(12) United States Patent
Caravella et al.

(10) Patent No.: US 11,247,987 B2
(45) Date of Patent: Feb. 15, 2022

(54) INHIBITING UBIQUITIN SPECIFIC PEPTIDASE 30

(71) Applicant: FORMA Therapeutics, Inc., Watertown, MA (US)

(72) Inventors: Justin Caravella, Cambridge, MA (US); Bingsong Han, Westwood, MA (US); Cuixian Liu, Madison, CT (US); Stephanos Ioannidis, Natick, MA (US); Alexandre Joseph Buckmelter, Acton, MA (US); David James Richard, Littleton, MA (US); Matthew W. Martin, Arlington, MA (US); Steven Mischke, Waltham, MA (US); Scot Mente, Watertown, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/753,439

(22) PCT Filed: Oct. 5, 2018

(86) PCT No.: PCT/US2018/054520
§ 371 (c)(1),
(2) Date: Apr. 3, 2020

(87) PCT Pub. No.: WO2019/071073
PCT Pub. Date: Apr. 11, 2019

(65) Prior Publication Data
US 2020/0317658 A1 Oct. 8, 2020

Related U.S. Application Data

(60) Provisional application No. 62/569,177, filed on Oct. 6, 2017.

(51) Int. Cl.
| C07D 417/04 | (2006.01) |
| C07D 417/12 | (2006.01) |
| C07C 261/04 | (2006.01) |
| C07D 231/40 | (2006.01) |
| C07D 241/04 | (2006.01) |

(Continued)

(52) U.S. Cl.
CPC .......... *C07D 417/12* (2013.01); *C07C 261/04* (2013.01); *C07D 231/40* (2013.01); *C07D 241/04* (2013.01); *C07D 265/30* (2013.01); *C07D 277/46* (2013.01); *C07D 277/56* (2013.01); *C07D 417/04* (2013.01)

(58) Field of Classification Search
CPC .. C07D 417/04; C07D 231/16; C07D 261/14; C07D 277/82; C07D 413/10; C07D 417/12; C07D 277/56; C07D 241/04; C07D 231/40; C07D 265/30; C07D 277/46; C07D 277/54; C07D 295/205

USPC ............... 548/953, 195, 371.7; 544/163, 386
See application file for complete search history.

(56) References Cited

U.S. PATENT DOCUMENTS

| 6,376,515 B2 | 4/2002 | Zhu et al. |
| 6,576,632 B1 | 6/2003 | Goldstein et al. |

(Continued)

FOREIGN PATENT DOCUMENTS

| CN | 101838264 A | 9/2010 |
| CN | 104045552 A | 9/2014 |

(Continued)

OTHER PUBLICATIONS

Rusilowicz-Jones, E. et al., A novel USP30 inhibitor recapitulates genetic loss of USP30 and sets the trigger for PINK1-PARKIN amplicfication of mitochondrial ubiquitylation, bioRxiv, doi: https://doi.org/10.1101/2020.04.16.044206, 1-35 (posted Apr. 20, 2020).
Rusilowicz-Jones, E. et al., USP30 sets a trigger threshold for PINK1-PARKIN amplification of mitochondrial ubiquitylation, Life Sci. Alli., 3(8):1-14 (2020).
Rusilowicz-Jones, E. V. et al., Benchmarking a highly selective USP30 inhibitor for enhancement of mitophagy and pexophagy, bioRxiv, doi:https://doi.org/10.1101/2021.04.28.441730, 1-19 (posted Apr. 28, 2021).

(Continued)

*Primary Examiner* — Jeffrey H Murray
(74) *Attorney, Agent, or Firm* — Choate, Hall & Stewart LLP; John P. Rearick; Erica M. D'Amato

(57) ABSTRACT

The present disclosure relates to chemical entities useful as inhibitors of Ubiquitin Specific Protease 30 (USP30), pharmaceutical compositions comprising the chemical entities, and methods of using the chemical entities. The chemical entities as disclosed herein can be useful in the treatment of a disease, disorder, or condition involving mitochondrial dysfunction, including neurodegenerative diseases, motor neuron diseases, metabolic disorders, and cancers, among other ailments. Chemical entities disclosed herein include compounds of Formula (II):

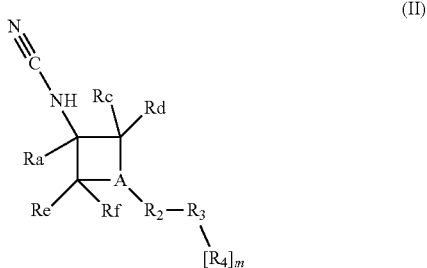

wherein A, $R_2$, $R_3$, $R_4$, $R_a$, $R_c$, $R_d$, $R_e$, $R_f$, and m are defined herein.

24 Claims, No Drawings

(51) Int. Cl.
  *C07D 265/30* (2006.01)
  *C07D 277/46* (2006.01)
  *C07D 277/56* (2006.01)

(56) References Cited

U.S. PATENT DOCUMENTS

| | | |
|---|---|---|
| 6,632,815 B2 | 10/2003 | Zhu et al. |
| 6,835,727 B2 | 12/2004 | Okamoto et al. |
| 7,425,354 B2 | 9/2008 | Yanai et al. |
| 7,687,504 B2 | 3/2010 | Jiaang et al. |
| 7,807,691 B2 | 10/2010 | Gavardinas et al. |
| 7,910,741 B2 | 3/2011 | Nishizawa et al. |
| 8,329,708 B2 | 12/2012 | Sim et al. |
| 8,815,924 B2 | 8/2014 | Dorsch et al. |
| 9,393,244 B2 | 7/2016 | Moussa |
| 9,511,142 B2 | 12/2016 | Burns et al. |
| 9,550,792 B2 | 1/2017 | Lu et al. |
| 9,926,307 B2 | 3/2018 | Jones et al. |
| 9,938,272 B2 | 4/2018 | Ding et al. |
| 9,997,717 B2 | 6/2018 | Kawamura et al. |
| 10,590,109 B2 | 3/2020 | Kong et al. |
| 10,615,343 B2 | 4/2020 | Stoessel et al. |
| 2003/0191279 A1 | 10/2003 | Goldstein et al. |
| 2009/0264499 A1 | 10/2009 | Deng et al. |
| 2016/0264548 A1 | 9/2016 | Qiu et al. |
| 2017/0247365 A1 | 8/2017 | Jones et al. |
| 2018/0228923 A1 | 8/2018 | Lai et al. |
| 2021/0198263 A1 | 7/2021 | Martin et al. |

FOREIGN PATENT DOCUMENTS

| | | |
|---|---|---|
| CN | 104557862 A | 4/2015 |
| CN | 106986859 A | 7/2017 |
| CN | 107619384 A | 1/2018 |
| DE | 102004054666 A1 | 5/2006 |
| EP | 3590931 A1 | 1/2020 |
| GB | 2424881 A | 10/2006 |
| JP | 2009/108152 A | 5/2009 |
| JP | 2009/149754 A | 7/2009 |
| JP | 2010/066630 A | 3/2010 |
| JP | 2011/006360 A | 1/2011 |
| JP | 2011/042606 A | 3/2011 |
| JP | 2012/123292 A | 6/2012 |
| JP | 5057056 B2 | 10/2012 |
| JP | 5219583 B2 | 6/2013 |
| JP | 5443720 B2 | 3/2014 |
| JP | 2014/232188 A | 12/2014 |
| JP | 5899607 B2 | 4/2016 |
| KR | 1077417 B1 | 10/2011 |
| KR | 1715090 B1 | 3/2017 |
| WO | WO-2001/019788 A2 | 3/2001 |
| WO | WO-2001/019798 A2 | 3/2001 |
| WO | WO-2001/029007 A1 | 4/2001 |
| WO | WO-2001/064642 A2 | 9/2001 |
| WO | WO-2001/064643 A2 | 9/2001 |
| WO | WO-2001/077073 A1 | 10/2001 |
| WO | WO-2002/046159 A1 | 6/2002 |
| WO | WO-2002/051831 A1 | 7/2002 |
| WO | WO-2003/007955 A2 | 1/2003 |
| WO | WO-2003/020217 A2 | 3/2003 |
| WO | WO-2004/002481 A1 | 1/2004 |
| WO | WO-2004/014370 A2 | 2/2004 |
| WO | WO-2004/014902 A2 | 2/2004 |
| WO | WO-2004/080966 A1 | 9/2004 |
| WO | WO-2004/085385 A2 | 10/2004 |
| WO | WO-2004/110350 A2 | 12/2004 |
| WO | WO-2005/000300 A1 | 1/2005 |
| WO | WO-2005/019200 A2 | 3/2005 |
| WO | WO-2005/044797 A1 | 5/2005 |
| WO | WO-2005/077345 A1 | 8/2005 |
| WO | WO-2005/077368 A2 | 8/2005 |
| WO | WO-2005/077373 A2 | 8/2005 |
| WO | WO-2005/080379 A1 | 9/2005 |
| WO | WO-2005/112540 A2 | 12/2005 |
| WO | WO-2005/115374 A1 | 12/2005 |
| WO | WO-2005/115382 A1 | 12/2005 |
| WO | WO-2006/014185 A1 | 2/2006 |
| WO | WO-2006/015279 A1 | 2/2006 |
| WO | WO-2006/024034 A1 | 3/2006 |
| WO | WO-2006/027076 A1 | 3/2006 |
| WO | WO-2006/045350 A1 | 5/2006 |
| WO | WO-2006/063113 A2 | 6/2006 |
| WO | WO-2006/074445 A2 | 7/2006 |
| WO | WO-2006/076202 A1 | 7/2006 |
| WO | WO-2006/113261 A2 | 10/2006 |
| WO | WO-2006/129199 A1 | 12/2006 |
| WO | WO-2007/024744 A2 | 3/2007 |
| WO | WO-2007/061923 A2 | 5/2007 |
| WO | WO-2007/144202 A1 | 12/2007 |
| WO | WO-2007/144204 A1 | 12/2007 |
| WO | WO-2007/146838 A2 | 12/2007 |
| WO | WO-2008/028553 A1 | 3/2008 |
| WO | WO-2008/035209 A2 | 3/2008 |
| WO | WO-2008/071456 A2 | 6/2008 |
| WO | WO-2008/073670 A2 | 6/2008 |
| WO | WO-2008/079291 A2 | 7/2008 |
| WO | WO-2008/141976 A1 | 11/2008 |
| WO | WO-2009/010156 A2 | 1/2009 |
| WO | WO-2009/011850 A2 | 1/2009 |
| WO | WO-2009/047105 A1 | 4/2009 |
| WO | WO-2009/078992 A1 | 6/2009 |
| WO | WO-2009/089042 A1 | 7/2009 |
| WO | WO-2009/129371 A1 | 10/2009 |
| WO | WO-2009/158571 A1 | 12/2009 |
| WO | WO-2010/048149 A2 | 4/2010 |
| WO | WO-2010/075376 A2 | 7/2010 |
| WO | WO-2011/025706 A2 | 3/2011 |
| WO | WO-2011/031934 A1 | 3/2011 |
| WO | WO-2011/053825 A2 | 5/2011 |
| WO | WO-2011/103091 A1 | 8/2011 |
| WO | WO-2011/126903 A2 | 10/2011 |
| WO | WO-2011/143495 A1 | 11/2011 |
| WO | WO-2011/161446 A1 | 12/2011 |
| WO | WO-2012/016217 A1 | 2/2012 |
| WO | WO-2012/078855 A1 | 6/2012 |
| WO | WO-2012/083048 A2 | 6/2012 |
| WO | WO-2012/083059 A1 | 6/2012 |
| WO | WO-2012/129562 A2 | 9/2012 |
| WO | WO-2012/139425 A1 | 10/2012 |
| WO | WO-2012/160015 A1 | 11/2012 |
| WO | WO-2012/166951 A1 | 12/2012 |
| WO | WO-2012/177782 A1 | 12/2012 |
| WO | WO-2012/177997 A1 | 12/2012 |
| WO | WO-2013/046136 A1 | 4/2013 |
| WO | WO-2013/052845 A1 | 4/2013 |
| WO | WO-2013/086229 A1 | 6/2013 |
| WO | WO-2013/106678 A1 | 7/2013 |
| WO | WO-2013/130890 A1 | 9/2013 |
| WO | WO-2013/132991 A1 | 9/2013 |
| WO | WO-2013/178816 A1 | 12/2013 |
| WO | WO-2013/182274 A1 | 12/2013 |
| WO | WO-2013/190212 A1 | 12/2013 |
| WO | WO-2014/000846 A1 | 1/2014 |
| WO | WO-2014/041111 A1 | 3/2014 |
| WO | WO-2014/068527 A1 | 5/2014 |
| WO | WO-2014/072261 A1 | 5/2014 |
| WO | WO-2014/108053 A1 | 7/2014 |
| WO | WO-2014/140059 A1 | 9/2014 |
| WO | WO-2014/159733 A1 | 10/2014 |
| WO | WO-2014/165232 A1 | 10/2014 |
| WO | WO-2015/003816 A2 | 1/2015 |
| WO | WO-2015/010297 A1 | 1/2015 |
| WO | WO-2015/011284 A2 | 1/2015 |
| WO | WO-2015/048547 A2 | 4/2015 |
| WO | WO-2015/048662 A2 | 4/2015 |
| WO | WO-2015/058832 A1 | 4/2015 |
| WO | WO-2015/085238 A1 | 6/2015 |
| WO | WO-2015/095104 A1 | 6/2015 |
| WO | WO-2015/106292 A1 | 7/2015 |
| WO | WO-2015/130790 A2 | 9/2015 |
| WO | WO-2015/173225 A1 | 11/2015 |
| WO | WO-2015/176625 A1 | 11/2015 |
| WO | WO-2015/189646 A1 | 12/2015 |
| WO | WO-2015/197028 A1 | 12/2015 |

(56) References Cited

FOREIGN PATENT DOCUMENTS

| | | |
|---|---|---|
| WO | WO-2016/007534 A1 | 1/2016 |
| WO | WO-2016/008011 A1 | 1/2016 |
| WO | WO-2016/016366 A1 | 2/2016 |
| WO | WO-2016/034262 A1 | 3/2016 |
| WO | WO-2016/040449 A1 | 3/2016 |
| WO | WO-2016/046530 A1 | 3/2016 |
| WO | WO-2016/109559 A2 | 7/2016 |
| WO | WO-2016/156816 A1 | 10/2016 |
| WO | WO-2016/172631 A2 | 10/2016 |
| WO | WO-2017/002120 A1 | 1/2017 |
| WO | WO-2017/009650 A1 | 1/2017 |
| WO | WO-2017/010399 A1 | 1/2017 |
| WO | WO-2017/019817 A1 | 2/2017 |
| WO | WO-2017/019822 A1 | 2/2017 |
| WO | WO-2017/019830 A1 | 2/2017 |
| WO | WO-2017/040194 A1 | 3/2017 |
| WO | WO-2017/040982 A1 | 3/2017 |
| WO | WO-2017/066705 A1 | 4/2017 |
| WO | WO-2017/093718 A1 | 6/2017 |
| WO | WO-2017/100558 A1 | 6/2017 |
| WO | WO-2017/103614 A1 | 6/2017 |
| WO | WO-2017/109488 A1 | 6/2017 |
| WO | WO-2017/141036 A1 | 8/2017 |
| WO | WO-2017/149313 A1 | 9/2017 |
| WO | WO-2017/158381 A1 | 9/2017 |
| WO | WO-2017/158388 A1 | 9/2017 |
| WO | WO-2017/161028 A1 | 9/2017 |
| WO | WO-2017/162007 A1 | 9/2017 |
| WO | WO-2017/163078 A1 | 9/2017 |
| WO | WO-2018/005591 A1 | 1/2018 |
| WO | WO-2018/010514 A1 | 1/2018 |
| WO | WO-2018/024188 A1 | 2/2018 |
| WO | WO-2018/039896 A1 | 3/2018 |
| WO | WO-2018/060689 A1 | 4/2018 |
| WO | WO-2018/060691 A1 | 4/2018 |
| WO | WO-2018/060742 A1 | 4/2018 |
| WO | WO-2018/065768 A1 | 4/2018 |
| WO | WO-2018/106818 A1 | 6/2018 |
| WO | WO-2018/106820 A1 | 6/2018 |
| WO | WO-2018/134352 A1 | 7/2018 |
| WO | WO-2018/146116 A1 | 8/2018 |
| WO | WO-2018/157856 A1 | 9/2018 |
| WO | WO-2018/160891 A1 | 9/2018 |
| WO | WO-2018/213150 A1 | 11/2018 |
| WO | WO-2018/220355 A1 | 12/2018 |
| WO | WO-2018/234775 A1 | 12/2018 |
| WO | WO-2019/071073 A1 | 4/2019 |
| WO | WO-2019/171042 A1 | 9/2019 |
| WO | WO-2019/222468 A1 | 11/2019 |
| WO | WO-2020/072964 A1 | 4/2020 |

OTHER PUBLICATIONS

Ahmed, H.E.A. and Bajorath, J., Methods for Computer-Aided Chemical Biology, Part 5: Rationalizing the Selectivity of Cathepsin Inhibitors on the Basis of Molecular Fragments and Topological Feature Distributions, Chemical Biology & Drug Design, (74): 129-141 (2009).

Bingol, B. et al., The mitochondrial deubiquitinase USP30 opposes parkin—mediated mitophagy, Nature, 510:370-375 (2014).

Buus, R. et al., Deubiquitinase Activities Required for Hepatocyte Growth Factor-Induced Scattering of Epithelial Cells, Current Bio., 19:1463-1466 (2009).

Dovlatyan, M. et al., A High-Content Live Imaging Mitophagy Assay to Evaluate Small Molecule Mitophagy Enhancers, Poster Abstract (Board No. B555) presented at ASCB EMBO (Dec. 2017).

Durcan, T. M. and Edward, A. F. The three 'P's of mitophagy: PARKIN, PINK1, and post-translational modifications, Genes and Development, 29:989-999 (2015).

International Search Report for PCT/US2018/054520, 4 pages (dated Feb. 5, 2019).

International Search Report for PCT/US2019/032619, 5 pages (dated Jul. 16, 2019).

International Search Report for PCT/US2019/054803, 6 pages (dated Nov. 27, 2019).

Iwashita, H. et al., Live Cell Imaging of Mitochondrial Autophagy with a Novel Fluorescent Small Molecule, ACS Chem. Biol., 12:2546-2551 (2017).

Ji, Y. et al., Innate C-H Trifluoromethylation of Heterocycles, PNAS, 108(35):14411-14415 (2011).

Kluge, A. F. et al., Novel Highly Selective Inhibitors of Ubiquitin Specific Protease 30 (USP30) Accelerate Mitophagy, Bioorg. and Medic. Chem. Lett., 28(15):2655-2659 (2018).

Lainé, D., et al., Discovery of Novel Cyanamide-Based Inhibitors of Cathepsin C, ACS Med. Chem. Lett., 2:142-147 (2011).

McWilliams, T. G. et al., mit-QC illuminates mitophagy and mitochondrial architecture in vivo, J. Cell Biol., 214:333-345 (2016).

Nakamura, N. and Hirose, S., Regulation of Mitochondrial Morphology by USP30, a Deubiquitinating Enzyme Present in the Mitochondrial Outer Membrane, Mole. Bio. Cell., 19:1903-1911 (2008).

Ndubaku, C. and Tsui, V., Inhibiting the Deubiquitinating Enzymes (DUBs), Jrnl. Med. Chem., 58:1581-1595 (2015).

Pollock, S.R., and Kashatus, D.F., A novel role for RaIA during PINK1-Parkin mitophagy, Poster Abstract (Board No. B3252) presented at ASCB EMBO (Dec. 2017).

PubChem CID 116045277, (3-Methylcyclobutyl)cyanamide, 2 pages, Date Created: Jan. 30, 2016, Date Modified: Aug. 8, 2020.

PubChem CID 116214356, (1-Ethylcyclobutyl)cyanamide, 2 pages, Date Created: Jan. 30, 2016, Date Modified: Aug. 8, 2020.

PubChem CID 21516572, (1-Methylcyclopropyl)cyanamide, 7 pages, Date Created: Dec. 5, 2007, Date Modified: Apr. 18, 2020.

Puri, R. et al., Mitochondrial Ubiquitin Ligase Mul1 Mediates an Early Stress Protection of Neuronal Mitochondria From Degradation by Parkin-Mediated Mitophagy, Poster Abstract (Board No. B482) presented at ASCB EMBO (Dec. 2017).

Sathe, M. et al., Efficient synthesis of N-cyano α and β-amino esters, Synthetic Communications: An International Journal for Rapid Communication of Synthetic Organic Chemistry, 38: 1375-1380 (2008).

Seiberlich, V. et al., The small molecule inhibitor PR-619 of deubiquitinating enzymes affects the microtubule network and causes protein aggregate formation in neural cells: Implications for neurodegenerative diseases, Biochem Biophys Acta., 1823 (11):2057-2068 (2012).

Silverman, R., "The Organic Chemistry of Drug Design and Drug Action", NY Elsevier, 29-32 (2004).

Thompson, J. E. et al., Discovery of MF-0094, a potent, selective and cell permeable inhibitor of USP30, Poster (2017).

U.S. Appl. No. 17/282,521, Buckmelter et al.

Deaton, D. N. et al., Novel and potent cyclic cyanamide-based cathepsin K inhibitors, Bioorg. Med. Chem. Lett., 15:1815-1819 (2005).

INHIBITING UBIQUITIN SPECIFIC PEPTIDASE 30

The present patent application is a U.S. National Stage Application of PCT/US18/54520, filed Oct. 5, 2018, which claims the benefit of U.S. Provisional Patent Application No. 62/569,177, filed Oct. 6, 2017, which is incorporated herein by reference in its entirety.

TECHNICAL FIELD

The present disclosure is directed to novel chemical entities, methods for their preparation, synthesis and manufacture, which can act as inhibitors of Ubiquitin Specific Peptidase 30 (USP30), a member of the deubiquitinating (DUB) enzyme family. The present disclosure also describes the use of these USP30 inhibitors in the treatment of diseases or disorders associated with USP30 enzymes, such as the treatment of mitochondrial dysfunction diseases or disorders, neurodegenerative diseases, and in the treatment of cancer. Specifically, the disclosure is concerned with chemical entities and compositions inhibiting USP30, methods of treating diseases or disorders associated with USP30, and methods of synthesis of these compounds.

BACKGROUND

The ubiquitination system is a highly-regulated process which affects a wide variety of cellular activities and physiological processes. Dysregulation of this system is commonly associated with several human diseases, including cancer, neurodegenerative disorders, muscle dystrophies, and cardiomyopathies, amongst others (Popovic, et al., *Nature Medicine* 2014, 20, 1242-1253). Ubiquitination is a reversible process, facilitated by a group of proteins known as deubiquitinating enzymes (DUBs), which deconjugate ubiquitin (Ub) from the substrate. DUBs are encoded by approximately 100 human genes and are divided into six families, with the largest family being the ubiquitin-specific proteases (USPs) with more than 50 members.

Ubiquitin regulates mitochondrial dynamics and biogenesis, affecting the abundance and function of these organelles. Many age-related diseases, particularly neurodegenerative disorders, have been linked to mitochondrial dysfunction and impairment of the ubiquitination system (Ross, et al., *Int J Mol Sci.* 2015, 16(8), 19458-19476).

Parkinson's disease (PD) is a neurodegenerative disorder that affects more than 10 million people worldwide, including 60,000 new diagnoses a year in the US alone (Parkinson's Disease Foundation, www.pdf.org). PD is characterized by the loss of dopaminergic neurons in the substantia nigra. Although the exact mechanism of neuronal loss is not yet fully elucidated, an increasing body of evidence links mitochondrial dysfunction with dopaminergic neuron vulnerability.

Mitophagy, the clearance of dysfunctional mitochondria through autophagy, appears to be specifically important in certain genetically defined subsets of Parkinson's patients. Loss-of-function mutations in PRKN (gene encoding the Parkin protein) present as a form of autosomal recessive juvenile Parkinsonism (AR-JP) (Shimura, et al., *Nat Genet.* 2000, 25(3), 302-305; Sriram, et al., *Hum Mol Genet.* 2005, 14(17), 2571-2586; Ekholm-Reed, et al., *Mol Cell Biol.* 2013, 33(18), 3627-3643). In the late 1990's genetic analysis of Japanese families revealed that mutations in PARK2 (nPRKN) were responsible for AR-JP (Matsumine, et al., *Am J Hum Genet.* 1997, 60(3), 588-596). Subsequent investigation of different ethnic populations independently replicated the association between PRKN mutations and early-onset PD. Later genetic work identified mutations in PINK1 which result in early-onset recessive PD (Valente, et al., *Science.* 2004, 304(5674), 1158-1160; Valente, et al., *Ann Neurol.* 2004, 56(3), 336-341).

Parkin (E3 ubiquitin ligase) and PINK1 (kinase) are key regulators of mitophagy. In healthy mitochondria, PINK1 localization to the mitochondrial outer membrane (MOM) and exposure to the cytosol is limited by rapid import to the mitochondrial inner membrane (MIM). Once localized to the MIM, PINK1 is processed by several proteases, such as presenilin associated rhomboid-like protease (PARL), to yield a truncated version of PINK1 which is subsequently degraded by the proteasome (Meissner et al., *Autophagy.* 2015, 11(9), 1484-1498). Upon mitochondrial depolarization or dysfunction, PINK1 accumulates in the mitochondrial outer membrane (MOM), recruiting and activating Parkin via PINK1-dependent phosphorylation of both ubiquitin and Parkin. Consequently, activated Parkin ubiquitinates MOM proteins like TOMM20 to trigger mitophagy (Pickrell et al., *Neuron.* 2015, 85(2), 257-273).

USP30 is embedded in the MOM with its catalytic DUB domain oriented towards the cytosol and has been shown to antagonize Parkin-mediated ubiquitination of common substrates, consequently opposing Parkin-mediated mitophagy. Genetic silencing of USP30 results in increased ubiquitination of several Parkin substrates followed by increased mitophagy. In model organisms, USP30 depletion is able to rescue mitophagy defects caused by pathogenic Parkin mutations, as well as restore mitochondria morphology and function, and dopamine levels. (Nakamura, et al., *Mol Biol Cell.* 2008, 19(5), 1903-1911: Bingol, et al., *Nature* 2014, 510(7505):370-5). Therefore, inhibition of USP30 could present a novel treatment paradigm for PD, by promoting mitochondrial turnover.

USP30 inhibition could also benefit patients with other indications which involve mitochondria function, including but not limited to, neurodegenerative diseases, motor neuron diseases, metabolic disorders, cardio-vascular diseases, psychiatric diseases, osteoarthritis, and cancer. For example, mitochondria play a central role in apoptotic cell death. The key event in this process is BAX/BAK-dependent mitochondrial outer-membrane permeabilization. USP30 regulates BAX/BAK-dependent apoptosis, and its depletion sensitizes cancer cells to ABT-737, a BCL-2 inhibitor/BH3-mimetic (Liang, et al., *EMBO reports* 2015, 16, 618-627). These studies suggest a utility for a USP30 inhibitor in anti-cancer therapy.

There remains a need for USP30 inhibitor compounds. Such compounds would be useful, for example, in the development of new therapies for Parkinson's disease.

SUMMARY

The present disclosure provides compounds of Formula (Ia):

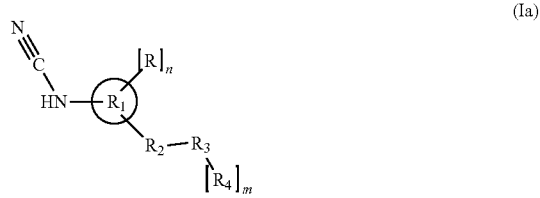

and pharmaceutically acceptable salts, solvates, prodrugs, stereoisomers, and tautomers thereof,
wherein:

R is independently chosen from hydrogen, OH, CN, $(C_1-C_6)$ alkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, and $(C_3-C_6)$ heterocycloalkyl groups;

n is 0, 1, or 2;

wherein, if n is 2, the R groups can combine to form a fused ring system with $R_1$;

$R_1$ is a 4-membered cyclic or heterocyclic group;

$R_2$, is chosen from $C(X)_n$, $S(O)_2$, $N(X)$, heteroatom linkers, $N(X)S(O)_2$, $N(X)S(O)_2N(X)$, carbonylalkyl groups, and carbonylheteroalkyl groups, wherein the alkyl portion of carbonylalkyl and carbonylheteroalkyl groups can optionally cyclize with R, $R_1$, or $R_3$;

X is independently chosen from hydrogen, alkyl groups, and heteroalkyl groups, wherein the alkyl and heteroalkyl groups can optionally cyclize with R, $R_1$, or $R_3$ or with another X group when multiple X groups are present;

$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;

$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

Y is independently chosen from hydrogen, OH, CN, $N(X)_2$, $(C_1-C_6)$ alkyl groups, $(C_1-C_6)$ heteroalkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, $(C_3-C_6)$ heterocycloalkyl groups, $(C_5-C_8)$ aryl groups, and $(C_4-C_8)$ heteroaryl groups; and m is 0, 1, or 2.

The present disclosure provides compounds of Formula (Ib):

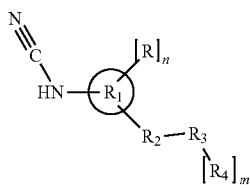

(Ib)

and pharmaceutically acceptable salts, solvates, prodrugs, stereoisomers, and tautomers thereof,
wherein:

R is independently chosen from hydrogen, OH, CN, $(C_1-C_6)$ alkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, and $(C_3-C_6)$ heterocycloalkyl groups;

n is 0, 1, or 2;

wherein, if n is 2, the R groups can combine to form a fused ring system with $R_1$;

$R_1$ is chosen from 3-6 membered cyclic or heterocyclic groups;

$R_2$ is chosen from carbonylheteroalkyl groups, wherein the alkyl portion of the carbonylheteroalkyl group can optionally cyclize with R, $R_1$, or $R_3$;

X is independently chosen from hydrogen, alkyl groups, and heteroalkyl groups, wherein the alkyl and heteroalkyl groups can optionally cyclize with R, $R_1$, or $R_3$ or with another X group when multiple X groups are present;

$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;

$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

Y is independently chosen from hydrogen, OH, CN, $N(X)_2$, $(C_1-C_6)$ alkyl groups, $(C_1-C_6)$ heteroalkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, $(C_3-C_6)$ heterocycloalkyl groups, $(C_5-C_8)$ aryl groups, and $(C_4-C_8)$ heteroaryl groups; and m is 0, 1, or 2.

The present disclosure provides compounds of Formula (Ic):

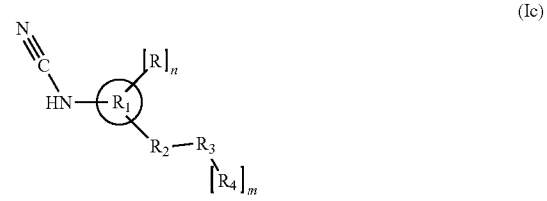

(Ic)

and pharmaceutically acceptable salts, solvates, prodrugs, stereoisomers, and tautomers thereof,
wherein:

R is independently chosen from hydrogen, OH, CN, $(C_1-C_6)$ alkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, and $(C_3-C_6)$ heterocycloalkyl groups;

n is 0, 1, or 2;

wherein, if n is 2, the R groups can combine to form a fused ring system with $R_1$;

$R_1$ is a 4-membered cyclic or heterocyclic group;

$R_2$, is a carbonylheteroalkyl group, wherein the alkyl portion of the carbonylheteroalkyl group can optionally cyclize with R, $R_1$, or $R_3$;

X is independently chosen from hydrogen, alkyl groups, and heteroalkyl groups, wherein the alkyl and heteroalkyl groups can optionally cyclize with R, $R_1$, or $R_3$ or with another X group when multiple X groups are present;

$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;

$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

Y is independently chosen from hydrogen, OH, CN, $N(X)_2$, $(C_1-C_6)$ alkyl groups, $(C_1-C_6)$ heteroalkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, $(C_3-C_6)$ heterocycloalkyl groups, $(C_5-C_8)$ aryl groups, and $(C_4-C_8)$ heteroaryl groups; and m is 0, 1, or 2.

The present disclosure provides compounds of Formula (II):

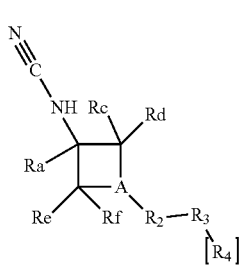

(II)

and pharmaceutically acceptable salts, solvates, prodrugs, stereoisomers, and tautomers thereof,
wherein:

A is N or $CR_b$;

$R_a$ is selected from the group consisting of hydrogen and $(C_1-C_6)$ alkyl groups;

$R_b$ is selected from the group consisting of: hydrogen, halogen, OH, $(C_1-C_6)$ alkyl groups optionally substituted with one or more $R_5$ and $(C_1-C_6)$ alkoxy groups optionally substituted with one or more $R_5$; or $R_b$ and X together form a $(C_3-C_6)$ spirocyclic cycloalkyl or $(C_3-C_6)$ spirocyclic heterocycloalkyl, each of $R_c$, $R_d$, $R_e$ and $R_f$ is independently selected from the group consisting of: hydrogen, halogen, —$OR_5$ and $(C_1-C_6)$ alkyl groups optionally substituted with one or more $R_5$;

$R_2$ is selected from the group consisting of: C(O)N(X), N(X)C(O);

X is independently chosen from hydrogen, alkyl groups, and heteroalkyl groups, wherein the alkyl and heteroalkyl groups can optionally cyclize with $R_b$, or $R_3$;

$R_3$ is selected from the group consisting of: $(C_1-C_6)$ alkyl (e.g., a linker to $R_4$, or when X forms a cycloalkyl together with $R_3$), $(C_3-C_6)$ cycloalkyl, $(C_1-C_6)$ heteroalkyl (e.g., when X forms a heterocyclyl together with $R_3$), aryl having 1 to 3 aromatic rings (including aryl groups optionally substituted with 1 or 2 R groups) and heteroaryl having 1 to 3 aromatic rings (including heteroaryl groups optionally substituted with 1 or 2 R groups);

$R_4$ (present when m is 1 or 2) is independently chosen from alkyl groups, cycloalkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

$R_5$ is selected from the group consisting of: hydrogen, halogen, OH, $(C_1-C_3)$ alkyl groups, and $(C_1-C_3)$ alkoxy groups;

R is independently chosen from hydrogen, OH, CN, $(C_1-C_6)$ alkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, $(C_3-C_6)$ heterocycloalkyl groups; $(C_3-C_6)$cycloalkyloxy groups and $(C_1-C_6)$ alkoxyalkyl groups;

Y is independently chosen from hydrogen, OH, CN, $N(X)_2$, $(C_1-C_6)$ alkyl groups, $(C_1-C_6)$ heteroalkyl groups, $(C_1-C_6)$ alkoxy groups, $(C_1-C_6)$ haloalkyl groups, $(C_1-C_6)$ haloalkoxy groups, halogen, $(C_3-C_6)$ cycloalkyl groups, $(C_3-C_6)$ heterocycloalkyl groups, $(C_5-C_8)$ aryl groups, $(C_4-C_8)$ heteroaryl groups, and $(C_4-C_8)$ heteroaryl groups substituted with $C_1-C_3$ alkyl; and m is 0, 1, or 2.

The present disclosure provides compounds of Formula (III):

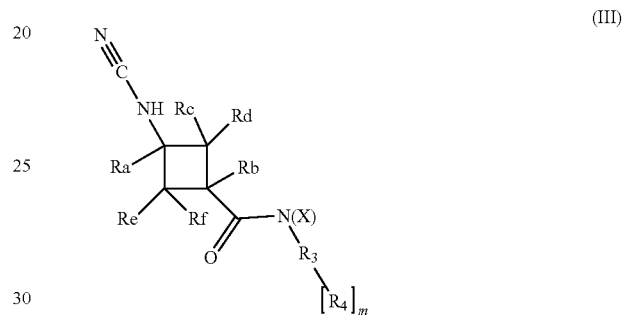

(III)

and pharmaceutically acceptable salts, solvates, prodrugs, stereoisomers, and tautomers thereof,
wherein:

$R_a$ is selected from the group consisting of hydrogen and $(C_1-C_6)$ alkyl groups;

$R_b$ is selected from the group consisting of: hydrogen, halogen, OH, $(C_1-C_6)$ alkyl groups optionally substituted with one or more $R_5$ and $(C_1-C_6)$ alkoxy groups optionally substituted with one or more $R_5$; or $R_b$ and X together form a $(C_3-C_6)$ spirocyclic cycloalkyl or $(C_3-C_6)$ spirocyclic heterocycloalkyl;

each of $R_c$, $R_d$, $R_e$ and $R_f$ is independently selected from the group consisting of: hydrogen, halogen, —$OR_5$ and $(C_1-C_6)$ alkyl groups optionally substituted with one or more $R_5$;

X is independently chosen from hydrogen, alkyl groups, and heteroalkyl groups, wherein the alkyl and heteroalkyl groups can optionally cyclize with $R_b$, or $R_3$;

$R_3$ is selected from the group consisting of: $(C_1-C_3)$ alkyl, $(C_1-C_3)$ heteroalkyl, and 5-10 membered cyclic, heterocyclic, aryl, and heteroaryl groups, wherein any of the rings can be optionally substituted with 1 or 2 R groups;

$R_4$ (present when m is 1 or 2) is independently chosen from alkyl groups, cycloalkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

$R_5$ is selected from the group consisting of: hydrogen, halogen, OH, $(C_1-C_3)$ alkyl groups, and $(C_1-C_3)$ alkoxy groups;

R is independently chosen from hydrogen, OH, CN, $(C_1-C_6)$ alkyl groups, $(C_1-C_6)$ alkoxy groups, $(C_1-C_6)$ haloalkyl groups, $(C_1-C_6)$ haloalkoxy groups, halogen, $(C_3-$ $C_6$) cycloalkyl groups, ($C_3$-$C_6$) heterocycloalkyl groups; ($C_3$-$C_6$)cycloalkyloxy groups and ($C_1$-$C_6$) alkoxyalkyl groups;

Y is independently chosen from hydrogen, OH, CN, $N(X)_2$, ($C_1$-$C_6$) alkyl groups, ($C_1$-$C_6$) heteroalkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, ($C_3$-$C_6$) heterocycloalkyl groups, ($C_5$-$C_8$) aryl groups, and ($C_4$-$C_8$) heteroaryl groups, and ($C_4$-$C_8$) heteroaryl groups substituted with $C_1$-$C_3$ alkyl; and m is 0, 1, or 2.

The present disclosure also provides compounds of Formula (I):

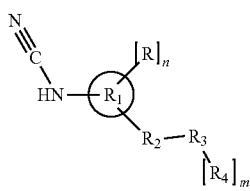

(I)

and pharmaceutically acceptable salts, solvates, prodrugs, stereoisomers, and tautomers thereof,
wherein:
R is independently chosen from hydrogen, OH, CN, ($C_1$-$C_6$) alkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, and ($C_3$-$C_6$) heterocycloalkyl groups;
n is 0, 1, or 2;
wherein, if n is 2, the R groups can combine to form a fused ring system with $R_1$;
$R_1$ is chosen from 3-6 membered cyclic or heterocyclic groups;
$R_2$ is chosen from $C(X)_n$, $S(O)_2$, $N(X)$, heteroatom linkers, $N(X)S(O)_2$, $N(X)S(O)_2N(X)$, carbonylalkyl groups, and carbonylheteroalkyl groups, wherein the alkyl portion of carbonylalkyl and carbonylheteroalkyl groups can optionally cyclize with R, $R_1$, or $R_3$;
X is independently chosen from hydrogen, alkyl groups, and heteroalkyl groups, wherein the alkyl and heteroalkyl groups can optionally cyclize with R, $R_1$, or $R_3$ or with another X group when multiple X groups are present;
$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;
$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;
Y is independently chosen from hydrogen, OH, CN, $N(X)_2$, ($C_1$-$C_6$) alkyl groups, ($C_1$-$C_6$) heteroalkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, ($C_3$-$C_6$) heterocycloalkyl groups, ($C_5$-$C_8$) aryl groups, and ($C_4$-$C_8$) heteroaryl groups; and
m is 0, 1, or 2.

Another aspect of the present disclosure relates to a method of treating a disease or disorder associated with inhibition of Ubiquitin Specific Peptidase 30 (USP30). The method comprises administering to a patient in need of a treatment for diseases or disorders associated with inhibition of USP30 an effective amount of at least one chemical entity chosen from compounds of Formula (I), and pharmaceutically acceptable salts, solvates, prodrugs, stereoisomers, and tautomers thereof.

Another aspect of the disclosure is directed to a method of inhibiting USP30. The method involves administering to a patient in need thereof an effective amount of at least one chemical entity chosen from compounds of Formula (I), and pharmaceutically acceptable salts, hydrates, solvates, prodrugs, stereoisomers, and tautomers thereof.

Another aspect of the disclosure relates to a method of treating neurodegenerative diseases. The method comprises administering to a patient in need thereof an effective amount of at least one chemical entity chosen from compounds of Formula (I), and pharmaceutically acceptable salts, solvates, prodrugs, stereoisomers, and tautomers thereof.

Preferably the compounds of the disclosure are for use in a method of treating Parkinson's disease, wherein the method comprises administering to a patient in need thereof an effective amount of at least one chemical entity of the disclosure or a pharmaceutically acceptable salt, solvate, prodrug, stereoisomer, or tautomer thereof.

Another aspect of the disclosure is directed to pharmaceutical compositions comprising at least one chemical entity chosen from compounds of Formula (I), and pharmaceutically acceptable salts, solvates, prodrugs, stereoisomers, and tautomers thereof, and a pharmaceutically acceptable carrier. The pharmaceutical acceptable carrier may further include an excipient, diluent, or surfactant.

Another aspect of the present disclosure relates to at least one chemical entity chosen from compounds of Formula (I), and pharmaceutically acceptable salts, solvates, prodrugs, stereoisomers, and tautomers thereof, for use in the manufacture of a medicament for treating a disease associated with inhibiting USP30.

Another aspect of the present disclosure relates to the use of at least one chemical entity chosen from compounds of Formula (I), and pharmaceutically acceptable salts, solvates, prodrugs, stereoisomers, and tautomers thereof, in the treatment of a disease associated with inhibiting USP30.

As summarized above, and as set forth in detail below, the present disclosure relates to chemical entities and compositions that are capable of inhibiting the activity of USP30. The disclosure also relates to methods of treating, preventing or ameliorating a disease or disorder in which USP30 plays a role by administering to a patient in need thereof a therapeutically effective amount of at least one chemical entity chosen from compounds of Formula (I), and pharmaceutically acceptable salts, solvates, prodrugs, stereoisomers, and tautomers thereof. The methods of the present disclosure can be used in the treatment of a variety of USP30 dependent diseases and disorders by inhibiting the activity of USP30. Inhibition of USP30 as disclosed herein provides a novel approach to the treatment, prevention, or amelioration of diseases including, but not limited to, cancer.

DETAILED DESCRIPTION

The present disclosure describes compounds that inhibit USP30. Compounds that inhibit USP30 are useful in the development of novel therapies for the treatment of diseases or disorders associated with USP30 enzymes, such as the treatment of mitochondrial dysfunction diseases or disorders, neurodegenerative diseases, and in the treatment of cancer. Specifically, the present disclosure is concerned with chemical entities and compositions inhibiting USP30, methods of treating diseases or disorders associated with USP30, and methods of synthesis of these compounds. In some embodiments the compounds of the invention are USP30 inhibitors having an IC$_{50}$ value of <10 µM and >0.001 µM when tested in the Biochemical Assay of Example A herein. Preferably, the compounds of the invention are USP30 inhibitors having an IC$_{50}$ value of <1 µM and >0.001 µM when tested in the Biochemical Assay of Example A herein.

In a first aspect of the disclosure, the chemical entities chosen from compounds of Formula (I):

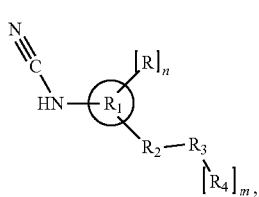

and pharmaceutically acceptable salts, solvates, prodrugs, stereoisomers, and tautomers thereof, are described wherein R, $R_1$, $R_2$, $R_3$, $R_4$, n, and m are as described herein above. In further aspects of the disclosure, compounds of Formula (Ia), (Ib), and (Ic) and pharmaceutically acceptable salts, solvates, prodrugs, stereoisomers, and tautomers thereof as described herein above are provided.

In a further aspect of the disclosure, compounds of Formula (II):

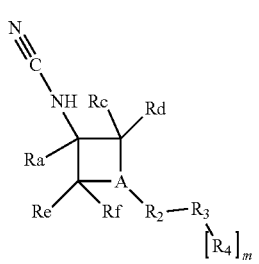

and pharmaceutically acceptable salts, solvates, prodrugs, stereoisomers, and tautomers thereof are provided, wherein A, $R_a$, $R_b$, $R_c$, $R_d$, $R_e$, $R_f$, R, $R_2$, $R_3$, $R_4$, $R_5$, X, Y, and m are as described herein above.

In a further aspect of the disclosure, compounds of Formula (III):

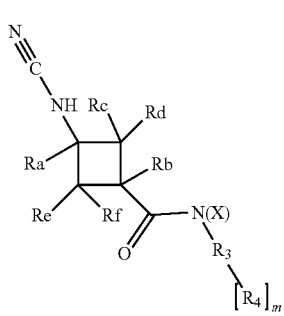

and pharmaceutically acceptable salts, solvates, prodrugs, stereoisomers, and tautomers thereof are provided, wherein $R_a$, $R_b$, $R_c$, $R_d$, $R_e$, $R_f$, R, $R_3$, $R_4$, $R_5$, X, Y, and m are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$) alkyl, (C$_1$-C$_6$) alkyl, (C$_1$-C$_6$) alkoxy, (C$_1$-C$_6$) haloalkyl, (C$_1$-C$_6$) haloalkoxy, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, —NH$_2$, —NH((C$_1$-C$_6$) alkyl), —N((C$_1$-C$_6$) alkyl)$_2$, —NHC(O)(C$_1$-C$_6$) alkyl, —C(O)NH(C$_1$-C$_6$) alkyl, —S(O)$_2$(C$_1$-C$_6$) alkyl, —S(O)NH(C$_1$-C$_6$) alkyl, and S(O)N((C$_1$-C$_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, and S, the remaining ring atoms being C. Heteroaryl as herein defined also means a bicyclic heteroaromatic group wherein the heteroatom is selected from N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, thieno[2,3-d]thiazole, 1a,2,3,7b-tetrahydro-1H-cyclopropa[c][1,8]naphthyridine, 3H-indolyl, and derivatives thereof. Furthermore the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, isoindolyl and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

The terms "alkylene" or "alkylenyl" refer to a divalent alkyl radical. Any of the above mentioned monovalent alkyl groups may be an alkylene by abstraction of a second hydrogen atom from the alkyl. As herein defined, alkylene may also be a $C_0$-$C_6$ alkylene. An alkylene may further be a $C_0$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "carbonylalkyl" means an alkyl group as defined above, where the alkyl group is substituted with one or more C(O) groups.

The term "carbonylheteroalkyl" is similar to the carbonylalkyl group as defined above, in that an alkyl group containing heteroatoms such as N, S, O ("heteroalkyl"), is substituted with one or more C(O) groups. Non-limiting examples of carbonylheteroalkyl groups include amide, reverse amide, and alkylamide-type groups such as NXC(O), C(X)$_2$NXC(O), C(O)NX, urea-type groups such as NXC(O)NX, wherein X is chosen from hydrogen, alkyl, and heteroalkyl groups, wherein the alkyl and heteroalkyl groups can optionally cyclize with other groups on the compound, such as R, $R_1$, $R_3$, or with another X group when multiple X groups are present.

"Cycloalkyl" or "carbocyclyl" means monocyclic or polycyclic saturated carbon rings containing 3-18 carbon atoms. One or two ring carbon atoms in the cycloalkyl ring can optionally be replaced by a —C(O)— group. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the entire ring carbon or heteroatoms. One or two ring carbon atoms in the heterocycloalkyl ring can optionally be replaced by a —C(O)— group. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. As used herein, "heterocyclyl" and "heterocycloalkyl" also includes bridged and spirocyclic ring systems where at least one atom is a heteroatom. A heterocyclic ring as a substituent may attach via a ring heteroatom (e.g. "N-linked") or via a ring carbon (e.g. "C-linked").

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The terms "administer", "administering", or "administration" as used in this disclosure refer to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

As used herein, the term "neurodegenerative disease" includes, but is not limited to, Alzheimer's disease and other dementias, Parkinson's disease and other synucleinopathies such as Multiple System Atrophy, dementia with Lewy Bodies and PD-related disorders, Prion disease, Corticobasal Degeneration, Frontotemporal Dementia, Posterior Cortical Atrophy, Primary Progressive Aphasia, Progressive Supranuclear Palsy, Pick's disease, Chronic Traumatic Encephelopathy, Dementia Pugilistica, Traumatic Brain Injury, Vascular Dementia, Peripheral Neuropathy and Multiple Sclerosis.

Formula I (and Formulae (Ia), (Ib), and (Ic))

The present disclosure relates to chemical entities chosen from compounds of Formula (I) and pharmaceutically acceptable salts, solvates, prodrugs, stereoisomers, and tautomers thereof, capable of inhibiting USP30, which are useful for the treatment of diseases and disorders associated with inhibition of USP30. The disclosure further relates to chemical entities chosen from compounds of Formula (I) and pharmaceutically acceptable salts, solvates, prodrugs, stereoisomers, and tautomers thereof, which are useful for inhibiting USP30.

The chemical entities disclosed are chosen from compounds of Formula (I):

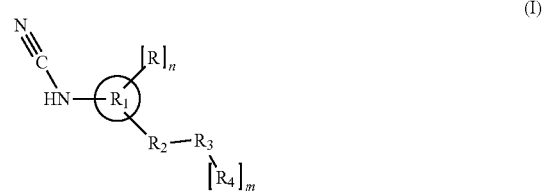

and pharmaceutically acceptable salts, solvates, prodrugs, stereoisomers, and tautomers thereof, wherein:

R is independently chosen from hydrogen, OH, CN, ($C_1$-$C_6$) alkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, and ($C_3$-$C_6$) heterocycloalkyl groups;

n is 0, 1, or 2;

wherein, if n is 2, the R groups can combine to form a fused ring system with $R_1$;

$R_1$ is chosen from 3-6 membered cyclic or heterocyclic groups;

$R_2$ is chosen from $C(X)_n$, $S(O)_2$, $N(X)$, heteroatom linkers, $N(X)S(O)_2$, $N(X)S(O)_2N(X)$, carbonylalkyl groups, and carbonylheteroalkyl groups, wherein the alkyl portion of carbonylalkyl and carbonylheteroalkyl groups can optionally cyclize with R, $R_1$, or $R_3$:

X is independently chosen from hydrogen, alkyl groups, and heteroalkyl groups, wherein the alkyl and heteroalkyl groups can optionally cyclize with R, $R_1$, or $R_3$ or with another X group when multiple X groups are present;

$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;

$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;

Y is independently chosen from hydrogen, OH, CN, $N(X)_2$, ($C_1$-$C_6$) alkyl groups, ($C_1$-$C_6$) heteroalkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, ($C_3$-$C_6$) heterocycloalkyl groups, ($C_5$-$C_8$) aryl groups, and ($C_4$-$C_8$) heteroaryl groups; and m is 0, 1, or 2.

In some embodiments of Formula (I) above, R is chosen from halogens.

In some embodiments of Formula (I) above, $R_1$ is chosen from cyclopropane, cyclobutane, cyclopentane, and cyclohexane. In some embodiments, $R_1$ is chosen from cyclobutane and cyclopentane. In some embodiments, $R_1$ is chosen from heterocyclic groups. In some embodiments, $R_1$ is a pyrrolidine. In some embodiments of Formula (I) above, $R_1$ is a cyclic group. In some embodiments of Formula (I) above, $R_1$ is a heterocyclic group. In some embodiments of Formula (I) above, $R_1$ is preferably cyclobutane.

In some embodiments of Formula (I) above, $R_2$ is chosen from carbonylalkyl and heterocarbonylalkyl groups. In some embodiments, $R_2$ is chosen from amides, reverse amides, and ureas.

In some embodiments of Formula (I) above, $R_2$ is chosen from carbonylalkyl and heterocarbonylalkyl groups wherein the groups optionally cyclize to adjacent groups. In some embodiments, $R_2$ is chosen from amides, reverse amides, and ureas, wherein the amides and reverse amides are optionally cyclized to adjacent groups.

In some embodiments of Formula (I) above, $R_2$ is a carbonylheteroalkyl group, wherein the alkyl portion of the carbonylheteroalkyl group can optionally cyclize with R, $R_1$, or $R_3$. In some embodiments of Formula (I) above, $R_2$ is an amide or reverse amide group. In some embodiments of Formula (I) above, $R_2$ is preferably an amide. In some embodiments of Formula (I) above, $R_2$ is a reverse amide. In some embodiments of Formula (I) above, $R_2$ is selected from C(O)N(X) and N(X)C(O). In some embodiments of Formula (I) above, $R_2$ is preferably C(O)N(X). In some embodiments of Formula (I) above, $R_2$ is N(X)C(O).

In some embodiments of Formula (I) above, $R_3$ is chosen from aryl and heteroaryl rings. In some embodiments, $R_3$ is chosen from thiazole, indenyl, pyrazole, and phenyl rings. In some embodiments, $R_3$ is chosen from cyclic and heterocyclic rings.

In some embodiments $R_3$ is chosen from thiazole, indenyl, pyrazole, phenyl, benzothiazole, and oxazole rings.

In some embodiments of Formula (I) above, $R_4$ is chosen from cyclic and heterocyclic rings optionally substituted with 1 or 2 R. In some embodiments, $R_4$ is chosen from alkyl, heteroalkyl, and haloalkyl groups. In some embodiments, $R_4$ is chosen from aryl and heteroaryl rings optionally substituted with 1 or 2 R.

In some embodiments of Formula (I) above, m is 0. In some embodiments, m is 1. In some embodiments, m is 2.

In some embodiments of Formula (I) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides or reverse amides; $R_3$ is chosen from $C_1$-$C_3$ alkyl linkers, thiazole, phenyl, benzothiazole, oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, ($C_3$-$C_6$) cycloalkyl groups.

In some embodiments of Formula (I) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides and reverse amides that form spirocyclic rings with $R_1$; $R_3$ is chosen from thiazole, phenyl, and oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, and ($C_3$-$C_6$) cycloalkyl groups.

In some embodiments of Formula (I) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from aryl and heteroaryl rings optionally substituted with 1 or 2 R.

In some embodiments of Formula (I) above, $R_1$ is a cyclobutane, $R_b$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from cyclic and heterocyclic rings optionally substituted with 1 or 2 R.

In some embodiments of Formula (I) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from alkyl, heteroalkyl, and haloalkyl groups.

Non-limiting illustrative compounds of the disclosure include:

| Example No. | Structure | Chemical Name |
|---|---|---|
| Compound 10-1 | 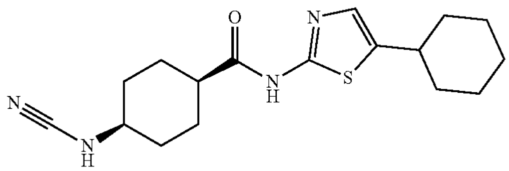 [SMILES: N#CN[C@H]1CC[C@@H](C(=O)Nc2ncc(C3CCCCC3)s2)CC1] | cis-4-(cyanoamino)-N-(5-cyclohexyl-1,3-thiazol-2-yl)cyclohexane-1-carboxamide |
| Compound 10-2 | 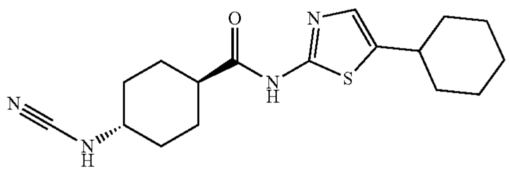 [SMILES: N#CN[C@H]1CC[C@H](C(=O)Nc2ncc(C3CCCCC3)s2)CC1] | trans-4-(cyanoamino)-N-(5-cyclohexyl-1,3-thiazol-2-yl)cyclohexane-1-carboxamide |
| Compound 10-3 | 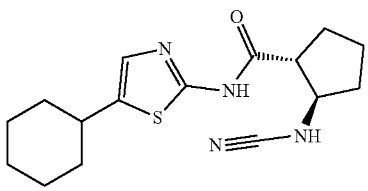 [SMILES: N#CN[C@@H]1CCC[C@H]1C(=O)Nc1ncc(C2CCCCC2)s1] | (1R,2R)-2-(cyanoamino)-N-(5-cyclohexyl-1,3-thiazol-2-yl)cyclopentane-1-carboxamide |
| Compound 10-4 | 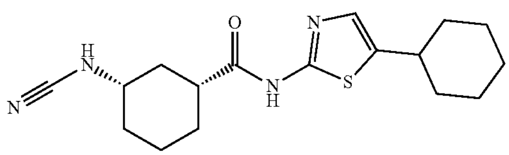 [SMILES: N#CN[C@H]1CCC[C@@H](C(=O)Nc2ncc(C3CCCCC3)s2)C1] | (1R,3S)-3-(cyanoamino)-N-(5-cyclohexyl-1,3-thiazol-2-yl)cyclohexane-1-carboxamide |
| Compound 10-5 | 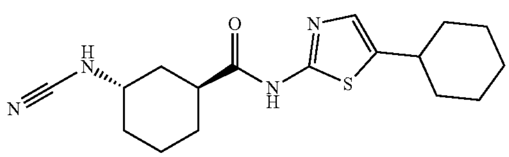 [SMILES: N#CN[C@H]1CCC[C@H](C(=O)Nc2ncc(C3CCCCC3)s2)C1] | (1S,3S)-3-(cyanoamino)-N-(5-cyclohexyl-1,3-thiazol-2-yl)cyclohexane-1-carboxamide |
| Compound 10-6 | 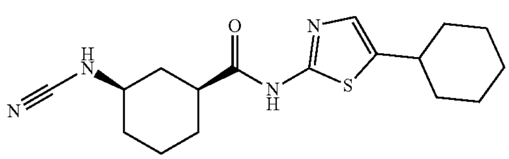 [SMILES: N#CN[C@@H]1CCC[C@H](C(=O)Nc2ncc(C3CCCCC3)s2)C1] | (1S,3R)-3-(cyanoamino)-N-(5-cyclohexyl-1,3-thiazol-2-yl)cyclohexane-1-carboxamide |
| Compound 10-7 | 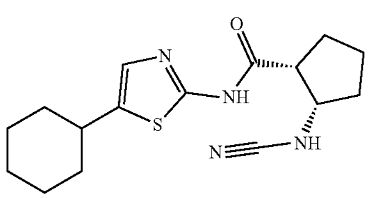 [SMILES: N#CN[C@H]1CCC[C@H]1C(=O)Nc1ncc(C2CCCCC2)s1] | (1R,2S)-2-(cyanoamino)-N-(5-cyclohexyl-1,3-thiazol-2-yl)cyclopentane-1-carboxamide |
| Compound 10-8 | 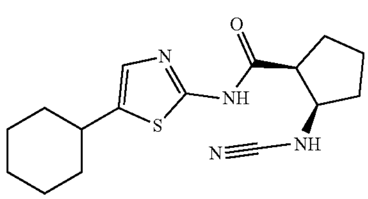 [SMILES: N#CN[C@@H]1CCC[C@@H]1C(=O)Nc1ncc(C2CCCCC2)s1] | (1S,2R)-2-(cyanoamino)-N-(5-cyclohexyl-1,3-thiazol-2-yl)cyclopentane-1-carboxamide |

-continued

| Example No. | Structure | Chemical Name |
|---|---|---|
| Compound 10-9 | 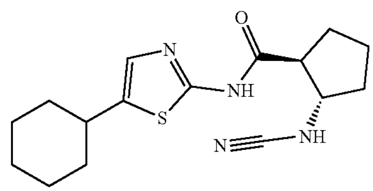 [SMILES: N#CN[C@H]1CCC[C@@H]1C(=O)Nc1ncc(C2CCCCC2)s1] | (1S,2S)-2-(cyanoamino)-N-(5-cyclohexyl-1,3-thiazol-2-yl)cyclopentane-1-carboxamide |
| Compound 1-1 | 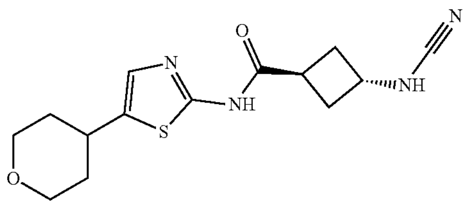 [SMILES: N#CN[C@H]1C[C@H](C(=O)Nc2ncc(C3CCOCC3)s2)C1] | trans-3-(cyanoamino)-N-[5-(oxan-4-yl)-1,3-thiazol-2-yl]cyclobutane-1-carboxamide |
| Compound 10-10 | 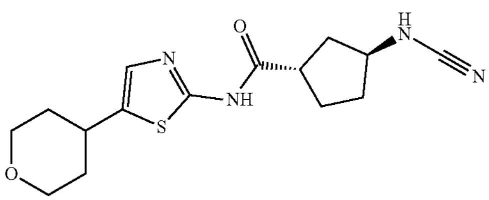 [SMILES: N#CN[C@H]1CC[C@H](C(=O)Nc2ncc(C3CCOCC3)s2)C1] | (1S,3S)-3-(cyanoamino)-N-[5-(oxan-4-yl)-1,3-thiazol-2-yl]cyclopentane-1-carboxamide |
| Compound 10-11 | 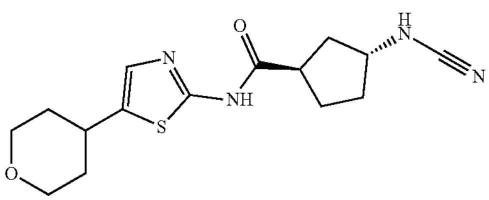 [SMILES: N#CN[C@@H]1CC[C@@H](C(=O)Nc2ncc(C3CCOCC3)s2)C1] | (1R,3R)-3-(cyanoamino)-N-[5-(oxan-4-yl)-1,3-thiazol-2-yl]cyclopentane-1-carboxamide |
| Compound 11-1 | 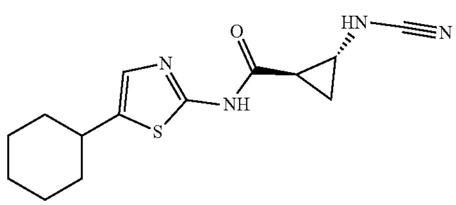 [SMILES: N#CN[C@@H]1C[C@H]1C(=O)Nc1ncc(C2CCCCC2)s1] | trans-2-(cyanoamino)-N-(5-cyclohexyl-1,3-thiazol-2-yl)cyclopropane-1-carboxamide |
| Compound 11-2 | 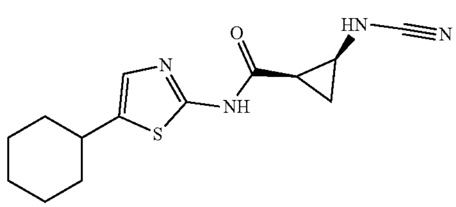 [SMILES: N#CN[C@H]1C[C@H]1C(=O)Nc1ncc(C2CCCCC2)s1] | cis-2-(cyanoamino)-N-(5-cyclohexyl-1,3-thiazol-2-yl)cyclopropane-1-carboxamide |
| Compound 2-1 | 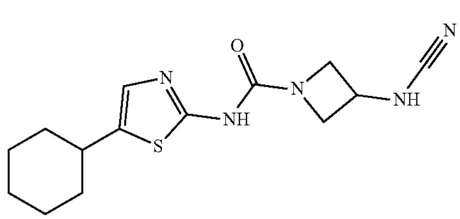 [SMILES: N#CNC1CN(C(=O)Nc2ncc(C3CCCCC3)s2)C1] | 3-(cyanoamino)-N-(5-cyclohexyl-1,3-thiazol-2-yl)azetidine-1-carboxamide |

-continued

| Example No. | Structure | Chemical Name |
|---|---|---|
| Compound 2-2 | 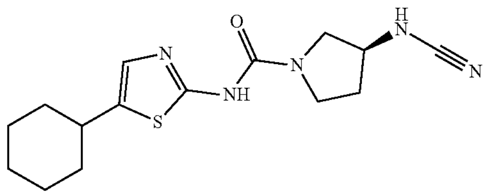 | (3S)-3-(cyanoamino)-N-(5-cyclohexyl-1,3-thiazol-2-yl)pyrrolidine-1-carboxamide |
| Compound 2-3 | 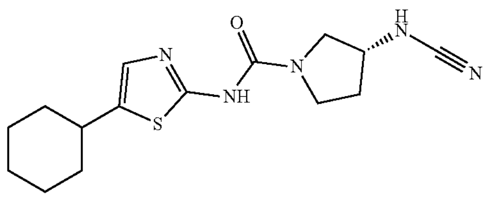 [SMILES: N#CN[C@@H]1CCN(C(=O)Nc2ncc(C3CCCCC3)s2)C1] | (3R)-3-(cyanoamino)-N-(5-cyclohexyl-1,3-thiazol-2-yl)pyrrolidine-1-carboxamide |
| Compound 3-1 | 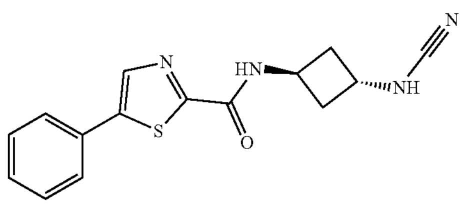 [SMILES: N#CN[C@H]1C[C@H](NC(=O)c2ncc(-c3ccccc3)s2)C1] | 5-phenyl-N-[(trans)-3-(cyanoamino)cyclobutyl]-1,3-thiazole-2-carboxamide |
| Compound 4-1 | 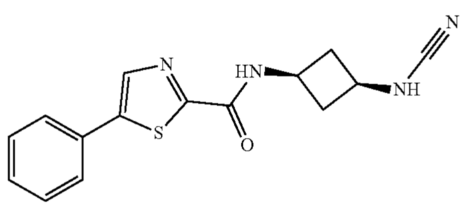 [SMILES: N#CN[C@H]1C[C@@H](NC(=O)c2ncc(-c3ccccc3)s2)C1] | 5-phenyl-N-[(cis)-3-(cyanoamino)cyclobutyl]-1,3-thiazole-2-carboxamide |
| Compound 12-1 | 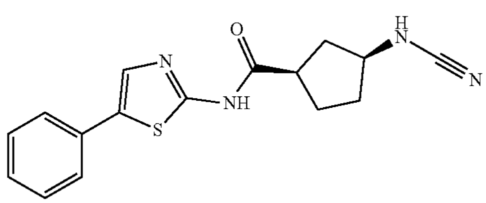 [SMILES: N#CN[C@H]1CC[C@@H](C(=O)Nc2ncc(-c3ccccc3)s2)C1] | (1R,3S)-3-(cyanoamino)-N-(5-phenyl-1,3-thiazol-2-yl)cyclopentane-1-carboxamide |
| Compound 12-2 | 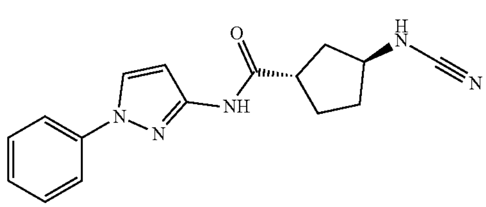 [SMILES: N#CN[C@H]1CC[C@H](C(=O)Nc2ccn(-c3ccccc3)n2)C1] | (1S,3S)-3-(cyanoamino)-N-(1-phenyl-1H-pyrazol-3-yl)cyclopentane-1-carboxamide |
| Compound 12-3 | 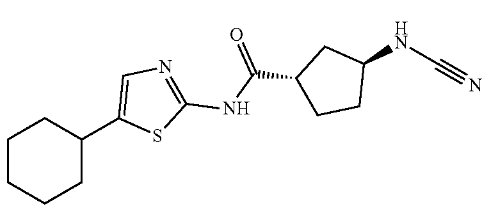 [SMILES: N#CN[C@H]1CC[C@H](C(=O)Nc2ncc(C3CCCCC3)s2)C1] | (1S,3S)-3-(cyanoamino)-N-(5-cyclohexyl-1,3-thiazol-2-yl)cyclopentane-1-carboxamide |

| Example No. | Structure | Chemical Name |
|---|---|---|
| Compound 12-4 | 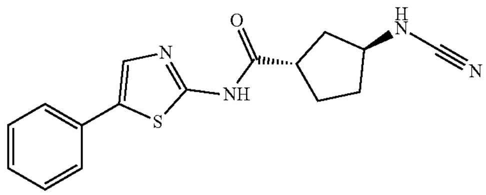 [SMILES: N#CN[C@H]1CC[C@H](C(=O)Nc2ncc(-c3ccccc3)s2)C1] | (1S,3S)-3-(cyanoamino)-N-(5-phenyl-1,3-thiazol-2-yl)cyclopentane-1-carboxamide |
| Compound 5-1 | 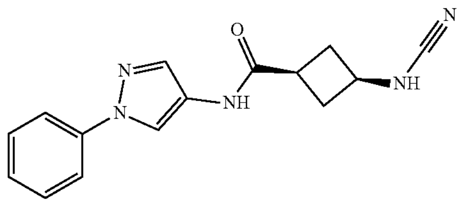 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide |
| Compound 5-2 | 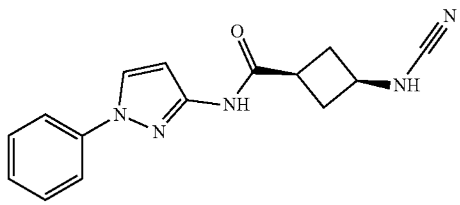 [SMILES: N#CN[C@H]1C[C@@H](C(=O)Nc2ccn(-c3ccccc3)n2)C1] | cis-3-(cyanoamino)-N-(1-phenyl-1H-pyrazol-3-yl)cyclobutane-1-carboxamide |
| Compound 5-3 | 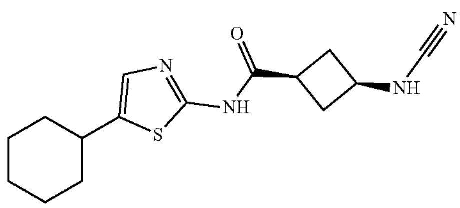 [SMILES: N#CN[C@H]1C[C@@H](C(=O)Nc2ncc(C3CCCCC3)s2)C1] | cis-3-(cyanoamino)-N-(5-cyclohexyl-1,3-thiazol-2-yl)cyclobutane-1-carboxamide |
| Compound 5-4 | 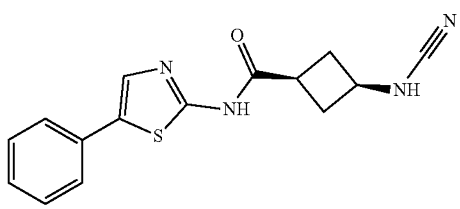 [SMILES: N#CN[C@H]1C[C@@H](C(=O)Nc2ncc(-c3ccccc3)s2)C1] | cis-3-(cyanoamino)-N-(5-phenyl-1,3-thiazol-2-yl)cyclobutane-1-carboxamide |
| Compound 5-5 | 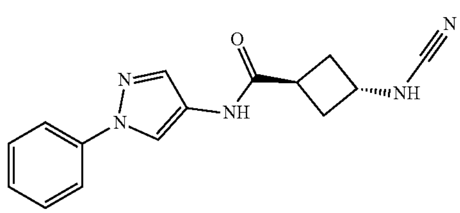 [SMILES: N#CN[C@H]1C[C@H](C(=O)Nc2cnn(-c3ccccc3)c2)C1] | trans-3-(cyanoamino)-N-(1-phenyl-1H-pyrazol-4-yl)cyclobutane-1-carboxamide |
| Compound 5-6 | 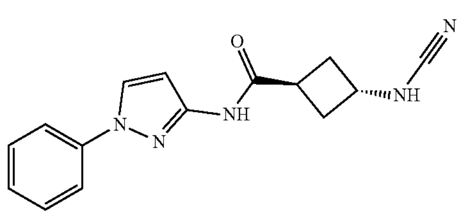 [SMILES: N#CN[C@H]1C[C@H](C(=O)Nc2ccn(-c3ccccc3)n2)C1] | trans-3-(cyanoamino)-N-(1-phenyl-1H-pyrazol-3-yl)cyclobutane-1-carboxamide |

-continued

| Example No. | Structure | Chemical Name |
|---|---|---|
| Compound 5-7 | 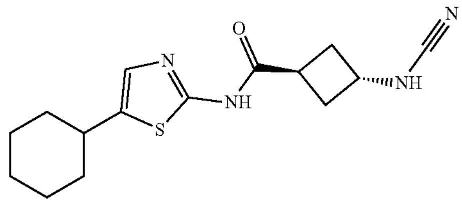 | trans-3-(cyanoamino)-N-(5-cyclohexyl-1,3-thiazol-2-yl)cyclobutane-1-carboxamide |
| Compound 5-8 | 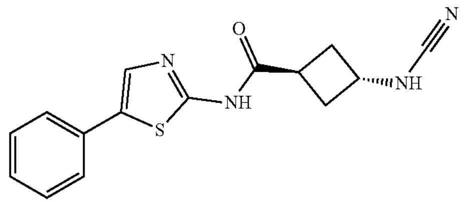 [SMILES: N#CN[C@H]1C[C@H](C(=O)Nc2ncc(-c3ccccc3)s2)C1] | trans-3-cyanoamino-N-(5-phenyl-1,3-thaizol-2-yl)cyclobutane-1-carboxamide |
| Compound 12-5 | 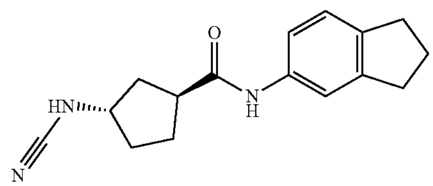 [SMILES: N#CN[C@H]1CC[C@H](C(=O)Nc2ccc3c(c2)CCC3)C1] | (1S,3S)-3-(cyanoamino)-N-(2,3-dihydro-1H-inden-5-yl)cyclopentane-1-carboxamide |
| Compound 12-6 | 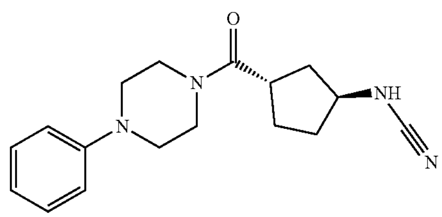 [SMILES: N#CN[C@H]1CC[C@H](C(=O)N2CCN(c3ccccc3)CC2)C1] | {[(1S,3S)-3-(4-phenylpiperazine-1-carbonyl)cyclopentyl]amino}carbonitrile |
| Compound 12-7 | 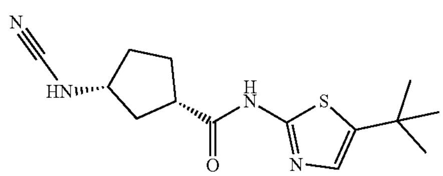 [SMILES: CC(C)(C)c1cnc(NC(=O)[C@H]2CC[C@@H](NC#N)C2)s1] | (1S,3R)-N-(5-tert-butyl-1,3-thiazol-2-yl)-3-(cyanoamino)cyclopentane-1-carboxamide |
| Compound 5-9 | 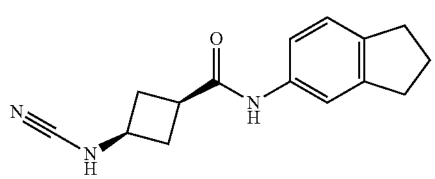 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide |
| Compound 5-10 | 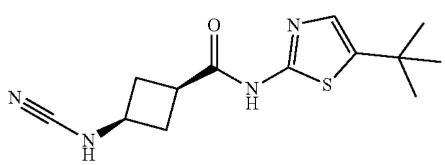 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide |
| Compound 5-11 | 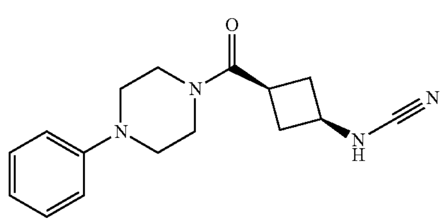 [SMILES: N#CN[C@H]1C[C@@H](C(=O)N2CCN(c3ccccc3)CC2)C1] | {[cis-3-(4-phenylpiperazine-1-carbonyl)cyclobutyl]amino}carbonitrile |

| Example No. | Structure | Chemical Name |
|---|---|---|
| Compound 5-12 | 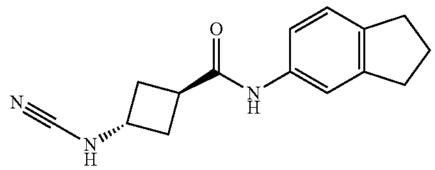 [SMILES: N#CN[C@H]1C[C@H](C(=O)Nc2ccc3c(c2)CCC3)C1] | trans-3-(cyanoamino)-N-(2,3-dihydro-1H-inden-5-yl)cyclobutane-1-carboxamide |
| Compound 5-13 | 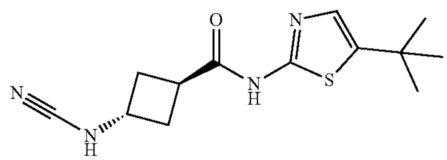 [SMILES: CC(C)(C)c1cnc(NC(=O)[C@H]2C[C@H](NC#N)C2)s1] | trans-N-(5-tert-butyl-1,3-thiazol-2-yl)-3-(cyanoamino)cyclobutane-1-carboxamide |
| Compound 5-14 | 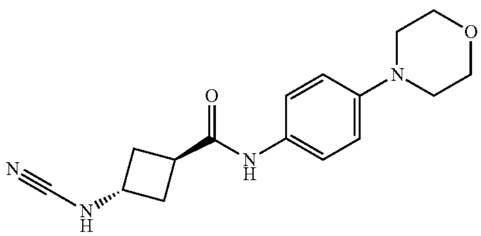 [SMILES: N#CN[C@H]1C[C@H](C(=O)Nc2ccc(N3CCOCC3)cc2)C1] | trans-3-(cyanoamino)-N-[4-(morpholin-4-yl)phenyl]cyclobutane-1-carboxamide |
| Compound 12-8 | 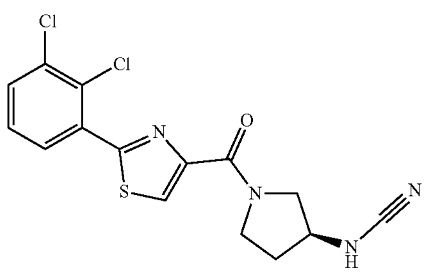 [SMILES: N#CN[C@H]1CCN(C(=O)c2csc(-c3cccc(Cl)c3Cl)n2)C1] | {[(3S)-1-[2-(2,3-dichlorophenyl)-1,3-thiazole-4-carbonyl]pyrolidin-3-yl]amino}carbonitrile |
| Compound 12-9 | 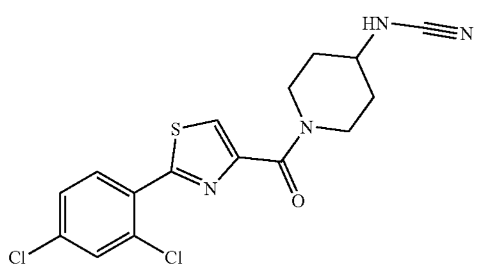 [SMILES: N#CNC1CCN(C(=O)c2csc(-c3ccc(Cl)cc3Cl)n2)CC1] | ({1-[2-(2,4-dichlorophenyl)-1,3-thiazole-4-carbonyl]piperidin-4-yl}amino)carbonitrile |

Any of the features disclosed above in the context of the compounds of Formula (I) may also be applied to any of the compounds of Formulae (Ia), (Ib), (Ic), (II), and (III) disclosed herein.

Formula (Ia)

In any of the embodiments of Formula (I) disclosed above, the compound of Formula (I) may be a compound of Formula (Ia) as described herein above. The compounds of Formula (Ia) correspond to compounds of Formula (I) wherein $R_1$ is a 4-membered cyclic or heterocyclic group.

In some embodiments of Formula (Ia) above, R is chosen from halogens

In some embodiments of Formula (Ia), $R_1$ is a cyclic group. In some embodiments of Formula (Ia), $R_1$ is a heterocyclic group. In some embodiments of Formula (Ia), $R_1$ is preferably cyclobutane.

In some embodiments of Formula (Ia), $R_2$ is chosen from carbonylalkyl and heterocarbonylalkyl groups. In some embodiments of Formula (Ia), $R_2$ is chosen from amides, reverse amides, and ureas.

In some embodiments of Formula (Ia), $R_2$ is chosen from carbonylalkyl and heterocarbonylalkyl groups wherein the groups optionally cyclize to adjacent groups. In some embodiments, $R_2$ is chosen from amides, reverse amides, and ureas, wherein the amides and reverse amides are optionally cyclized to adjacent groups.

In some embodiments of Formula (I) above, $R_2$ is a carbonylheteroalkyl group, wherein the alkyl portion of the carbonylheteroalkyl group can optionally cyclize with R, $R_1$, or $R_3$. In some embodiments of Formula (Ia), $R_2$ is an amide or reverse amide group. In some embodiments of Formula (Ia), $R_2$ is preferably an amide. In some embodiments of Formula (Ia), $R_2$ is a reverse amide. In some embodiments of Formula (Ia), $R_2$ is selected from C(O)N(X) and N(X)C(O). In some embodiments of Formula (Ia), $R_2$ is preferably C(O)N(X). In some embodiments of Formula (Ia), $R_2$ is N(X)C(O).

In some embodiments of Formula (Ia), $R_3$ is chosen from aryl and heteroaryl rings. In some embodiments of Formula (Ia), $R_3$ is chosen from thiazole, indenyl, pyrazole, and phenyl rings. In some embodiments of Formula (Ia), $R_3$ is chosen from cyclic and heterocyclic rings.

In some embodiments of Formula (Ia), $R_3$ is chosen from thiazole, indenyl, pyrazole, phenyl, benzothiazole, and oxazole rings.

In some embodiments of Formula (Ia), $R_4$ is chosen from cyclic and heterocyclic rings optionally substituted with 1 or 2 R. In some embodiments of Formula (Ia), $R_4$ is chosen from alkyl, heteroalkyl, and haloalkyl groups. In some embodiments of Formula (Ia), $R_a$ is chosen from aryl and heteroaryl rings optionally substituted with 1 or 2 R.

In some embodiments of Formula (Ia), m is 0. In some embodiments of Formula (Ia), m is 1. In some embodiments of Formula (Ia), m is 2.

In some embodiments of Formula (Ia) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides or reverse amides; $R_3$ is chosen from $C_1$-$C_3$ alkyl linkers, thiazole, phenyl, benzothiazole, oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, ($C_3$-$C_6$) cycloalkyl groups.

In some embodiments of Formula (Ia) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides and reverse amides that form spirocyclic rings with $R_1$; $R_3$ is chosen from thiazole, phenyl, and oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, and ($C_3$-$C_6$) cycloalkyl groups.

In some embodiments of Formula (Ia) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from aryl and heteroaryl rings optionally substituted with 1 or 2 R.

In some embodiments of Formula (Ia) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_3$ is chosen from cyclic and heterocyclic rings optionally substituted with 1 or 2 R.

In some embodiments of Formula (Ia) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from alkyl, heteroalkyl, and haloalkyl groups.

Any of the features disclosed above in the context of the compounds of Formula (Ia) may also be applied to any of the compounds of Formulae (I), (Ib), (Ic), (II), and (III) disclosed herein.

Formula (Ib)

In any of the embodiments disclosed above, the compound of Formula (I) may be a compound of Formula (Ib) as described herein above. The compounds of Formula (Ib) correspond to compounds of Formula (I) wherein $R_2$ is carbonylheteroalkyl group, wherein the alkyl portion of the carbonylheteroalkyl group can optionally cyclize with R, $R_1$, or $R_3$.

In some embodiments of Formula (Ib) above, R is chosen from halogens

In some embodiments of Formula (Ib), $R_1$ is a 4-membered cyclic or heterocyclic group. In some embodiments of Formula (Ib), $R_1$ is a cyclic group. In some embodiments of Formula (Ib), $R_1$ is a heterocyclic group. In some embodiments of Formula (Ib), $R_1$ is preferably cyclobutane.

In some embodiments of Formula (Ib), $R_2$ is chosen from amides, reverse amides, and ureas. In some embodiments of Formula (Ib), $R_2$ is chosen from heterocarbonylalkyl groups wherein the group optionally cyclizes to adjacent groups. In some embodiments, $R_2$ is chosen from amides, reverse amides, and ureas, wherein the amides and reverse amides are optionally cyclized to adjacent groups.

In some embodiments of Formula (Ib) above, $R_2$ is a carbonylheteroalkyl group, wherein the alkyl portion of the carbonylheteroalkyl group can optionally cyclize with R, $R_1$, or $R_3$. In some embodiments of Formula (Ib), $R_2$ is an amide or reverse amide group. In some embodiments of Formula (Ib), $R_2$ is preferably an amide. In some embodiments of Formula (Ib), $R_2$ is a reverse amide. In some embodiments of Formula (Ib), $R_2$ is selected from C(O)N(X) and N(X)C(O). In some embodiments of Formula (Ib), $R_2$ is preferably C(O)N(X). In some embodiments of Formula (Ib), $R_2$ is N(X)C(O).

In some embodiments of Formula (Ib), $R_1$ is chosen from aryl and heteroaryl rings. In some embodiments of Formula (Ib), $R_3$ is chosen from thiazole, indenyl, pyrazole, and phenyl rings. In some embodiments of Formula (Ib), $R_3$ is chosen from cyclic and heterocyclic rings.

In some embodiments of Formula (Ib), $R_3$ is chosen from thiazole, indenyl, pyrazole, phenyl, benzothiazole, and oxazole rings.

In some embodiments of Formula (Ib), $R_4$ is chosen from cyclic and heterocyclic rings optionally substituted with 1 or 2 R. In some embodiments of Formula (Ib), $R_4$ is chosen from alkyl, heteroalkyl, and haloalkyl groups. In some embodiments of Formula (Ib), $R_4$ is chosen from aryl and heteroaryl rings optionally substituted with 1 or 2 R.

In some embodiments of Formula (Ib), m is 0. In some embodiments of Formula (Ib), m is 1. In some embodiments of Formula (Ib), m is 2.

In some embodiments of Formula (Ib) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides or reverse amides; $R_3$ is chosen from $C_1$-$C_3$ alkyl linkers, thiazole, phenyl, benzothiazole, oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, ($C_3$-$C_6$) cycloalkyl groups.

In some embodiments of Formula (Ib) above, $R_1$ is a cyclobutane optionally substituted with 1 or 2 R; R is chosen from ($C_1$-$C_6$) alkyl groups, ($C_1$-$C_6$) haloalkyl groups, ($C_1$-

$C_6$) alkoxy groups, and halogens; $R_2$ is chosen from amides and reverse amides that form spirocyclic rings with $R_1$; $R_3$ is chosen from thiazole, phenyl, and oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, and ($C_3$-$C_6$) cycloalkyl groups.

In some embodiments of Formula (Ib) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_a$ is chosen from aryl and heteroaryl rings optionally substituted with 1 or 2 R.

In some embodiments of Formula (Ib) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from cyclic and heterocyclic rings optionally substituted with 1 or 2 R.

In some embodiments of Formula (Ib) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from alkyl, heteroalkyl, and haloalkyl groups.

Any of the features disclosed above in the context of the compounds of Formula (Ib) may also be applied to any of the compounds of Formulae (I), (Ia), (Ic), (II), and (II) disclosed herein.

Formula (Ic)

In any of the embodiments disclosed above, the compound of Formula (I) may be a compound of Formula (Ic) as described herein above. The compounds of Formula (Ic) correspond to compounds of Formula (I) wherein $R_1$ is a 4-membered cyclic or heterocyclic group; and $R_2$ is carbonylheteroalkyl group, wherein the alkyl portion of the carbonylheteroalkyl group can optionally cyclize with R, $R_1$, or $R_3$.

In some embodiments of Formula (Ic) above, R is chosen from halogens.

In some embodiments of Formula (Ic), $R_1$ is a cyclic group. In some embodiments of Formula (Ic), $R_1$ is a heterocyclic group. In some embodiments of Formula (Ic), $R_1$ is preferably cyclobutane.

In some embodiments of Formula (Ic), $R_2$ is chosen from amides, reverse amides, and ureas. In some embodiments of Formula (Ic), $R_2$ is chosen from heterocarbonylalkyl groups wherein the group optionally cyclizes to adjacent groups. In some embodiments, $R_2$ is chosen from amides, reverse amides, and ureas, wherein the amides and reverse amides are optionally cyclized to adjacent groups.

In some embodiments of Formula (Ic), $R_2$ is an amide or reverse amide group. In some embodiments of Formula (Ic), $R_2$ is preferably an amide. In some embodiments of Formula (Ic), $R_2$ is a reverse amide. In some embodiments of Formula (Ic), $R_2$ is selected from C(O)N(X) and N(X)C(O). In some embodiments of Formula (Ic), $R_2$ is preferably C(O)N(X). In some embodiments of Formula (Ic), $R_2$ is N(X)C(O).

In some embodiments of Formula (Ic), $R_3$ is chosen from aryl and heteroaryl rings. In some embodiments of Formula (Ic), $R_3$ is chosen from thiazole, indenyl, pyrazole, and phenyl rings. In some embodiments of Formula (Ic), $R_3$ is chosen from cyclic and heterocyclic rings.

In some embodiments of Formula (Ic), $R_3$ is chosen from thiazole, indenyl, pyrazole, phenyl, benzothiazole, and oxazole rings.

In some embodiments of Formula (Ic), $R_4$ is chosen from cyclic and heterocyclic rings optionally substituted with 1 or 2 R. In some embodiments of Formula (Ic), $R_4$ is chosen from alkyl, heteroalkyl, and haloalkyl groups. In some embodiments of Formula (Ic), $R_4$ is chosen from aryl and heteroaryl rings optionally substituted with 1 or 2 R.

In some embodiments of Formula (Ic), m is 0. In some embodiments of Formula (Ic), m is 1. In some embodiments of Formula (Ic), m is 2.

In some embodiments of Formula (Ic) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides or reverse amides; $R_3$ is chosen from $C_1$-$C_3$ alkyl linkers, thiazole, phenyl, benzothiazole, oxazole groups optionally substituted with 1 or 2 R; $R_4$ is chosen from cyclic rings, alkyl groups, and heteroaryl groups optionally substituted with 1 or 2 Y;

Y is chosen from ($C_1$-$C_6$) alkyl groups, ($C_3$-$C_6$) cycloalkyl groups.

In some embodiments of Formula (Ic) above, $R_1$ is a cyclobutane optionally substituted with 1 or 2 R; R is chosen from ($C_1$-$C_6$) alkyl groups, ($C_1$-$C_6$) haloalkyl groups, ($C_1$-$C_6$) alkoxy groups, and halogens; $R_2$ is chosen from amides and reverse amides that form spirocyclic rings with $R_1$; $R_3$ is chosen from thiazole, phenyl, and oxazole groups optionally substituted with 1 or 2 R; $R_4$ is chosen from cyclic rings, alkyl groups, and heteroaryl groups optionally substituted with 1 or 2 Y; Y is chosen from ($C_1$-$C_6$) alkyl groups, and ($C_3$-$C_6$) cycloalkyl groups.

In some embodiments of Formula (Ic) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from aryl and heteroaryl rings optionally substituted with 1 or 2 R.

In some embodiments of Formula (Ic) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from cyclic and heterocyclic rings optionally substituted with 1 or 2 R.

In some embodiments of Formula (Ic) above, $R_1$ is a cyclobutane, $R_2$ is chosen from carbonylalkyl and heterocarbonylalkyl groups (e.g. amides, reverse amides, and ureas, preferably amides), $R_3$ is chosen from aryl and heteroaryl rings (e.g. thiazole, indenyl, pyrazole, and phenyl rings) preferably heteroaryl rings, and $R_4$ is chosen from alkyl, heteroalkyl, and haloalkyl groups.

Any of the features disclosed above in the context of the compounds of Formula (Ic) may also be applied to any of the compounds of Formulae (I), (Ia), (Ib), (II), and (III) disclosed herein.

Non-limiting illustrative compounds of the disclosure include:

| Example No. | Structure | Chemical Name |
|---|---|---|
| Compound 1-1 | 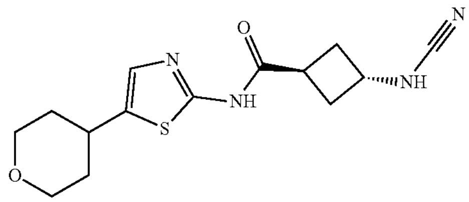 [SMILES: N#CN[C@H]1C[C@H](C(=O)Nc2ncc(C3CCOCC3)s2)C1] | trans-3-(cyanoamino)-N-[5-(oxan-4-yl)-1,3-thiazol-2-yl]cyclobutane-1-carboxamide |
| Compound 2-1 | 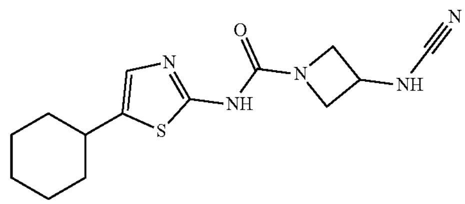 [SMILES: N#CNC1CN(C(=O)Nc2ncc(C3CCCCC3)s2)C1] | 3-(cyanoamino)-N-(5-cyclohexyl-1,3-thiazol-2-yl)azetidine-1-carboxamide |
| Compound 3-1 | 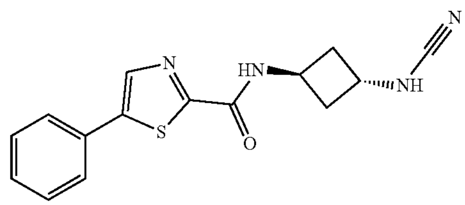 [SMILES: N#CN[C@H]1C[C@H](NC(=O)c2ncc(-c3ccccc3)s2)C1] | 5-phenyl-N-[(trans)-3-(cyanoamino)cyclobutyl]-1,3-thiazole-2-carboxamide |
| Compound 4-1 | 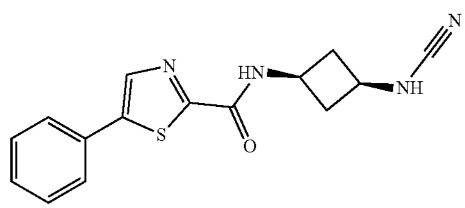 [SMILES: N#CN[C@H]1C[C@@H](NC(=O)c2ncc(-c3ccccc3)s2)C1] | 5-phenyl-N-[(cis)-3-(cyanoamino)cyclobutyl]-1,3-thiazole-2-carboxamide |
| Compound 5-1 | 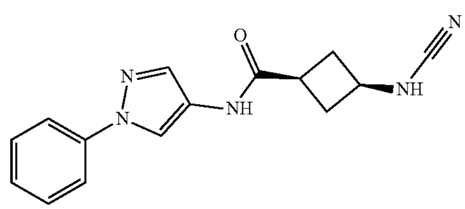 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide |
| Compound 5-2 | 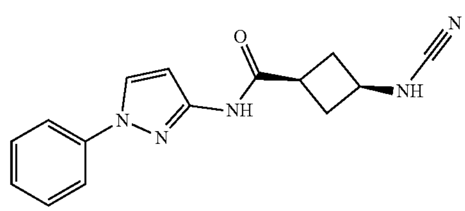 [SMILES: N#CN[C@H]1C[C@@H](C(=O)Nc2ccn(-c3ccccc3)n2)C1] | cis-3-(cyanoamino)-N-(1-phenyl-1H-pyrazol-3-yl)cyclobutane-1-carboxamide |
| Compound 5-3 | 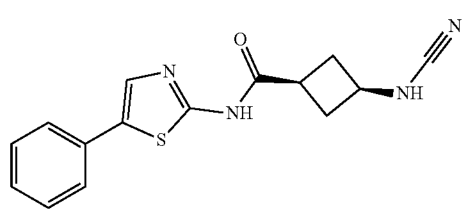 [SMILES: N#CN[C@H]1C[C@@H](C(=O)Nc2ncc(-c3ccccc3)s2)C1] | cis-3-(cyanoamino)-N-(5-cyclohexyl-1,3-thiazol-2-yl)cyclobutane-1-carboxamide |

-continued

| Example No. | Structure | Chemical Name |
|---|---|---|
| Compound 5-4 | 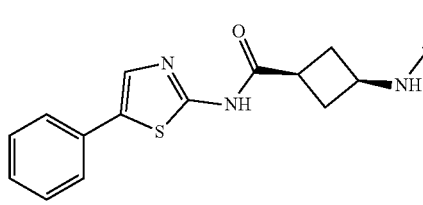 | cis-3-(cyanoamino)-N-(5-phenyl-1,3-thiazol-2-yl)cyclobutane-1-carboxamide |
| Compound 5-5 | 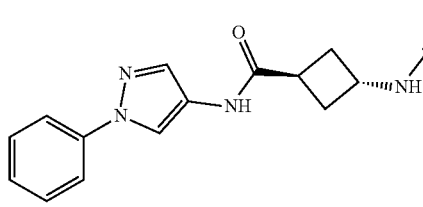 | trans-3-(cyanoamino)-N-(1-phenyl-1H-pyrazol-4-yl)cyclobutane-1-carboxamide |
| Compound 5-6 | 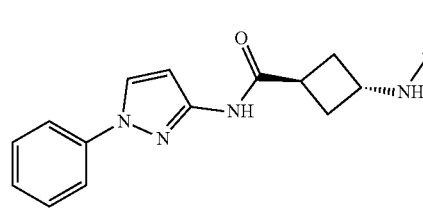 | trans-3-(cyanoamino)-N-(1-phenyl-1H-pyrazol-3-yl)cyclobutane-1-carboxamide |
| Compound 5-7 | 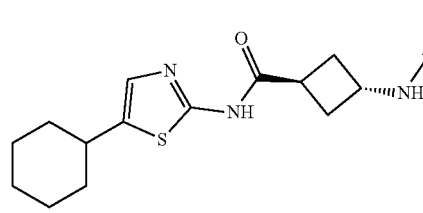 | trans-3-(cyanoamino)-N-(5-cyclohexyl-1,3-thiazol-2-yl)cyclobutane-1-carboxamide |
| Compound 5-8 | 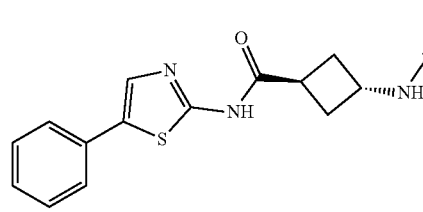 | trans-3-(cyanoamino)-N-(5-phenyl-1,3-thiazol-2-yl)cyclobutane-1-carboxamide |
| Compound 5-9 | 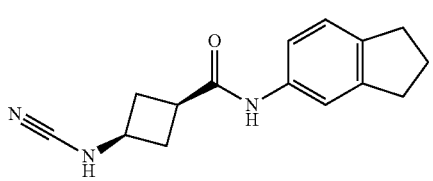 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide |
| Compound 5-10 | 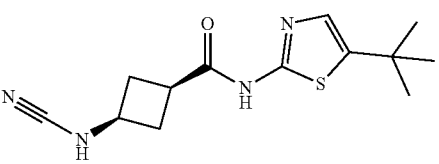 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide |

| Example No. | Structure | Chemical Name |
|---|---|---|
| Compound 5-11 | 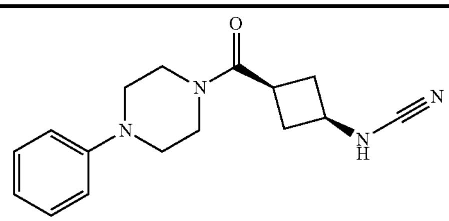 | {[cis-3-(4-phenylpiperazine-1-carbonyl)cyclobutyl]amino}carbonitrile |
| Compound 5-12 | 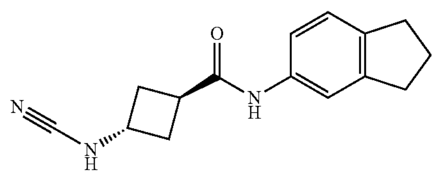 [SMILES: N#CN[C@H]1C[C@H](C(=O)Nc2ccc3c(c2)CCC3)C1] | trans-3-(cyanoamino)-N-(2,3-dihydro-1H-inden-5-yl)cyclobutane-1-carboxamide |
| Compound 5-13 | 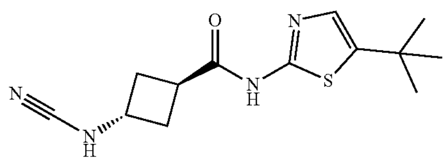 [SMILES: CC(C)(C)c1cnc(NC(=O)[C@H]2C[C@H](NC#N)C2)s1] | trans-N-(5-tert-butyl-1,3-thiazol-2-yl)-3-(cyanoamino)cyclobutane-1-carboxamide |
| Compound 5-14 | | trans-3-(cyanoamino)-N-[4-(morphoin-4-yl)phenyl]cyclobutane-1-carboxamide | and pharmaceutically acceptable salts, solvates, prodrugs, stereoisomers, and tautomers thereof.

Non-limiting illustrative compounds of the disclosure also include:

| Example No. | Structure | Chemical Name |
|---|---|---|
| Compound 1-2 | 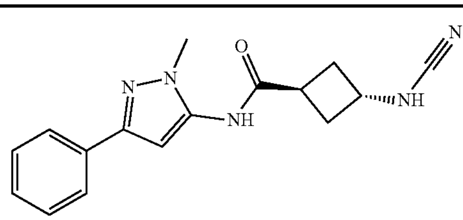 | (1r,3r)-3-(cyanoamino)-N-(1-methyl-3-phenyl-1H-pyrazol-5-yl)cyclobutane-1-carboxamide |
| Compound 1-3 | 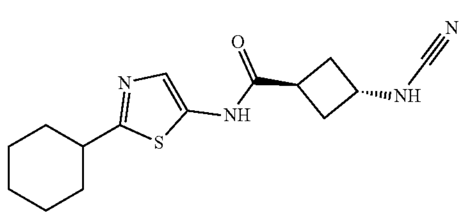 [SMILES: N#CN[C@H]1C[C@H](C(=O)Nc2cnc(C3CCCCC3)s2)C1] | (1r,3r)-3-(cyanoamino)-N-(2-cyclohexyl-1,3-thiazol-5-yl)cyclobutane-1-carboxamide |

| Example No. | Structure | Chemical Name |
|---|---|---|
| Compound 1-4 | 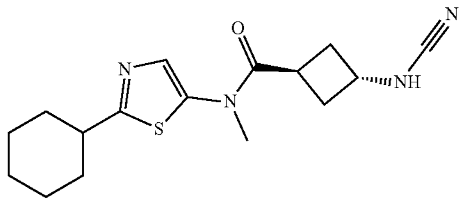 [SMILES: CN(c1cnc(C2CCCCC2)s1)C(=O)[C@H]1C[C@H](NC#N)C1] | (1r,3r)-3-(cyanoamino)-N-(2-cyclohexyl-1,3-thiazol-5-yl)-N-methylcyclobutane-1-carboxamide |
| Compound 1-5 | 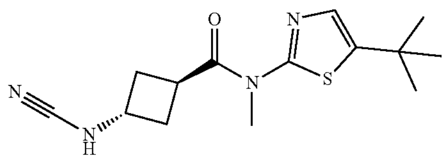 [SMILES: CN(c1ncc(C(C)(C)C)s1)C(=O)[C@H]1C[C@H](NC#N)C1] | (1r,3r)-N-(5-tert-butyl-1,3-thiazol-2-yl)-3-(cyanoamino)-N-methylcyclobutane-1-carboxamide |
| Compound 1-6 | 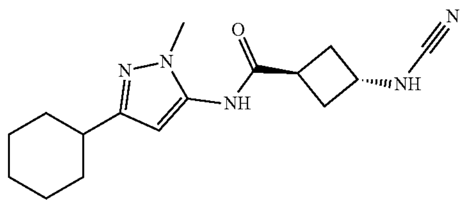 [SMILES: Cn1nc(C2CCCCC2)cc1NC(=O)[C@H]1C[C@H](NC#N)C1] | (1r,3r)-3-(cyanoamino)-N-(3-cyclohexyl-1-methyl-1H-pyrazol-5-yl)cyclobutane-1-carboxamide |
| Compound 1-7 | 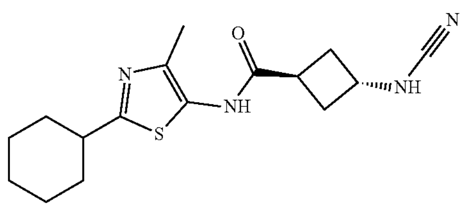 [SMILES: Cc1nc(C2CCCCC2)sc1NC(=O)[C@H]1C[C@H](NC#N)C1] | (1r,3r)-3-(cyanoamino)-N-(2-cyclohexyl-4-methyl-1,3-thiazol-5-yl)cyclobutane-1-carboxamide |
| Compound 1-8 | 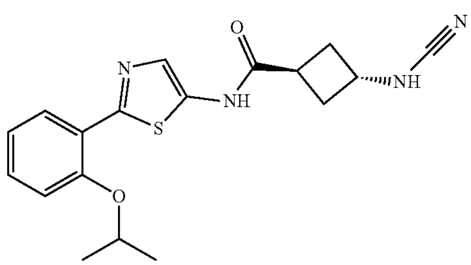 [SMILES: CC(C)Oc1ccccc1-c1ncc(NC(=O)[C@H]2C[C@H](NC#N)C2)s1] | (1r,3r)-3-(cyanoamino)-N-{2-[2-(propan-2-yloxy)phenyl]-1,3-thiazol-5-yl}cyclobutane-1-carboxamide |
| Compound 1-9 | 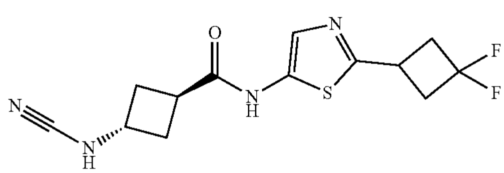 [SMILES: N#CN[C@H]1C[C@H](C(=O)Nc2cnc(C3CC(F)(F)C3)s2)C1] | (1r,3r)-3-(cyanoamino)-N-[2-(3,3-difluorocyclobutyl)-1,3-thiazol-5-yl]cyclobutane-1-carboxamide |
| Compound 1-10 | 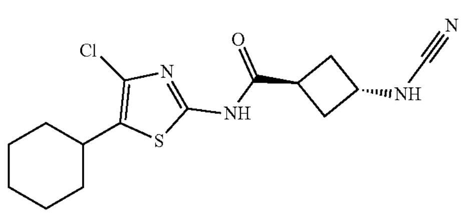 [SMILES: N#CN[C@H]1C[C@H](C(=O)Nc2nc(Cl)c(C3CCCCC3)s2)C1] | (1r,3r)-N-(4-chloro-5-cyclohexyl-1,3-thiazol-2-yl)-3-(cyanoamino)cyclobutane-1-carboxamide |

-continued

| Example No. | Structure | Chemical Name |
|---|---|---|
| Compound 1-11 | 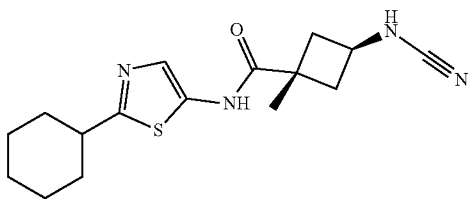 [SMILES: C[C@]1(C(=O)Nc2cnc(C3CCCCC3)s2)C[C@H](NC#N)C1] | (1r,3r)-3-(cyanoamino)-N-(2-cyclohexyl-1,3-thiazol-5-yl)-1-methylcyclobutane-1-carboxamide |
| Compound 1-12 | 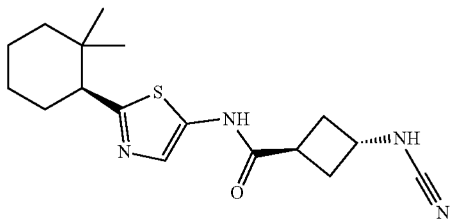 [SMILES: CC1(C)CCCC[C@@H]1c1ncc(NC(=O)[C@H]2C[C@H](NC#N)C2)s1] | (1r,3r)-3-(cyanoamino)-N-{2-[(1S)-2,2-dimethylcyclohexyl]-1,3-thiazol-5-yl}cyclobutane-1-carboxamide |
| Compound 1-13 | 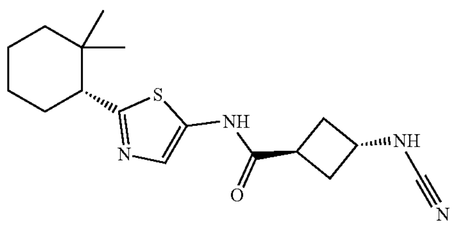 [SMILES: CC1(C)CCCC[C@H]1c1ncc(NC(=O)[C@H]2C[C@H](NC#N)C2)s1] | (1r,3r)-3-(cyanoamino)-N-{2-[(1R)-2,2-dimethylcyclohexyl]-1,3-thiazol-5-yl}cyclobutane-1-carboxamide |
| Compound 1-14 | 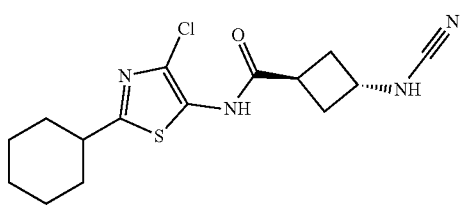 [SMILES: N#CN[C@H]1C[C@H](C(=O)Nc2sc(C3CCCCC3)nc2Cl)C1] | (1r,3r)-N-(4-chloro-2-cyclohexyl-1,3-thiazol-5-yl)-3-(cyanoamino)cyclobutane-1-carboxamide |
| Compound 1-15 | 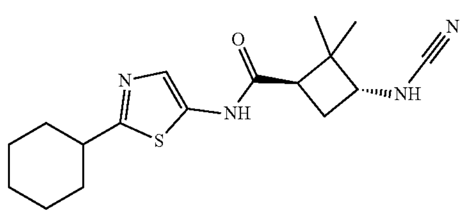 [SMILES: CC1(C)[C@H](NC#N)C[C@H]1C(=O)Nc1cnc(C2CCCCC2)s1] | (1R,3R)-3-(cyanoamino)-N-(2-cyclohexyl-1,3-thiazol-5-yl)-2,2-dimethylcyclobutane-1-carboxamide |
| Compound 1-16 | 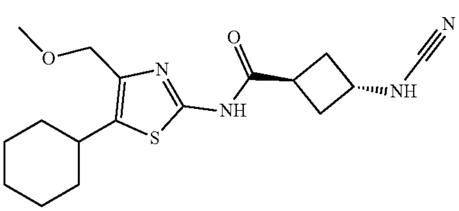 [SMILES: COCc1nc(NC(=O)[C@H]2C[C@H](NC#N)C2)sc1C1CCCCC1] | (1r,3r)-3-(cycanoamino)-N-[5-cyclohexyl-4-(methoxymethyl)-1,3-thiazol-2-yl]cyclobutane-1-carboxamide |
| Compound 1-17 | 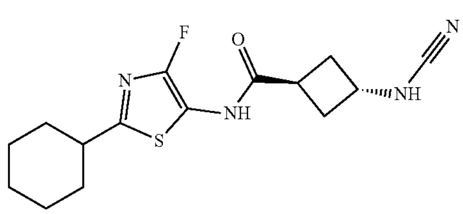 [SMILES: N#CN[C@H]1C[C@H](C(=O)Nc2sc(C3CCCCC3)nc2F)C1] | (1r,3r)-3-(cyanoamino)-N-(2-cyclohexyl-4-fluoro-1,3-thiazol-5-yl)cyclobutane-1-carboxamide |

| Example No. | Structure | Chemical Name |
|---|---|---|
| Compound 1-18 | 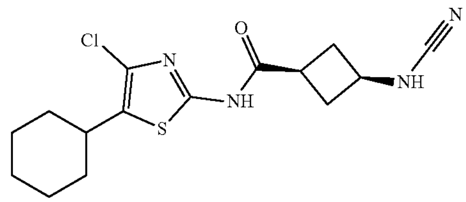 [SMILES: N#CN[C@H]1C[C@@H](C(=O)Nc2nc(Cl)c(C3CCCCC3)s2)C1] | (1s,3s)-N-(4-chloro-5-cyclohexyl-1,3-thiazol-2-yl)-3-(cyanoamino)cyclobutane-1-carboxamide |
| Compound 1-19 | 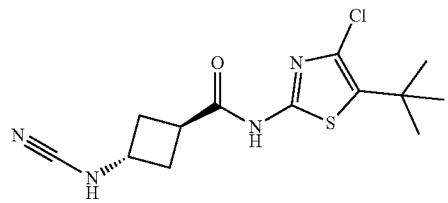 [SMILES: CC(C)(C)c1sc(NC(=O)[C@H]2C[C@H](NC#N)C2)nc1Cl] | (1r,3r)-N-(5-tert-butyl-4-chloro-1,3-thiazol-2-yl)-3-(cyanoamino)cyclobutane-1-carboxamide |
| Compound 1-20 | 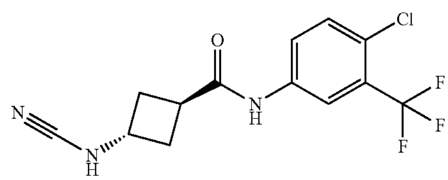 [SMILES: N#CN[C@H]1C[C@H](C(=O)Nc2ccc(Cl)c(C(F)(F)F)c2)C1] | (1r,3r)-N-[4-chloro-3-(trifluoromethyl)phenyl]-3-(cyanoamino)cyclobutane-1-carboxamide |
| Compound 1-21 | 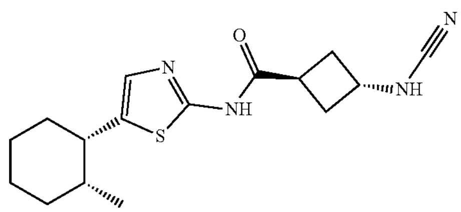 [SMILES: C[C@@H]1CCCC[C@@H]1c1cnc(NC(=O)[C@H]2C[C@H](NC#N)C2)s1] | (1r,3r)-3-(cyanoamino)-N-{5-[(1S,2R)-2-methylcyclohexyl]-1,3-thiazol-2-yl}cyclobutane-1-carboxamide |
| Compound 1-22 | 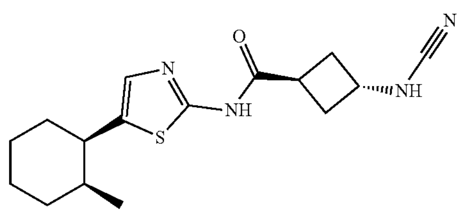 [SMILES: C[C@H]1CCCC[C@H]1c1cnc(NC(=O)[C@H]2C[C@H](NC#N)C2)s1] | (1r,3r)-3-(cyanoamino)-N-{5-[(1R,2S)-2-methylcyclohexyl]-1,3-thiazol-2-yl}cyclobutane-1-carboxamide |
| Compound 1-23 | 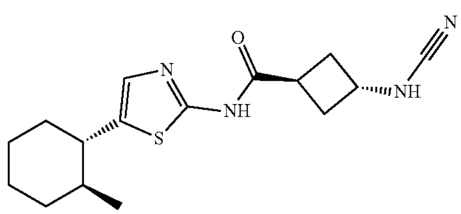 [SMILES: C[C@H]1CCCC[C@@H]1c1cnc(NC(=O)[C@H]2C[C@H](NC#N)C2)s1] | (1r,3r)-3-(cyanoamino)-N-{5-[(1S,2S)-2-methylcyclohexyl]-1,3-thiazol-2-yl}cyclobutane-1-carboxamide |
| Compound 1-24 | 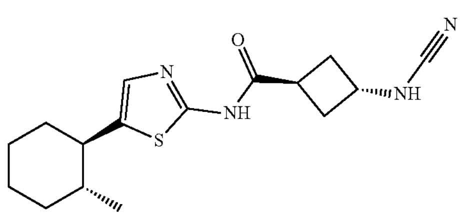 [SMILES: C[C@@H]1CCCC[C@H]1c1cnc(NC(=O)[C@H]2C[C@H](NC#N)C2)s1] | (1r,3r)-3-(cyanoamino)-N-{5-[(1R,2R)-2-methylcyclohexyl]-1,3-thiazol-2-yl}cyclobutane-1-carboxamide |

-continued

| Example No. | Structure | Chemical Name |
|---|---|---|
| Compound 1-25 | 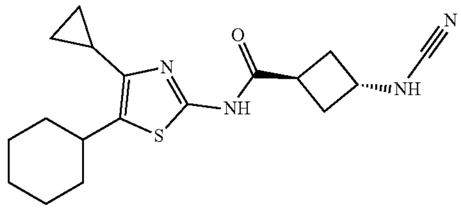 [SMILES: N#CN[C@H]1C[C@H](C(=O)Nc2nc(C3CC3)c(C3CCCCC3)s2)C1] | (1r,3r)-3-(cyanoamino)-N-(5-cyclohexyl-4-cyclopropyl-1,3-thiazol-2-yl)cyclobutane-1-carboxamide |
| Compound 1-26 | 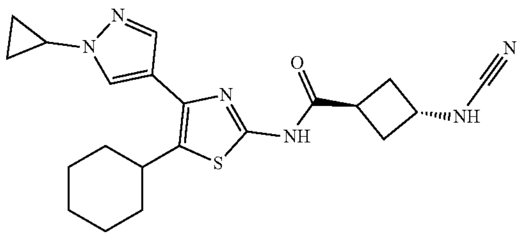 [SMILES: N#CN[C@H]1C[C@H](C(=O)Nc2nc(-c3cnn(C4CC4)c3)c(C3CCCCC3)s2)C1] | (1r,3r)-3-(cyanoamino)-N-[5-cyclohexyl-4-(1-cyclopropyl-1H-pyrazol-4-yl)-1,3-thiazol-2-yl]cyclobutane-1-carboxamide |
| Compound 1-27 | 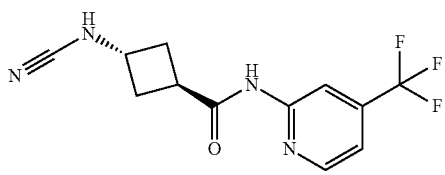 | (1r,3r)-3-(cyanoamino)-N-[4-(trifluoromethyl)pyridin-2-yl]cyclobutane-1-carboxamide |
| Compound 1-28 | 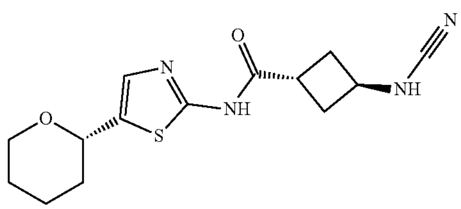 [SMILES: N#CN[C@H]1C[C@H](C(=O)Nc2ncc([C@@H]3CCCCO3)s2)C1] | (1r,3r)-3-(cyanoamino)-N-{5-[(2S)-oxan-2-yl]-1,3-thiazol-2-yl}cyclobutane-1-carboxamide |
| Compound 1-29 | 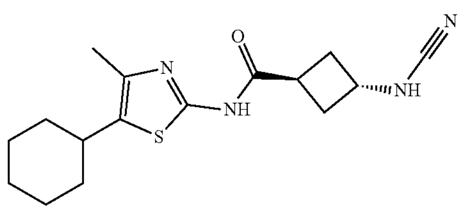 [SMILES: Cc1nc(NC(=O)[C@H]2C[C@H](NC#N)C2)sc1C1CCCCC1] | (1r,3r)-3-(cyanoamino)-N-(5-cyclohexyl-4-methyl-1,3-thiazol-2-yl)cyclobutane-1-carboxamide |
| Compound 1-30 | 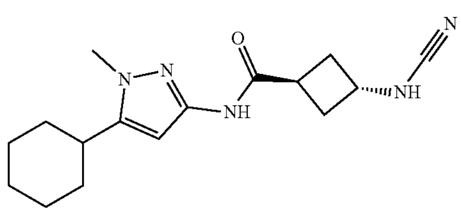 [SMILES: Cn1nc(NC(=O)[C@H]2C[C@H](NC#N)C2)cc1C1CCCCC1] | (1r,3r)-3-(cyanoamino)-N-(5-cyclohexyl-1-methyl-1H-pyrazol-3-yl)cyclobutane-1-carboxamide |
| Compound 1-31 | 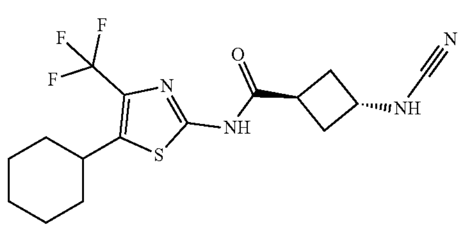 [SMILES: N#CN[C@H]1C[C@H](C(=O)Nc2nc(C(F)(F)F)c(C3CCCCC3)s2)C1] | (1r,3r)-3-(cyanoamino)-N-[5-cyclohexyl-4-(trifluoromethyl)-1,3-thiazol-2-yl]cyclobutane-1-carboxamide |

-continued

| Example No. | Structure | Chemical Name |
|---|---|---|
| Compound 1-32 | 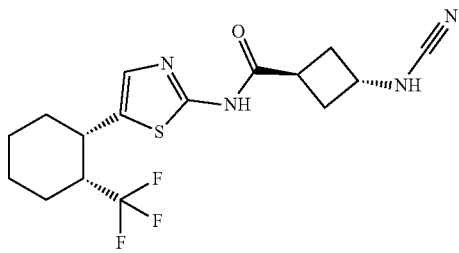 [SMILES: N#CN[C@H]1C[C@H](C(=O)Nc2ncc([C@H]3CCCC[C@H]3C(F)(F)F)s2)C1] | (1r,3r)-3-(cyanoamino)-N-{5-[(1S,2R)-2-(trifluoromethyl)cyclohexyl]-1,3-thiazol-2-yl}cyclobutane-1-carboxamide |
| Compound 1-33 | 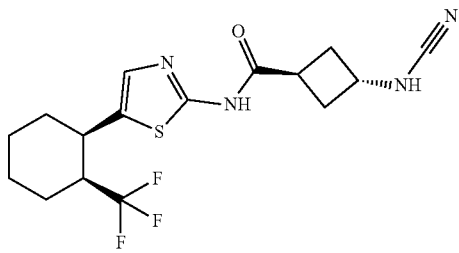 [SMILES: N#CN[C@H]1C[C@H](C(=O)Nc2ncc([C@@H]3CCCC[C@@H]3C(F)(F)F)s2)C1] | (1r,3r)-3-(cyanoamino)-N-{5-[(1R,2S)-2-(trifluoromethyl)cyclohexyl]-1,3-thiazol-2-yl}cyclobutane-1-carboxamide |
| Compound 1-34 | 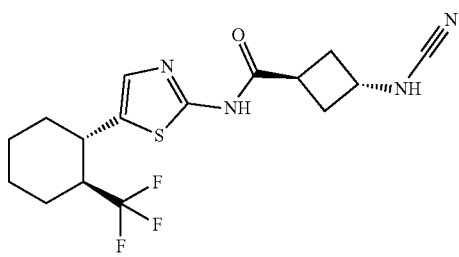 [SMILES: N#CN[C@H]1C[C@H](C(=O)Nc2ncc([C@H]3CCCC[C@@H]3C(F)(F)F)s2)C1] | (1r,3r)-3-(cyanoamino)-N-{5-[(1S,2S)-2-(trifluoromethyl)cyclohexyl]-1,3-thiazol-2-yl}cyclobutane-1-carboxamide |
| Compound 1-35 | 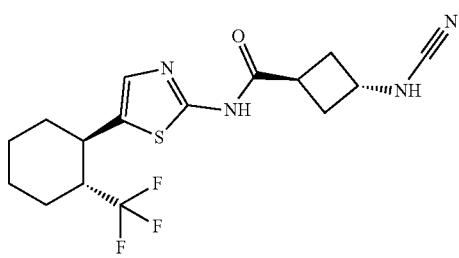 [SMILES: N#CN[C@H]1C[C@H](C(=O)Nc2ncc([C@@H]3CCCC[C@H]3C(F)(F)F)s2)C1] | (1r,3r)-3-(cyanoamino)-N-{5-[(1R,2R)-2-(trifluoromethyl)cyclohexyl]-1,3-thiazol-2-yl}cyclobutane-1-carboxamide |
| Compound 1-36 | 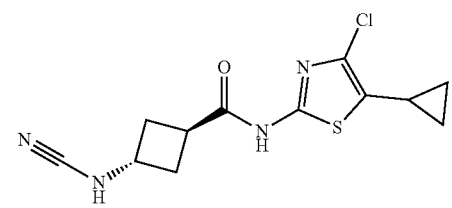 [SMILES: N#CN[C@H]1C[C@H](C(=O)Nc2nc(Cl)c(C3CC3)s2)C1] | (1r,3r)-N-(4-chloro-5-cyclopropyl-1,3-thiazol-2-yl)-3-(cyanoamino)cyclobutane-1-carboxamide |
| Compound 1-37 | 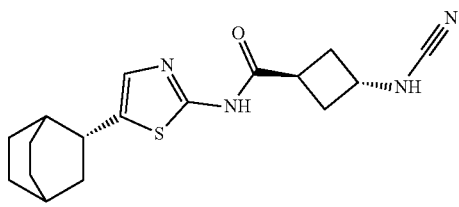 [SMILES: N#CN[C@H]1C[C@H](C(=O)Nc2ncc([C@@H]3CC4CCC3CC4)s2)C1] | (1r,3r)-N-{5-[(2R)-bicyclo[2.2.2]octan-2-yl]-1,3-thiazol-2-yl}-3-(cyanoamino)cyclobutane-1-carboxamide |

-continued

| Example No. | Structure | Chemical Name |
|---|---|---|
| Compound 1-38 | 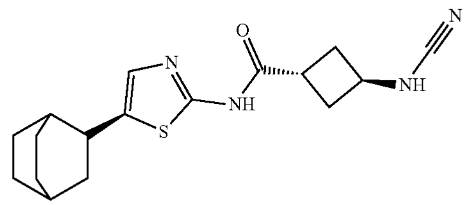 | (1r,3r)-N-{5-[(2S)-bicyclo[2.2.2]octan-2-yl]-1,3-thiazol-2-yl}-3-(cyanoamino)cyclobutane-1-carboxamide |
| Compound 1-39 | 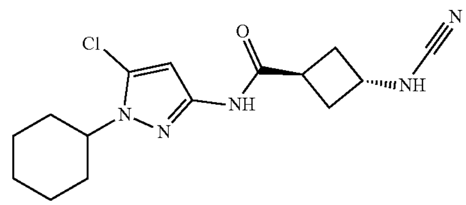 [SMILES: N#CN[C@H]1C[C@H](C(=O)Nc2cc(Cl)n(C3CCCCC3)n2)C1] | (1r,3r)-N-(5-chloro-1-cyclohexyl-1H-pyrazol-3-yl)-3-(cyanoamino)cyclobutane-1-carboxamide |
| Compound 1-40 | 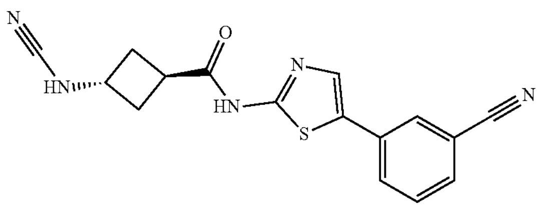 [SMILES: N#CN[C@H]1C[C@H](C(=O)Nc2ncc(-c3cccc(C#N)c3)s2)C1] | (1r,3r)-3-(cyanoamino)-N-[5-(3-cyanophenyl)-1,3-thiazol-2-yl]cyclobutane-1-carboxamide |
| Compound 1-41 | 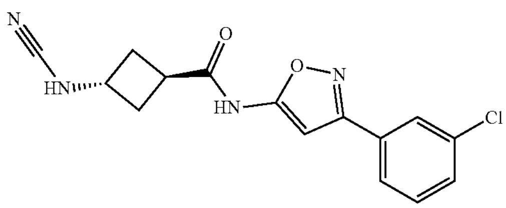 [SMILES: N#CN[C@H]1C[C@H](C(=O)Nc2cc(-c3cccc(Cl)c3)no2)C1] | (1r,3r)-N-[3-(3-chlorophenyl)-1,2-oxazol-5-yl]-3-(cyanoamino)cyclobutane-1-carboxamide |
| Compound 1-42 | 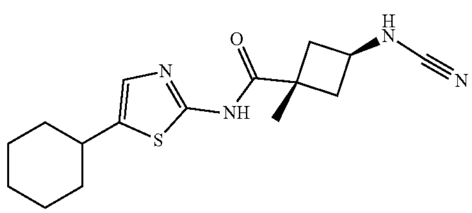 [SMILES: C[C@]1(C(=O)Nc2ncc(C3CCCCC3)s2)C[C@H](NC#N)C1] | (1r,3s)-3-(cyanoamino)-N-(5-cyclohexyl-1,3-thiazol-2-yl)-1-methylcyclobutane-1-carboxamide |
| Compound 1-43 | 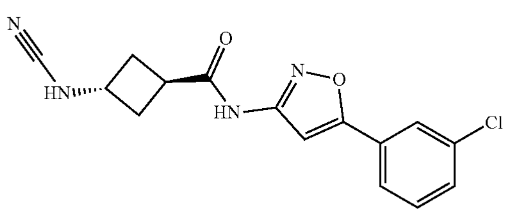 [SMILES: N#CN[C@H]1C[C@H](C(=O)Nc2cc(-c3cccc(Cl)c3)on2)C1] | (1r,3r)-N-[5-(3-chlorophenyl)-1,2-oxazol-3-yl]-3-(cyanoamino)cyclobutane-1-carboxamide |
| Compound 1-44 | 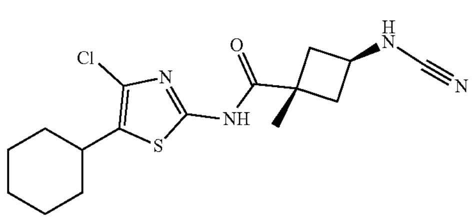 [SMILES: C[C@]1(C(=O)Nc2nc(Cl)c(C3CCCCC3)s2)C[C@H](NC#N)C1] | (1r,3s)-N-(4-chloro-5-cyclohexyl-1,3-thiazol-2-yl)-3-(cyanoamino)-1-methylcyclobutane-1-carboxamide |

-continued

| Example No. | Structure | Chemical Name |
|---|---|---|
| Compound 1-45 | 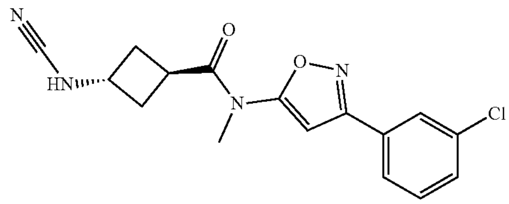 [SMILES: CN(c1cc(-c2cccc(Cl)c2)no1)C(=O)[C@H]1C[C@H](NC#N)C1] | (1r,3r)-N-[3-(3-chlorophenyl)-1,2-oxazol-5-yl]-3-(cyanoamino)-N-methylcyclobutane-1-carboxamide |
| Compound 1-46 | 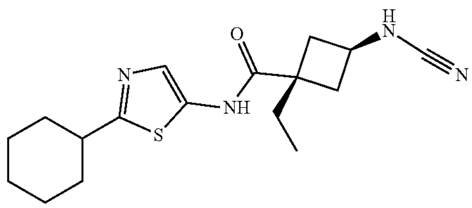 [SMILES: CC[C@]1(C(=O)Nc2cnc(C3CCCCC3)s2)C[C@H](NC#N)C1] | (1r,3s)-3-(cyanoamino)-N-(2-cyclohexyl-1,3-thiazol-5-yl)-1-ethylcyclobutane-1-carboxamide |
| Compound 1-47 | 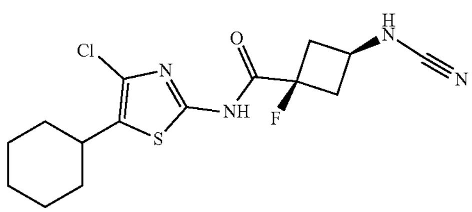 [SMILES: N#CN[C@H]1C[C@](F)(C(=O)Nc2nc(Cl)c(C3CCCCC3)s2)C1] | (1s,3s)-N-(4-chloro-5-cyclohexyl-1,3-thiazol-2-yl)-3-(cyanoamino)-1-fluorocyclobutane-1-carboxamide |
| Compound 1-48 | 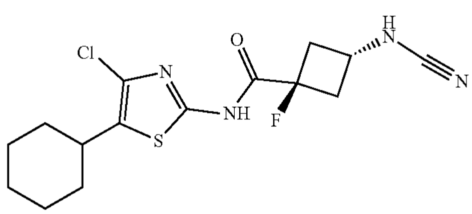 [SMILES: N#CN[C@H]1C[C@@](F)(C(=O)Nc2nc(Cl)c(C3CCCCC3)s2)C1] | (1r,3r)-N-(4-chloro-5-cyclohexyl-1,3-thiazol-2-yl)-3-(cyanoamino)-1-fluorocyclobutane-1-carboxamide |
| Compound 1-49 | 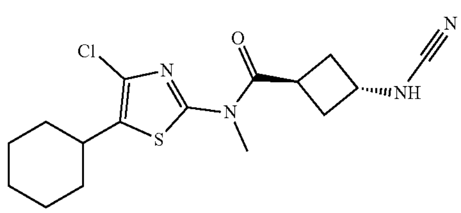 [SMILES: CN(c1nc(Cl)c(C2CCCCC2)s1)C(=O)[C@H]1C[C@H](NC#N)C1] | (1r,3r)-N-(4-chloro-5-cyclohexyl-1,3-thiazol-2-yl)-3-(cyanoamino)-N-methylcyclobutane-1-carboxamide |
| Compound 1-50 | 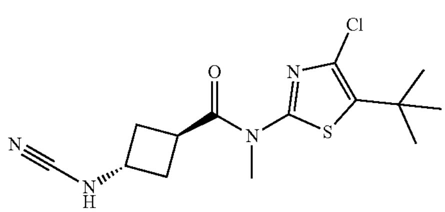 | (1r,3r)-N-(5-tert-butyl-4-chloro-1,3-thiazol-2-yl)-3-(cyanoamino)-N-methylcyclobutane-1-carboxamide |
| Compound 1-51 | 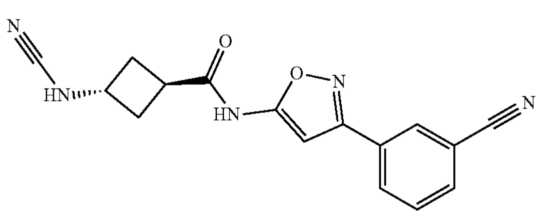 [SMILES: N#CN[C@H]1C[C@H](C(=O)Nc2cc(-c3cccc(C#N)c3)no2)C1] | (1r,3r)-3-(cyanamino)-N-[3-(3-cyanophenyl)-1,2-oxazol-5-yl]cyclobutane-1-carboxamide |

-continued

| Example No. | Structure | Chemical Name |
|---|---|---|
| Compound 1-52 | 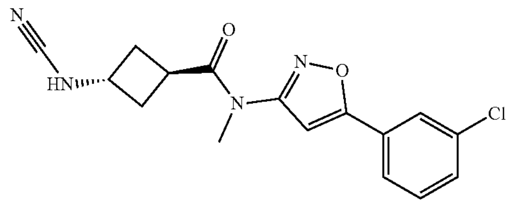 [SMILES: CN(c1cc(-c2cccc(Cl)c2)on1)C(=O)[C@H]1C[C@H](NC#N)C1] | (1r,3r)-N-[5-(3-chlorophenyl)-1,2-oxazol-3-yl]-3-(cyanoamino)-N-methylcyclobutane-1-carboxamide |
| Compound 1-53 | 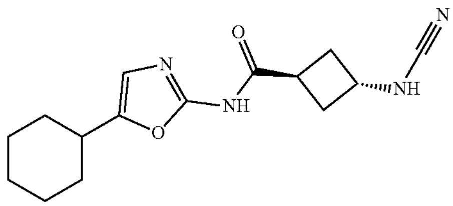 [SMILES: N#CN[C@H]1C[C@H](C(=O)Nc2ncc(C3CCCCC3)o2)C1] | (1r,3r)-3-(cyanoamino)-N-(5-cyclohexyl-1,3-oxazol-2-yl)cyclobutane-1-carboxamide |
| Compound 1-54 | 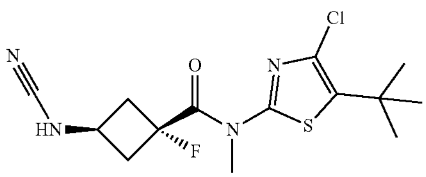 [SMILES: CN(c1nc(Cl)c(C(C)(C)C)s1)C(=O)[C@]1(F)C[C@H](NC#N)C1] | (1r,3r)-N-(5-tert-butyl-4-chloro-1,3-thiazol-2-yl)-3-(cyanoamino)-1-fluoro-N-methylcyclobutane-1-carboxamide |
| Compound 1-55 | 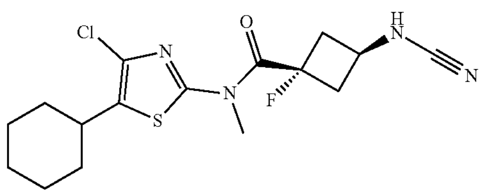 [SMILES: CN(c1nc(Cl)c(C2CCCCC2)s1)C(=O)[C@]1(F)C[C@H](NC#N)C1] | (1r,3r)-N-(4-chloro-5-cyclohexyl-1,3-thiazol-2-yl)-3-(cyanoamino)-1-fluoro-N-methylcyclobutane-1-carboxamide |
| Compound 1-56 | 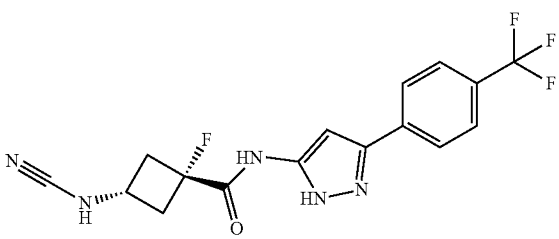 [SMILES: N#CN[C@H]1C[C@](F)(C(=O)Nc2cc(-c3ccc(C(F)(F)F)cc3)n[nH]2)C1] | (1s,3s)-3-(cyanoamino)-1-fluoro-N-{3-[4-(trifluoromethyl)phenyl]-1H-pyrazol-5-yl}cyclobutane-1-carboxamide |
| Compound 1-57 | 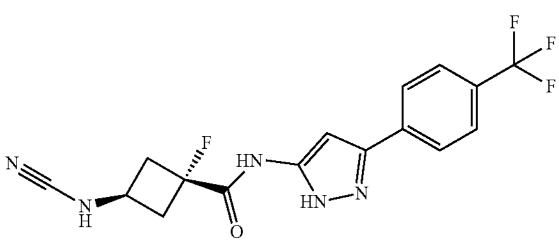 [SMILES: N#CN[C@H]1C[C@@](F)(C(=O)Nc2cc(-c3ccc(C(F)(F)F)cc3)n[nH]2)C1] | (1r,3r)-3-(cyanoamino)-1-fluoro-N-{3-[4-(trifluoromethyl)phenyl]-1H-pyrazol-5-yl}cyclobutane-1-carboxamide |
| Compound 1-58 | 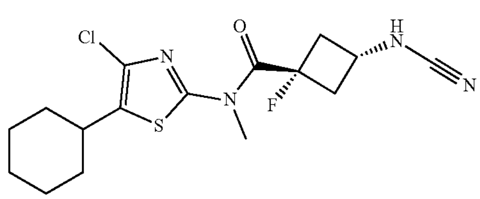 [SMILES: CN(c1nc(Cl)c(C2CCCCC2)s1)C(=O)[C@]1(F)C[C@@H](NC#N)C1] | (1s,3s)-N-(4-chloro-5-cyclohexyl-1,3-thiazol-2-yl)-3-(cyanoamino)-1-fluoro-N-methylcyclobutane-1-carboxamide |

-continued

| Example No. | Structure | Chemical Name |
|---|---|---|
| Compound 1-59 | 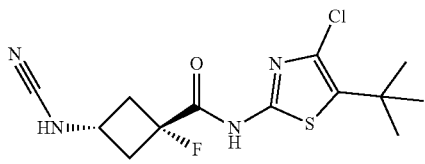 [SMILES: CC(C)(C)c1sc(NC(=O)[C@]2(F)C[C@@H](NC#N)C2)nc1Cl] | (1s,3s)-N-(5-tert-butyl-4-chloro-1,3-thiazol-2-yl)-3-(cyanoamino)-1-fluorocyclobutane-1-carboxamide |
| Compound 1-60 | 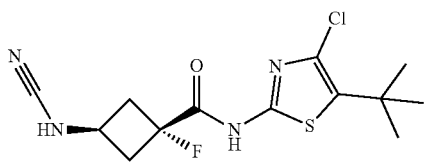 | (1r,3s)-N-(5-tert-butyl-4-chloro-1,3-thiazol-2-yl)-3-(cyanoamino)-1-fluorocyclobutane-1-carboxamide |
| Compound 1-61 | 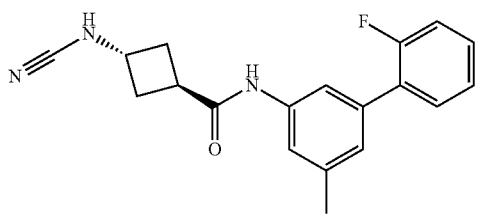 [SMILES: Cc1cc(NC(=O)[C@H]2C[C@H](NC#N)C2)cc(-c2ccccc2F)c1] | (1r,3r)-3-(cyanoamino)-N-[3-(2-fluorophenyl)-5-methylphenyl]cyclobutane-1-carboxamide |
| Compound 1-62 | 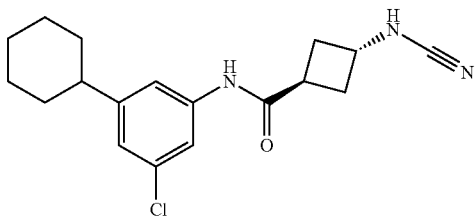 [SMILES: N#CN[C@H]1C[C@H](C(=O)Nc2cc(Cl)cc(C3CCCCC3)c2)C1] | (1r,3r)-N-(3-chloro-5-cyclohexylphenyl)-3-(cyanoamino)cyclobutane-1-carboxamide |
| Compound 1-63 | 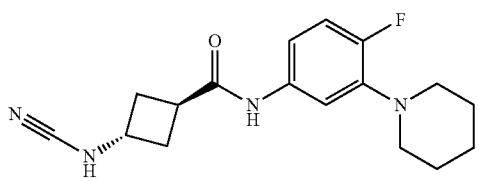 [SMILES: N#CN[C@H]1C[C@H](C(=O)Nc2ccc(F)c(N3CCCCC3)c2)C1] | (1r,3r)-3-(cyanoamino)-N-[4-fluoro-3-(piperidin-1-yl)phenyl]cyclobutane-1-carboxamide |
| Compound 1-64 | 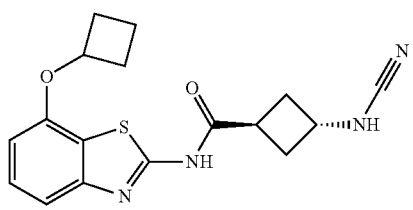 | (1r,3r)-3-(cyanoamino)-N-(7-cyclobutoxy-1,3-benzothiazol-2-yl)cyclobutane-1-carboxamide |
| Compound 1-65 | 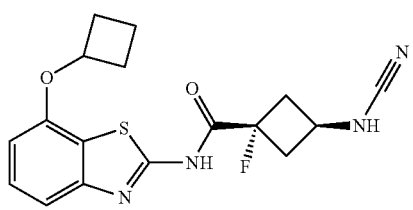 [SMILES: N#CN[C@H]1C[C@@](F)(C(=O)Nc2nc3cccc(OC4CCC4)c3s2)C1] | (1r,3r)-3-(cyanoamino)-N-(7-cyclobutoxy-1,3-benzothiazol-2-yl)-1-fluorocyclobutane-1-carboxamide |

-continued

| Example No. | Structure | Chemical Name |
|---|---|---|
| Compound 1-66 | 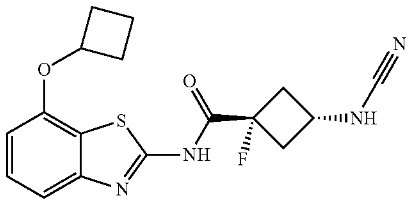 [SMILES: N#CN[C@H]1C[C@](F)(C(=O)Nc2nc3cccc(OC4CCC4)c3s2)C1] | (1s,3s)-3-(cyanoamino)-N-(7-cyclobutoxy-1,3-benzothiazol-2-yl)-1-fluorocyclobutane-1-carboxamide |
| Compound 1-67 | 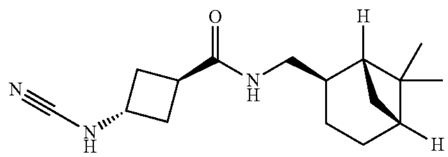 [SMILES: CC1(C)[C@@H]2CC[C@@H](CNC(=O)[C@H]3C[C@H](NC#N)C3)[C@H]1C2] | (1r,3r)-3-(cyanoamino)-N-{[(1R,2R,5R)-6,6-dimethylbicyclo[3.1.1]heptan-2-yl]methyl}cyclobutane-1-carboxamide |
| Compound 1-68 | 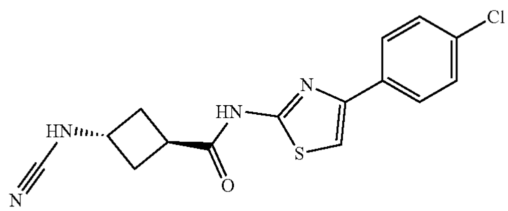 [SMILES: N#CN[C@H]1C[C@H](C(=O)Nc2nc(-c3ccc(Cl)cc3)cs2)C1] | (1r,3r)-N-[4-(4-chlorophenyl)-1,3-thiazol-2-yl]-3-(cyanoamino)cyclobutane-1-carboxamide |
| Compound 1-69 | 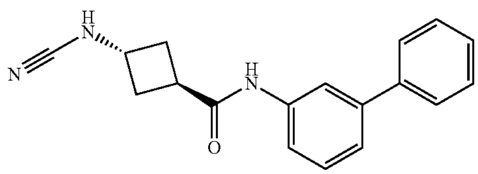 [SMILES: N#CN[C@H]1C[C@H](C(=O)Nc2cccc(-c3ccccc3)c2)C1] | (1r,3r)-3-(cyanoamino)-N-(3-phenylphenyl)cyclobutane-1-carboxamide |
| Compound 1-70 | 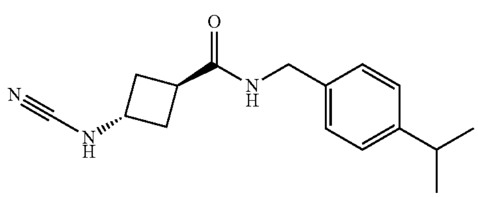 [SMILES: CC(C)c1ccc(CNC(=O)[C@H]2C[C@H](NC#N)C2)cc1] | (1r,3r)-3-(cyanoamino)-N-{[4-(propan-2-yl)phenyl]methyl}cyclobutane-1-carboxamide |
| Compound 1-71 | 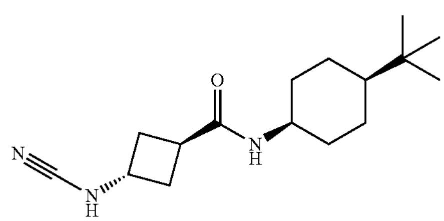 [SMILES: CC(C)(C)[C@H]1CC[C@@H](NC(=O)[C@H]2C[C@H](NC#N)C2)CC1] | (1r,3r)-3-(cyanoamino)-N-[(1s,4s)-4-tert-butylcyclohexyl]cyclobutane-1-carboxamide |
| Compound 1-72 | 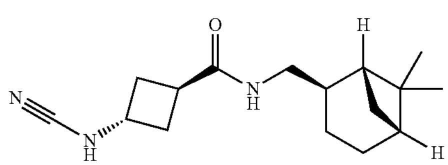 [SMILES: CC1(C)[C@@H]2CC[C@@H](CNC(=O)[C@H]3C[C@H](NC#N)C3)[C@H]1C2] | (1r,3r)-3-(cyanoamino)-N-{[(1R,2R,5R)-6,6-dimethylbicyclo[3.1.1]heptan-2-yl]methyl}cyclobutane-1-carboxamide |
| Compound 1-73 | 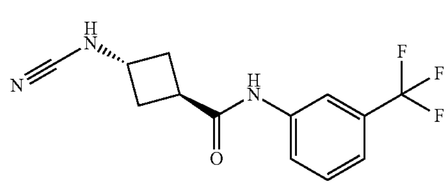 [SMILES: N#CN[C@H]1C[C@H](C(=O)Nc2cccc(C(F)(F)F)c2)C1] | (1r,3r)-3-(cyanoamino)-N-[3-(trifluoromethyl)phenyl]cyclobutane-1-carboxamide |

-continued

| Example No. | Structure | Chemical Name |
|---|---|---|
| Compound 3-2 | 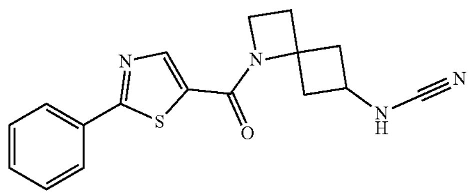 [SMILES: N#CNC1CC2(CCN2C(=O)c2cnc(-c3ccccc3)s2)C1] | {[1-(2-phenyl-1,3-thiazole-5-carbonyl)-1-azaspiro[3.3]heptan-6-yl]amino}carbonitrile |
| Compound 3-3 | 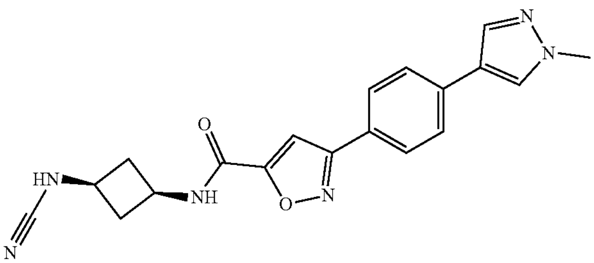 [SMILES: Cn1cc(-c2ccc(-c3cc(C(=O)N[C@H]4C[C@@H](NC#N)C4)on3)cc2)cn1] | 3-[4-(1-methyl-1H-pyrazol-4-yl)phenyl]-N-[(1s,3s)-3-(cyanoamino)cyclobutyl]-1,2-oxazole-5-carboxamide |
| Compound 3-4 | 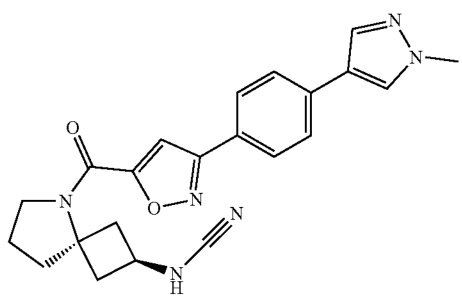 [SMILES: Cn1cc(-c2ccc(-c3cc(C(=O)N4CCC[C@]45C[C@H](NC#N)C5)on3)cc2)cn1] | {[(2r,4s)-5-{3-[4-(1-methyl-1H-pyrazol-4-yl)phenyl]-1,2-oxazole-5-carbonyl}-5-azaspiro[3.4]octan-2-yl]amino}carbonitrile |
| Compound 3-5 | 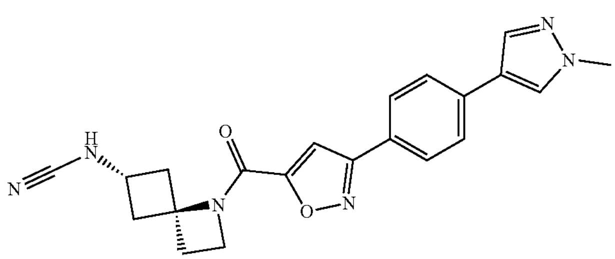 [SMILES: Cn1cc(-c2ccc(-c3cc(C(=O)N4CC[C@]45C[C@@H](NC#N)C5)on3)cc2)cn1] | {[(4r,6s)-1-{3-[4-(1-methyl-1H-pyrazol-4-yl)phenyl]-1,2-oxazole-5-carbonyl}-1-azaspiro[3.3]heptan-6-yl]amino}carbonitrile |
| Compound 3-6 | 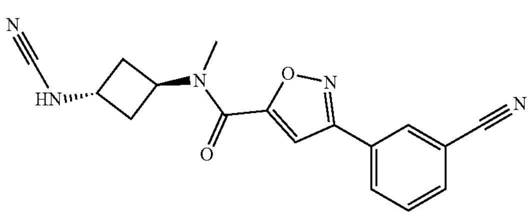 [SMILES: CN(C(=O)c1cc(-c2cccc(C#N)c2)no1)[C@H]1C[C@H](NC#N)C1] | 3-(3-cyanophenyl)-N-methyl-N-[(1r,3r)-3-(cyanoamino)cyclobutyl]-1,2-oxazole-5-carboxamide |
| Compound 6-1 | 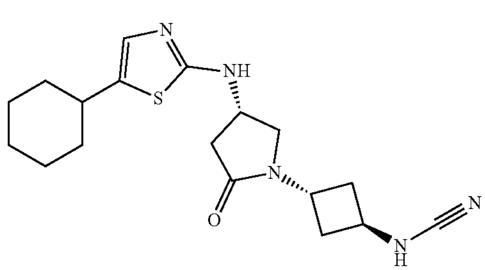 [SMILES: N#CN[C@H]1C[C@H](N2C[C@@H](Nc3ncc(C4CCCCC4)s3)CC2=O)C1] | {[(1r,3r)-3-[(4S)-4-[(5-cyclohexyl-1,3-thiazol-2-yl)amino]-2-oxopyrrolidin-1-yl]cyclobutyl]amino}carbonitrile |

-continued

| Example No. | Structure | Chemical Name |
|---|---|---|
| Compound 7-1 | 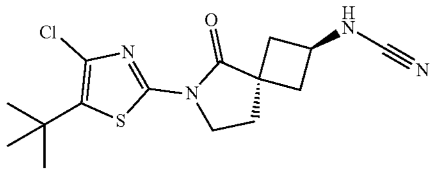 [SMILES: CC(C)(C)c1sc(N2CC[C@]3(C[C@H](NC#N)C3)C2=O)nc1Cl] | {[(2r,4s)-6-(5-tert-butyl-4-chloro-1,3-thiazol-2-yl)-5-oxo-6-azaspiro[3.4]octan-2-yl]amino}carbonitrile |
| Compound 7-2 | 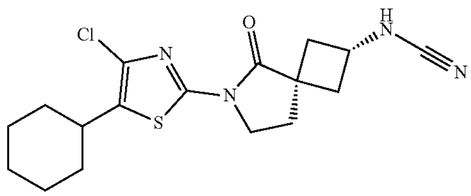 [SMILES: N#CN[C@H]1C[C@@]2(CCN(c3nc(Cl)c(C4CCCCC4)s3)C2=O)C1] | {[(2s,4r)-6-(4-chloro-5-cyclohexyl-1,3-thiazol-2-yl)-5-oxo-6-azaspiro[3.4]octan-2-yl]amino}carbonitrile |
| Compound 7-3 | 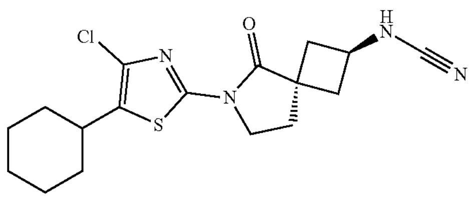 [SMILES: N#CN[C@H]1C[C@]2(CCN(c3nc(Cl)c(C4CCCCC4)s3)C2=O)C1] | {[(2r,4s)-6-(4-chloro-5-cyclohexyl-1,3-thiazol-2-yl)-5-oxo-6-azaspiro[3.4]octan-2-yl]amino}carbonitrile |
| Compound 8-1 | 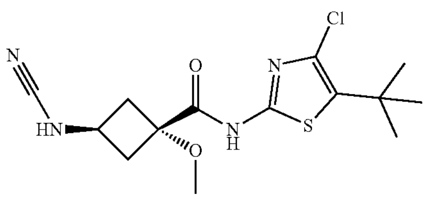 [SMILES: CO[C@]1(C(=O)Nc2nc(Cl)c(C(C)(C)C)s2)C[C@@H](NC#N)C1] | (1r,3r)-N-(5-tert-butyl-4-chloro-1,3-thiazol-2-yl)-3-(cyanoamino)-1-methoxycyclobutane-1-carboxamide |
| Compound 9-1 | 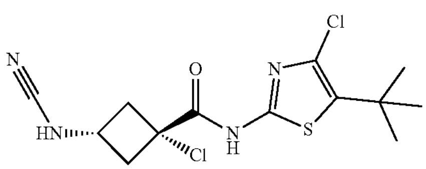 | (1s,3s)-N-(5-tert-butyl-4-chloro-1,3-thiazol-2-yl)-1-chloro-3-(cyanoamino)cyclobutane-1-carboxamide |
| Compound 9-2 | | (1r,3r)-N-(5-tert-butyl-4-chloro-1,3-thiazol-2-yl)-1-chloro-3-(cyanoamino)cyclobutane-1-carboxamide | and pharmaceutically acceptable salts, solvates, prodrugs, stereoisomers, and tautomers thereof.

Formula II

The disclosure also provides compounds of Formula II:

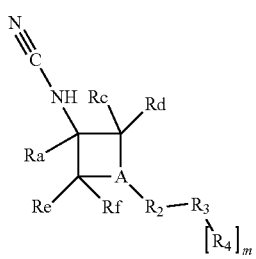

(II)

wherein A, $R_a$, $R_b$, $R_c$, $R_d$, $R_e$, $R_f$, R, $R_2$, $R_3$, $R_4$, $R_5$, X, Y, and m are as described herein above.

The disclosure provides compounds of Formula (H), wherein preferably A is $CR_b$.

The disclosure provides compounds of Formula (H), wherein $R_a$ is hydrogen.

The disclosure provides compounds of Formula (II), wherein $R_b$ is selected from hydrogen, halogen, $(C_1$-$C_6)$ alkyl groups optionally substituted with one or more $R_5$, and $(C_1$-$C_6)$ alkoxy groups optionally substituted with one or more $R_5$.

The disclosure provides compounds of formula (II), wherein both $R_a$ and $R_b$ are each hydrogen.

The disclosure provides compounds of Formula (II), wherein each of $R_c$, $R_d$, $R_e$, and $R_f$ is independently selected from the group consisting of hydrogen and $(C_1$-$C_6)$ alkyl groups optionally substituted with one or more $R_f$. In some embodiments of Formula (II), each of $R_c$, $R_d$, $R_e$, and $R_f$ in the compounds of Formula (II) is hydrogen.

The disclosure provides compounds of Formula (II) wherein $R_2$ is selected from amides and reverse amides. The disclosure provides compounds of Formula (II) wherein $R_2$ is an amide. The disclosure provides compounds of Formula (II) wherein $R_2$ is a reverse amide. The disclosure provides compounds of Formula (II) wherein $R_2$ is selected from C(O)N(X) and N(X)C(O). The disclosure provides compounds of Formula (II), wherein $R_2$ is preferably C(O)N(X). The disclosure provides compounds of Formula (II), wherein $R_2$ is N(X)C(O).

In a preferred embodiment of Formula (II), A is $CR_b$ and $R_2$ is selected from amides and reverse amides. In one embodiment A is $CR_b$ and $R_2$ is a reverse amide. More preferably, A is $CR_b$ and $R_2$ is an amide.

In a preferred embodiment of Formula (II), A is $CR_b$ and $R_2$ is selected from C(O)N(X) and N(X)C(O). In one embodiment A is $CR_b$ and $R_2$ is N(X)C(O). More preferably, A is $CR_b$ and $R_2$ is C(O)N(X).

The disclosure provides compounds of Formula (II), wherein X is selected from hydrogen and alkyl groups. In some embodiments of Formula (H) X is H.

The disclosure provides compounds of Formula (II), wherein X is selected from alkyl groups and heteroalkyl groups, and the alkyl and heteroalkyl groups cyclize with $R_b$ or $R_3$.

The disclosure provides compounds of Formula (II) wherein $R_3$ is selected from the group consisting of aryl having 1 to 3 aromatic rings (including aryl groups optionally substituted with 1 or 2 R groups) and heteroaryl having 1 to 3 aromatic rings (including heteroaryl groups optionally substituted with 1 or 2 R groups). In some embodiments of Formula (II) $R_3$ is a heteroaryl group having 1 to 3 aromatic rings (including heteroaryl groups optionally substituted with 1 or 2 R groups). In some embodiments of Formula (II), $R_3$ is a heteroaryl group having 1 aromatic ring optionally substituted with 1 or 2 R groups. In some embodiments of Formula (II) $R_3$ is a heteroaryl group having 1 aromatic ring optionally substituted with 1 or 2 R groups wherein the aromatic ring features two heteroatoms, preferably one nitrogen and one sulphur atom. In some embodiments of Formula (II) $R_3$ is a heteroaryl group having 1 aromatic ring optionally substituted with 1 or 2 R groups wherein the aromatic ring is a 5 membered ring featuring one nitrogen and one sulphur atom, preferably a thiazole ring. In some embodiments of Formula (II) $R_3$ is chosen from thiazole, indenyl, pyrazole, phenyl, benzothiazole, and oxazole rings.

The disclosure provides compounds of Formula (II), wherein $R_4$ is a cyclic group, e.g. a cycloalkyl group optionally substituted with 1 or 2 Y groups. The disclosure provides compounds of Formula (II), wherein $R_4$ is an aryl group optionally substituted with 1 or 2 Y groups. The disclosure provides compounds of Formula (II), wherein $R_4$ is a cyclohexyl group or phenyl group. The disclosure provides compounds of Formula (II) wherein $R_4$ is a cyclohexyl group. The disclosure provides compounds of Formula (II), wherein $R_4$ is a phenyl group.

The disclosure provides compounds of Formula (II) wherein, A is $CR_b$, $R_b$ is selected from hydrogen and $(C_1-C_6)$alkyl groups, each of $R_a$, $R_c$, $R_d$, $R_e$, and $R_f$ is hydrogen, $R_2$ is C(O)N(X), X is selected from hydrogen and alkyl groups, and $R_3$ is a heteroaryl group having 1 aromatic ring optionally substituted with 1 or 2 R groups wherein the aromatic ring features one nitrogen and one sulphur atom; and $R_4$ is a cyclic group or aryl group optionally substituted with 1 or 2 Y groups.

The disclosure provides compounds of Formula (II) wherein, A is $CR_b$, $R_b$ is selected from hydrogen and $(C_1-C_6)$alkyl groups, each of R, $R_c$, $R_d$, $R_e$, and $R_f$ is hydrogen, $R_2$ is C(O)N(X), X is selected from hydrogen and alkyl groups, and $R_3$ is a thiazole ring optionally substituted with 1 or 2 R groups; and $R_a$ is a 6-membered cyclic group or aryl group optionally substituted with 1 or 2 Y groups.

Any of the features disclosed above in the context of the compounds of Formula (II) may also be applied to any of the compounds of Formulae (I), (Ia), (Ib), (Ic), and (III) disclosed herein.

Formula III

The disclosure also provides compounds of Formula (III):

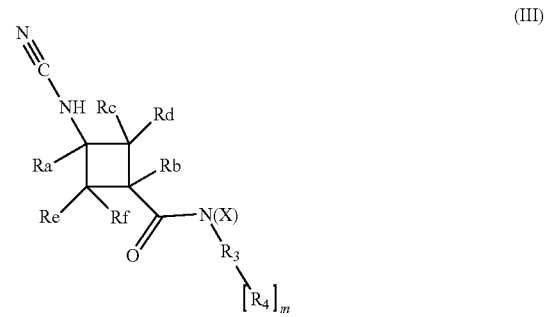

(III)

wherein $R_a$, $R_b$, $R_c$, $R_d$, $R_e$, $R_f$, R, $R_3$, $R_4$, $R_5$, X, Y, and m are as described herein above.

The disclosure provides compounds of Formula (III), wherein $R_a$ is hydrogen.

The disclosure provides compounds of Formula (III), wherein $R_b$ is selected from hydrogen, halogen, $(C_1-C_6)$ alkyl groups optionally substituted with one or more $R_5$, and $(C_1-C_6)$ alkoxy groups optionally substituted with one or more $R_5$.

The disclosure provides compounds of formula (III), wherein both $R_a$ and $R_b$ are each hydrogen.

The disclosure provides compounds of Formula (III), wherein each of R, $R_d$, $R_e$, and $R_f$ is independently selected from the group consisting of hydrogen and $(C_1-C_6)$ alkyl groups optionally substituted with one or more $R_5$. In some embodiments of the disclosure, each of $R_c$, $R_d$, $R_e$, and $R_f$ in the compounds of Formula (III) is hydrogen.

The disclosure provides compounds of Formula (III), wherein X is selected from hydrogen and alkyl groups. In some embodiments of the compounds of Formula (III) X is H.

The disclosure provides compounds of Formula (III), wherein X is selected from alkyl groups and heteroalkyl groups, and the alkyl and heteroalkyl groups cyclize with $R_b$ or $R_3$.

The disclosure provides compounds of Formula (III) wherein $R_3$ is selected from the group consisting of aryl having 1 to 3 aromatic rings (including aryl groups optionally substituted with 1 or 2 R groups) and heteroaryl having 1 to 3 aromatic rings (including heteroaryl groups optionally substituted with 1 or 2 R groups). In some embodiments of the disclosure $R_3$ in the compounds of Formula (III) is a heteroaryl group having 1 to 3 aromatic rings (including heteroaryl groups optionally substituted with 1 or 2 R groups). In some embodiments, $R_3$ is a heteroaryl group having 1 aromatic ring optionally substituted with 1 or 2 R groups. In some embodiments $R_3$ is a heteroaryl group having 1 aromatic ring optionally substituted with 1 or 2 R groups wherein the aromatic ring features two heteroatoms, preferably one nitrogen and one sulphur atom. In some embodiments $R_3$ is a heteroaryl group having 1 aromatic ring optionally substituted with 1 or 2 R groups wherein the aromatic ring is a 5 membered ring featuring one nitrogen and one sulphur atom, preferably a thiazole ring. In some embodiments of Formula (III) $R_3$ is chosen from thiazole, indenyl, pyrazole, phenyl, benzothiazole, and oxazole rings.

The disclosure provides compounds of Formula (III), wherein $R_4$ is a cyclic group, e.g. a cycloalkyl group optionally substituted with 1 or 2 Y groups. The disclosure provides compounds of Formula (III), wherein $R_4$ is an aryl group optionally substituted with 1 or 2 Y groups. The disclosure provides compounds of Formula (III), wherein $R_a$ is a cyclohexyl group or phenyl group. The disclosure provides compounds of Formula (III) wherein $R_4$ is a cyclohexyl group.

The disclosure provides compounds of Formula (III) wherein, $R_b$ is selected from hydrogen and $(C_1-C_6)$alkyl groups, each of $R_a$, $R_c$, $R_d$, $R_e$, and $R_f$ is hydrogen, X is selected from hydrogen and alkyl groups, and $R_1$ is a heteroaryl group having 1 aromatic ring optionally substituted with 1 or 2 R groups wherein the aromatic ring features one nitrogen and one sulphur atom; and $R_4$ is a cyclic group or aryl group optionally substituted with 1 or 2 Y groups.

The disclosure provides compounds of Formula (III) wherein, $R_b$ is selected from hydrogen and $(C_1-C_6)$alkyl groups, each of $R_a$, $R_c$, $R_d$, $R_e$, and $R_e$ is hydrogen, X is selected from hydrogen and alkyl groups, and $R_3$ is a thiazole ring optionally substituted with 1 or 2 R groups; and $R_4$ is a 6-membered cyclic group or aryl group optionally substituted with 1 or 2 Y groups.

Any of the features disclosed above in the context of the compounds of Formula (III) may also be applied to any of the compounds of Formulae (I), (Ia), (Tb), (Ic), and (II) disclosed herein.

In this disclosure, statements relating to compounds of Formula (I) may also be applied to any of the compounds of Formula (Ia), (Ib), (Ic), (II), and (III).

In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the compounds disclosed herein.

The compounds disclosed herein may form salts which are also within the scope of this disclosure.

The present disclosure relates to compounds which can be inhibitors of USP30.

The disclosure provides compounds having a USP30 $IC_{50}$ (µM) of 1 µM or less. Non-limiting examples of compounds of the disclosure having a USP30 $IC_{50}$ (µM) of 1 µM or less include those exemplified in tables A1 to A3 below having an activity reported as "+++" or "++++".

The disclosure provides compounds having a USP30 $IC_{50}$ (µM) of less than 0.5 µM.

The disclosure also provides compounds having a USP30 $IC_{50}$ (μM) of less than 0.1 μM. Non-limiting examples of compounds of the disclosure having a USP30 $IC_{50}$ (μM) of 1 μM or less include those exemplified in tables A1 to A3 below having an activity reported as "++++".

The present disclosure is directed to chemical entities chosen from compounds as described herein and pharmaceutically acceptable salts, solvates, prodrugs, stereoisomers, and tautomers thereof, and pharmaceutical compositions comprising at least one chemical entity chosen from compounds as described herein, and pharmaceutically acceptable salts, solvates, prodrugs, stereoisomers, and tautomers thereof.

In some embodiments of the methods described herein, neurodegenerative disease is chosen from Alzheimer's disease and other dementias, Parkinson's disease and other synucleinopathies such as Multiple System Atrophy, dementia with Lewy Bodies and PD-related disorders, Prion disease, Corticobasal Degeneration, Frontotemporal Dementia, Posterior Cortical Atrophy, Primary Progressive Aphasia, Progressive Supranuclear Palsy, Pick's disease, Chronic Traumatic Encephelopathy, Dementia Pugilistica, Traumatic Brain Injury, Vascular Dementia, Peripheral Neuropathy and Multiple Sclerosis.

Another aspect of the disclosure is directed to pharmaceutical compositions comprising a chemical entity chosen from compounds of Formula (I), and pharmaceutically acceptable salts, solvates, prodrugs, stereoisomers, and tautomers thereof and a pharmaceutically acceptable carrier. The pharmaceutical acceptable carrier may further include an excipient, diluent, or surfactant.

The disclosed compounds of the disclosure can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

The present disclosure also relates to a pharmaceutical composition comprising a compound disclosed herein and a pharmaceutically acceptable carrier. The pharmaceutical acceptable carrier may further include an excipient, diluent, additive, or surfactant. The compounds or pharmaceutical compositions of the disclosure may be administered via any mode of administration for therapeutic agents. These modes include systemic or local administration such as oral administration. Depending on the intended mode of administration, the disclosed compounds or compositions can be in solid dosage form, such as, for example, tablets, or pills or the like, sometimes in unit dosages and consistent with conventional pharmaceutical practices. Likewise, they can also be administered using forms well known to those skilled in the pharmaceutical arts.

The compounds of the disclosure can be administered in effective amounts to treat or prevent a disorder and/or prevent the development thereof in subjects.

In one embodiment, the present disclosure relates to a method of preparing a pharmaceutical composition of the present disclosure by mixing at least one pharmaceutically acceptable compound of the present disclosure, and, optionally, one or more pharmaceutically acceptable carriers, additives, or excipients. Pharmaceutical compositions comprising a compound of the disclosure can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume. The dosage forms of the present disclosure, may contain a mixture of one or more compounds of this disclosure, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. In one embodiment, the stabilizing additives are gum acacia, gelatin and methyl cellulose.

The compounds of the disclosure provided herein are preferably administered in a therapeutically effective amount (e.g., an amount having a suitable favorable therapeutic index). The amount and frequency of administration of the compounds of the disclosure and/or the pharmaceutically acceptable salts thereof will be regulated according to the judgment of the attending clinician considering such factors as age, condition and size of the patient as well as severity of the symptoms medical condition being treated. The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Another aspect of the disclosure is directed to pharmaceutical compositions comprising a chemical entity chosen from compounds of Formula (I), and pharmaceutically acceptable salts, solvates, prodrugs, stereoisomers, and tautomers thereof and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed chemical entity, or, in a range of from one amount to another amount in the list of doses. In one embodiment, the compositions are in the form of a tablet that can be scored.

Method of Synthesizing the Compounds

The compounds of the present disclosure may be made by a variety of methods, including standard chemistry. Suitable synthetic routes are depicted in the Schemes given below.

The compounds disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways known to those skilled in the art of organic synthesis. By way of example, compounds of the present disclosure can be synthesized using the methods described below, together with synthetic methods known in the art of synthetic organic chemistry, or variations thereof as appreciated by those skilled in the art. Preferred methods include but are not limited to those methods described below. General procedures to prepare compounds of the instant invention are described in General Schemes 1 and 2.

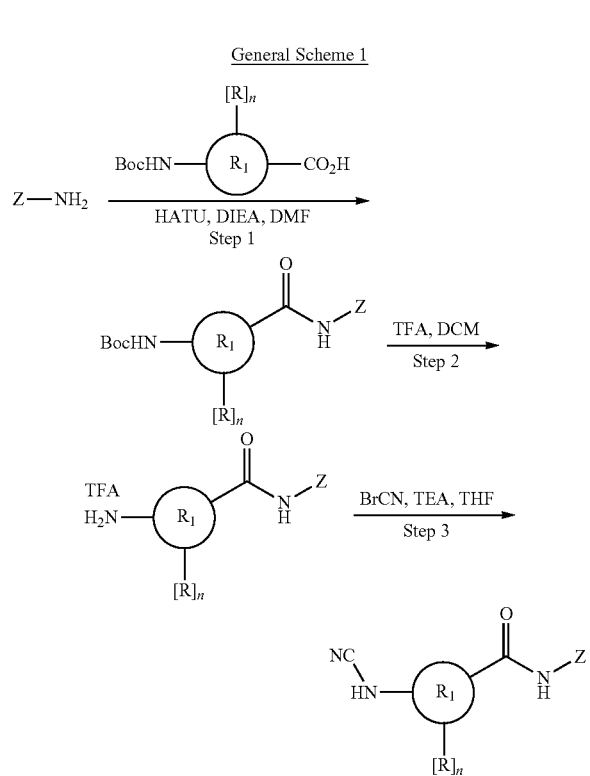

General Scheme 1

General Procedure. A Boc-protected amino acid can be coupled to an amine (i.e., Z—NH$_2$) using a standard coupling reagent (i.e., HATU) and base (i.e., DIEA) in a suitable solvent (i.e., DMF). The Boc group can then be removed using either TFA or HCl in a suitable solvent (i.e., DCM) to yield the corresponding crude amine salt. Finally, the crude amine salt can be reacted with cyanogen bromide in an appropriate solvent (i.e., THF) with excess base (i.e., TEA or NaHCO$_3$) at a range of temperatures (i.e., −20° C. to 25° C.) to afford the final product after purification.

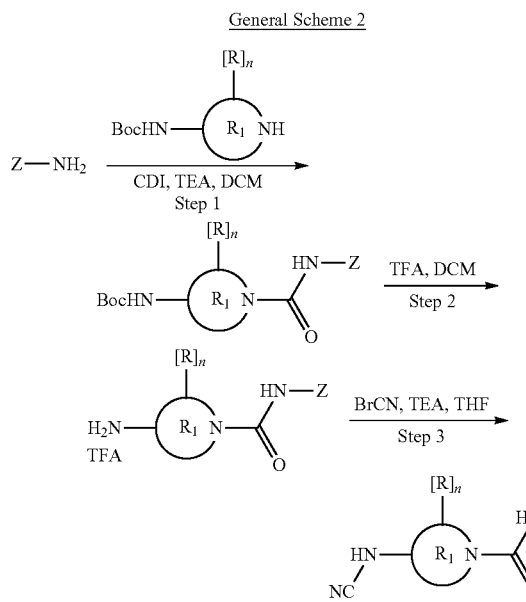

General Scheme 2

General Procedure: A mono-Boc-protected diamine can be treated with CDI and another amine (i.e., Z—NH$_2$) in the presence of a base (i.e., DIEA) in a suitable solvent (i.e., DCM) to afford the corresponding urea intermediate. The Boc group can then be removed using either TFA or HCl in a suitable solvent (i.e., DCM) to yield the corresponding crude amine salt. Finally, the crude amine salt can be reacted with cyanogen bromide in an appropriate solvent (i.e., THF) with excess base (i.e., TEA or NaHCO$_3$) at a range of temperatures (i.e., −20° C. to 25° C.) to afford the final product after purification.

Examples

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Unless otherwise noted, reactions were conducted under an inert atmosphere of nitrogen. Proton nuclear magnetic resonance (NMR) spectra were obtained on either Brüker or Varian spectrometers at 300 or 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 μm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted as designated below. The absolute configuration of the separated enantiomers of the compounds in the examples described herein was occasionally determined. In all other cases the absolute configuration of the separated enantiomers was not determined and in those instances the configuration of the resolved materials were arbitrarily assigned as R or S in each case.

Abbreviations Used in the Following Examples and Elsewhere Herein are:

| Abbreviation | Name |
| --- | --- |
| atm | atmospheres |
| AcOH | acetic acid |
| Boc | t-butoxycarbonyl |
| CDI | 1,1'-Carbonyldiimidazole |
| CDCl$_3$ | deuterated chloroform |
| Cs$_2$CO$_3$ | cesium carbonate |
| DAST | Diethylaminosulfur trifluoride |
| DBU | 1,8-Diazabicyclo[5.4.0]undec-7-ene |
| DCM | Dichloromethane, methylene chloride |
| DIEA | diisopropylethylamine |
| DMA | N,N-dimethylacetamide |
| DMF | N,N-dimethylformamide |
| DMSO | dimethylsulfoxide |
| DPPA | Diphenylphosphoryl azide |
| EDCI | 1-Ethyl-3-(3-dimethylaminopropyl)carbodiimide |
| ES | electrospray |
| Et$_3$N | triethylamine |
| Et$_2$O | diethyl ether |
| EtOAc | ethyl acetate |
| EtOH | ethanol |
| h or hr | hours |
| H$_2$O | water |
| HATU | 1-[Bis(dimethylamino)methylene]-1H-1,2,3-triazolo[4,5-b]pyridinium 3-oxid hexafluorophosphate |
| HBTU | N,N,N',N'-tetramethyl-O-(1H-benzotriazol-1-yl) uronium hexafluorophosphate |
| HCl | hydrochloric acid |
| HOBt | Hydroxybenzotriazole |
| IPA | isopropanol |
| K$_2$CO$_3$ | potassium carbonate |
| LDA | Lithium diisopropylamide |
| MeCN | acetonitrile |
| MeOH | methanol |
| MgSO$_4$ | magnesium sulfate |
| min | minutes |
| MS | mass spectrometry |
| MTBE | Methyl tert-butyl ether |
| Na$_2$CO$_3$ | Sodium carbonate |
| Na$_2$SO$_4$ | sodium sulfate |
| NaH | sodium hydride |
| NaHCO$_3$ | sodium bicarbonate |
| NaOH | sodium hydroxide |
| N.D. | Not determined |
| NH$_4$HCO$_3$ | ammonium bicarbonate |
| NH$_4$OH | ammonium hydroxide |
| NMP | N-methyl-2-pyrrolidone |
| Pd/C | palladium on carbon |
| Pd(dppf)Cl$_2$ | [1,1'-bis(diphenylphosphino)ferrocene] dichloropalladium(II) |

| Abbreviation | Name |
|---|---|
| Pd(dppf)Cl$_2$·CH$_2$Cl$_2$ | [1,1'-bis(diphenylphosphino)ferrocene] dichloropalladium(II)-dichloromethane adduct |
| pet. ether | petroleum ether |
| PhI(OAc)$_2$ | (diacetoxyiodo)benzene |
| prep-HPLC | preparatory high pressure liquid chromatography |
| prep-TLC | preparatory thin layer chromatography |
| rt | Room temperature |
| RT | Retention time |
| RuPhos | 2-dicyclohexylphosphino-2',6'-diisopropoxybiphenyl |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| SFC | Supercritical Fluid Chromatography |
| t-BuOH | Tert-butanol |
| TBS | tert-butyl(dimethyl)silyl |
| TEA | triethylamine |
| TFA | trifluoroacetic acid |
| THF | tetrahydrofuran |

Synthetic Examples of Compounds of Formula (I)

Example 1. trans-3-(cyanoamino)-N-[5-(oxan-4-yl)-1,3-thiazol-2-yl]cyclobutane-1-carboxamide (Compound 1-1)

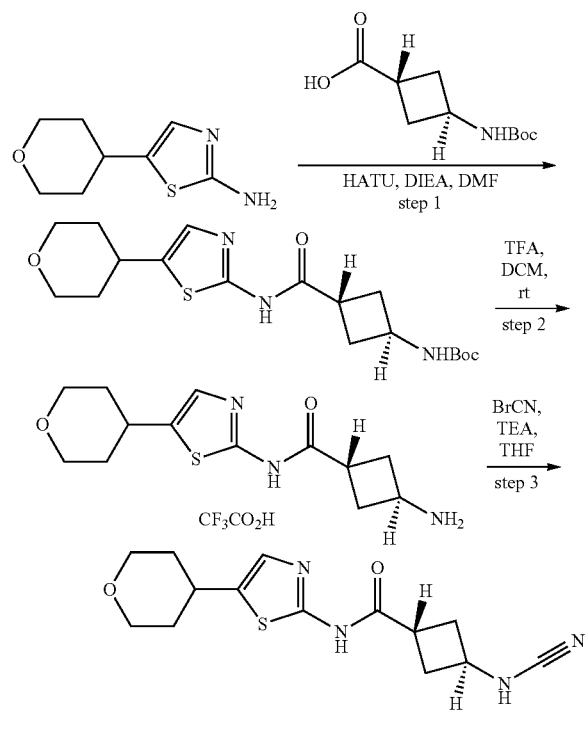

Step 1. tert-butyl (trans-(tetrahydro-2H-pyran-4-yl)thiazol-2-ylcarbamoyl)cyclobutylcarbamate A solution of trans-3-(tert-butoxycarbonylamino)cyclobutanecarboxylic acid (169 mg, 0.786 mmol), HATU (298 mg, 0.790 mmol), 5-(tetrahydro-2H-pyran-4-yl)thiazol-2-amine (120 mg, 0.650 mmol) and DIEA (0.320 mL, 1.96 mmol) in N,N-dimethylformamide (3 mL) was stirred for 30 min at 25° C. The reaction was then quenched by the addition of water (10 mL). The resulting mixture was extracted with ethyl acetate (3×10 mL). The organic layers were combined, dried over anhydrous sodium sulfate, filtered and concentrated under vacuum. The residue was purified by Prep-TLC plate (developing solvent: 20:1 dichloromethane/methanol) to afford tert-butyl (trans-(tetrahydro-2H-pyran-4-yl)thiazol-2-ylcarbamoyl)cyclobutylcarbamate as a yellow solid (80.0 mg). LCMS (ES, m/z) 382 [M+H]$^+$.

Step 2. trans-3-amino-N-(5-(tetrahydro-2H-pyran-4-yl)thiazol-2-yl)cyclobutanecarboxamide 2,2,2-trifluoroacetate A solution of tert-butyl (trans-(tetrahydro-2H-pyran-4-yl)thiazol-2-ylcarbamoyl)cyclobutylcarbamate (80.0 mg, 0.210 mmol) and trifluoroacetic acid (1 mL) in dichloromethane (3 mL) was stirred for 2 h at 25° C. The resulting mixture was concentrated under vacuum to afford trans-3-amino-N-(5-(tetrahydro-2H-pyran-4-yl)thiazol-2-yl)cyclobutanecarboxamide 2,2,2-trifluoroacetate as yellow oil (90.0 mg,). LCMS (ES, m/z) 282 [M+H]$^+$.

Step 3. trans-3-(cyanoamino)-N-[5-(oxan-4-yl)-1,3-thiazol-2-yl]cyclobutane-1-carboxamide Cyanogen bromide (19.0 mg, 0.180 mmol) was added into a stirring solution of trans-3-amino-N-(5-(tetrahydro-2H-pyran-4-yl)thiazol-2-yl)cyclobutanecarboxamide 2,2,2-trifluoroacetate (70.0 mg, 0.180 mmol) and TEA (0.074 mL, 0.530 mmol) in tetrahydrofuran (5 mL) at −20° C. The resulting solution was stirred for 30 min at −20° C. The reaction was then quenched by the addition of water (10 mL). The resulting mixture was extracted with ethyl acetate (3×15 mL). The organic layers were combined, dried over anhydrous sodium sulfate, filtered and concentrated under vacuum. The residue was purified by Prep-HPLC (Column: XBridge BEH130 RP18 OBD Column, 130 Å, 5 μm, 19 mm*150 mm; Mobile phase, A: water (10 mM NH$_4$HCO$_3$) and B: ACN (10% up to 40% over 7 min); Flow rate: 20 mL/min; Detector: 254 & 220 nm) to afford trans-3-(cyanoamino)-N-[5-(oxan-4-yl)-1,3-thiazol-2-yl]cyclobutane-1-carboxamide as a white solid (5.40 mg). $^1$H NMR (300 MHz, DMSO-d6), δ 11.92 (s, 1H), 7.22 (s, 1H), 7.19 (s, 1H), 3.92-3.79 (m, 3H), 3.46-3.42 (m, 2H), 3.28-3.19 (m, 1H), 3.07-2.98 (m, 1H), 2.47-2.42 (m, 2H), 2.27-2.17 (m, 2H), 1.88-1.83 (m, 2H), 1.68-1.55 (m, 2H). LC-MS (ESI) m/z 307.2 [M+H]$^+$ The following compounds were synthesized according to General Scheme 1:

| Example No. | Structure | Chemical Name | MS m/z [M + H]+ | 1H NMR |
|---|---|---|---|---|
| Compound 1-2 | 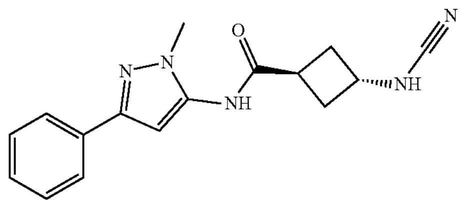 [SMILES: Cn1nc(-c2ccccc2)cc1NC(=O)[C@H]1C[C@H](NC#N)C1] | (1r,3r)-3-(cyanoamino)-N-(1-methyl-3-phenyl-1H-pyrazol-5-yl)cyclobutane-1-carboxamide | 296 | 10.01 (s, 1H), 7.75 (d, J = 8.0 Hz, 2H), 7.41-7.37 (m, 2H), 7.30-7.24 (m, 2H), 6.66 (s, 1H), 3.87-3.80 (m, 1H), 3.70 (s, 3H), 3.26-3.21 (m, 1H), 2.51-2.47 (m, 2H), 2.29-2.21 (m, 2H) |
| Compound 1-3 | 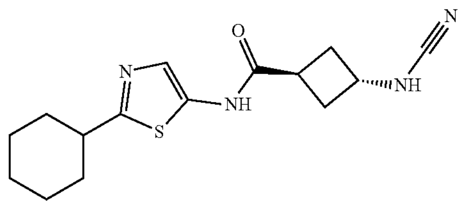 [SMILES: N#CN[C@H]1C[C@H](C(=O)Nc2cnc(C3CCCCC3)s2)C1] | (1r,3r)-3-(cyanoamino)-N-(2-cyclohexyl-1,3-thiazol-5-yl)cyclobutane-1-carboxamide | 305 | 11.13 (br s, 1H), 7.31 (s, 1H), 7.22 (br s, 1H), 3.85-3.76 (m, 1H), 3.17-3.08 (m, 1H), 2.89-2.79 (m, 1H), 2.48-2.39 (m, 2H), 2.27-2.17 (m, 2H), 2.05-1.95 (m, 2H), 1.80-1.70 (m, 2H), 1.70-1.61 (m, 1H), 1.51-1.31 (m, 4H), 1.31-1.15 (m, 1H) |
| Compound 1-4 | 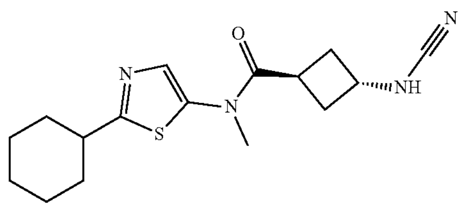 [SMILES: CN(c1cnc(C2CCCCC2)s1)C(=O)[C@H]1C[C@H](NC#N)C1] | (1r,3r)-3-(cyanoamino)-N-(2-cyclohexyl-1,3-thiazol-5-yl)-N-methylcyclobutane-1-carboxamide | 319 | 7.56-7.38 (m, 1H), 7.28-7.05 (m, 1H), 3.72-3.53 (m, 2H), 3.32 (s, 2H), 3.17-3.05 (m, 1H), 2.97-2.80 (m, 1H), 2.46-2.35 (m, 1H), 2.35-2.25 (m, 2H), 2.08-1.87 (m, 3H), 1.80-1.62 (m, 3H), 1.51-1.29 (m, 4H), 1.29-1.19 (m, 1H) |
| Compound 1-5 | 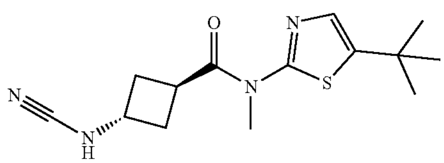 [SMILES: CN(c1ncc(C(C)(C)C)s1)C(=O)[C@H]1C[C@H](NC#N)C1] | (1r,3r)-N-(5-tert-butyl-1,3-thiazol-2-yl)-3-(cyanoamino)-N-methylcyclobutane-1-carboxamide | 293 | 7.33-7.20 (m, 2H), 3.71-3.61 (m, 2H), 347 (s, 3H), 2.60-2.51 (m, 2H), 2.35-2.28 (m, 2H), 1.33 (s, 9H) |
| Compound 1-6 | 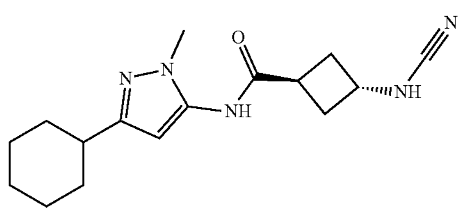 [SMILES: Cn1nc(C2CCCCC2)cc1NC(=O)[C@H]1C[C@H](NC#N)C1] | (1r,3r)-3-(cyanoamino)-N-(3-cyclohexyl-1-methyl-1H-pyrazol-5-yl)cyclobutane-1-carboxamide | 302 | 9.80 (br s, 1H), 7.22 (br s, 1H), 6.00 (s, 1H), 3.84-3.76 (m, 1H), 3.55 (s, 3H), 3.33-3.15 (m, 1H), 2.50-2.45 (m, 3H), 2.25-2.18 (m, 2H), 1.85-1.83 (m, 2H), 1.73-1.72 (m, 2H), 1.65 (d, J = 12.8 Hz, 1H), 1.37-1.26 (m, 4H), 1.25-1.15 (m, 1H) |
| Compound 1-7 | 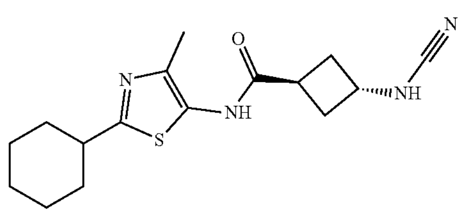 [SMILES: Cc1nc(C2CCCCC2)sc1NC(=O)[C@H]1C[C@H](NC#N)C1] | (1r,3r)-3-(cyanoamino)-N-(2-cyclohexyl-4-methyl-1,3-thiazol-5-yl)cyclobutane-1-carboxamide | 319 | 10.19 (br s, 1H), 7.22 (br s, 1H), 3.90-3.75 (m, 1H), 3.30-3.22 (m, 1H), 2.82-2.75 (m, 1H), 2.43-2.37 (m, 2H), 2.25-2.15 (m, 5H), 2.00-1.90 (m, 2H), 1.75-1.70 (m, 2H), 1.70-1.60 (m, 1H), 1.43-1.27 (m, 4H), 1.25-1.13 (m, 1H) |
| Compound 1-8 | 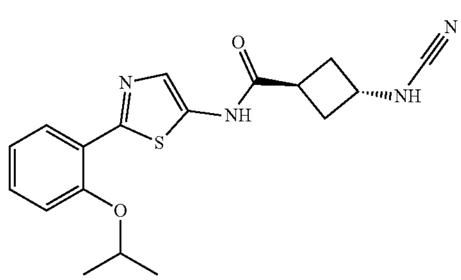 [SMILES: CC(C)Oc1ccccc1-c1ncc(NC(=O)[C@H]2C[C@H](NC#N)C2)s1] | (1r,3r)-3-(cyanoamino)-N-{2-[2-(propan-2-yloxy)phenyl]-1,3-thiazol-5-yl}cyclobutane-1-carboxamide | 357 | 8.22 (d, J = 7.2 Hz, 1H), 7.60 (s, 1H), 7.37-7.33 (m, 1H), 7.22-7.20 (m, 1H), 4.93-4.91 (m, 1H), 3.88-3.84 (m, 1H), 3.28-3.12 (m, 1H), 2.51-2.43 (m, 2H), 2.33-2.08 (m, 2H), 1.43 (d, J = 5.6 Hz, 6H) |

-continued

| Example No. | Structure | Chemical Name | MS m/z [M + H]+ | 1H NMR |
|---|---|---|---|---|
| Compound 1-9 | 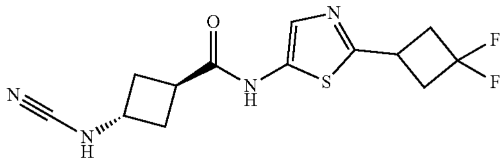 [SMILES: N#CN[C@H]1C[C@H](C(=O)Nc2cnc(C3CC(F)(F)C3)s2)C1] | (1r,3r)-3-(cyanoamino)-N-[2-(3,3-difluoro-cyclobutyl)-1,3-thiazol-5-yl]cyclobutane-1-carboxamide | 313 | 11.28 (br s, 1H), 7.39 (s, 1H), 7.24 (br s, 1H), 3.82 (s, 1H), 3.73-3.64 (m, 1H), 3.20-3.10 (m, 1H), 3.09-2.97 (m, 1H), 2.95-2.77 (m, 1H), 2.86 (s, 2H), 2.45 (s, 2H), 2.29-2.19 (m, 2H |
| Compound 1-10 | 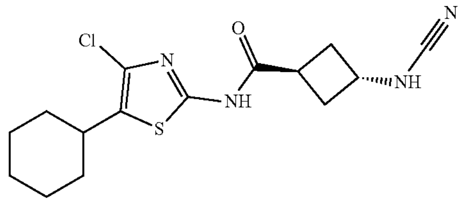 [SMILES: N#CN[C@H]1C[C@H](C(=O)Nc2nc(Cl)c(C3CCCCC3)s2)C1] | (1r,3r)-N-(4-chloro-5-cyclohexyl-1,3-thiazol-2-yl)-3-(cyanoamino)cyclo-butane-1-carboxamide | 339, 341 | 12.10 (br s, 1H), 7.22 (d, J = 5.5 Hz, 1H), 3.85-3.74 (m, 1H), 3.27-3.16 (m, 1H), 2.86-2.76 (m, 1H), 2.48-2.41 (m, 2H), 2.28-2.16 (m, 2H), 1.92-1.82 (m, 2H), 1.82-1.72 (m, 2H), 1.71-1.63 (m, 1H), 1.42-1.17 (m, 5H) |
| Compound 1-11 | 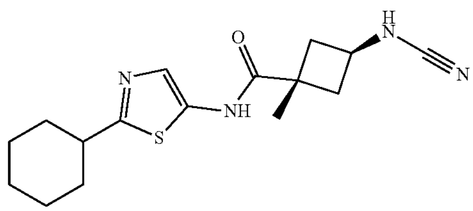 [SMILES: C[C@]1(C(=O)Nc2cnc(C3CCCCC3)s2)C[C@H](NC#N)C1] | (1r,3s)-3-(cyanoamino)-N-(2-cyclohexyl-1,3-thiazol-5-yl)-1-methylcyclobutane-1-carboxamide | 319 | 11.83 (br s, 1H), 7.17 (s, 2H), 3.50-3.46 (m, 1H), 2.86-2.73 (m, 3H), 1.94-1.89 (m, 4H), 1.77-1.67 (m, 3H), 1.44 (s, 3H), 1.40-1.35 (m, 4H), 1.26-1.20 (m, 1H) |
| Compound 1-12 | 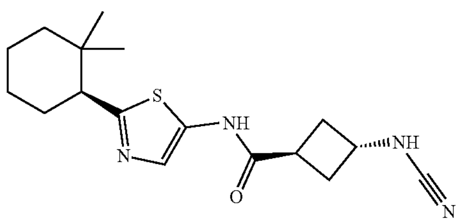 [SMILES: CC1(C)CCCC[C@@H]1c1ncc(NC(=O)[C@H]2C[C@H](NC#N)C2)s1] | (1r,3r)-3-(cyanoamino)-N-{2-[(1S)-2,2-dimethylcyclohexyl]-1,3-thiazol-5-yl}cyclobutane-1-carboxamide | 333 | 11.15 (br s, 1H), 7.35 (s, 1H), 7.23 (br s, 1H), 3.90-3.78 (m, 1H), 3.19-3.09 (m, 1H), 2.77-2.69 (m, 1H), 2.49-2.40 (m, 2H), 2.29-2.17 (m, 2H), 1.87-1.72 (m, 2H), 1.70-1.61 (m, 1H), 1.55-1.43 (m, 3H), 1.36-1.21 (m, 2H), 0.87 (d, J = 9.4 Hz, 6H) |
| Compound 1-13 | 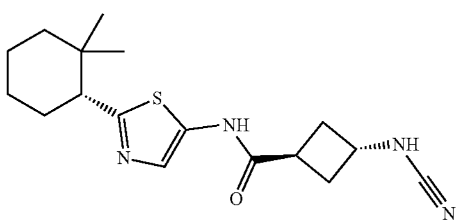 [SMILES: CC1(C)CCCC[C@H]1c1ncc(NC(=O)[C@H]2C[C@H](NC#N)C2)s1] | (1r,3r)-3-(cyanoamino)-N-{2-[(1R)-2,2-dimethylcyclohexyl]-1,3-thiazol-5-yl}cyclobutane-1-carboxamide | 333 | 11.15 (br s, 1H), 7.35 (s, 1H), 7.23 (br s, 1H), 3.90-3.78 (m, 1H), 3.19-3.09 (m, 1H), 2.77-2.69 (m, 1H), 2.49-2.40 (m, 2H), 2.29-2.17 (m, 2H), 1.87-1.72 (m, 2H), 1.70-1.61 (m, 1H), 1.55-1.43 (m, 3H), 1.36-1.21 (m, 2H), 0.87 (d, J = 9.4 Hz, 6H) |
| Compound 1-14 | 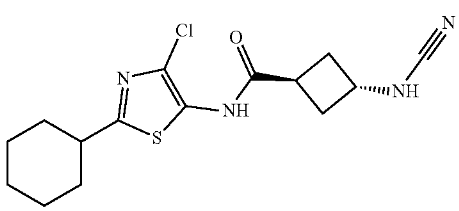 | (1r,3r)-N-(4-chloro-2-cyclohexyl-1,3-thiazol-5-yl)-3-(cyanoamino)cyclo-butane-1-carboxamide | 339, 341 | 10.7 (br s, 1H), 7.25 (br s, 1H), 3.62-3.58 (m, 1H), 3.09-3.04 (m, 1H), 2.88-2.83 (m, 1H), 2.45-2.39 (m, 2H), 2.18-2.10 (m, 2H), 2.00-1.87 (m, 2H), 1.77-1.74 (m, 2H), 1.68-1.65 (m, 1H), 1.47-1.31 (m, 4H), 1.26-1.21 (m, 1H). |
| Compound 1-15 | 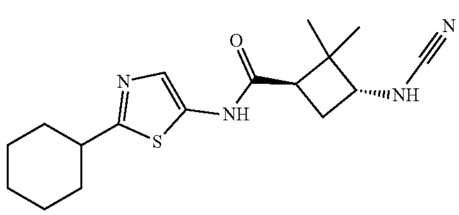 [SMILES: CC1(C)[C@H](NC#N)C[C@H]1C(=O)Nc1cnc(C2CCCCC2)s1] | (1R,3R)-3-(cyanoamino)-N-(2-cyclohexyl-1,3-thiazol-5-yl)-2,2-dimethylcyclobutane-1-carboxamide | 333 | 1H-NMR (CD3OD, 400 MHz) δ (ppm): 7.11 (s, 1H), 3.46-3.42 (m, 1H), 2.83-2.79 (m, 2H), 2.49-2.41 (m, 1H), 2.34-2.27 (m, 1H), 2.05-2.00 (m, 2H), 1.86-1.85 (m, 2H), 1.77-1.74 (m, 1H), 1.52-1.40 (m, 4H), 1.38-1.28 (m, 4H), 1.02 (s, 3H). |

-continued

| Example No. | Structure | Chemical Name | MS m/z [M + H]+ | 1H NMR |
|---|---|---|---|---|
| Compound 1-16 | 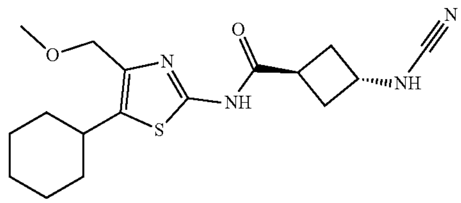 [SMILES: COCc1nc(NC(=O)[C@H]2C[C@H](NC#N)C2)sc1C1CCCCC1] | (1r,3r)-3-(cyanoamino)-N-[5-cyclohexyl-4-(methoxymethyl)-1,3-thiazol-2-yl]cyclobutane-1-carboxamide | 349 | 11.9 (br s, 1H), 7.23 (br s, 1H), 4.33 (s, 2H), 3.84-3.79 (m, 1H), 3.26-3.19 (m, 4H), 2.97-2.92 (m, 1H), 2.48-2.44 (m, 2H), 2.34-2.19 (m, 2H), 1.88-1.85 (m, 2H), 1.78-1.76 (m, 2H), 1.71-1.60 (m, 1H), 1.44-1.19 (m, 5H). |
| Compound 1-17 | 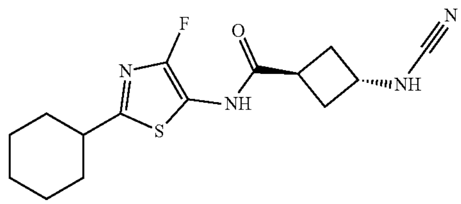 | (1r,3r)-3-(cyanoamino)-N-(2-cyclohexyl-4-fluoro-1,3-thiazol-5-yl)cyclobutane-1-carboxamide | 323 | 10.9 (br s, 1H), 7.24 (br s, 1H), 3.84-3.80 (m, 1H), 3.27-3.02 (m, 1H), 2.84-2.77 (m, 1H), 2.47-2.42 (m, 2H), 2.25-2.20 (m, 2H), 1.99-1.96 (m, 2H), 1.76-1.74 (m, 2H), 1.67-1.64 (m, 1H), 1.47-1.31 (m, 4H), 1.27-1.18 (m, 1H). |
| Compound 1-18 | 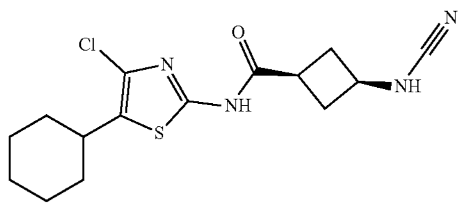 [SMILES: N#CN[C@H]1C[C@@H](C(=O)Nc2nc(Cl)c(C3CCCCC3)s2)C1] | (1s,3s)-N-(4-chloro-5-cyclohexyl-1,3-thiazol-2-yl)-3-(cyanoamino)cyclobutane-1-carboxamide | 339, 341 | 11.50 (br s, 1H), 7.22 (br s, 1H), 3.67-3.55 (m, 1H), 2.96-2.76 (m, 2H), 2.47-2.37 (m, 2H), 2.20-2.08 (m, 2H), 1.92-1.82 (m, 2H), 1.82-1.73 (m, 2H), 1.72-1.65 (m, 1H), 1.42-1.17 (m, 5H) |
| Compound 1-19 | 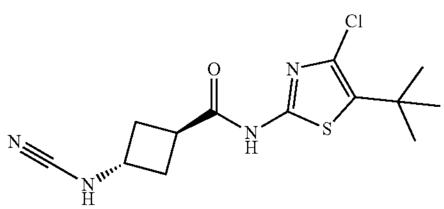 [SMILES: CC(C)(C)c1sc(NC(=O)[C@H]2C[C@H](NC#N)C2)nc1Cl] | (1r,3r)-N-(5-tert-butyl-4-chloro-1,3-thiazol-2-yl)-3-(cyanoamino)cyclobutane-1-carboxamide | 313, 315 | 11.40 (br s, 1H), 7.27 (br s, 1H), 3.82-3.78 (m, 1H), 3.22-3.17 (m, 1H), 2.51-2.43 (m, 2H), 2.26-2.20 (m, 2H), 1.41 (s, 9H) |
| Compound 1-20 | 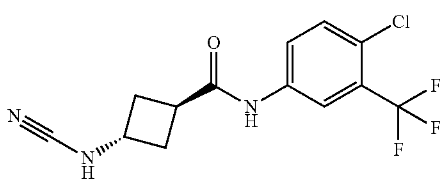 [SMILES: N#CN[C@H]1C[C@H](C(=O)Nc2ccc(Cl)c(C(F)(F)F)c2)C1] | (1r,3r)-N-[4-chloro-3-(trifluoromethyl)phenyl]-3-(cyanoamino)cyclobutane-1-carboxamide | 318, 320 | 10.40 (br s, 1H), 8.24 (s, 1H), 7.83 (d, J = 8.4 Hz, 1H), 7.66 (d, J = 8.8 Hz, 1H), 7.25 (br s, 1H), 3.86-3.79 (m, 1H), 3.18-3.13 (m, 1H), 2.51-2.47 (m, 2H), 2.27-2.20 (m, 2H) |
| Compound 1-21 | 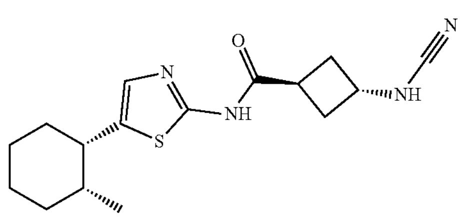 [SMILES: C[C@@H]1CCCC[C@@H]1c1cnc(NC(=O)[C@H]2C[C@H](NC#N)C2)s1] | (1r,3r)-3-(cyanoamino)-N-{5-[(1S,2R)-2-methylcyclohexyl]-1,3-thiazol-2-yl}cyclobutane-1-carboxamide | 319 | 11.87 (br s, 1H), 7.20 (d, J = 5.2 Hz, 1H), 7.14 (s, 1H), 3.86-3.75 (m, 1H), 3.27-3.17 (m, 1H), 2.48-2.34 (m, 3H), 2.27-2.16 (m, 2H), 1.88-1.64 (m, 4H), 1.47-1.21 (m, 4H), 1.12-0.96 (m, 1H), 0.73 (d, J = 6.4 Hz, 3H) |
| Compound 1-22 | 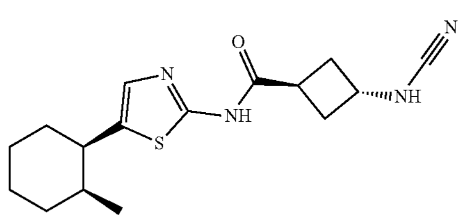 [SMILES: C[C@H]1CCCC[C@H]1c1cnc(NC(=O)[C@H]2C[C@H](NC#N)C2)s1] | (1r,3r)-3-(cyanoamino)-N-{5-[(1R,2S)-2-methylcyclohexyl]-1,3-thiazol-2-yl}cyclobutane-1-carboxamide | 319 | 11.87 (br, 1H), 7.20 (d, J = 5.2 Hz, 1H), 7.14 (s, 1H), 3.86-3.75 (m, 1H), 3.27-3.17 (m, 1H), 2.48-2.34 (m, 3H), 2.27-2.16 (m, 2H), 1.88-1.64 (m, 4H), 1.47-1.21 (m, 4H), 1.12-0.96 (m, 1H), 0.73 (d, J = 6.4 Hz, 3H) |

-continued

| Example No. | Structure | Chemical Name | MS m/z [M+H]+ | 1H NMR |
|---|---|---|---|---|
| Compound 1-23 | 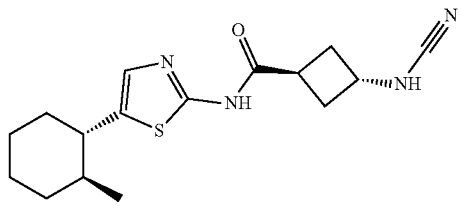 [SMILES: C[C@H]1CCCC[C@@H]1c1cnc(NC(=O)[C@H]2C[C@H](NC#N)C2)s1] | (1r,3r)-3-(cyanoamino)-N-{5-[(1S,2S)-2-methylcyclohexyl]-1,3-thiazol-2-yl}cyclobutane-1-carboxamide | 319 | 11.88 (br s, 1H), 7.23 (s, 1H), 7.11 (s, 1H), 3.88-3.76 (m, 1H), 3.29-3.18 (m, 1H), 3.15-3.03 (m, 1H), 2.49-2.41 (m, 2H), 2.27-2.17 (m, 2H), 2.04-1.94 (m, 1H), 1.77-1.46 (m, 6H), 1.46-1.34 (m, 2H), 0.75 (d, J = 6.8 Hz, 3H) |
| Compound 1-24 | 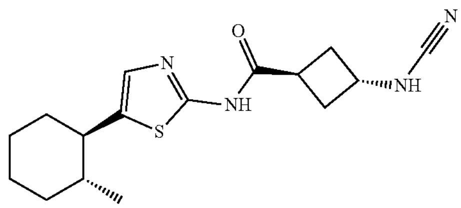 [SMILES: C[C@@H]1CCCC[C@H]1c1cnc(NC(=O)[C@H]2C[C@H](NC#N)C2)s1] | (1r,3r)-3-(cyanoamino)-N-{5-[(1R,2R)-2-methylcyclohexyl]-1,3-thiazol-2-yl}cyclobutane-1-carboxamide | 319 | 11.88 (br s, 1H), 7.23 (s, 1H), 7.11 (s, 1H), 3.88-3.76 (m, 1H), 3.29-3.18 (m, 1H), 3.15-3.03 (m, 1H), 2.49-2.41 (m, 2H), 2.27-2.17 (m, 2H), 2.04-1.94 (m, 1H), 1.77-1.46 (m, 6H), 1.46-1.34 (m, 2H), 0.75 (d, J = 6.8 Hz, 3H) |
| Compound 1-25 | 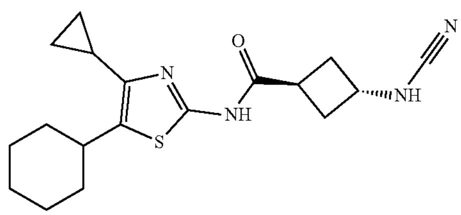 [SMILES: N#CN[C@H]1C[C@H](C(=O)Nc2nc(C3CC3)c(C3CCCCC3)s2)C1] | (1r,3r)-3-(cyanoamino)-N-(5-cyclohexyl-4-cyclopropyl-1,3-thiazol-2-yl)cyclobutane-1-carboxamide | 345 | 11.80 (s, 1H), 7.22 (d, J = 5.6 Hz, 1H), 3.80-3.77 (m, 1H), 3.20-3.16 (m, 1H), 3.00-2.91 (m, 1H), 2.45-2.35 (m, 2H), 2.25-2.12 (m, 2H), 1.96-1.89 (m, 2H), 1.79-1.68 (m, 3H), 1.21-1.41 (m, 5H), 1.79-1.68 (m, 3H), 0.85-0.73 (m, 4H |
| Compound 1-26 | 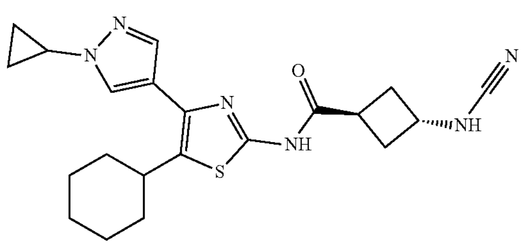 [SMILES: N#CN[C@H]1C[C@H](C(=O)Nc2nc(-c3cnn(C4CC4)c3)c(C3CCCCC3)s2)C1] | (1r,3r)-3-(cyanoamino)-N-[5-cyclohexyl-4-(1-cyclopropyl-1H-pyrazol-4-yl)-1,3-thiazol-2-yl]cyclobutane-1-carboxamide | 411 | 11.90-12.05 (m, 1H), 7.91 (s, 1H), 7.63 (s, 1H), 7.24 (d, J = 4.8 Hz, 1H), 3.85-3.80 (m, 2H), 3.24-3.21 (m, 1H), 3.02-2.98 (m, 2H), 2.48-2.43 (m, 2H), 2.26-2.19 (m, 2H), 1.94-1.91 (m, 2H), 1.79-1.70 (m, 3H), 1.46-1.11 (m, 5H), 1.09-0.96 (m, 4H) |
| Compound 1-27 | 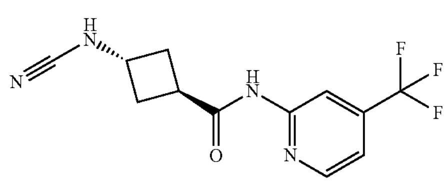 [SMILES: N#CN[C@H]1C[C@H](C(=O)Nc2cc(C(F)(F)F)ccn2)C1] | (1r,3r)-3-(cyanoamino)-N-[4-(trifluoro-methyl)pyridin-2-yl]cyclobutane-1-carboxamide | 285 | 11.99 (br s, 1H), 8.59 (d, J = 5.2 Hz, 1H), 8.46 (s, 1H), 7.46 (d, J = 5.2 Hz, 1H), 7.22 (d, J = 5.6 Hz, 1H), 3.84-3.78 (m, 1H), 3.29-3.26 (m, 1H), 2.48-2.46 (m, 2H), 2.27-2.20 (m, 2H) |
| Compound 1-28 | 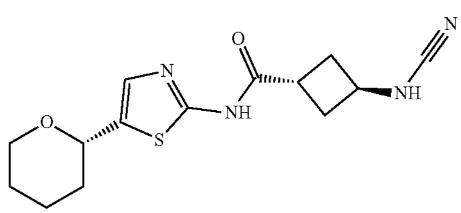 [SMILES: N#CN[C@H]1C[C@H](C(=O)Nc2ncc([C@@H]3CCCCO3)s2)C1] | (1r,3r)-3-(cyanoamino)-N-{5-[(2S)-oxan-2-yl]-1,3-thiazol-2-yl}cyclobutane-1-carboxamide | 307 | 11.97 (br s, 1H), 7.30 (s, 1H), 7.23 (br s, 1H), 4.57-4.55 (m, 1H), 3.96-3.93 (m, 1H), 3.84-3.81 (m, 1H), 3.56-3.46 (m, 1H), 3.27-3.22 (m, 1H), 2.51-2.44 (m, 2H), 2.33-2.19 (m, 2H), 1.90-1.84 (m, 2H), 1.70-1.50 (m, 4H) |
| Compound 1-29 | 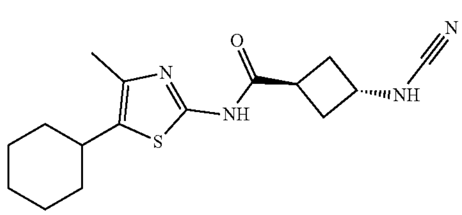 [SMILES: Cc1nc(NC(=O)[C@H]2C[C@H](NC#N)C2)sc1C1CCCCC1] | (1r,3r)-3-(cyanoamino)-N-(5-cyclohexyl-4-methyl-1,3-thiazol-2-yl)cyclobutane-1-carboxamide | 319 | 7.26 (br s, 1H), 3.85-3.77 (m, 1H), 3.22-3.16 (m, 1H), 2.81-2.75 (m, 1H), 2.52-2.41 (m, 2H), 2.25-2.19 (m, 2H), 2.17 (s, 3H), 1.86-1.80 (m, 2H), 1.80-1.70 (m, 2H), 1.70-1.60 (m, 1H), 1.40-1.20 (m, 5H) |

-continued

| Example No. | Chemical Name | MS m/z [M + H]+ | 1H NMR |
|---|---|---|---|
| Compound 1-30 | (1r,3r)-3-(cyanoamino)-N-(5-cyclohexyl-1-methyl-1H-pyrazol-3-yl)cyclobutane-1-carboxamide | 302 | 10.23 (br s, 1H), 7.30-6.80 (br s, 1H), 6.30 (s, 1H), 3.82-3.79 (m, 1H), 3.63 (s, 3H), 3.11-3.07 (m, 1H), 2.65-2.59 (m, 1H), 2.41-2.35 (m, 2H), 2.19-2.12 (m, 2H), 1.87-1.83 (m, 2H), 1.78-1.75 (m, 2H), 1.71-1.68 (m, 1H), 1.43-1.20 (m, 5H) |
| Compound 1-31 | (1r,3r)-3-(cyanoamino)-N-[5-cyclohexyl-4-(trifluoromethyl)-1,3-thiazol-2-yl]cyclobutane-1-carboxamide | 373 | 7.24 (s, 1H), 3.84-3.76 (m, 1H), 3.27-3.14 (m, 1H), 3.13-3.00 (m, 1H), 2.48-2.45 (m, 2H), 2.28-2.17 (m, 2H), 1.97-1.87 (m, 2H), 1.83-1.73 (m, 2H), 1.73-1.64 (m, 1H), 1.44-1.29 (m, 4H) |
| Compound 1-32 | (1r,3r)-3-(cyanoamino)-N-{5-[(1S,2R)-2-(trifluoromethyl)cyclohexyl]-1,3-thiazol-2-yl}cyclobutane-1-carboxamide | 373 | 11.57-11.08 (br s, 1H), 7.22-7.21 (br s, 1H), 4.90-4.85 (m, 1H), 4.36-4.31 (m, 1H), 3.79-3.70 (m, 1H), 3.39-3.33 (m, 1H), 3.16-3.11 (m, 1H), 2.43-2.37 (m, 2H), 2.21-2.17 (m, 4H), 2.08-1.95 (m, 1H), 1.80-1.70 (m, 1H), 1.59-1.42 (m, 3H), 1.29-1.24 (m, 1H) |
| Compound 1-33 | (1r,3r)-3-(cyanoamino)-N-{5-[(1R,2S)-2-(trifluoromethyl)cyclohexyl]-1,3-thiazol-2-yl}cyclobutane-1-carboxamide | 373 | 11.32 (br s, 1H), 7.22-7.21 (br s, 1H), 4.76-4.71 (m, 1H), 4.53-4.48 (m, 1H), 3.79-3.70 (m, 1H), 3.15-3.10 (m, 1H), 3.04-2.97 (m, 1H), 2.40-2.37 (m, 3H), 2.22-2.14 (m, 2H), 2.02-1.90 (m, 2H), 1.77-1.74 (m, 1H), 1.68-1.52 (m, 2H), 1.49-1.43 (m, 1H), 1.30-1.24 (m, 1H) |
| Compound 1-34 | (1r,3r)-3-(cyanoamino)-N-{5-[(1S,2S)-2-(trifluoromethyl)cyclohexyl]-1,3-thiazol-2-yl}cyclobutane-1-carboxamide | 373 | 11.28 (br s, 1H), 7.22 (br s, 1H), 4.91-4.85 (m, 1H), 4.36-4.31 (m, 1H), 3.79-3.70 (m, 1H), 3.41-3.35 (m, 1H), 3.16-3.11 (m, 1H), 2.40-2.37 (m, 2H), 2.21-2.08 (m, 4H), 1.99-1.95 (m, 1H), 1.77-1.73 (m, 1H), 1.59-1.42 (m, 3H), 1.33-1.24 (m, 1H) |
| Compound 1-35 | (1r,3r)-3-(cyanoamino)-N-{5-[(1R,2R)-2-(trifluoromethyl)cyclohexyl]-1,3-thiazol-2-yl}cyclobutane-1-carboxamide | 373 | 11.20 (br s, 1H), 7.22 (br s, 1H), 4.76-4.71 (m, 1H), 4.53-4.48 (m, 1H), 3.76-3.72 (m, 1H), 3.15-3.10 (m, 1H), 3.06-2.90 (m, 1H), 2.40-2.37 (m, 3H), 2.26-2.08 (m, 2H), 2.02-1.90 (m, 2H), 1.77-1.74 (m, 1H), 1.67-1.60 (m, 2H), 1.52-1.43 (m, 1H), 1.30-1.24 (m, 1H) |

| Example No. | Structure | Chemical Name | MS m/z [M+H]+ | 1H NMR |
|---|---|---|---|---|
| Compound 1-36 | 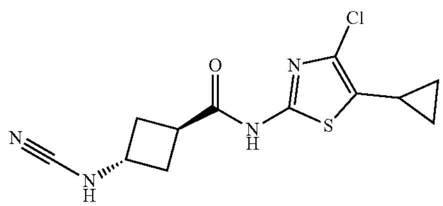 [SMILES: N#CN[C@H]1C[C@H](C(=O)Nc2nc(Cl)c(C3CC3)s2)C1] | (1r,3r)-N-(4-chloro-5-cyclopropyl-1,3-thiazol-2-yl)-3-(cyanoamino)cyclobutane-1-carboxamide | 297, 299 | 12.19 (br s, 1H), 7.24 (br s, 1H), 3.82-3.76 (m, 1H), 3.24-3.18 (m, 1H), 2.50-2.42 (m, 2H), 2.26-2.18 (m, 2H), 2.00-1.90 (m, 1H), 1.10-1.00 (m, 2H), 1.70-1.60 (m, 2H) |
| Compound 1-37 | 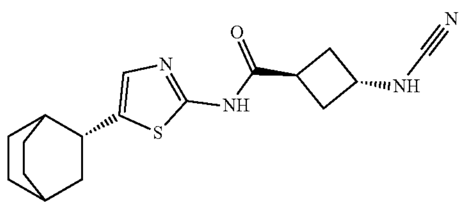 [SMILES: N#CN[C@H]1C[C@H](C(=O)Nc2ncc([C@@H]3CC4CCC3CC4)s2)C1] | (1r,3r)-N-{5-[(2R)-bicyclo[2.2.2]octan-2-yl]-1,3-thiazol-2-yl}-3-(cyanoamino)cyclobutane-1-carboxamide | 331 | 7.25 (br s, 1H), 7.22 (s, 1H), 3.84-3.79 (m, 1H), 3.25-3.20 (m, 1H), 3.15-3.11 (m, 1H), 2.51-2.43 (m, 2H), 2.25-2.18 (m, 2H), 2.05-2.00 (m, 1H), 1.70-1.56 (m, 11H) |
| Compound 1-38 | 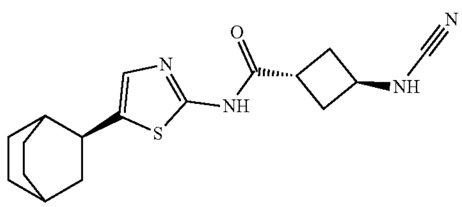 [SMILES: N#CN[C@H]1C[C@H](C(=O)Nc2ncc([C@H]3CC4CCC3CC4)s2)C1] | (1r,3r)-N-{5-[(2S)-bicyclo[2.2.2]octan-2-yl]-1,3-thiazol-2-yl}-3-(cyanoamino)cyclobutane-1-carboxamide | 331 | 7.25 (br s, 1H), 7.22 (s, 1H), 3.86-3.77 (m, 1H), 3.25-3.21 (m, 1H), 3.15-3.11 (m, 1H), 2.51-2.43 (m, 2H), 2.25-2.18 (m, 2H), 2.05-2.00 (m, 1H), 1.70-1.61 (m, 11H) |
| Compound 1-39 | 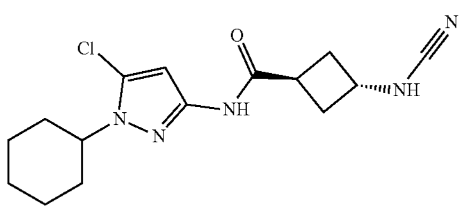 [SMILES: N#CN[C@H]1C[C@H](C(=O)Nc2cc(Cl)n(C3CCCCC3)n2)C1] | (1r,3r)-N-(5-chloro-1-cyclohexyl-1H-pyrazol-3-yl)-3-(cyanoamino)cyclobutane-1-carboxamide | 322, 324 | 10.60 (br s, 1H), 7.20 (br s, 1H), 6.57 (s, 1H), 4.23-4.15 (m, 1H), 3.84-3.77 (m, 1H), 3.15-3.08 (m, 1H), 2.43-2.37 (m, 2H), 2.20-2.12 (m, 2H), 1.82-1.74 (m, 4H), 1.73-1.65 (m, 3H), 1.45-1.35 (m, 2H), 1.20-1.10 (m, 1H) |
| Compound 1-40 | 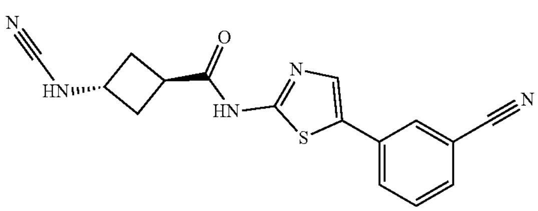 [SMILES: N#CN[C@H]1C[C@H](C(=O)Nc2ncc(-c3cccc(C#N)c3)s2)C1] | (1r,3r)-3-(cyanoamino)-N-[5-(3-cyanophenyl)-1,3-thiazol-2-yl]cyclobutane-1-carboxamide | 324 | 12.27 (br s, 1H), 8.17 (s, 1H), 8.06 (s, 1H), 7.93 (d, J = 8.4 Hz, 1H), 7.76 (d, J = 7.6 Hz, 1H), 7.63 (t, J = 8.0 Hz, 1H), 7.28 (br s, 1H), 3.87-3.80 (m, 1H), 3.31-3.28 (m, 1H), 2.55-2.52 (m, 1H), 2.52-2.49 (m, 1H), 2.30-2.23 (m, 2H) |
| Compound 1-41 | 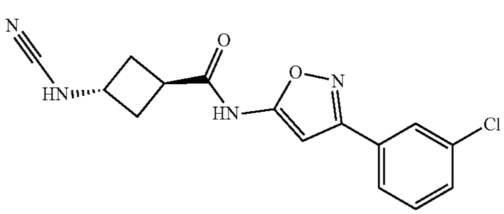 [SMILES: N#CN[C@H]1C[C@H](C(=O)Nc2cc(-c3cccc(Cl)c3)no2)C1] | (1r,3r)-N-[3-(3-chlorophenyl)-1,2-oxazol-5-yl]-3-(cyanoamino)cyclobutane-1-carboxamide | 317, 319 | 11.75 (br s, 1H), 7.92 (s, 1H), 7.83 (d, J = 7.2 Hz, 1H), 7.59-7.52 (m, 2H), 7.26 (br s, 1H), 6.85 (s, 1H), 3.85-3.77 (m, 1H), 3.26-3.19 (m, 1H), 2.53-2.49 (m, 1H), 2.49-2.47 (m, 1H), 2.29-2.21 (m, 2H) |
| Compound 1-42 | 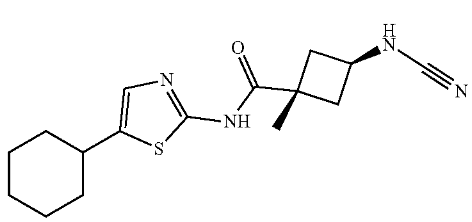 [SMILES: C[C@]1(C(=O)Nc2ncc(C3CCCCC3)s2)C[C@H](NC#N)C1] | (1r,3s)-3-(cyanoamino)-N-(5-cyclohexyl-1,3-thiazol-2-yl)-1-methylcyclobutane-1-carboxamide | 305 | 12.06 (s, 1H), 7.24 (d, J = 6 Hz, 1H), 6.72 (s, 1H), 3.66-3.56 (m, 1H), 2.95-2.87 (m, 1H), 2.68-2.56 (m, 1H), 2.45-2.41 (m, 2H), 2.19-2.12 (m, 2H), 1.93-1.84 (m, 2H), 1.79-1.68 (m, 3H), 1.45-1.27 (m, 4H), 1.26-1.13 (m, 1H) |

-continued

| Example No. | Structure | Chemical Name | MS m/z [M + H]+ | 1H NMR |
|---|---|---|---|---|
| Compound 1-43 | 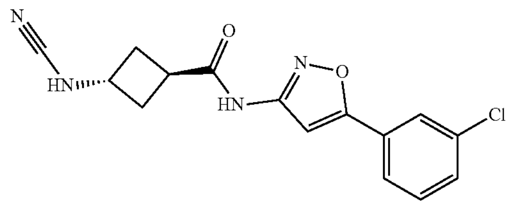 [SMILES: N#CN[C@H]1C[C@H](C(=O)Nc2cc(-c3cccc(Cl)c3)on2)C1] | (1r,3r)-N-[5-(3-chlorophenyl)-1,2-oxazol-3-yl]-3-(cyanoamino)cyclobutane-1-carboxamide | 317, 319 | 11.09 (br s, 1H), 7.99 (s, 1H), 7.88-7.85 (m, 1H), 7.58-7.57 (m, 2H), 7.57-7.52 (m, 1H), 7.25-7.23 (br s, 1H), 3.83-3.79 (m, 1H), 3.23-3.21 (m, 1H), 2.48-2.45 (m, 2H), 2.27-2.20 (m, 2H) |
| Compound 1-44 | 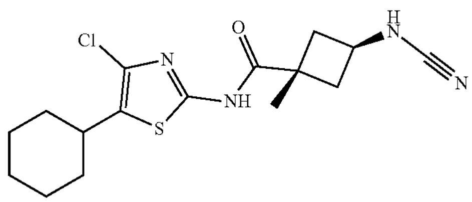 | (1r,3s)-N-(4-chloro-5-cyclohexyl-1,3-thiazol-2-yl)-3-(cyanoamino)-1-methylcyclobutane-1-carboxamide | 353, 355 | 12.19 (br s, 1H), 7.19-7.18 (br s, 1H), 3.52-3.44 (m, 1H), 2.85-2.80 (m, 3H), 1.94-1.89 (m, 4H), 1.79-1.70 (m, 2H), 1.70-1.67 (m, 1H), 1.43 (s, 3H), 1.39-1.30 (m, 4H), 1.30-1.20 (m, 1H) |
| Compound 1-45 | 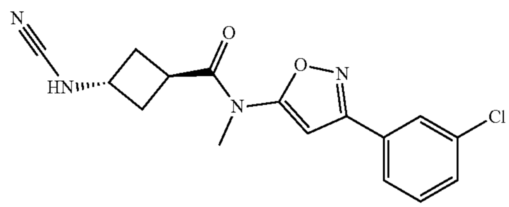 [SMILES: CN(c1cc(-c2cccc(Cl)c2)no1)C(=O)[C@H]1C[C@H](NC#N)C1] | (1r,3r)-N-[3-(3-chlorophenyl)-1,2-oxazol-5-yl]-3-(cyanoamino)-N-methylcyclobutane-1-carboxamide | 331, 333 | 7.94 (s, 1H), 7.86 (d, J = 7.2 Hz, 1H), 7.60-7.57 (m, 2H), 7.23 (br s, 1H), 7.01 (s, 1H), 3.80-3.40 (m, 5H), 2.60-2.40 (m, 2H), 2.30-2.20 (m, 2H) |
| Compound 1-46 | 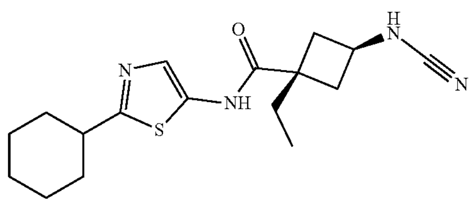 [SMILES: CC[C@]1(C(=O)Nc2cnc(C3CCCCC3)s2)C[C@H](NC#N)C1] | (1r,3s)-3-(cyanoamino)-N-(2-cyclohexyl-1,3-thiazol-5-yl)-1-ethylcyclobutane-1-carboxamide | 333 | 10.92 (br s, 1H), 7.40 (s, 1H), 7.21 (br s 1H), 3.40-3.38 (m, 1H), 2.86-2.82 (m, 1H), 2.78-2.73 (m, 2H), 2.01-1.67 (m, 9H), 1.52-1.36 (m, 4H), 1.32-1.22 (m, 1H), 0.71 (t, J = 7.2 Hz, 3H) |
| Compound 1-47 | 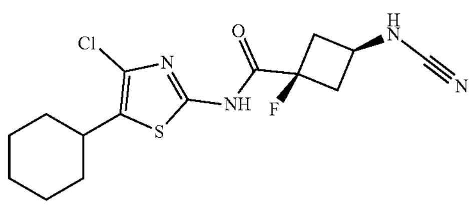 [SMILES: N#CN[C@H]1C[C@](F)(C(=O)Nc2nc(Cl)c(C3CCCCC3)s2)C1] | (1s,3s)-N-(4-chloro-5-cyclohexyl-1,3-thiazol-2-yl)-3-(cyanoamino)-1-fluorocyclobutane-1-carboxamide | 357, 359 | 12.63 (br s, 1H), 7.44 (br s, 1H), 4.07-4.00 (m, 1H), 2.87-2.82 (m, 1H), 2.76-2.59 (m, 4H), 1.95-1.89 (m, 2H), 1.79-1.77 (m, 2H), 1.73-1.67 (m, 1H), 1.42-1.17 (m, 5H) |
| Compound 1-48 | 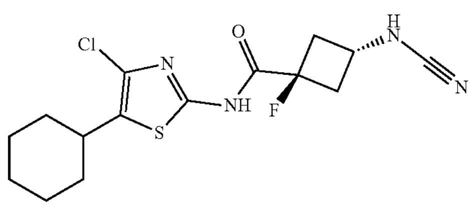 [SMILES: N#CN[C@H]1C[C@@](F)(C(=O)Nc2nc(Cl)c(C3CCCCC3)s2)C1] | (1r,3r)-N-(4-chloro-5-cyclohexyl-1,3-thiazol-2-yl)-3-(cyanoamino)-1-fluorocyclobutane-1-carboxamide | 357, 359 | 12.64 (br s, 1H), 7.47 (br s, 1H), 3.52-3.49 (m, 1H), 3.04-2.97 (m, 2H), 2.87-2.82 (m, 1H), 2.48-2.42 (m, 2H), 1.92-1.89 (m, 2H), 1.79-1.77 (m, 2H), 1.71-1.67 (m, 1H), 1.42-1.17 (m, 5H) |
| Compound 1-49 | 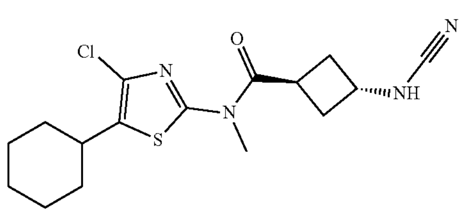 [SMILES: CN(c1nc(Cl)c(C2CCCCC2)s1)C(=O)[C@H]1C[C@H](NC#N)C1] | (1r,3r)-N-(4-chloro-5-cyclohexyl-1,3-thiazol-2-yl)-3-(cyanoamino)-N-methylclycobutane-1-carboxamide | 353, 355 | 7.28 (br s, 1H), 3.71-3.63 (m, 2H), 3.43 (s, 3H), 2.82-2.77 (m, 1H), 2.58-2.51 (m, 2H), 2.35-2.28 (m, 2H), 1.90-1.88 (m, 2H), 1.77-1.72 (m, 2H), 1.70-1.67 (m, 1H), 1.42-1.22 (m, 5H) |

| Example No. | Structure | Chemical Name | MS m/z [M + H]+ | 1H NMR |
|---|---|---|---|---|
| Compound 1-50 | 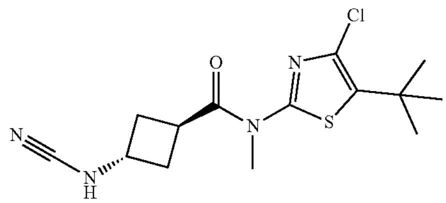 | (1r,3r)-N-(5-tert-butyl-4-chloro-1,3-thiazol-2-yl)-3-(cyanoamino)-N-methylcyclobutane-1-carboxamide | 327, 329 | 7.28 (br s, 1H), 3.69-3.63 (m, 2H), 3.42 (s, 3H), 2.60-2.51 (m, 2H), 2.35-2.28 (m, 2H), 1.41 (s, 9H) |
| Compound 1-51 | 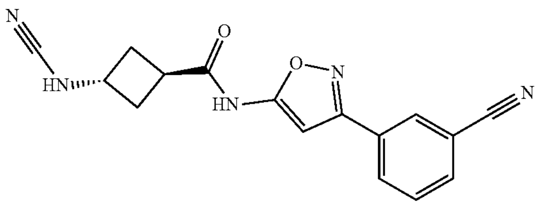 [SMILES: N#CN[C@H]1C[C@H](C(=O)Nc2cc(-c3cccc(C#N)c3)no2)C1] | (1r,3r)-3-(cyanoamino)-N-[3-(3-cyanophenyl)-1,2-oxazol-5-yl]cyclobutane-1-carboxamide | 308 | 11.80 (br s, 1H), 8.37 (s, 1H), 8.22 (d, J = 8.0 Hz, 1H), 7.99 (d, J = 7.6 Hz, 1H), 7.73 (t, J = 8.0 Hz, 1H), 7.27 (br s, 1H), 6.95 (s, 1H), 3.85-3.80 (m, 1H), 3.26-3.22 (m, 1H), 2.55-2.49 (m, 2H), 2.30-2.23 (m, 2H) |
| Compound 1-52 | 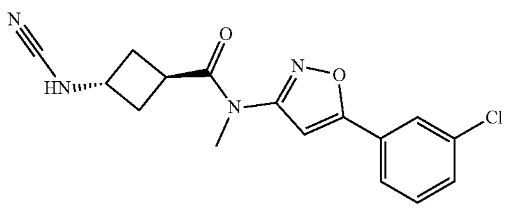 [SMILES: CN(c1cc(-c2cccc(Cl)c2)on1)C(=O)[C@H]1C[C@H](NC#N)C1] | (1r,3r)-N-[5-(3-chlorophenyl)-1,2-oxazol-3-yl]-3-(cyanoamino)-N-methylcyclobutane-1-carboxamide | 331, 333 | 8.01 (s, 1H), 7.89-7.86 (m, 1H), 7.61-7.57 (m, 3H), 7.26 (br s, 1H), 3.74-3.69 (m, 1H), 3.59-3.55 (m, 1H), 3.32 (s, 3H), 2.52-2.51 (m, 2H), 2.34-2.27 (m, 2H) |
| Compound 1-53 | 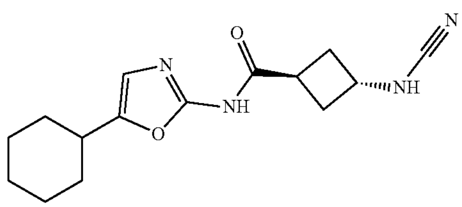 [SMILES: N#CN[C@H]1C[C@H](C(=O)Nc2ncc(C3CCCCC3)o2)C1] | (1r,3r)-3-(cyanoamino)-N-(5-cyclohexyl-1,3-oxazol-2-yl)cyclobutane-1-carboxamide | 289 | 7.25 (br s, 2H), 6.91 (s, 1H), 3.78-3.75 (m, 1H), 3.22-3.17 (m, 1H), 2.68-2.62 (m, 1H), 2.47-2.40 (m, 2H), 2.34-2.15 (m, 2H), 1.92-1.86 (m, 2H), 1.78-1.71 (m, 2H), 1.70-1.64 (m, 1H), 1.40-1.15 (m, 5H) |
| Compound 1-54 | 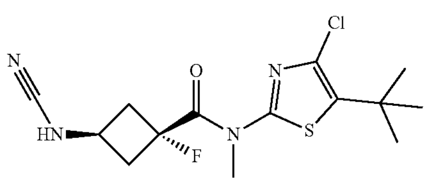 [SMILES: CN(c1nc(Cl)c(C(C)(C)C)s1)C(=O)[C@]1(F)C[C@H](NC#N)C1] | (1r,3r)-N-(5-tert-butyl-4-chloro-1,3-thiazol-2-yl)-3-(cyanoamino)-1-fluoro-N-methylcyclobutane-1-carboxamide | 345, 347 | 7.40 (br s, 1H), 3.51 (s, 3H), 3.50-3.25 (m, 3H) 2.58-2.51 (m, 2H), 1.41 (s, 9H) |
| Compound 1-55 | 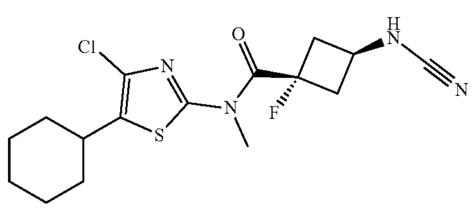 [SMILES: CN(c1nc(Cl)c(C2CCCCC2)s1)C(=O)[C@]1(F)C[C@H](NC#N)C1] | (1r,3r)-N-(4-chloro-5-cyclohexyl-1,3-thiazol-2-yl)-3-(cyanoamino)-1-fluoro-N-methylcyclobutane-1-carboxamide | 370, 373 | 7.51 (br s, 1H), 3.52 (s, 3H), 3.34-3.24 (m, 3H), 2.88-2.84 (m, 1H), 2.58-2.51 (m, 2H), 1.92-1.89 (m, 2H), 1.79-1.74 (m, 2H), 1.71-1.68 (m, 1H), 1.43-1.23 (m, 5H) |
| Compound 1-56 | 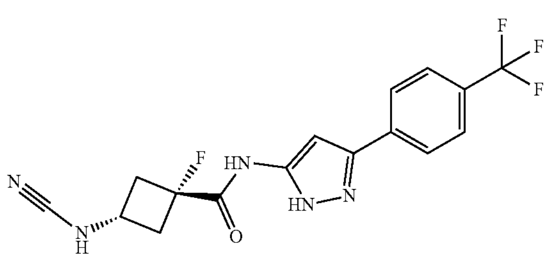 [SMILES: N#CN[C@H]1C[C@](F)(C(=O)Nc2cc(-c3ccc(C(F)(F)F)cc3)n[nH]2)C1] | (1s,3s)-3-(cyanoamino)-1-fluoro-N-{3-[4-(trifluoromethyl)phenyl]-1H-pyrazol-5-yl}cyclobutane-1-carboxamide | 368 | 13.3 (br s, 1H), 10.6 (br s, 1H), 7.97 (d, J = 8.0 Hz, 2H), 7.83 (d, J = 8.4 Hz, 2H), 7.45 (br s, 1H), 7.08 (s, 1H), 4.07-4.01 (m, 1H), 2.72-2.61 (m, 4H). |

-continued

| Example No. | Structure | Chemical Name | MS m/z [M+H]+ | 1H NMR |
|---|---|---|---|---|
| Compound 1-57 | 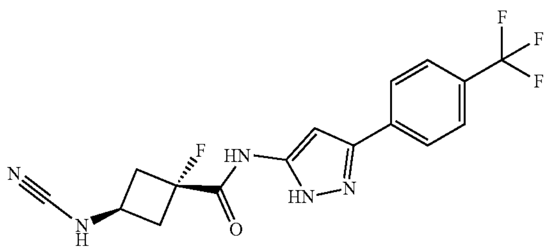 [SMILES: N#CN[C@H]1C[C@@](F)(C(=O)Nc2cc(-c3ccc(C(F)(F)F)cc3)n[nH]2)C1] | (1r,3r)-3-(cyanoamino)-1-fluoro-N-{3-[4-(trifluoromethyl)phenyl]-1H-pyrazol-5-yl}cyclobutane-1-carboxamide | 368 | 13.2 (br s, 1H), 10.6 (br s, 1H), 7.97 (d, J = 8.0 Hz, 2H), 7.83 (d, J = 8.4 Hz, 2H), 7.47 (br s, 1H), 7.07 (s, 1H), 4.05-3.98 (m, 1H), 3.02-2.97 (m, 2H), 2.51-2.42 (m, 2H). |
| Compound 1-58 | 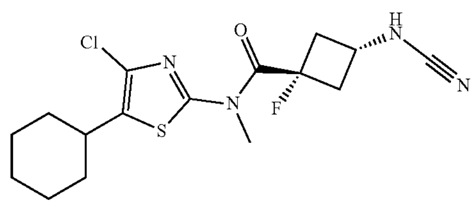 [SMILES: CN(c1nc(Cl)c(C2CCCCC2)s1)C(=O)[C@]1(F)C[C@@H](NC#N)C1] | (1s,3s)-N-(4-chloro-5-cyclohexyl-1,3-thiazol-2-yl)-3-(cyanoamino)-1-fluoro-N-methylcyclobutane-1-carboxamide | 371, 373 | 751 (br s, 1H), 3.52 (s, 3H), 3.34-3.24 (m, 3H), 2.88-2.84 (m, 1H), 2.58-2.51 (m, 2H), 1.92-1.89 (m, 2H), 1.79-1.74 (m, 2H), 1.71-1.68 (m, 1H), 1.43-1.23 (m, 5H) |
| Compound 1-59 | 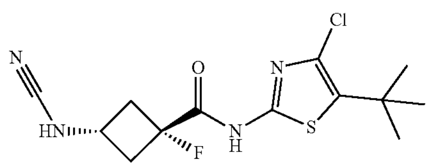 [SMILES: CC(C)(C)c1sc(NC(=O)[C@]2(F)C[C@@H](NC#N)C2)nc1Cl] | (1s,3s)-N-(5-tert-butyl-4-chloro-1,3-thiazol-2-yl)-3-(cyanoamino)-1-fluorocyclobutane-1-carboxamide | 331, 333 | 12.57 (br s, 1H), 7.43 (br s, 1H), 4.07-3.98 (m, 1H), 2.72-2.61 (m, 4H), 1.41 (s, 9H) |
| Compound 1-60 | 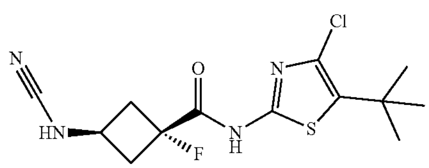 [SMILES: CC(C)(C)c1sc(NC(=O)[C@]2(F)C[C@H](NC#N)C2)nc1Cl] | (1r,3r)-N-(5-tert-butyl-4-chloro-1,3-thiazol-2-yl)-3-(cyanoamino)-1-fluorocyclobutane-1-carboxamide | 331, 333 | 12.57 (br s, 1H), 7.48 (br s, 1H), 3.51-3.48 (m, 1H), 3.00-2.97 (m, 2H), 2.50-2.41 (m, 2H), 1.41 (s, 9H). |
| Compound 1-61 | 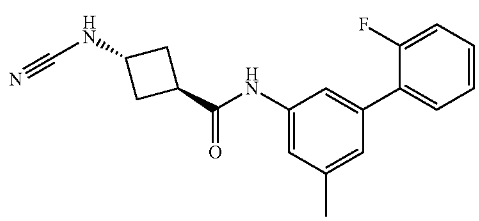 [SMILES: Cc1cc(NC(=O)[C@H]2C[C@H](NC#N)C2)cc(-c2ccccc2F)c1] | (1r,3r)-3-(cyanoamino)-N-[3-(2-fluorophenyl)-5-methylphenyl]cyclobutane-1-carboxamide | 324 | 9.96 (br s, 1H), 7.63 (s, 1H), 7.50-7.40 (m, 3H), 7.33-7.28 (m, 2H), 7.24 (br s, 1H), 7.04 (s, 1H), 3.85-3.80 (m, 1H), 3.17-3.12 (m, 1H), 2.49-2.43 (m, 2H), 2.34 (s, 3H), 2.25-2.18 (m, 2H). |
| Compound 1-62 | 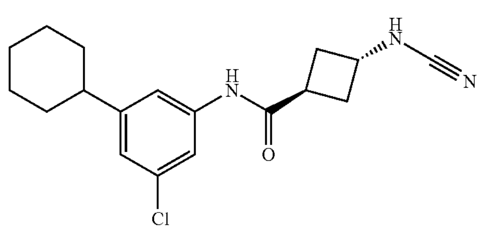 [SMILES: N#CN[C@H]1C[C@H](C(=O)Nc2cc(Cl)cc(C3CCCCC3)c2)C1] | (1r,3r)-N-(3-chloro-5-cyclohexylphenyl)-3-(cyanoamino)cyclobutane-1-carboxamide | 332, 334 | 10.0 (br s, 1H), 7.62 (s, 1H), 7.35 (s, 1H), 7.24 (br s, 1H), 6.95 (s, 1H), 3.85-3.80 (m, 1H), 3.15-3.08 (m, 1H), 2.48-2.42 (m, 3H), 2.24-2.17 (m, 2H), 1.78-1.68 (m, 5H), 1.40-1.20 (m, 5H). |
| Compound 1-63 | 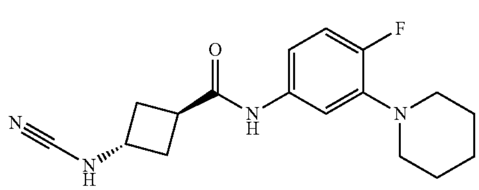 [SMILES: N#CN[C@H]1C[C@H](C(=O)Nc2ccc(F)c(N3CCCCC3)c2)C1] | (1r,3r)-3-(cyanoamino)-N-[4-fluoro-3-(piperidin-1-yl)phenyl]cyclobutane-1-carboxamide | 317 | 9.85 (br s, 1H), 7.37 (dd, J = 8.0, 2.4 Hz, 1H), 7.17-7.13 (m, 1H), 7.04-6.99 (m, 1H), 3.84-3.80 (m, 1H), 3.12-3.07 (m, 1H), 2.94-2.92 (m, 4H), 2.48-2.42 (m, 2H), 2.21-2.18 (m, 2H), 1.69-1.64 (m, 4H), 1.54-1.51 (m, 2H). |

| Example No. | Structure | Chemical Name | MS m/z [M+H]+ | 1H NMR |
|---|---|---|---|---|
| Compound 1-64 | 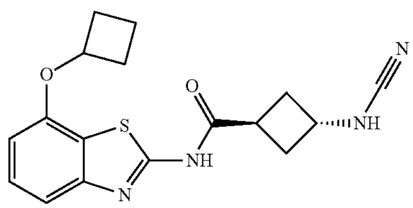 [SMILES: N#CN[C@H]1C[C@H](C(=O)Nc2nc3cccc(OC4CCC4)c3s2)C1] | (1r,3r)-3-(cyanoamino)-N-(7-cyclobutoxy-1,3-benzothiazol-2-yl)cyclobutane-1-carboxamide | 343 | 7.35-7.30 (m, 2H), 6.74-6.72 (m, 1H), 4.89-4.82 (m, 1H), 3.84-3.70 (m, 1H), 3.32-3.25 (m, 1H), 2.49-2.45 (m, 4H), 2.30-2.22 (m, 2H), 2.14-2.09 (m, 1H), 0.86-0.79 (m, 1H), 0.74-0.65 (m, 1H). |
| Compound 1-65 | 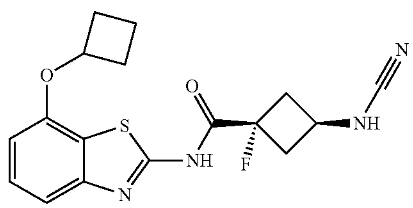 [SMILES: N#CN[C@H]1C[C@@](F)(C(=O)Nc2nc3cccc(OC4CCC4)c3s2)C1] | (1r,3r)-3-(cyanoamino)-N-(7-cyclobutoxy-1,3-benzothiazol-2-yl)-1-fluorocyclobutane-1-carboxamide | 361 | 7.45 (brs, 1H), 7.34-7.32 (m, 2H), 6.75-6.74 (m, 1H), 4.90-4.87 (m, 1H), 3.62-3.57 (m, 1H), 3.08-2.98 (m, 2H), 2.47-2.42 (m, 4H), 2.15-2.08 (m, 2H), 1.85-1.82 (m, 1H), 1.72-1.65 (m, 2H). |
| Compound 1-66 | 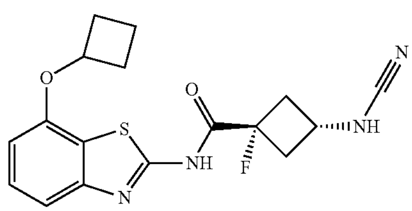 [SMILES: N#CN[C@H]1C[C@](F)(C(=O)Nc2nc3cccc(OC4CCC4)c3s2)C1] | (1s,3s)-3-(cyanoamino)-N-(7-cyclobutoxy-1,3-benzothiazol-2-yl)-1-fluorocyclobutane-1-carboxamide | 361 | 7.16-7.14 (m, 2H), 6.63-6.54 (m, 2H), 6.09 (br s, 1H), 4.83-4.80 (m, 1H), 3.95-3.92 (m, 1H), 2.70-2.58 (m, 4H), 2.47-2.33 (m, 2H), 2.14-2.09 (m, 2H), 1.83-1.81 (m, 1H), 1.70-1.63 (m, 2H), |
| Compound 1-67 | 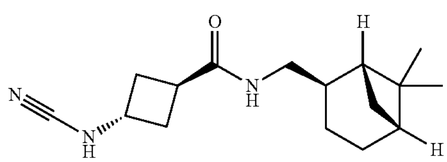 [SMILES: CC1(C)[C@@H]2CC[C@@H](CNC(=O)[C@H]3C[C@H](NC#N)C3)[C@H]1C2] | (1r,3r)-3-(cyanoamino)-N-{[(1R,2R,5R)-6,6-dimethylbicyclo[3.1.1]heptan-2-yl]methyl}cyclobutane-1-carboxamide | 276 | |
| Compound 1-68 | 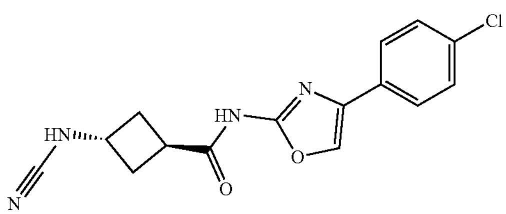 | (1r,3r)-N-[4-(4-chlorophenyl)-1,3-thiazol-2-yl]-3-(cyanoamino)cyclobutane-1-carboxamide | 333 | |
| Compound 1-69 | 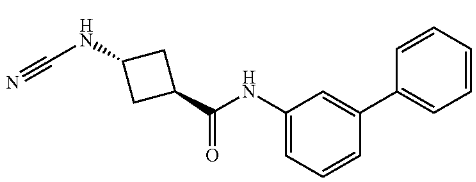 [SMILES: N#CN[C@H]1C[C@H](C(=O)Nc2cccc(-c3ccccc3)c2)C1] | (1r,3r)-3-(cyanoamino)-N-(3-phenylphenyl)cyclobutane-1-carboxamide | 292 | |
| Compound 1-70 | 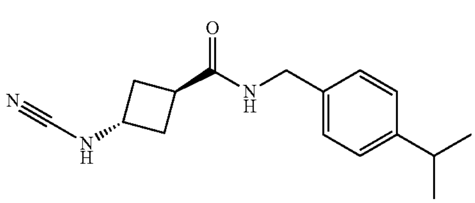 [SMILES: CC(C)c1ccc(CNC(=O)[C@H]2C[C@H](NC#N)C2)cc1] | (1r,3r)-3-(cyanoamino)-N-{[4-(propan-2-yl)phenyl]methyl}cyclobutane-1-carboxamide | 272 | |

| Example No. | Structure | Chemical Name | MS m/z [M + H]+ | 1H NMR |
|---|---|---|---|---|
| Compound 1-71 | 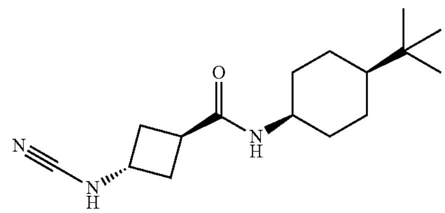 [SMILES: CC(C)(C)[C@H]1CC[C@@H](NC(=O)[C@H]2C[C@H](NC#N)C2)CC1] | (1r,3r)-3-(cyanoamino)-N-[(1s,4s)-4-tert-butylcyclohexyl]cyclobutane-1-carboxamide | 278 | |
| Compound 1-72 | 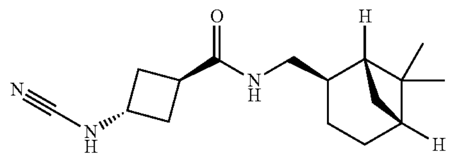 [SMILES: CC1(C)[C@@H]2CC[C@@H](CNC(=O)[C@H]3C[C@H](NC#N)C3)[C@H]1C2] | (1r,3r)-3-(cyanoamino)-N-{[1R,2R,5R)-6,6-dimethylbicyclo[3.1.1]heptan-2-yl]methyl}cyclobutane-1-carboxamide | 276 | |
| Compound 1-73 | 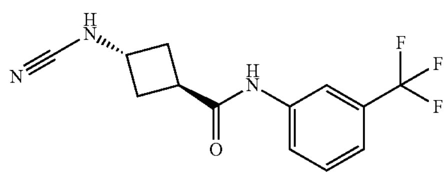 | (1r,3r)-3-(cyanoamino)-N-[3-(trifluoromethyl)phenyl]cyclobutane-1-carboxamide | 284 | |

Example 2-1. 3-(cyanoamino)-N-(5-cyclohexyl-1,3-thiazol-2-yl)azetidine-1-carboxamide (Compound 2-1)

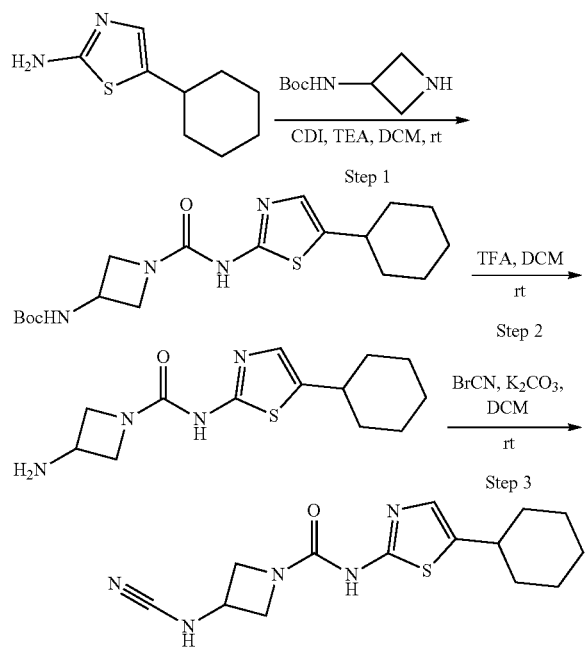

Step 1. tert-butyl (1-((5-cyclohexylthiazol-2-yl)carbamoyl)azetidin-3-yl)carbamate Into a 50 mL round-bottom flask was placed 5-cyclohexylthiazol-2-amine (300 mg, 1.65 mmol), dichloromethane (5 mL) and triethylamine (833 mg, 8.23 mmol). This was followed by the addition of N,N'-carbonyldiimidazole (348 mg, 2.15 mmol). The resulting solution was stirred for 2 h at room temperature. Then tert-butyl azetidin-3-ylcarbamate (369 mg, 2.14 mmol) was added. The resulting solution was stirred overnight at room temperature. The reaction mixture was poured into water (5 mL) and then extracted with ethyl acetate (3×10 mL). The organic layers were combined, dried over anhydrous sodium sulfate, filtered and concentrated under vacuum. The residue was purified by silica gel chromatography (eluting with 1:1 ethyl acetate/petroleum ether) to afford tert-butyl (1-((5-cyclohexylthiazol-2-yl)carbamoyl)azetidin-3-yl)carbamate as a yellow solid. LC-MS (ESI) m/z 381.2[M+H]+

Step 2. 3-amino-N-(5-cyclohexylthiazol-2-yl)azetidine-1-carboxamide TFA salt Into a 50 mL round-bottom flask was placed tert-butyl (1-((5-cyclohexylthiazol-2-yl)carbamoyl)azetidin-3-yl)carbamate (190 mg, 0.50 mmol), dichloromethane (3 mL) and trifluoroacetic acid (1 mL). The resulting solution was stirred for 2 h at room temperature. The reaction mixture was concentrated under vacuum. The residue was treated with ethyl ether and dried under vacuum to afford 3-amino-N-(5-cyclohexylthiazol-2-yl)azetidine-1-carboxamide TFA salt as a yellow oil. LC-MS (ESI) m/z 281.2[M+H]+

Step 3. 3-(cyanoamino)-N-(5-cyclohexyl-1,3-thiazol-2-yl)azetidine-1-carboxamide Into a 50 mL round-bottom flask was placed 3-amino-N-(5-cyclohexylthiazol-2-yl)azetidine-1-carboxamide TFA salt (160 mg, 0.41 mmol), dichloromethane (5 mL), potassium carbonate (169 mg, 1.22 mmol) and cyanogen bromide (44 mg, 0.42 mmol). The resulting solution was stirred for 2 h at room temperature. The reaction mixture was poured into water (5 mL) and then extracted with ethyl acetate (3×10 mL). The organic layers were combined, dried over anhydrous sodium sulfate, filtered and concentrated under vacuum. The residue was purified by prep-HPLC (Column: XBridge Shield RP18 OBD Column, 130 Å, 5 μm, 19 mm×150 mm; Mobile phase: water (10 mM NH$_4$HCO$_3$), MeCN (30% MeCN up to 50% over 10 min); Flow rate: 20 mL/min; Detector: 254 & 220 nm) to afford 3-cyanamido-N-(5-cyclohexylthiazol-2-yl)azetidine-1-carboxamide as a white solid. $^1$H NMR (300 MHz, DMSO-d6) δ 6.96 (s, 1H), 4.43-4.38 (m, 2H), 4.21-4.10 (m, 3H), 2.77-2.73 (m, 1H), 1.81 (s, 4H), 1.45-1.32 (m, 7H). LC-MS (ESI) m/z 306.2 [M+H]$^+$ Example 3-1. 5-phenyl-N-[(trans)-3-(cyanoamino)cyclobutyl]-1,3-thiazole-2-carboxamide (Compound 3-1)

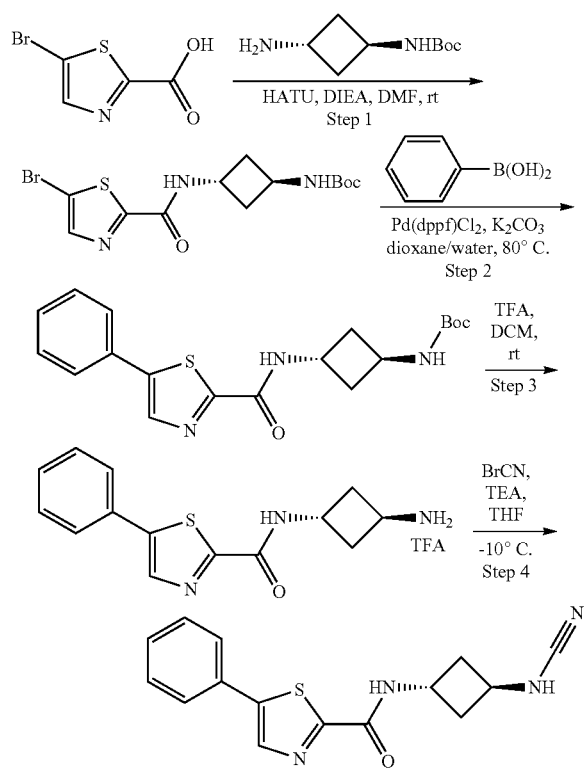

Step 1. tert-butyl ((trans)-3-(5-bromothiazole-2-carboxamido)cyclobutyl)carbamate Into a 100 mL round-bottom flask was placed 5-bromothiazole-2-carboxylic acid (300 mg, 1.41 mmol), N,N-dimethylformamide (5 mL), tert-butyl N-[(trans)-3-aminocyclobutyl]carbamate (270 mg, 1.42 mmol), N,N-diisopropylethylamine (560 mg, 4.33 mmol) and HATU (661 mg, 1.74 mmol). The resulting solution was stirred for 1 h at room temperature. The reaction mixture was poured into water (5 mL) and then extracted with ethyl acetate (3×10 mL). The organic layers were combined, dried over anhydrous sodium sulfate, filtered and concentrated under vacuum. The residue was purified by prep-TLC (eluting with 1:1 ethyl acetate/petroleum ether) to afford tert-butyl ((trans)-3-(5-bromothiazole-2-carboxamido)cyclobutyl)carbamate as a yellow solid. LC-MS (ESI) m-z 320.0, 322.0 [M+H-tBu]$^+$ Step 2. tert-butyl ((trans)-3-(5-phenylthiazole-2-carboxamido)cyclobutyl)carbamate Into a 100 mL round-bottom flask purged and maintained with an inert atmosphere of nitrogen was placed tert-butyl ((trans)-3-(5-bromothiazole-2-carboxamido)cyclobutyl)carbamate (200 mg, 0.51 mmol), 1,4-dioxane (15 mL), water (5 mL), phenylboronic acid (78 mg, 0.63 mmol, 1.23), potassium carbonate (219 mg, 1.58 mmol) and Pd(dppf)C$_{12}$ (39 mg, 0.05 mmol). The resulting mixture was stirred overnight at 80° C. After cooling to room temperature, the reaction mixture was poured into water (10 mL) and then extracted with ethyl acetate (3×10 mL). The organic layers were combined, dried over anhydrous sodium sulfate, filtered and concentrated under vacuum. The residue was purified by silica gel chromatography (eluting with 1:1 ethyl acetate/petroleum ether) to afford tert-butyl ((trans)-3-(5-phenylthiazole-2-carboxamido)cyclobutyl)carbamate as a white solid. LC-MS (ESI) m/z 374.2 [M+H]$^+$ Step 3. N-((trans)-3-aminocyclobutyl)-5-phenylthiazole-2-carboxamide TFA salt Into a 50 mL round-bottom flask was placed tert-butyl ((trans)-3-(5-phenylthiazole-2-carboxamido)cyclobutyl)carbamate (60 mg, 0.15 mmol), dichloromethane (3 mL) and trifluoroacetic acid (0.6 mL). The resulting solution was stirred for 1 h at room temperature. The reaction mixture was concentrated under vacuum. The residue was treated with ethyl ether and dried under vacuum to afford N-((trans)-3-aminocyclobutyl)-5-phenylthiazole-2-carboxamide TFA salt as a yellow oil. LC-MS (ESI) m/z 274.2 [M+H]$^+$ Step 4. 5-phenyl-N-[(trans)-3-(cyanoamino)cyclobutyl]-1,3-thiazole-2-carboxamide Into a 50 mL round-bottom flask was placed N-((trans)-3-aminocyclobutyl)-5-phenylthiazole-2-carboxamide TFA salt (50 mg, 0.12 mmol), tetrahydrofuran (5 mL) and triethylamine (16 mg, 0.16 mmol). After cooling to −10° C., to this solution was added cyanogen bromide (17 mg, 0.16 mmol). The resulting solution was stirred for 30 min at −10° C. The reaction mixture was poured into water (5 mL) and then extracted with ethyl acetate (3×10 mL). The organic layers were combined, dried over anhydrous sodium sulfate, filtered and concentrated under vacuum. The residue was purified by prep-HPLC (Column: XBridge Shield RP8 OBD Column, 130 Å, 5 μm, 19 mm×150 mm; Mobile phase: water (10 mM NH$_4$HCO$_3$), MeCN (25% MeCN up to 55% over 7 min); Flow rate: 20 mL/min; Detector: 254 & 220 nm) to afford N-((trans)-3-cyanamidocyclobutyl)-5-phenylthiazole-2-carboxamide as a white solid. $^1$H NMR (400 MHz, DMSO-d6) δ 9.31 (d, J=7.60 Hz, 1H), 8.44 (s, 1H), 7.80-7.77 (m, 2H), 7.51-7.41 (m, 3H), 7.22 (s, 1H), 4.56-4.50 (m, 1H), 3.85 (d, J=3.20 Hz, 1H), 2.51-2.46 (m, 2H), 2.33-2.08 (in, 2H). LC-MS (ESI) m/z 299.2 [M+H]$^+$ The following compounds were synthesized in a manner analogous to Compound 3-1:

| Example No. | Structure | Chemical Name | MS m/z [M + H]+ | 1H NMR |
|---|---|---|---|---|
| Compound 3-2 | 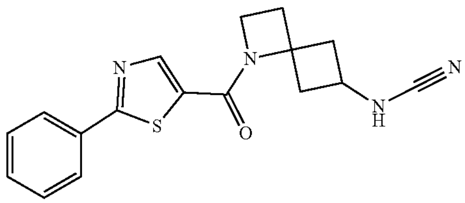 [SMILES: N#CNC1CC2(CCN2C(=O)c2cnc(-c3ccccc3)s2)C1] | {[1-(2-phenyl-1,3-thiazole-5-carbonyl)-1-azaspiro[3.3]heptan-6-yl]amino}carbonitrile | 325 | 8.25 (s, 1H), 8.03-7.98 (m, 2H), 7.57-7.52 (m, 3H), 6.52 (s, 1H), 4.43-4.39 (m, 2H), 3.47-3.41 (m, 1H), 3.06-3.01 (m, 2H), 2.55-2.42 (m, 4H) |
| Compound 3-3 | 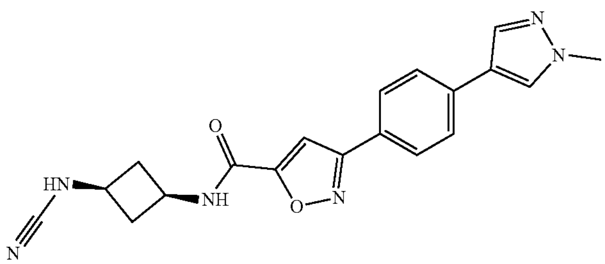 [SMILES: Cn1cc(-c2ccc(-c3cc(C(=O)N[C@H]4C[C@@H](NC#N)C4)on3)cc2)cn1] | 3-[4-(1-methyl-1H-pyrazol-4-yl)phenyl]-N-[(1s,3s)-3-(cyanoamino)cyclobutyl]-1,2-oxazole-5-carboxamide | 363 | 1H-NMR (CD3OD, 400 MHz) δ (ppm): 8.09 (s, 1H), 7.92-7.89 (m, 3H), 7.72 (dd, J = 6.8, 2.0 Hz, 2H), 7.40 (s, 1H), 4.21-4.17 (m, 1H), 3.97 (s, 3H), 3.56-3.48 (m, 1H), 2.81-2.75 (m, 2H), 2.26-2.18 (m, 2H). |
| Compound 3-4 | 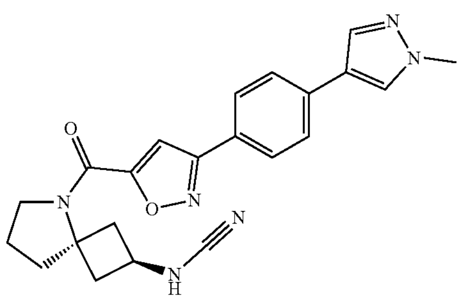 [SMILES: Cn1cc(-c2ccc(-c3cc(C(=O)N4CCC[C@]45C[C@H](NC#N)C5)on3)cc2)cn1] | {[(2r,4s)-5-{3-[4-(1-methyl-1H-pyrazol-4-yl)phenyl]-1,2-oxazole-5-carbonyl}-5-azaspiro[3.4]octan-2-yl]amino}carbonitrile | 403 | 1H-NMR (CDCl3, 400 MHz) δ (ppm): 7.85-7.83 (m, 3H), 7.71 (s, 1H), 7.61 (d, J = 8.0 Hz, 2H), 7.18 (s, 1H), 4.40-4.34 (m, 1H), 4.00 (s, 3H), 3.96-3.92 (m, 2H), 3.47-4.41 (m, 2H), 2.37-2.241 (m, 4H), 1.96-1.91 (m, 2H). |
| Compound 3-5 | 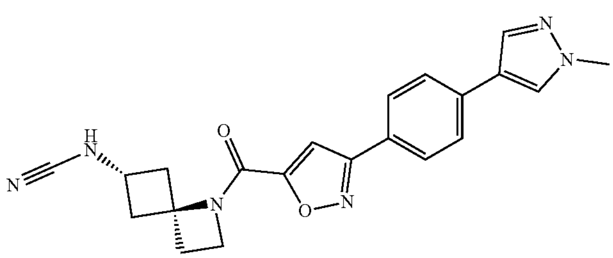 [SMILES: Cn1cc(-c2ccc(-c3cc(C(=O)N4CC[C@]45C[C@@H](NC#N)C5)on3)cc2)cn1] | {[(4r,6s)-1-{3-[4-(1-methyl-1H-pyrazol-4-yl)phenyl]-1,2-oxazole-5-carbonyl}-1-azaspiro[3.3]heptan-6-yl]amino}carbonitrile | 389 | 8.27(s, 1H), 7.98 (s, 1H), 7.93(d, J = 8.4 Hz, 2H),7.73(d, J = 8.4 Hz, 2H), 7.60(s, 1H), 7.30 (d, J = 6.0 Hz, 1H), 4.46-4.42 (m, 2H), 3.89(s, 3H), 3.48-3.44(m, 1H), 3.06-3.00 (m, 2H), 2.48-2.42 (m, 4H) |

| Example No. | Structure | Chemical Name | MS m/z [M + H]+ | 1H NMR |
|---|---|---|---|---|
| Compound 3-6 | 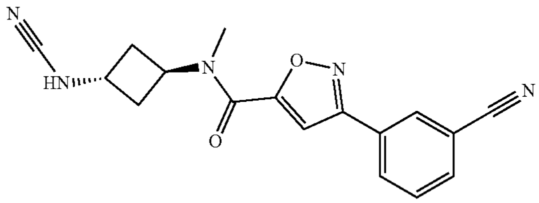 [SMILES: CN(C(=O)c1cc(-c2cccc(C#N)c2)no1)[C@H]1C[C@H](NC#N)C1] | 3-(3-cyanophenyl)-N-methyl-N-[(1r,3r)-3-(cyanoamino)cyclobutyl]-1,2-oxazole-5-carboxamide | 322 | 8.45 (s, 1H), 8.31 (d, J = 7.6 Hz, 1H), 8.04 (d, J = 7.6 Hz, 1H), 7.78 (t, J = 8.0 Hz, 1H), 7.71-7.59 (m, 1H), 7.24 (br s, 1H), 5.12-5.08 (m, 0.5H), 4.74-4.70 (m, 0.5H), 3.82-3.78 (m, 1H), 3.14-3.06 (m, 3H), 2.73-2.60 (m, 2H), 2.45-2.22 (m, 2H) |

Example 4-1. 5-phenyl-N-[(cis)-3-(cyanoamino)cyclobutyl]-1,3-thiazole-2-carboxamide (Compound 4-1)

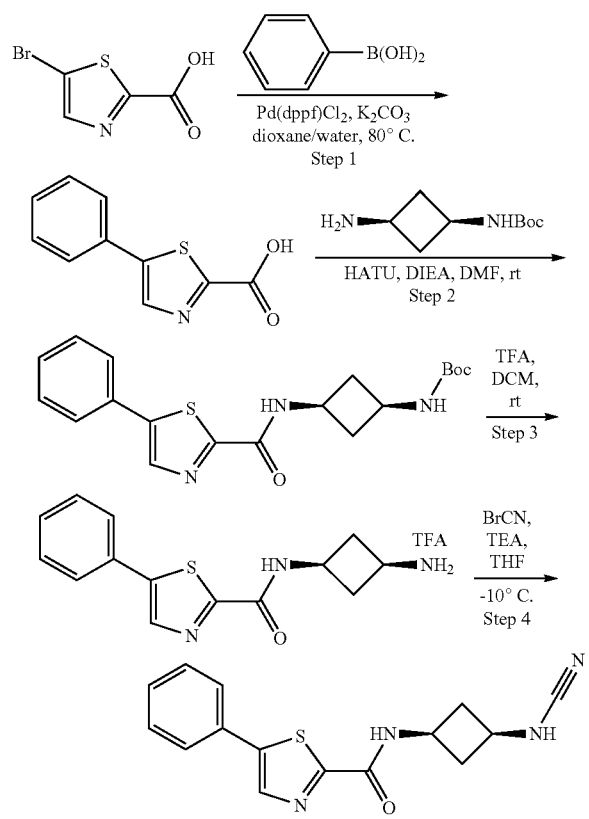

Step 1. 5-phenylthiazole-2-carboxylic acid

Into a 100 mL round-bottom flask purged and maintained with an inert atmosphere of nitrogen was placed 5-bromothiazole-2-carboxylic acid (1 g, 4.71 mmol), phenylboronic acid (707 mg, 5.68 mmol), potassium carbonate (2 g, 14.47 mmol), 1,4-dioxane (20 mL), water (2 mL) and Pd(dppf)C$_{12}$ (352 mg, 0.48 mmol). The resulting mixture was stirred for 16 h at 80° C. After cooling to room temperature, the reaction mixture was poured into water (5 mL) and then washed with ethyl ether (2×5 mL). The aqueous layer was acidified to pH 5 with hydrochloric acid (1N) and then extracted with ethyl acetate (3×20 mL). The organic layers were combined, dried over anhydrous sodium sulfate, filtered and concentrated under vacuum to afford 5-phenylthiazole-2-carboxylic acid as a brown solid. LC-MS (ESI) m/z 206.1 [M+H]$^+$ Step 2. tert-butyl ((cis)-3-(5-phenylthiazole-2-carboxamido)cyclobutyl)carbamate Into a 100 mL round-bottom flask was placed 5-phenylthiazole-2-carboxylic acid (120 mg, 0.56 mmol), N,N-dimethylformamide (20 mL), tert-butyl N-[(cis)-3-aminocyclobutyl]carbamate (109 mg, 0.57 mmol), N,N-diisopropylethylamine (227 mg, 1.76 mmol) and HATU (267 mg, 0.70 mmol). The resulting solution was stirred for 1 h at room temperature. The reaction mixture was poured into water (10 mL) and then extracted with ethyl acetate (3×20 mL). The organic layers were combined, dried over anhydrous sodium sulfate, filtered and concentrated under vacuum. The residue was purified by silica gel chromatography (eluting with 1:3 ethyl acetate/petroleum ether) to afford tert-butyl ((cis)-3-(5-phenylthiazole-2-carboxamido)cyclobutyl)carbamate as a white solid. LC-MS (ESI) m/z 374.2 [M+H]$^+$ Step 3. N-(cis)-3-aminocyclobutyl)-5-phenylthiazole-2-carboxamide TFA salt Into a 50 mL round-bottom flask was placed tert-butyl (cis)-3-(5-phenylthiazole-2-carboxamido)cyclobutyl)carbamate (200 mg, 0.51 mmol), dichloromethane (5 mL) and trifluoroacetic acid (1 mL). The resulting solution was stirred for 1 h at room temperature. The reaction mixture was concentrated under vacuum. The residue was treated with ethyl ether and dried under vacuum to afford N-(cis)-3-aminocyclobutyl)-5-phenylthiazole-2-carboxamide TFA salt as a yellow oil. LC-MS (ESI) m/z 274.2 [M+H]$^+$ Step 4. 5-phenyl-N-[(cis)-3-(cyanoamino)cyclobutyl]-1,3-thiazole-2-carboxamide Into a 50 mL round-bottom flask was placed N-(cis)-3-aminocyclobutyl)-5-phenylthiazole-2-carboxamide TFA salt (120 mg, 0.29 mmol), tetrahydrofuran (10 mL) and triethylamine (54 mg, 0.53 mmol). After cooling to −10° C., to this solution was added cyanogen bromide (56 mg, 0.52 mmol). The resulting solution was stirred for 30 min at −10° C. The reaction mixture was poured into water (5 mL) and then extracted with ethyl acetate (3×10 mL). The organic layers were combined, dried over anhydrous sodium sulfate, filtered and concentrated under vacuum. The residue was purified by prep-HPLC (Column. XBridge Shield RP18 OBD Column, 130 Å, 5 μm, 19 mm×150 mm; Mobile phase: water (10 mM $NH_4HCO_3$), MeCN (25% MeCN up to 55% over 7 min); Flow rate: 20 mL/min; Detector: 254 & 220 nm) to afford N-(cis)-3-cyanamidocyclobutyl)-5-phenylthiazole-2-carboxamide as a white solid. $^1$H NMR (400 MHz, DMSO-d6) δ 9.30 (d, J=7.60 Hz, 1H), 8.43 (s, 1H), 7.78 (d, J=7.20 Hz, 2H), 7.51-7.43 (m, 3H), 7.17 (d, J=4.40 Hz, 1H), 4.06-4.04 (m, 1H), 3.39-3.33 (m, 1H), 2.56-2.50 (m, 2H), 2.23-2.16 (m, 2H). LC-MS (ESI) m/z 299.2 $[M+H]^+$ Example 5: cis-3-(cyanoamino)-N-(5-cyclohexyl-1,3-thiazol-2-yl)cyclobutane-1-carboxamide (Compound 5-3)

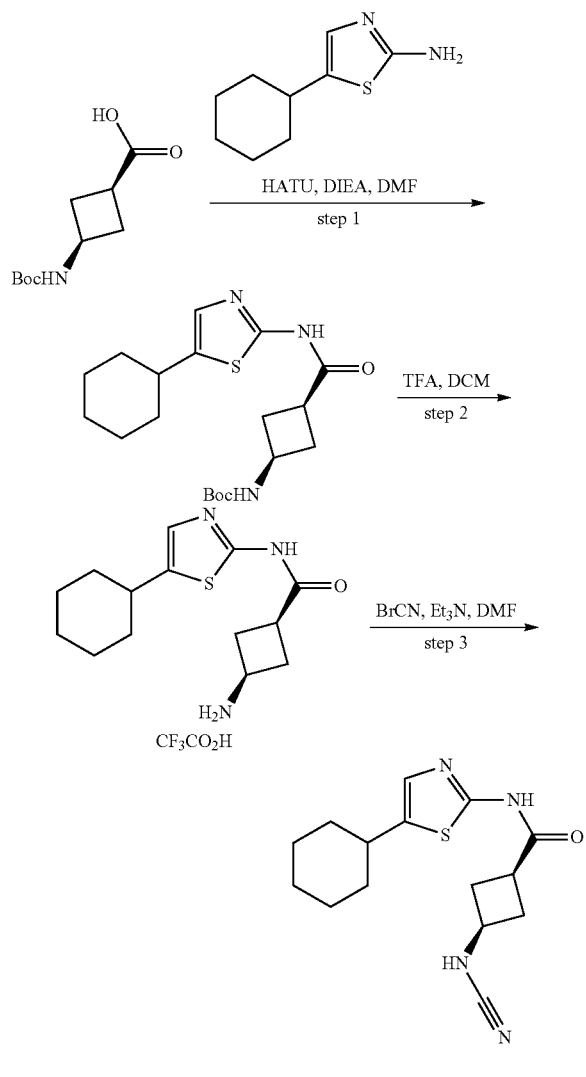

Step 1. tert-butyl N-[cis-3-[(5-cyclohexyl-1,3-thiazol-2-yl)carbamoyl]cyclobutyl]carbamate To a stirring mixture of cis-3-[[(tert-butoxy)carbonyl]amino]cyclobutane-1-carboxylic acid (100 mg, 0.465 mmol) in DMF (4 mL) was added HATU (212 mg, 0.560 mmol), DIEA (0.230 mL, 1.39 mmol) and 5-cyclohexyl-1,3-thiazol-2-amine (93.0 mg, 0.510 mmol) at 25° C. The resulting solution was stirred for 1.5 h at 25° C. The resulting mixture was diluted with water (10 mL) and extracted with DCM (3×15 mL). The combined organic layer was washed with brine (4×30 mL), dried over anhydrous sodium sulfate, filtered and concentrated under reduced pressure. The residue was purified by silica gel column chromatography (eluting with 1/1 with ethyl acetate/petroleum ether) to afford tert-butyl N-[cis-3-[(5-cyclohexyl-1,3-thiazol-2-yl)carbamoyl]cyclobutyl]carbamate as a white solid (98.0 mg). LCMS (ES, m/z): 380 $[M+H]^+$.

Step 2. cis-3-amino-N-(5-cyclohexyl-1,3-thiazol-2-yl)cyclobutane-1-carboxamide 2,2,2-trifluoroacetate A solution of tert-butyl N-[(cis)-3-[(5-cyclohexyl-1,3-thiazol-2-yl)carbamoyl]cyclobutyl]carbamate (98.0 mg, 0.258 mmol) and TFA (1 mL) in DCM (5 mL) was stirred for 1 h at 25° C. The resulting mixture was concentrated under reduced pressure to give cis-3-amino-N-(5-cyclohexyl-1,3-thiazol-2-yl)cyclobutane-1-carboxamide 2,2,2-trifluoroacetate as yellow oil (102 mg). LCMS (ES, m/z): 280 $[M+H]^+$.

Step 3. cis-3-(cyanoamino)-N-(5-cyclohexyl-1,3-thiazol-2-yl)cyclobutane-1-carboxamide To a stirring mixture of cis-3-amino-N-(5-cyclohexyl-1,3-thiazol-2-yl)cyclobutane-1-carboxamide 2,2,2-trifluoroacetate (102 mg. 0.271 mmol) in DMF (2 mL) was added $Et_3N$ (0.072 mL, 0.520 mmol) dropwise at 0° C. Then BrCN (28.0 mg, 0.260 mmol) was added. The mixture was stirred for 2 h at 25° C. and then poured into ice/water (5 mL). The resulting mixture was extracted with DCM (3×10 mL). The combined organic layer was washed with brine (20 mL), dried over anhydrous sodium sulfate, filtered and concentrated under reduced pressure. The residue was purified by Prep-HPLC (Column, Kinetex EVO C18 Column, 21.2×150 mm, 5 μm; Mobile phase, A: water (10 mmol/L $NH_4HCO_3$) and B: ACN (27% up to 46% in 10 min); Detector, UV 254/220 nm). The collected fraction was lyophilized to give cis-3-(cyanoamino)-N-(5-cyclohexyl-1,3-thiazol-2-yl)cyclobutane-1-carboxamide as a white solid (14.9 mg). $^1$H-NMR (DMSO-$d_6$, 400 MHz) δ (ppm): 11.88 (br s, 1H), 7.20 (br s, 1H), 7.14 (s, 1H), 3.67-3.55 (m, 1H), 2.97-2.85 (m, 1H), 2.83-2.71 (m. 1H), 2.47-2.36 (m, 2H), 2.20-2.10 (m, 2H), 2.00-1.88 (m, 2H), 1.81-1.71 (m, 2H), 1.71-1.62 (m, 1H), 1.44-1.29 (m, 4H), 1.28-1.15 (m, 1H). LCMS (ES, m/z): 305 $[M+H]^+$ The following compounds were synthesized according to Example 5:

| Example No. | Structure | Chemical Name | MS m/z [M + H]+ |
|---|---|---|---|
| Compound 5-1 | 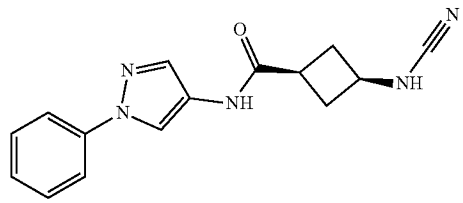 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide | LC-MS (ESI) m/z 282.2 [M + H ]+ |
| Compound 5-2 | 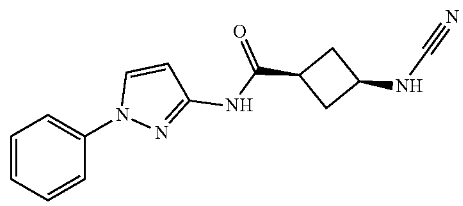 [SMILES: N#CN[C@H]1C[C@@H](C(=O)Nc2ccn(-c3ccccc3)n2)C1] | cis-3-(cyanoamino)-N-(1-phenyl-1H-pyrazol-3-yl)cyclobutane-1-carboxamide | LC-MS (ESI) m/z 282.2 [M + H ]+ |
| Compound 5-4 | 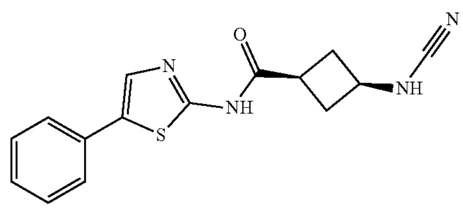 [SMILES: N#CN[C@H]1C[C@@H](C(=O)Nc2ncc(-c3ccccc3)s2)C1] | cis-3-(cyanoamino)-N-(5-phenyl-1,3-thiazol-2-yl)cyclobutane-1-carboxamide | LC-MS (ESI) m/z 299.1 [M + H ]+ |
| Compound 5-5 | 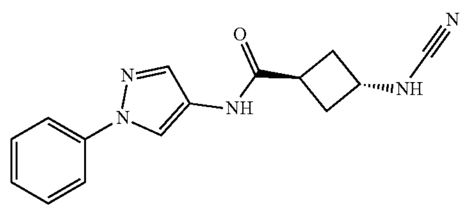 [SMILES: N#CN[C@H]1C[C@H](C(=O)Nc2cnn(-c3ccccc3)c2)C1] | trans-3-(cyanoamino)-N-(1-phenyl-1H-pyrazol-4-yl)cyclobutane-1-carboxamide | LC-MS (ESI) m/z 282.2 [M + H ]+ |
| Compound 5-6 | 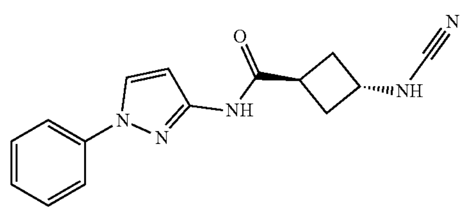 [SMILES: N#CN[C@H]1C[C@H](C(=O)Nc2ccn(-c3ccccc3)n2)C1] | trans-3-(cyanoamino)-N-(1-phenyl-1H-pyrazol-3-yl)cyclobutane-1-carboxamide | LC-MS (ESI) m/z 282.2 [M + H ]+ |
| Compound 5-7 | 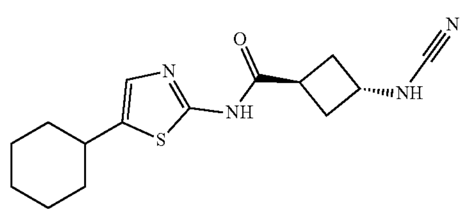 [SMILES: N#CN[C@H]1C[C@H](C(=O)Nc2ncc(C3CCCCC3)s2)C1] | trans-3-(cyanoamino)-N-(5-cyclohexyl-1,3-thiazol-2-yl)cyclobutane-1-carboxamide | LC-MS (ESI) m/z 305.2 [M + H ]+ |
| Compound 5-8 | 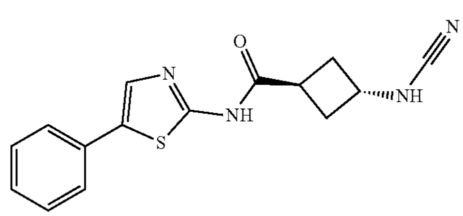 [SMILES: N#CN[C@H]1C[C@H](C(=O)Nc2ncc(-c3ccccc3)s2)C1] | trans-3-(cyanoamino)-N-(5-phenyl-1,3-thiazol-2-yl)cyclobutane-1-carboxamide | LC-MS (ESI) m/z 299.2 [M + H ]+ |

-continued

| Example No. | Structure | Chemical Name | MS m/z [M + H]+ |
|---|---|---|---|
| Compound 5-9 | 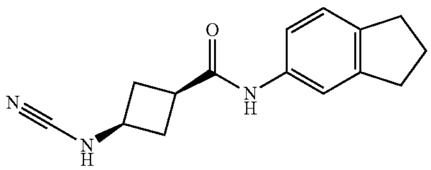 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide | LC-MS (ESI) m/z 256.2 [M + H]+ |
| Compound 5-10 | 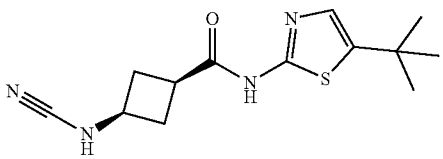 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide | LC-MS (ESI) m/z 279.2 [M + H]+ |
| Compound 5-11 | 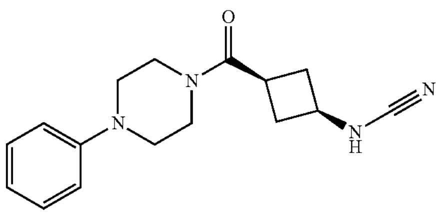 [SMILES: N#CN[C@H]1C[C@@H](C(=O)N2CCN(c3ccccc3)CC2)C1] | {[cis-3-(4-phenylpiperazine-1-carbonyl)cyclobutyl]amino}carbonitrile | LC-MS (ESI) m/z 285.3 [M + H]+ |
| Compound 5-12 | 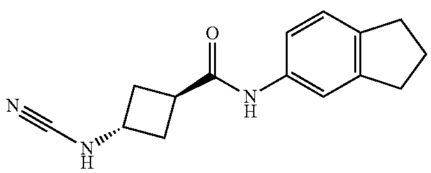 [SMILES: N#CN[C@H]1C[C@H](C(=O)Nc2ccc3c(c2)CCC3)C1] | trans-3-(cyanoamio)-N-(2,3-dihydro-1H-inden-5-yl)cyclobutane-1-carboxamide | LC-MS (ESI) m/z 256.2 [M + H]+ |
| Compound 5-13 | 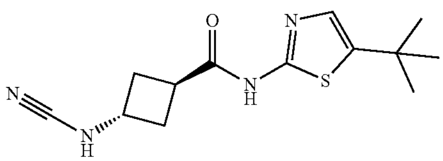 [SMILES: CC(C)(C)c1cnc(NC(=O)[C@H]2C[C@H](NC#N)C2)s1] | trans-N-(5-tert-butyl-1,3-thiazol-2-yl)-3-(cyanoamino)cyclobutane-1-carboxamide | LC-MS (ESI) m/z 279.2 [M + H]+ |
| Compound 5-14 | 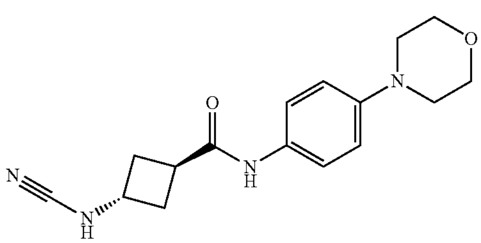 [SMILES: N#CN[C@H]1C[C@H](C(=O)Nc2ccc(N3CCOCC3)cc2)C1] | trans-3-(cyanoamino)-N-[4-(morpholin-4-yl)phenyl]cylobutane-1-carboxamide | LC-MS (ESI) m/z 301.2 [M + H]+ |

Example 6: {[(1r,3r)-3-[(4S)-4-[(5-cyclohexyl-1,3-thiazol-2-yl)amino]-2-oxopyrrolidin-1-yl]cyclobutyl]amino}formonitrile (Compound 6-1)

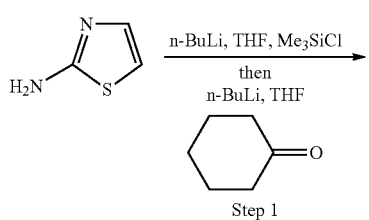

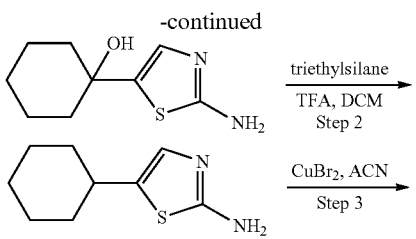

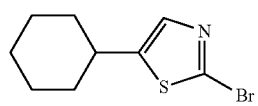

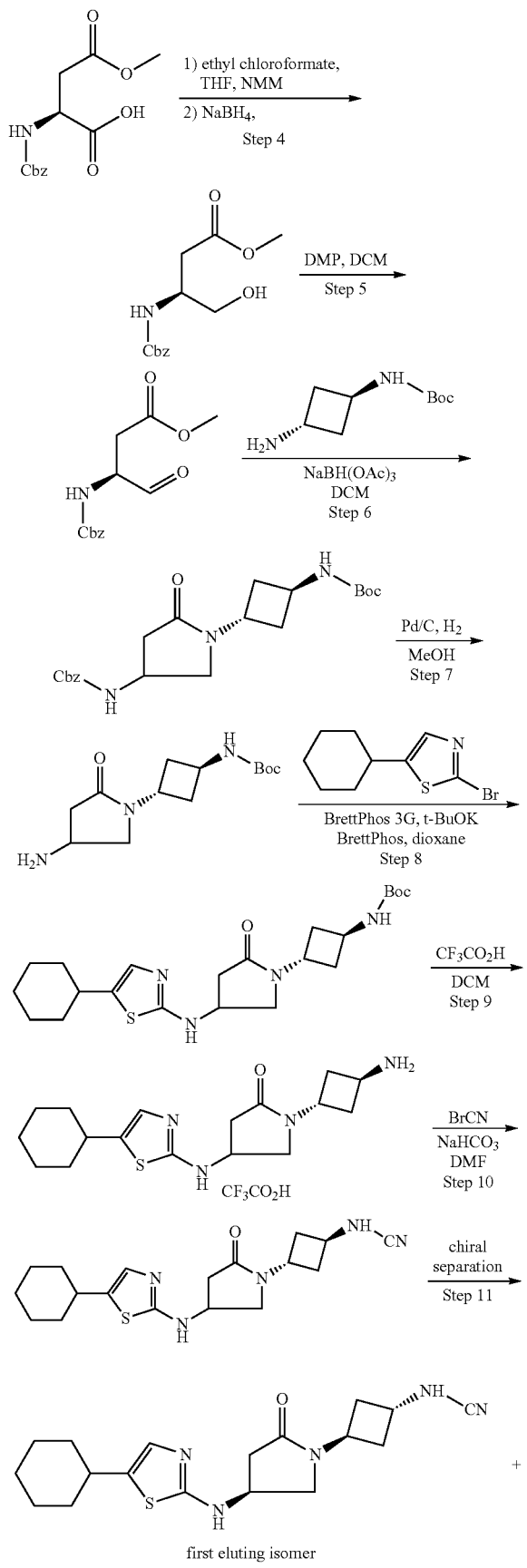

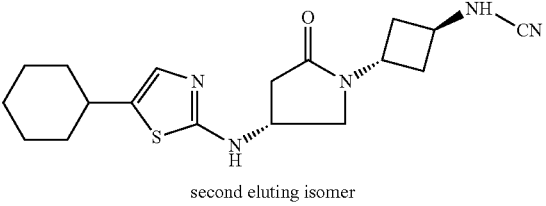

second eluting isomer

Step 1.
1-(2-Amino-1,3-thiazol-5-yl)cyclohexan-1-ol

A solution of n-BuLi (2.5 M in hexane)(200 mL) was added to a solution of 1,3-thiazol-2-amine (25.0 g, 0.250 mol) in THF (200 mL) at −78° C. and then the mixture was stirred for 15 min at −78° C. Trimethylchlorosilane (54.5 g, 0.500 mol) was added at −78° C. The resulting mixture was stirred for 30 min at −25° C. A solution of n-BuLi (2.5 M in hexane) (100 mL) was added at −78° C. and the mixture was stirred for 15 min at −78° C. Cyclohexanone (27.0 g, 0.275 mol) was added and the resulting mixture was stirred for an additional 30 min at −78° C. The reaction was quenched with ammonium chloride (200 mL sat.) at −78° C. The resulting mixture was extracted with ethyl acetate (3×200 mL). The combined organic layers were washed with brine (200 mL), dried over anhydrous sodium sulfate, filtered and concentrated under vacuum to afford 1-(2-amino-1,3-thiazol-5-yl)cyclohexan-1-ol as a brown solid (26.0 g). LCMS (ES, m/z) 199 [M+H]$^+$.

Step 2. 5-Cyclohexyl-1,3-thiazol-2-amine

Triethylsilane (122 g, 1.05 mol) and TFA (90 mL) were added to a solution of 1-(2-amino-1,3-thiazol-5-yl)cyclohexan-1-ol (23.0 g, 115 mmol) in DCM (500 mL), and the reaction mixture stirred for 1 h at 25° C. The resulting mixture was concentrated under vacuum. The residue was re-crystallized from ethyl ether (50 mL). The solids were collected by filtration to afford 5-cyclohexyl-1,3-thiazol-2-amine as an off-white solid (18.0 g). LCMS (ES, m/z): 183 [M+H]$^+$.

Step 3. 2-Bromo-5-cyclohexyl-1,3-thiazole tert-Butyl nitrite (8.83 mL, 81.4 mmol) was added into a stirring mixture of 5-cyclohexyl-1,3-thiazol-2-amine (10.0 g, 54.9 mmol) and CuBr$_2$(24.5 g, 108 mmol) in ACN (200 mL) at 0° C. The resulting mixture was stirred for 1.5 h at 25° C. The reaction was quenched by the addition of water (100 mL). The solvent was removed under vacuum. The residue was extracted with dichloromethane (3×300 mL). The combined organic layers were dried over anhydrous sodium sulfate. After filtration, the filtrate was concentrated under reduced pressure. The residue was purified by silica gel chromatography (eluting with 1:10 ethyl acetate/petroleum ether) to afford 2-bromo-5-cyclohexyl-1,3-thiazole as yellow oil (10.8 g). LCMS (ES, m/z): 246,248 [M+H]$^+$.

Step 4. Methyl (3S)-3-[[(benzyloxy)carbonyl]amino]-4-hydroxybutanoate

A solution of (2S)-2-[[(benzyloxy)carbonyl]amino]-4-methoxy-4-oxobutanoic acid (8.00 g, 27.1 mmol), NMM (2.88 g, 27.1 mmol), and ethyl chloroformate (4.01 g, 35.1 mmol) in THF (50 mL) was stirred for 10 min at −10° C. To the above mixture was added NaBH$_4$ (5.38 g, 135 mmol) in one portion at −10° C. Methanol (70 mL) was added dropwise at −10° C., and the resulting mixture was stirred for additional 30 min at 0° C. The solvent was removed under vacuum. The pH value of the residue was adjusted to 6 with hydrochloric acid (1 N) at 0° C. The resulting mixture was extracted with DCM (3×50 mL). The combined organic layers were dried over anhydrous sodium sulfate, filtered, and concentrated under vacuum. The residue was purified by reverse phase chromatography (Column, C18 silica gel; Mobile phase, A: water (containing 10 mM NH$_4$HCO$_3$) and B: ACN (10% to 50% in 10 min); Detector, UV 254/220 nm) to afford methyl (3S)-3-[[(benzyloxy)carbonyl]amino]-4-hydroxybutanoate as colorless oil (3.00 g). LCMS (ES, m/z) 268 [M+H]$^+$.

Step 5. Methyl (3S)-3-[[(benzyloxy)carbonyl]amino]-4-oxobutanoate

DMP (6.77 g, 15.2 mmol) was added in portions to a 0° C. solution of methyl (3S)-3-[[(benzyloxy)carbonyl]amino]-4-hydroxybutanoate (3.00 g, 10.1 mmol) in DCM (40 mL). The mixture was stirred for 2 h at 25° C. The reaction was quenched with saturated aqueous sodium thiosulfate (10 mL). The solids were filtered out and the filter cake was washed with DCM (3×10 mL). The filtrate was washed with sodium bicarbonate (2×20 mL, sat.). The combined organic layers were dried over anhydrous sodium sulfate. After filtration, the filtrate was concentrated under reduced pressure. The residue was purified by reverse phase chromatography (Column, C18 silica gel; Mobile phase, A: water (containing 10 mM NH$_4$HCO$_3$) and B: ACN (5% to 50% in 5 min); Detector, UV 254/220 nm) to afford methyl (3S)-3-[[(benzyloxy)carbonyl]amino]-4-oxobutanoate as yellow oil (2.00 g). LCMS (ES, m/z) 266 [M+H]$^+$.

Step 6. Benzyl N-[(3S)-5-oxo-1-[(1r,3r)-3-[[(tert-butoxy)carbonyl]amino]cyclobutyl]pyrrolidin-3-yl]carbamate A solution of tert-butyl N-[(trans)-3-aminocyclobutyl]carbamate (545 mg, 2.78 mmol) and methyl (3S)-3-[[(benzyloxy)carbonyl]amino]-4-oxobutanoate (820 mg, 2.78 mmol) in DCM (30 mL) was stirred for 1 h at 25° C. Sodium triacetoxyborohydride (807 mg, 3.62 mmol) was added in two portions, and the resulting mixture was stirred for additional 14 h at 25° C. The reaction was quenched by the addition of water/ice (30 mL). The resulting mixture was extracted with DCM (2×50 mL). The combined organic layers were washed with brine (50 mL), dried over anhydrous sodium sulfate, filtered and concentrated under vacuum. The residue was treated with DMF (5 mL). The solids were collected by filtration, washed with MeOH (3×10 mL) and dried in an oven to afford benzyl N-[(3S)-5-oxo-1-[(trans)-3-[[(tert-butoxy)carbonyl]amino]cyclobutyl]pyrrolidin-3-yl]carbamate as a white solid (800 mg). LCMS (ES, m/z) 404 [M+H]$^+$.

Step 7. tert-butyl N-[(1r,3r)-3-(4-amino-2-oxopyrrolidin-1-yl)cyclobutyl]carbamate A mixture of benzyl N-[(3S)-5-oxo-1-[(1r,3r)-3-[[(tert-butoxy)carbonyl]amino]cyclobutyl]pyrrolidin-3-yl]carbamate (800 mg, 1.99 mmol) and palladium on carbon (500 mg, 10%) in methanol (30 mL) was stirred for 4 h at 25° C. under hydrogen atmosphere (balloon). The solids were filtered out and the filter cake was washed with methanol (2×5 mL). The filtrate was concentrated under reduced pressure to afford tert-butyl N-[(trans)-3-(4-amino-2-oxopyrrolidin-1-yl)cyclobutyl]carbamate as colorless oil (480 mg). LCMS (ES, m/z) 270 [M+H]$^+$.

Step 8. tert-butyl N-[(trans)-3-[4-[(5-cyclohexyl-1,3-thiazol-2-yl)amino]-2-oxopyrrolidin-1-yl]cyclobutyl]carbamate A mixture of tert-butyl N-[(trans)-3-(4-amino-2-oxopyrrolidin-1-yl)cyclobutyl]carbamate (300 mg, 1.12 mmol), 2-bromo-5-cyclohexyl-1,3-thiazole (360 mg, 1.32 mmol), BrettPhos (120 mg, 0.220 mmol), 3$^{rd}$ generation BrettPhos precatalyst (100 mg, 0.100 mmol), and t-BuOK (180 mg, 1.52 mmol) in dioxane (20 mL) was stirred for 1 h at 100° C. After cooling to 25° C., the reaction was quenched by the addition of water (30 mL). The resulting mixture was extracted with ethyl acetate (2×30 mL). The combined organic layers were washed with brine (30 mL), dried over anhydrous sodium sulfate, filtered and concentrated under vacuum. The residue was purified by reverse phase chromatography (Column, C18 silica gel; Mobile phase, A: water (containing 10 mM NH$_4$HCO$_3$) and B: ACN (30% to 70% in 10 min); Detector, UV 254/220 nm) to afford tert-butyl N-[(trans)-3-[4-[(5-cyclohexyl-1,3-thiazol-2-yl)amino]-2-oxopyrrolidin-1-yl]cyclobutyl]carbamate as a yellow solid (300 mg). LCMS (ES, m/z) 435 [M+H]$^+$.

Step 9. 4-[(5-cyclohexyl-1,3-thiazol-2-yl)amino]-1-[(trans)-3-aminocyclobutyl]pyrrolidin-2-one 2,2,2-trifluroacetate A solution of tert-butyl N-[(trans)-3-[4-[(5-cyclohexyl-1,3-thiazol-2-yl)amino]-2-oxopyrrolidin-1-yl]cyclobutyl]carbamate (180 mg, 0.331 mmol) and TFA (1 mL) in DCM (5 mL) was stirred for 1 h at 25° C. The resulting mixture was concentrated under vacuum to afford 4-[(5-cyclohexyl-1,3-thiazol-2-yl)amino]-1-[(trans)-3-aminocyclobutyl]pyrrolidin-2-one 2,2,2-trifluoroacetate as yellow oil (200 mg). LCMS (ES, m/z) 335 [M+H]$^+$.

Step 10. [[(trans)-3-[4-[(5-cyclohexyl-1,3-thiazol-2-yl)amino]-2-oxopyrrolidin-1-yl]cyclobutyl]amino]formonitrile A mixture of 4-[(5-cyclohexyl-1,3-thiazol-2-yl)amino]-1-[(trans)-3-aminocyclobutyl]pyrrolidin-2-one 2,2,2-trifluoroacetate (200 mg, 0.464 mmol) and NaHCO$_3$ (315 mg, 3.56 mmol) in DMF (4 mL) was stirred for 30 min at 0° C. A solution of cyanogen bromide (40.0 mg, 0.360 mmol) in DMF (1 mL) was added dropwise at 0° C. The resulting mixture was stirred for 14 h at 25° C. The reaction was quenched by the addition of water/ice (10 mL). The resulting mixture was extracted with ethyl acetate (2×20 mL). The combined organic layers were washed with brine (20 mL), dried over anhydrous sodium sulfate, filtered and concentrated under vacuum. The residue was purified by Prep-HPLC (Column: XBridge Shield RP18 OBD, 5 µm, 19×150 mm; Mobile Phase, A: water (containing 10 mM ammonium bicarbonate) and B: CH$_3$CN (2% to 40% over 1 min); Detector: UV 254/220 nm). The product fractions were lyophilized to afford [[(1r,3r)-3-[4-[(5-cyclohexyl-1,3-thiazol-2-yl)amino]-2-oxopyrrolidin-1-yl]cyclobutyl]amino]formonitrile as a white solid (70 mg). LCMS (ES, m/z) 360 [M+H]$^+$.

Step 11. {[(1r,3r)-3-[(4S)-4-[(5-cyclohexyl-1,3-thi-azol-2-yl)amino]-2-oxopyrrolidin-1-yl]cyclobutyl]amino}formonitrile

[[(1r,3r)-3-[4-[(5-Cyclohexyl-1,3-thiazol-2-yl)amino]-2-oxopyrrolidin-1-yl]cyclobutyl]amino]formonitrile (70.0 mg, 0.175 mmol) was separated by Chiral-HPLC (Column: CHIRALPAK IE, 2×25 cm, 5 μm; Mobile Phase A: MTBE (containing 0.2% IPA) and B: EtOH (hold 20% in 14 min); Flow rate: 17 mL/min; Detector: 220/254 nm; $RT_1$: 9.148 min; $RT_2$: 11.792 min). The first eluting isomer ($RT_1$=9.148 min) was collected and lyophilized to afford a yellow oil arbitrarily assigned as {[(1r,3r)-3-[(4S)-4-[(5-cyclohexyl-1,3-thiazol-2-yl)amino]-2-oxopyrrolidin-1-yl]cyclobutyl]amino}formonitrile (28.3 mg). $^1$H-NMR (DMSO-d6, 400 MHz) δ (ppm): 7.68 (br s, 1H), 7.24 (br s, 1H), 6.72 (s, 1H), 4.73-4.69 (m, 1H), 4.26-4.24 (m, 1H), 3.80-3.72 (m, 2H), 3.26-3.21 (m, 1H), 2.71-2.59 (m, 2H), 2.51-2.46 (m, 1H), 2.25-2.20 (m, 1H), 2.11-2.06 (m, 2H), 1.89-1.87 (m, 2H), 1.74-1.71 (m, 2H), 1.66-1.63 (m, 1H), 1.37-1.13 (m, 6H). LCMS (ES, m/z) 360 [M+H]$^+$. The second eluting isomer (RT=11.792 min) was collected and lyophilized to afford a yellow oil arbitrarily assigned as {[(1r,3r)-3-[(4R)-4-[(5-cyclohexyl-1,3-thiazol-2-yl)amino]-2-oxopyrrolidin-1-yl]cyclobutyl]amino}formonitrile (26.2 mg). LCMS (ES, m/z) 360 [M+H]$^+$.

Example 7. ([(2r,4s)-6-(5-tert-butyl-4-chloro-1,3-thiazol-2-yl)-5-oxo-6-azaspiro[3.4]octan-2-yl]amino)carbonitrile (Compound 7-1)

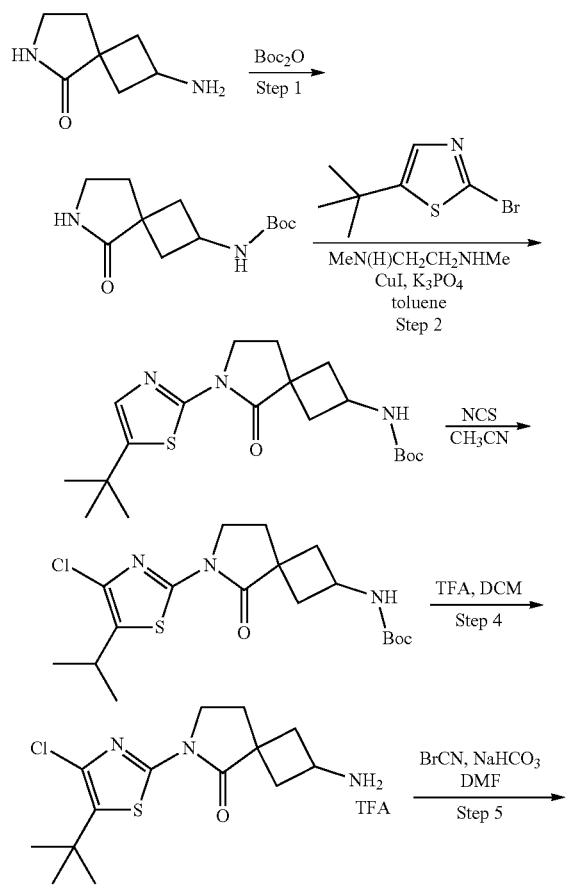

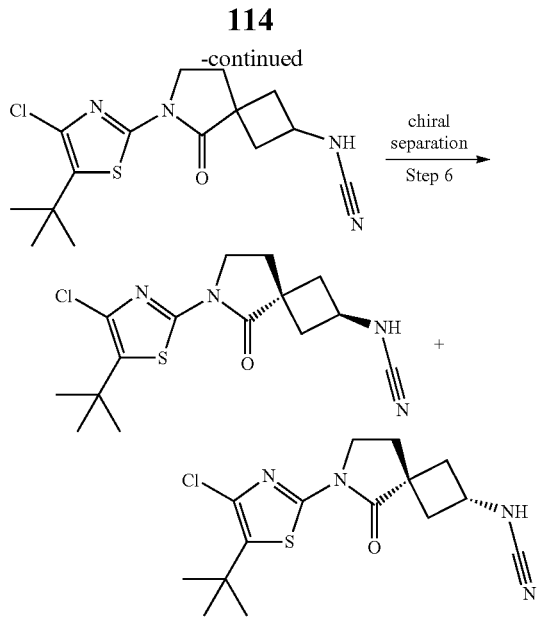

Step 1. tert-butyl N-[5-oxo-6-azaspiro[3.4]octan-2-yl]carbamate

Di-tert-butyl dicarbonate (0.600 mL, 2.73 mmol) was added to a solution of 2-amino-6-azaspiro[3.4]octan-5-one (300 mg, 2.14 mmol) and $Na_2CO_3$ (454 mg, 4.24 mmol) in dioxane (5 mL) and water (0.5 mL) and the solution stirred for 4 h at 25° C. The resulting mixture was diluted with water (10 mL) and extracted with ethyl acetate (3×50 mL). The combined organic layers were dried over anhydrous sodium sulfate, filtered and concentrated under vacuum. The residue was purified by reverse phase chromatography (Column, C18 silica gel; Mobile phase, A: water (containing 10 mM $NH_4HCO_3$) and B: ACN (5% to 50% in 5 min); Detector, UV 254/220 nm) to afford tert-butyl N-[5-oxo-6-azaspiro[3.4]octan-2-yl]carbamate as a white solid (400 mg). LCMS (ES, m/z) 241 [M+H]$^+$.

Step 2. tert-butyl N-[6-(5-tert-butyl-1,3-thiazol-2-yl)-5-oxo-6-azaspiro[3.4]octan-2-yl]carbamate A mixture of tert-butyl N-[5-oxo-6-azaspiro[3.4]octan-2-yl]carbamate (654 mg, 2.59 mmol), 2-bromo-5-tert-butyl-1,3-thiazole (600 mg, 2.59 mmol), $K_3PO_4$ (1.67 g, 7.79 mmol), CuI (99.6 mg, 0.518 mmol), and methyl[2-(methylamino)ethyl]amine (115 mg, 1.30 mmol) in toluene (12 mL) was stirred for 16 h at 100° C. After cooling to 25° C., the reaction was quenched by the addition of water (50 mL). The resulting mixture was extracted with ethyl acetate (3×100 mL). The combined organic layers were washed with brine (100 mL), dried over anhydrous sodium sulfate. After filtration, the filtrate was concentrated under reduced pressure. The residue was purified by silica gel chromatography (eluting with 3:7 petroleum ether/ethyl acetate) to afford N-[6-(5-tert-butyl-1,3-thiazol-2-yl)-5-oxo-6-azaspiro[3.4]octan-2-yl]carbamate as a yellow solid (690 mg). LCMS (ES, m/z): 380 [M+H]$^+$.

Step 3. tert-butyl N-[6-(5-tert-butyl-4-chloro-1,3-thiazol-2-yl)-5-oxo-6-azaspiro[3.4]octan-2-yl]carbamate A solution of tert-butyl N-[6-(5-tert-butyl-1,3-thiazol-2-yl)-5-oxo-6-azaspiro[3.4]octan-2-yl]carbamate (600 mg, 1.50 mmol) and NCS (300 mg, 2.25 mmol) in acetonitrile (10 mL) was stirred for 16 h at 60° C. The mixture was allowed to cool down to 25° C. The reaction was quenched by the addition of water (20 mL). The resulting mixture was extracted with ethyl acetate (3×50 mL). The combined organic layers were dried over anhydrous sodium sulfate. After filtration, the filtrate was concentrated under reduced pressure. The residue was purified by silica gel chromatography (eluting with 1:1 petroleum ether/ethyl acetate) to afford tert-butyl N-[6-(5-tert-butyl-4-chloro-1,3-thiazol-2-yl)-5-oxo-6-azaspiro[3.4]octan-2-yl]carbamate as yellow oil (270 mg). LCMS (ES, m/z): 414, 416 [M+H]+.

Step 4. 2-amino-6-(5-tert-butyl-4-chloro-1,3-thiazol-2-yl)-6-azaspiro[3.4]octan-5-one 2,2,2-trifluoroacetate A solution of tert-butyl N-[6-(5-tert-butyl-4-chloro-1,3-thiazol-2-yl)-5-oxo-6-azaspiro[3.4]octan-2-yl]carbamate (200 mg, 0.460 mmol) and TFA (2 mL) in DCM (5 mL) was stirred for 1 h at 25° C. The resulting mixture was concentrated under vacuum to afford 2-amino-6-(5-tert-butyl-4-chloro-1,3-thiazol-2-yl)-6-azaspiro[3.4]octan-5-one 2,2,2-trifluroacetate as yellow oil (210 mg). LCMS (ES, m/z): 314, 316 [M+H]+.

Step 5. [[6-(5-tert-butyl-4-chloro-1,3-thiazol-2-yl)-5-oxo-6-azaspiro[3.4]octan-2-yl]amino]formonitrile A mixture of 2-amino-6-(5-tert-butyl-4-chloro-1,3-thiazol-2-yl)-6-azaspiro[3.4]octan-5-one 2,2,2-trifluroacetate (150 mg, 0.365 mmol), NaHCO₃ (132 mg, 1.58 mmol) and BrCN (33.4 mg, 0.320 mmol) in DMF (3 mL) was stirred for 4 h at 25° C. The reaction was quenched by the addition of water (10 mL). The resulting mixture was extracted with ethyl acetate (3×30 mL). The combined organic layers were washed with brine (30 mL), dried over anhydrous sodium sulfate. After filtration, the filtrate was concentrated under reduced pressure. The residue was purified by Prep-HPLC (Column: XBridge Prep Phenyl OBD Column, 5 μm, 19×150 mm; Mobile Phase, A: water (containing 0.05% ammonium bicarbonate) and B: CH₃CN (13% to 37% in 7 min); Detector: UV 254 nm). The product fractions were lyophilized to afford [[6-(5-tert-butyl-4-chloro-1,3-thiazol-2-yl)-5-oxo-6-azaspiro[3.4]octan-2-yl]amino]formonitrile as a white solid (70.0 mg). LCMS (ES, m/z): 314, 316 [M+H]+.

Step 6. [[(2s,4r)-6-(5-tert-butyl-4-chloro-1,3-thiazol-2-yl)-5-oxo-6-azaspiro[3.4]octan-2-yl]amino]formonitrile and [[(2r,4s)-6-(5-tert-butyl-4-chloro-,3-thiazol-2-yl)-5-oxo-6-azaspiro[3.4]octan-2-yl]amino]formonitrile

[[6-(5-tert-butyl-4-chloro-1,3-thiazol-2-yl)-5-oxo-6-azaspiro[3.4]octan-2-yl]amino]formonitrile (70.0 mg, 0.223 mmol) was separated by Chiral-HPLC (Column, CHIRAL-PAK IA, 5 μm, 2×25 cm; Mobile phase, A: hexane and B: ethanol (hold 30% in 10 min); flow rate: 20 m/min; Detector: 254 and 220 nm; RT₁: 7.043 min; RT₂: 8.368 min). The product fraction (RT: 7.043 min) was lyophilized to afford a white solid arbitrarily assigned as [[(2s,4r)-6-(5-tert-butyl-4-chloro-1,3-thiazol-2-yl)-5-oxo-6-azaspiro[3.4]octan-2-yl]amino]formonitrile (22.6 mg). ¹H-NMR (DMSO-d6, 400 MHz) δ (ppm): 7.35 (br s, 1H), 3.89-3.86 (m, 2H), 3.83-3.82 (m, 1H), 2.34-2.23 (m, 6H), 1.41 (s, 9H). LCMS (ES, m/z): 339, 341[M+H]+.

The product fraction (RT: 8.368 min) was lyophilized to afford a white solid arbitrarily assigned as [[(2r,4s)-6-(5-tert-butyl-4-chloro-1,3-thiazol-2-yl)-5-oxo-6-azaspiro[3.4]octan-2-yl]amino]formonitrile (15.1 mg). ¹H-NMR (DMSO-d6, 400 MHz) δ (ppm): 7.30 (br s, 1H), 3.88-3.85 (m, 2H), 3.81-3.80 (m, 1H), 2.63-2.62 (m, 2H), 2.28-2.24 (m, 2H), 2.16-2.12 (m, 2H), 1.42 (s, 9H). LCMS (ES, m/z): 339, 341[M+H]+.

The following compounds were synthesized according to Example 7:

| Example No. | Structure | Chemical Name | MS m/z [M + H]+ | 1H NMR |
|---|---|---|---|---|
| Compound 7-2 | 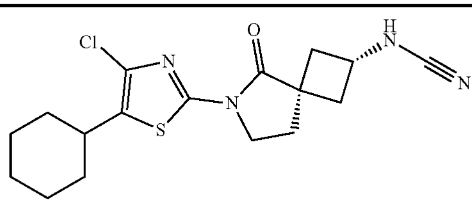 | {[(2s,4r)-6-(4-chloro-5-cyclohexyl-1,3-thiazol-2-yl)-5-oxo-6-azaspiro[3.4]octan-2-yl]amino}carbonitrile | 365, 367 | 7.35 (br s, 1H), 3.92-3.88 (m, 2H), 3.83-3.79 (m, 1H), 2.86-2.85 (m, 1H), 2.32-2.24 (m, 6H), 1.90-1.87 (m, 2H), 1.79-1.76 (m, 2H), 1.70-1.67 (m, 1H), 1.38-1.18 (m, 5H) |
| Compound 7-3 | 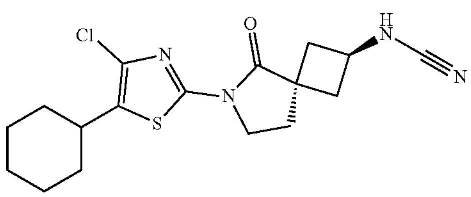 [SMILES: N#CN[C@H]1C[C@]2(CCN(c3nc(Cl)c(C4CCCCC4)s3)C2=O)C1] | {[(2r,4s)-6-(4-chloro-5-cyclohexyl-1,3-thiazol-2-yl)-5-oxo-6-azaspiro[3.4]octan-2-yl]amino}carbonitrile | 365, 367 | 7.28 (br s, 1H), 3.90-3.87 (m, 2H), 3.84-3.78 (m, 1H), 2.86-2.85 (m, 1H), 2.66-2.61 (m, 2H), 2.28-2.25 (m, 2H), 2.15-2.08 (m, 2H), 1.90-1.87 (m, 2H), 1.79-1.76 (m, 2H), 1.70-1.67 (m, 1H), 1.41-1.18 (m, 5H) |

Example 8. N-(5-tert-butyl-4-chloro-1,3-thiazol-2-yl)-3-(cyanoamino)-1-methoxycyclobutane-1-carboxamide (Compound 8-1)

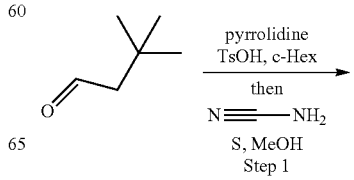

S, MeOH
Step 1

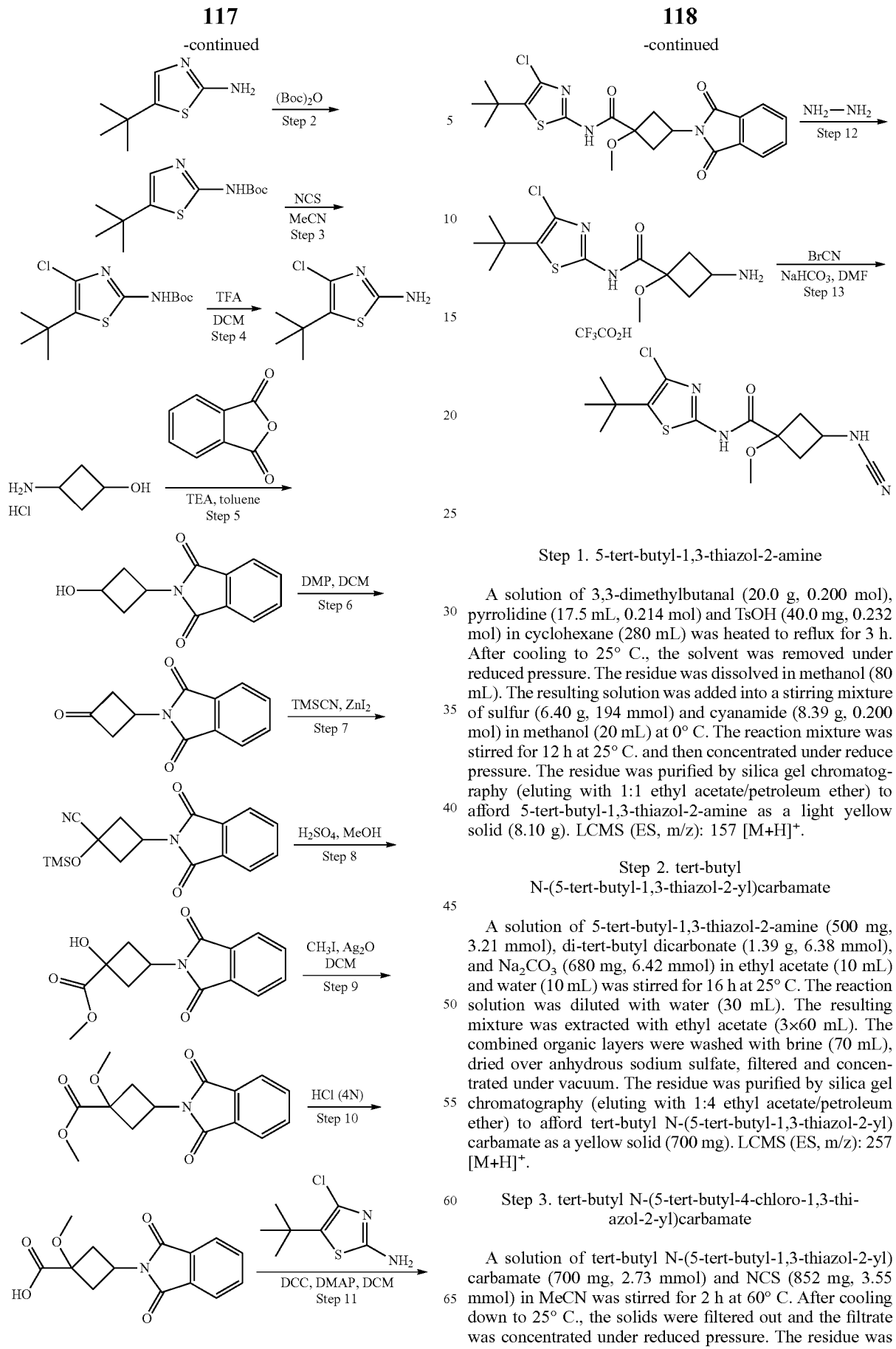

Step 1. 5-tert-butyl-1,3-thiazol-2-amine

A solution of 3,3-dimethylbutanal (20.0 g, 0.200 mol), pyrrolidine (17.5 mL, 0.214 mol) and TsOH (40.0 mg, 0.232 mol) in cyclohexane (280 mL) was heated to reflux for 3 h. After cooling to 25° C., the solvent was removed under reduced pressure. The residue was dissolved in methanol (80 mL). The resulting solution was added into a stirring mixture of sulfur (6.40 g, 194 mmol) and cyanamide (8.39 g, 0.200 mol) in methanol (20 mL) at 0° C. The reaction mixture was stirred for 12 h at 25° C. and then concentrated under reduce pressure. The residue was purified by silica gel chromatography (eluting with 1:1 ethyl acetate/petroleum ether) to afford 5-tert-butyl-1,3-thiazol-2-amine as a light yellow solid (8.10 g). LCMS (ES, m/z): 157 [M+H]$^+$.

Step 2. tert-butyl N-(5-tert-butyl-1,3-thiazol-2-yl)carbamate

A solution of 5-tert-butyl-1,3-thiazol-2-amine (500 mg, 3.21 mmol), di-tert-butyl dicarbonate (1.39 g, 6.38 mmol), and Na$_2$CO$_3$ (680 mg, 6.42 mmol) in ethyl acetate (10 mL) and water (10 mL) was stirred for 16 h at 25° C. The reaction solution was diluted with water (30 mL). The resulting mixture was extracted with ethyl acetate (3×60 mL). The combined organic layers were washed with brine (70 mL), dried over anhydrous sodium sulfate, filtered and concentrated under vacuum. The residue was purified by silica gel chromatography (eluting with 1:4 ethyl acetate/petroleum ether) to afford tert-butyl N-(5-tert-butyl-1,3-thiazol-2-yl)carbamate as a yellow solid (700 mg). LCMS (ES, m/z): 257 [M+H]$^+$.

Step 3. tert-butyl N-(5-tert-butyl-4-chloro-1,3-thiazol-2-yl)carbamate

A solution of tert-butyl N-(5-tert-butyl-1,3-thiazol-2-yl)carbamate (700 mg, 2.73 mmol) and NCS (852 mg, 3.55 mmol) in MeCN was stirred for 2 h at 60° C. After cooling down to 25° C., the solids were filtered out and the filtrate was concentrated under reduced pressure. The residue was diluted with water (50 mL) at 25° C. The resulting mixture was extracted with ethyl acetate (2×50 mL). The organic layers were combined, washed with brine (40 mL), dried over anhydrous sodium sulfate, filtered and concentrated under vacuum. The residue was purified by silica gel chromatography (eluting with 1:5 ethyl acetate/petroleum ether) to afford tert-butyl N-(5-tert-butyl-4-chloro-1,3-thiazol-2-yl)carbamate as a white solid (530 mg). LCMS (ES, m/z): 291, 293 [M+H]$^+$.

Step 4. 5-tert-butyl-4-chloro-1,3-thiazol-2-amine

A solution of tert-butyl N-(5-tert-butyl-4-chloro-1,3-thiazol-2-yl)carbamate (525 mg, 1.80 mmol) and TFA (2 mL) in DCM (5 mL) was stirred for 14 h at 25° C. The resulting mixture was concentrated under vacuum. The residue was purified by reverse phase chromatography (Column, C18 silica gel; Mobile phase, A: water (containing 10 Mm NH$_4$HCO$_3$) and B: ACN (10% to 50% in 8 min); Detector, UV 254/220 nm) to afford 5-tert-butyl-4-chloro-1,3-thiazol-2-amine as a yellow solid (310 mg). LCMS (ES, m/z): 191, 193 [M+H]$^+$.

Step 5. 2-(3-Hydroxycyclobutyl)-2,3,3a,7a-tetrahydro-1H-isoindole-1,3-dione

Triethylamine (20.2 mL, 192 mmol) was added to a solution of 3-aminocyclobutan-1-ol hydrochloride (10.0 g, 76.8 mmol) and 1,3-dihydro-2-benzofuran-1,3-dione (15.5 g, 100 mmol) in toluene (400 mL). The resulting mixture was stirred for 6 h at 120° C. After cooling to 25° C., the resulting mixture was concentrated under reduced pressure. The residue was purified by silica gel chromatography (eluting with 1:1 ethyl acetate/petroleum ether) to afford 2-(3-hydroxycyclobutyl)-2,3,3a,7a-tetrahydro-1H-isoindole-1,3-dione as a white solid (8.00 g). LCMS (ES, m/z): 218 [M+H]$^+$.

Step 6. 2-(3-Oxocyclobutyl)-2,3-dihydro-1H-isoindole-1,3-dione

DMP (7.91 g, 18.6 mmol) was added in portions to a 0° C. solution of 2-(3-hydroxycyclobutyl)-2,3-dihydro-1H-isoindole-1,3-dione (3.00 g, 12.4 mmol) in DCM (60 mL). The resulting mixture was stirred for 2 h at 25° C. The solids were filtered out and the filter cake was washed with DCM (3×20 mL). The filtrate was concentrated under reduced pressure. The residue was treated with ethyl acetate (20 mL). The solids were collected by filtration and dried in an oven to give 2-(3-oxocyclobutyl)-2,3-dihydro-1H-isoindole-1,3-dione as a white solid (2.70 g). LCMS (ES, m/z): 216 [M+H]$^+$.

Step 7. 3-(1,3-Dioxo-2,3-dihydro-1H-isoindol-2-yl)-1-hydroxycyclobutane-1-carbonitrile ZnI$_2$ (210 mg, 0.630 mmol) was added to a 0° C. solution of 2-(3-oxocyclobutyl)-2,3-dihydro-1H-isoindole-1,3-dione (7.50 g, 31.4 mmol) and TMSCN (200 mL). The resulting mixture was stirred for 20 h at 25° C., and then concentrated under vacuum. The residue was purified by silica gel chromatography (eluting with 1:1 ethyl acetate/petroleum ether) to afford 3-(1,3-dioxo-2,3-dihydro-1H-isoindol-2-yl)-1-hydroxycyclobutane-1-carbonitrile as a white solid (5.50 g). LCMS (ES, m/z): 315 [M+H]$^+$.

Step 8. Methyl 3-(1,3-dioxo-2,3-dihydro-1H-isoindol-2-yl)-1-hydroxycyclobutane-1-carboxylate H$_2$SO$_4$ (25.0 mL, con.) was added to a 0° C. solution of 3-(1,3-dioxo-2,3-dihydro-1H-isoindol-2-yl)-1-[(trimethylsilyl)oxy]cyclobutane-1-carbonitrile (6.00 g, 17.2 mmol) in MeOH (100 mL). The reaction mixture stirred for 3 h at 90° C. After cooling to 25° C., the solvent was removed under vacuum. The pH value of the residue was adjusted to 7-8 with saturated aqueous Na$_2$CO$_3$ solution. The resulting mixture was extracted with DCM (2×100 mL). The combined organic layers were dried over anhydrous sodium sulfate. After filtration, the filtrate was concentrated under reduced pressure. The residue was purified by reverse phase chromatography (Column, C18 silica gel; Mobile phase, A: water (containing 0.05% TFA) and B: ACN (10% to 50% in 10 min); Detector, UV 254/220 nm) to afford methyl 3-(1,3-dioxo-2,3-dihydro-1H-isoindol-2-yl)-1-hydroxycyclobutane-1-carboxylate (2.10 g) as a yellow solid. LCMS (ES, m/z): 276 [M+H]$^+$.

Step 9. Methyl 3-(1,3-dioxo-2,3-dihydro-1H-isoindol-2-yl)-1-methoxycyclobutane-1-carboxylate A mixture of methyl 3-(1,3-dioxo-2,3-dihydro-1H-isoindol-2-yl)-1-hydroxycyclobutane-1-carboxylate (500 mg, 1.64 mmol), CH$_3$I (0.540 mL, 8.21 mmol) and Ag$_2$O (4.00 g, 16.4 mmol) in DCM (8 mL) was stirred for 20 h at 40° C. The solids were filtered out and the filter cake was washed with DCM (2×10 mL). The filtrate was concentrated under reduced pressure. The residue was purified by reverse phase chromatography (Column, C18 silica gel; Mobile phase, A: water (containing 0.05% TFA) and B: ACN (40% to 80% in 10 min); Detector, UV 254/220 nm) to afford methyl 3-(1,3-dioxo-2,3-dihydro-1H-isoindol-2-yl)-1-methoxycyclobutane-1-carboxylate (200 mg) as a white solid. LCMS (ES, m/z): 290 [M+H]$^+$.

Step 10. 3-(1,3-Dioxo-2,3-dihydro-1H-isoindol-2-yl)-1-methoxycyclobutane-1-carboxylic acid A mixture of methyl 3-(1,3-dioxo-2,3-dihydro-1H-isoindol-2-yl)-1-methoxycyclobutane-1-carboxylate (400 mg, 1.38 mmol) and hydrochloric acid (8 mL, 4N) was stirred for 4 h at 90° C. After cooling to 25° C., the resulting mixture was concentrated under reduced pressure. The residue was purified by reverse phase chromatography (Column, C18 silica gel; Mobile Phase, A: water (containing 0.05% TFA) and B: CH$_3$CN (18% to 25% over 8 min); Detector: UV 220/254 nm) to afford 3-(1,3-dioxo-2,3-dihydro-1H-isoindol-2-yl)-1-methoxycyclobutane-1-carboxylic acid as a white solid (200 mg). LCMS (ES, m/z): 276 [M+H]$^+$.

Step 11. N-(5-tert-butyl-4-chloro-1,3-thiazol-2-yl)-3-(1,3-dioxo-2,3-dihydro-1H-isoindol-2-yl)-1-methoxycyclobutane-1-carboxamide A mixture of 3-(1,3-dioxo-2,3-dihydro-1H-isoindol-2-yl)-1-methoxycyclobutane-1-carboxylic acid (290 mg, 0.948 mmol), 5-tert-butyl-4-chloro-1,3-thiazol-2-amine (301 mg, 1.42 mmol), DCC (515 mg, 2.37 mmol) and DMAP (305 mg, 2.37 mmol) in DCM (10 mL) was stirred for 30 h at 25° C. The solids were filtered out and the filtrate was diluted with water (40 mL). The resulting mixture was extracted with DCM (2×40 mL). The combined organic layers were dried over anhydrous sodium sulfate, filtered, and concentrated under vacuum. The residue was purified by silica gel chromatography (eluting with 1:1 ethyl acetate/petroleum ether) to afford N-(5-tert-butyl-4-chloro-1,3-thiazol-2-yl)-3-(1,3-dioxo-2,3-dihydro-1H-isoindol-2-yl)-1-methoxycyclobutane-1-carboxamide as a yellow solid (150 mg). LCMS (ES, m/z): 448, 450 [M+H]+.

Step 12. 3-amino-N-(5-tert-butyl-4-chloro-1,3-thiazol-2-yl)-1-methoxycyclobutane-1-carboxamide 2,2,2-trifluoroacetate A solution of N-(5-tert-butyl-4-chloro-1,3-thiazol-2-yl)-3-(1,3-dioxo-2,3-dihydro-1H-isoindol-2-yl)-1-methoxycyclobutane-1-carboxamide (140 mg, 0.281 mmol) and hydrazine hydrate solution (0.140 mL, 80% in water) in EtOH (4 mL) stirred for 4 h at 50° C. After cooling to 25° C., the resulting mixture was concentrated under vacuum. The residue was purified by reverse phase chromatography (Column, C18 silica gel; Mobile phase, A: water (containing 0.05% TFA) and B: ACN (10% to 50/6 in 10 min); Detector, UV 254/220 nm) to afford 3-amino-N-(5-tert-butyl-4-chloro-1,3-thiazol-2-yl)-1-methoxycyclobutane-1-carboxamide 2,2,2-trifluoroacetate as a yellow solid (70.0 mg). LCMS (ES, m/z): 318, 320 [M+H]+.

Step 13. N-(5-tert-butyl-4-chloro-1,3-thiazol-2-yl)-3-(cyanoamino)-1-methoxycyclobutane-1-carboxamide A mixture of 3-amino-N-(5-tert-butyl-4-chloro-1,3-thiazol-2-yl)-1-methoxycyclobutane-1-carboxamide 2,2,2-trifluoroacetate (70.0 mg, 0.220 mmol), NaHCO3 (185 mg, 2.20 mmol) and BrCN (23.3 mg, 0.220 mmol) in DMF (2 mL) was stirred for 2 h at 25° C. The reaction was quenched by the addition of water/ice (5 mL). The resulting mixture was extracted with ethyl acetate (3×10 mL). The combined organic layers were washed with brine (5 mL), dried over anhydrous sodium sulfate. After filtration, the filtrate was concentrated under reduced pressure. The residue was purified by Prep-HPLC (Column: XBridge Shield RP18 OBD Column, 5 µm, 19×150 mm; Mobile Phase, A: water (containing 10 mM ammonium bicarbonate) and B: acetonitrile (65% to 75% in 7 min); Detector: UV 254 nm). The product fractions were lyophilized to afford N-(5-tert-butyl-4-chloro-1,3-thiazol-2-yl)-3-(cyanoamino)-1-methoxycyclobutane-1-carboxamide as a white solid (27.3 mg). 1H-NMR (DMSO-d6, 400 MHz) δ (ppm): 10.28 (br s, 1H), 7.30 (br s, 1H), 3.10 (s, 3H), 2.77-2.76 (m, 2H), 2.51-2.50 (m, 2H), 1.41 (s, 9H). LCMS (ES, m/z): 343, 345 [M+H]+.

Example 9. (1s,3s)-N-(5-tert-butyl-4-chloro-1,3-thiazol-2-yl)-1-chloro-3-(cyanoamino)cyclobutane-1-carboxamide (Compound 9-1) and (1r,3r)-N-(5-tert-butyl-4-chloro-1,3-thiazol-2-yl)-1-chloro-3-(cyanoamino)cyclobutane-1-carboxamide (Compound 9-2)

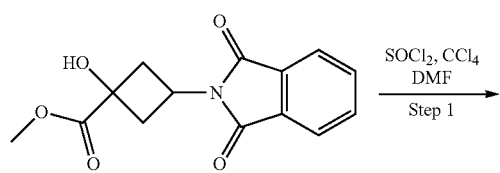

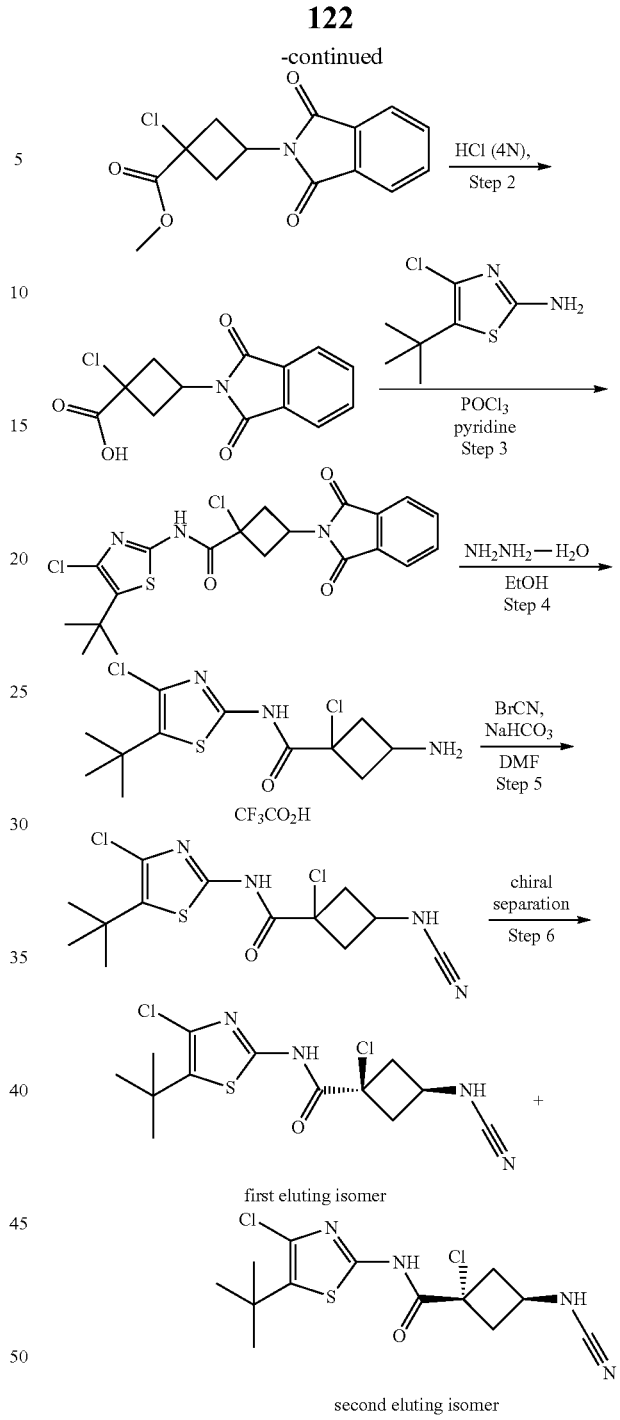

Step 1. Methyl 1-chloro-3-(1,3-dioxo-2,3-dihydro-1H-isoindol-2-yl)cyclobutane-1-carboxylate A solution of methyl 3-(1,3-dioxo-2,3-dihydro-1H-isoindol-2-yl)-1-hydroxycyclobutane-1-carboxylate (1.50 g, 4.90 mmol), DMF (3 mL) and SOCl2 (30 mL) in CCl4 (30 mL) was stirred for 30 h at 100° C. After cooling to 25° C., the resulting mixture was concentrated under reduced pressure. The residue was purified by reverse phase chromatography (Column, C18 silica gel; Mobile phase, A: water (0.05% TFA) and B: ACN (10% to 50% in 10 min); Detector, UV 254/220 nm) to afford methyl 1-chloro-3-(1,3-dioxo-2,3- dihydro-1H-isoindol-2-yl)cyclobutane-1-carboxylate as a white solid (500 mg). LCMS (ES, m/z): 294, 296 [M+H]$^+$.

Step 2. 1-Chloro-3-(1,3-dioxo-2,3-dihydro-1H-isoindol-2-yl)cyclobutane-1-carboxylic acid A mixture of methyl 1-chloro-3-(1,3-dioxo-2,3-dihydro-1H-isoindol-2-yl)cyclobutane-1-carboxylate (500 mg, 1.70 mmol) and hydrochloric acid (3 mL, 4 N) was stirred for 1 h at 90° C. After cooling down to 25° C., the resulting mixture was concentrated under vacuum. The residue was purified by reverse phase chromatography (Column, C18 silica gel; Mobile phase, A: water (containing 0.05% TFA) B: ACN (10% to 80% in 10 min); Detector, UV 254/220 nm) to afford 1-chloro-3-(1,3-dioxo-2,3-dihydro-1H-isoindol-2-yl)cyclobutane-1-carboxylic acid as a white solid (360 mg). LCMS (ES, m/z): 280, 282 [M+H]$^+$.

Step 3. N-(5-tert-butyl-4-chloro-1,3-thiazol-2-yl)-1-chloro-3-(1,3-dioxo-2,3-dihydro-1H-isoindol-2-yl)cyclobutane-1-carboxamide A solution of 1-chloro-3-(1,3-dioxo-2,3-dihydro-1H-isoindol-2-yl)cyclobutane-1-carboxylic acid (360 mg, 1.28 mmol) and 5-tert-butyl-4-chloro-1,3-thiazol-2-amine (294 mg, 1.39 mmol) in pyridine (10 mL) was stirred for 5 min at 0° C. POCl$_3$ (0.46 mL, 9.23 mmol) was added at 0° C., and the resulting mixture stirred for an additional 14 h at 0° C. The reaction was then quenched by the addition of ice/water (20 mL). The resulting mixture was extracted with ethyl acetate (2×40 mL). The combined organic layers were dried over anhydrous sodium sulfate, filtered and concentrated under vacuum. The residue was purified by silica gel chromatography (eluting with 1.1 ethyl acetate/petroleum ether) to afford N-(5-tert-butyl-4-chloro-1,3-thiazol-2-yl)-1-chloro-3-(1,3-dioxo-2,3-dihydro-1H-isoindol-2-yl)cyclobutane-1-carboxamide as a yellow solid (280 mg). LCMS (ES, m/z): 452, 454 [M+H]$^+$.

Step 4. 3-amino-N-(5-tert-butyl-4-chloro-1,3-thiazol-2-yl)-1-chlorocyclobutane-1-carboxamide 2,2,2-trifluoroacetate A solution of N-(5-tert-butyl-4-chloro-1,3-thiazol-2-yl)-1-chloro-3-(1,3-dioxo-2,3-dihydro-1H-isoindol-2-yl)cyclobutane-1-carboxamide (280 mg, 0.619 mmol) and hydrazine hydrate solution (0.29 mL, 80% in water) in EtOH (5 mL) was stirred for 2 h at 50° C. After cooling down to 25° C., the resulting mixture was concentrated under vacuum. The residue was purified by reverse phase chromatography (Column, C18 silica gel; Mobile phase, A: water (containing 0.05% TFA) and B: ACN (10% to 50% in 10 min); Detector, UV 254/220 nm) to afford 3-amino-N-(5-tert-butyl-4-chloro-1,3-thiazol-2-yl)-1-chlorocyclobutane-1-carboxamide 2,2,2-trifluoroacetate as a white solid (100 mg,). LCMS (ES, m/z): 322, 324 [M+H]$^+$.

Step 5. N-(5-tert-butyl-4-chloro-,3-thiazol-2-yl)-1-chloro-3-(cyanoamino)cyclobutane-1-carboxamide Sodium bicarbonate (182 mg, 2.06 mmol) was added into a stirring solution of 3-amino-N-(5-tert-butyl-4-chloro-1,3-thiazol-2-yl)-1-chlorocyclobutane-1-carboxamide 2,2,2-trifluoroacetate (100 mg, 0.228 mmol) in DMF (3 mL). The resulting solution was stirred for 0.5 h at 25° C. A solution of BrCN (23.0 mg, 0.206 mmol) in DMF (0.5 mL) was added at 0° C., and the resulting solution stirred for 14 h at 25° C. The reaction was then quenched by the addition of ice/water (10 mL). The resulting mixture was extracted with ethyl acetate (2×20 mL). The combined organic layers were dried over anhydrous sodium sulfate, filtered and concentrated under vacuum. The residue was purified by Prep-HPLC (Column: XBridge Prep C18 OBD Column, 5 μm, 19×150 mm; Mobile Phase, A: water (containing 10 mM ammonium bicarbonate) and B: CH$_3$CN (45% to 75% over 7 min); Detector: UV 254 nm). The product fractions were lyophilized to afford N-(5-tert-butyl-4-chloro-1,3-thiazol-2-yl)-1-chloro-3-(cyanoamino)cyclobutane-1-carboxamide as a white solid (30.0 mg). LCMS (ES, m/z): 347, 349 [M+H]$^+$.

Step 6. (1s,3s)-N-(5-tert-butyl-4-chloro-1,3-thiazol-2-yl)-1-chloro-3-(cyanoamino)cyclobutane-1-carboxamide N-(5-tert-butyl-4-chloro-1,3-thiazol-2-yl)-1-chloro-3-(cyanoamino)cyclobutane-1-carboxamide (30.0 mg, 0.086 mmol,) was separated by Chiral-HPLC (Column: CHIRAL-PAK IG, 2×25 cm, 5 μm; Mobile Phase A: n-hexane and B: EtOH (hold 10% in 30 min); Flow rate: 20 mL/min; Detector: 220 and 254 nm; RT$_1$: 18.708 min; RT$_2$: 21.346 min). The first product fractions (RT=18.708 min) were lyophilized to afford a white solid arbitrarily assigned as (1s,3s)-N-(5-tert-butyl-4-chloro-1,3-thiazol-2-yl)-1-chloro-3-(cyanoamino)cyclobutane-1-carboxamide (1.40 mg). $^1$H-NMR (DMSO-d6, 400 MHz) δ (ppm): 12.78 (br s, 1H), 7.50 (br s, 1H), 3.48-3.38 (m, 1H), 2.60-2.52 (m, 4H), 1.42 (s, 9H). LCMS (ES, m/z): 347,349 [M+H]$^+$. The second product fractions (RT=21.346 min) were lyophilized to afford a white solid arbitrarily assigned as (1r,3r)-N-(5-tert-butyl-4-chloro-1,3-thiazol-2-yl)-1-chloro-3-(cyanoamino)cyclobutane-1-carboxamide (25.0 mg). $^1$H-NMR (DMSO-d$_6$, 400 MHz) δ (ppm): 12.77 (br s, 1H), 7.31 (br s, 1H), 4.04-3.99 (m, 1H), 2.85-2.75 (m, 4H), 1.42 (s, 9H). LCMS (ES, m/z): 347, 349 [M+H]$^+$.

Example 10-1. cis-4-(cyanoamino)-N-(5-cyclohexyl-1,3-thiazol-2-yl)cyclohexane-1-carboxamide (Compound 10-1)

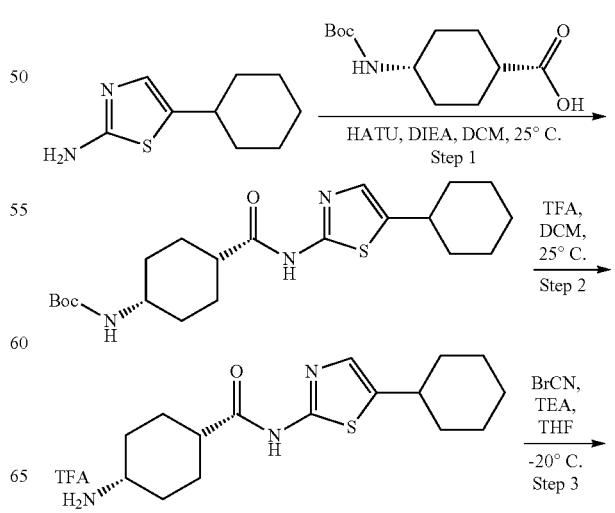

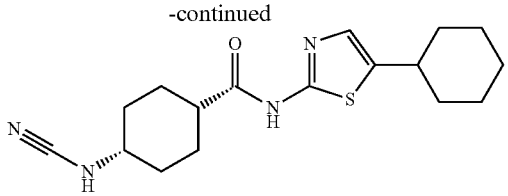

Step 1. cis-tert-butyl N-[4-[(5-cyclohexyl-1,3-thiazol-2-yl)carbamoyl]cyclohexyl]carbamate Into a 25 mL round-bottom flask was placed cis-4-[(tert-butoxy)carbonyl]aminocyclohexane-1-carboxylic acid (160 mg, 0.66 mmol), N,N-dimethylformamide (5 mL), N,N-diisopropylethylamine (212 mg, 1.64 mmol), HATU (417 mg, 1.10 mmol) and 5-cyclohexylthiazol-2-amine (100 mg, 0.49 mmol). The resulting solution was stirred for 18 h at 25° C. The resulting solution was poured into water (10 mL) and then extracted with ethyl acetate (3×10 mL). The organic layers were combined, dried over anhydrous sodium sulfate, filtered and concentrated under vacuum. The residue was purified by silica gel chromatography (eluting with 1:1 ethyl acetate/petroleum ether) to afford cis-tert-butyl N-[4-[(5-cyclohexyl-1,3-thiazol-2-yl)carbamoyl]cyclohexyl]carbamate as a yellow oil. LC-MS (ESI) m/z 408.2 [M+H]$^+$

Step 2. cis-4-amino-N-(5-cyclohexyl-1,3-thiazol-2-yl)cyclohexane-1-carboxamide TFA salt Into a 25 mL round-bottom flask was placed cis-tert-butyl N-[4-[(5-cyclohexyl-1,3-thiazol-2-yl)carbamoyl]cyclohexyl]carbamate (70 mg, 0.15 mmol), dichloromethane (4 mL) and trifluoroacetic acid (1 mL). The resulting solution was stirred for 2 h at 25° C. The reaction mixture was concentrated under vacuum. The residue was treated with ethyl ether and dried under vacuum to afford cis-4-amino-N-(5-cyclohexyl-1,3-thiazol-2-yl)cyclohexane-1-carboxamide TFA salt as a yellow oil. LC-MS (ESI) m/z 308.2 [M+H]$^+$

Step 3. cis-4-(cyanoamino)-N-(5-cyclohexyl-1,3-thiazol-2-yl)cyclohexane-1-carboxamide Into a 25 mL round-bottom flask was placed cis-4-amino-N-(5-cyclohexyl-1,3-thiazol-2-yl)cyclohexane-1-carboxamide TFA salt (40 mg, 0.12 mmol), tetrahydrofuran (5 mL) and triethylamine (26 mg, 0.26 mmol). Then cyanogen bromide (13 mg, 0.12 mmol) was added at −20° C. The resulting solution was stirred for 1 h at −20° C. The reaction mixture was poured into water (5 mL) and then extracted with ethyl acetate (3×5 mL). The residue was purified by prep-TLC (eluting with 10:1 dichloromethane/methanol), and further purified by prep-HPLC (Column: XBridge Shield RP18 OBD Column, 130 Å, 5 μm, 19 mm×150 mm; Mobile phase: water (10 mM NH$_4$HCO$_3$), MeCN (40% MeCN up to 65% over 7 min); Flow rate: 20 mL/min; Detector: 254 & 220 nm) to afford cis-4-(cyanoamino)-N-(5-cyclohexyl-1,3-thiazol-2-yl)cyclohexane-1-carboxamide. $^1$H NMR (300 MHz, DMSO-d6) δ11.83 (br s, 1H), 7.14 (s, 1H), 6.77 (s, 1H), 2.76-2.68 (m, 1H), 2.65-2.50 (m, 1H), 1.95-1.81 (m, 2H), 1.76-1.49 (m, 11H), 1.43-1.31 (m, 4H), 1.29-1.22 (m, 2H). LC-MS (ESI) m/z 333.2 [M+H]$^+$ The following compounds were prepared according to Example 10-1:

Compound 10-2. trans-4-(cyanoamino)-N-(5-cyclohexyl-1,3-thiazol-2-yl)cyclohexane-1-carboxamide

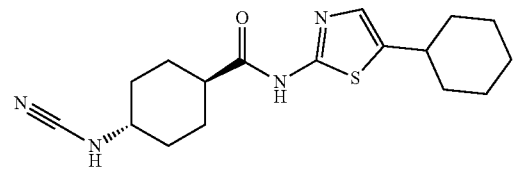 [SMILES: N#CN[C@H]1CC[C@H](C(=O)Nc2ncc(C3CCCCC3)s2)CC1]

$^1$H NMR (300 MHz, DMSO-d6), δ 11.85 (s, 1H), 7.14 (s, 1H), 6.86 (d, J=4.80 Hz, 1H), 3.00-2.91 (m, 1H), 2.75 (s, 1H), 2.44-2.36 (m, 1H), 1.94-1.84 (m, 6H), 1.73-1.64 (m, 3H), 1.54-1.42 (m, 2H), 1.38-1.23 (m, 7H).

LC-MS (ESI) m/z 333.2 [M+H]$^+$

Compound 10-3. (1R,2R)-2-(cyanoamino)-N-(5-cyclohexyl-1,3-thiazol-2-yl)cyclopentane-1-carboxamide

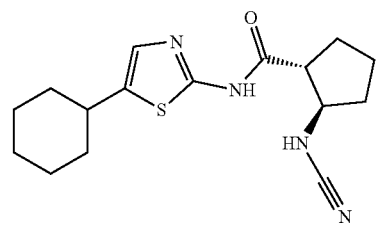 [SMILES: N#CN[C@@H]1CCC[C@H]1C(=O)Nc1ncc(C2CCCCC2)s1]

$^1$H NMR (300 MHz, DMSO-d6) δ 7.15 (s, 1H), 3.77-3.70 (m, 1H), 2.90-2.76 (m, 2H), 2.27-1.92 (m, 4H), 1.74-1.60 (m, 7H), 1.43-1.01 (m, 5H).

LC-MS (ESI) m/z 319.2 [M+H]$^+$

Compound 10-4. (1R,3S)-3-(cyanoamino)-N-(5-cyclohexyl-1,3-thiazol-2-yl)cyclohexane-1-carboxamide

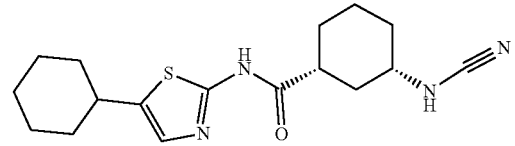 [SMILES: N#CN[C@H]1CCC[C@@H](C(=O)Nc2ncc(C3CCCCC3)s2)C1]

$^1$H NMR (300 MHz, DMSO-d$_6$) δ 11.88 (s, 1H), 7.14 (d, J=0.60 Hz, 1H), 6.91 (d, J=4.80 Hz, 1H), 2.98-2.97 (m, 1H), 2.76-2.53 (m, 1H), 2.50-2.49 (m, 1H), 1.97-1.64 (m, 9H), 1.30-1.26 (m, 9H).

LC-MS (ESI) m/z 333.1 [M+H]$^+$

Compound 10-5. (1S,3S)-3-(cyanoamino)-N-(5-cyclohexyl-1,3-thiazol-2-yl)cyclohexane-1-carboxamide

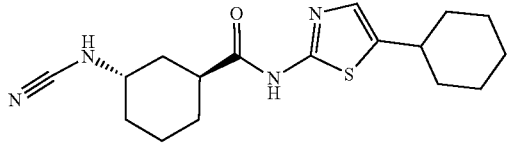 [SMILES: N#CN[C@H]1CCC[C@H](C(=O)Nc2ncc(C3CCCCC3)s2)C1]

¹H NMR (300 MHz, DMSO-d6) δ 11.88 (s, 1H), 7.14 (d, 0.1=0.60 Hz, 1H), 6.91 (d, 0.1=4.80 Hz, 1H), 2.98-2.97 (m, 1H), 2.76-2.53 (m, 1H), 2.50-2.49 (m, 1H), 1.97-1.64 (m, 9H), 1.30-1.26 (m, 9H).

LC-MS (ESI) m/z 333.1 [M+H]⁺

Compound 10-6. (1S,3R)-3-(cyanoamino)-N-(5-cyclohexyl-1,3-thiazol-2-yl)cyclohexane-1-carboxamide

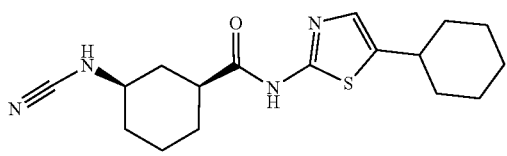 [SMILES: N#CN[C@@H]1CCC[C@H](C(=O)Nc2ncc(C3CCCCC3)s2)C1]

¹H NMR (300 MHz, DMSO-d₆), δ 11.88 (s, 1H), 7.14 (s, 1H), 6.92 (d, J=4.80 Hz, 1H), 3.03-2.93 (m, 1H), 2.76-2.74 (m, 1H), 2.58-2.54 (m, 1H), 2.01-1.64 (m, 9H), 1.42-1.39 (m, 9H).

LC-MS (ESI) m/z 333.1 [M+H]⁺

Compound 10-7. (1R,2S)-2-(cyanoamino)-N-(5-cyclohexyl-1,3-thiazol-2-yl)cyclopentane-1-carboxamide

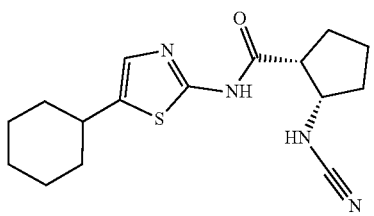 [SMILES: N#CN[C@H]1CCC[C@H]1C(=O)Nc1ncc(C2CCCCC2)s1]

¹H NMR (300 MHz, DMSO-d6) δ 7.09 (s, 1H), 3.75-3.62 (m, 1H), 2.95-2.70 (m, 2H), 2.13-1.88 (m, 4H), 1.67-1.42 (m, 7H), 1.47-0.82 (m, 5H).

LC-MS (ESI) m/z 319.2 [M+H]⁺

Compound 10-8. (1S,2R)-2-(cyanoamino)-N-(5-cyclohexyl-1,3-thiazol-2-yl)cyclopentane-1-carboxamide

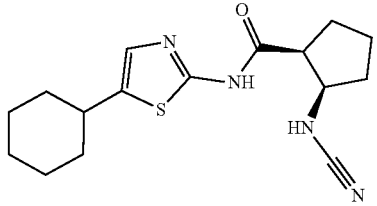 [SMILES: N#CN[C@@H]1CCC[C@@H]1C(=O)Nc1ncc(C2CCCCC2)s1]

¹H NMR (300 MHz, DMSO-d6) δ 7.09 (s, 1H), 3.72-3.68 (m, 1H), 2.87-2.78 (m, 2H), 2.00-1.80 (m, 4H), 1.68-1.39 (m, 7H), 1.36-0.96 (m, 5H).

LC-MS (ESI) m/z 319.2 [M+H]⁺

Compound 10-9. (1S,2S)-2-(cyanoamino)-N-(5-cyclohexyl-1,3-thiazol-2-yl)cyclopentane-1-carboxamide

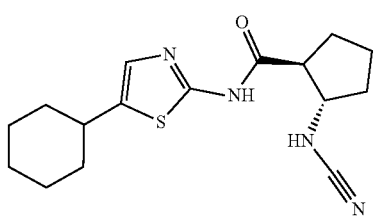 [SMILES: N#CN[C@H]1CCC[C@@H]1C(=O)Nc1ncc(C2CCCCC2)s1]

¹H NMR (300 MHz, DMSO-d6) δ 7.16 (s, 1H), 3.78-3.70 (m, 1H), 2.90-2.73 (m, 2H), 2.10-1.92 (m, 4H), 1.75-1.52 (m, 7H), 1.42-1.18 (m, 5H).

LC-MS (ESI) m/z 319.2 [M+H]⁺

Compound 10-10. (1S,3S)-3-(cyanoamino)-N-[5-(oxan-4-yl)-1,3-thiazol-2-yl]cyclopentane-1-carboxamide

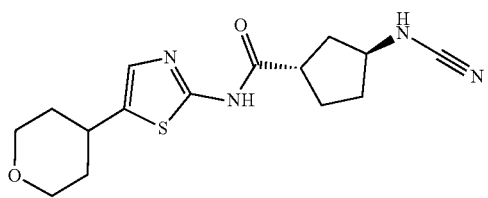 [SMILES: N#CN[C@H]1CC[C@H](C(=O)Nc2ncc(C3CCOCC3)s2)C1]

¹H NMR (300 MHz, DMSO-d6), δ 12.00 (s, 1H), 7.20 (s, 1H), 6.85 (s, 1H), 3.92-3.89 (m, 2H), 3.88 (s, 1H), 3.73-3.39 (m, 2H), 3.15-3.03 (m, 2H), 2.08-1.96 (m, 3H), 1.92-1.83 (m, 3H), 1.82-1.73 (m, 1H), 1.67-1.66 (m, 3H).

LC-MS (ESI) m/z 321.2 [M+H]⁺

Compound 10-11. (1R,3R)-3-(cyanoamino)-N-[5-(oxan-4-yl)-1,3-thiazol-2-yl]cyclopentane-1-carboxamide

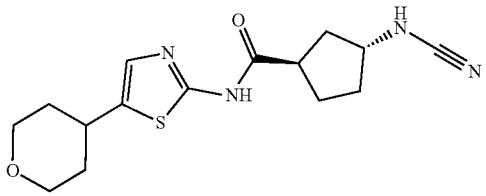 [SMILES: N#CN[C@@H]1CC[C@@H](C(=O)Nc2ncc(C3CCOCC3)s2)C1]

1H NMR (300 MHz, DMSO-d6), δ 11.99 (s, 1H), 7.19 (s, 1H), 6.86 (s, 1H), 3.92-3.87 (m, 2H), 3.72 (s, 1H), 3.46-3.39 (m, 2H), 3.13-3.03 (m, 2H), 2.08-1.97 (m, 2H), 1.88-1.82 (m, 4H), 1.77-1.55 (m, 4H).
LC-MS (ESI) m/z 321.2 [M+H]+

Example 11-1. trans-2-(cyanoamino)-N-(5-cyclohexyl-1,3-thiazol-2-yl)cyclopropane-1-carboxamide (Compound 11-1)

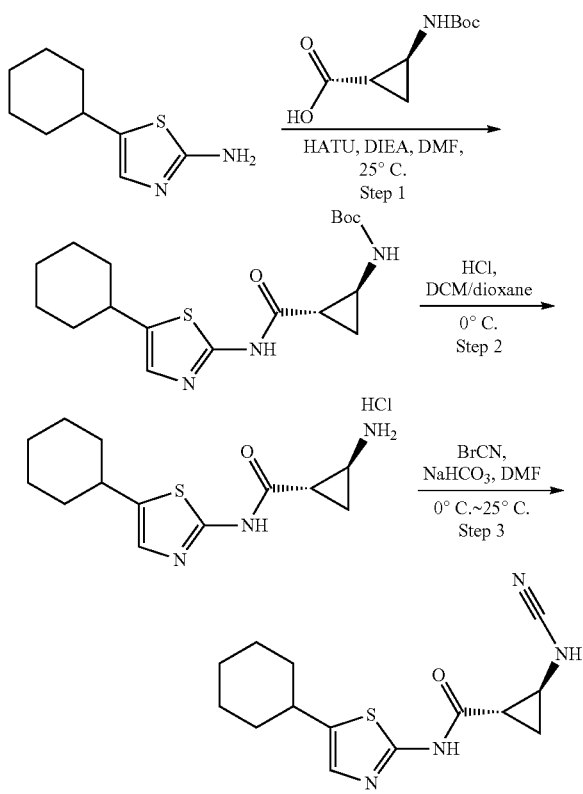

Step 1. tert-butyl N-[(trans)-2-[(5-cyclohexyl-1,3-thiazol-2-yl)carbamoyl]cyclopropyl]carbamate Into a 8 mL vial was placed (trans)-2-[(tert-butoxy)carbonyl]aminocyclopropane-1-carboxylic acid (132 mg, 0.62 mmol), N,N-dimethylformamide (1 mL), N,N-diisopropylethylamine (212 mg, 1.64 mmol), HATU (417 mg, 1.10 mmol) and 5-cyclohexyl-1,3-thiazol-2-amine (100 mg, 0.55 mmol). The resulting solution was stirred for 2 h at 25° C. The reaction mixture was poured into water (2 mL) and then extracted with ethyl acetate (3×2 mL). The organic layers were combined, dried over anhydrous sodium sulfate, filtered and concentrated under vacuum. The residue was purified by silica gel chromatography (eluting with 1:1 ethyl acetate/petroleum ether) to afford tert-butyl N-[(trans)-2-[(5-cyclohexyl-1,3-thiazol-2-yl)carbamoyl]cyclopropyl]carbamate as a white solid. LC-MS (ESI) m/z 366.1 [M+H]+

Step 2. (trans)-2-amino-N-(5-cyclohexyl-1,3-thiazol-2-yl)cyclopropane-1-carboxamide HCl salt Into a 8 mL vial was placed tert-butyl N-[(trans)-2-[(5-cyclohexyl-1,3-thiazol-2-yl)carbamoyl]cyclopropyl]carbamate (100 mg, 0.25 mmol), dichloromethane (2.4 mL) and a solution of HCl in 1,4-dioxane (4 M, 0.9 mL). The resulting solution was stirred for 6 h at 0° C. The resulting mixture was concentrated under vacuum, washed with ethyl ether, filtered and concentrated under vacuum to afford (trans)-2-amino-N-(5-cyclohexyl-1,3-thiazol-2-yl)cyclopropane-1-carboxamide HCl salt as a white solid. LC-MS (ESI) m/z 266.1 [M+H]+

Step 3. trans-2-(cyanoamino)-N-(5-cyclohexyl-1,3-thiazol-2-yl)cyclopropane-1-carboxamide Into a 8 mL vial was placed (trans)-2-amino-N-(5-cyclohexyl-1,3-thiazol-2-yl)cyclopropane-1-carboxamide HCl salt (70 mg, 0.21 mmol), N,N-dimethylformamide (1 mL) and sodium bicarbonate (35 mg, 0.42 mmol). After cooling to 0° C., cyanogen bromide (22 mg, 0.21 mmol) was added. The resulting solution was stirred for 1 h at 0° C. and 18 h at room temperature. The reaction mixture was poured into water (2 mL) and then extracted with ethyl acetate (3×2 mL). The organic layers were combined, dried over anhydrous sodium sulfate, filtered and concentrated under vacuum. The residue was purified by prep-TLC (eluting with 1:1 ethyl acetate/petroleum ether), and further purified by prep-HPLC (Column: XBridge Shield RP18 OBD Column, 130 Å, 5 μm, 19 mm×150 mm; Mobile phase: water (10 mM NH4HCO3), MeCN (35% MeCN up to 65% over 7 min); Flow rate: 20 mL/min; Detector: 254 & 220 nm). This resulted in (trans)-2-(cyanoamino)-N-(5-cyclohexyl-1,3-thiazol-2-yl)cyclopropane-1-carboxamide as a white solid. 1H NMR (400 MHz, DMSO-d6) δ 8.15 (s, 1H), 7.29 (s, 1H), 5.67-5.64 (m, 1H), 2.82-2.71 (m, 2H), 2.68-2.53 (m, 2H), 2.16-2.06 (m, 1H), 1.97-1.92 (m, 2H), 1.77-1.75 (m, 2H), 1.69-1.66 (m, 1H), 1.47-1.33 (m, 4H), 1.32-1.24 (m, 1H).
LC-MS (ESI) m/z 291.2[M+H]+

The following compounds were prepared according to Example 11-1:

Compound 11-2. cis-2-(cyanoamino)-N-(5-cyclohexyl-1,3-thiazol-2-yl)cyclopropane-1-carboxamide

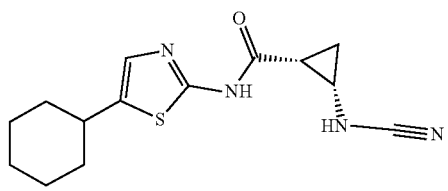 [SMILES: N#CN[C@H]1C[C@H]1C(=O)Nc1ncc(C2CCCCC2)s1]

¹H NMR (400 MHz, DMSO-d6) δ 7.98 (br s, 1H), 7.29 (s, 1H), 5.67-5.64 (m, 1H), 2.83-2.80 (m, 2H), 2.68-2.53 (m, 2H), 2.13-2.06 (m, 1H), 1.97-1.90 (m, 2H), 1.77-1.74 (m, 2H), 1.69-1.61 (m, 1H), 1.47-1.33 (m, 4H), 1.27-1.24 (m, 1H).

LC-MS (ESI) m/z 291.2[M+H]⁺

The following compounds were also prepared according to previous Example 2-1 above:

Compound 2-2. (3S)-3-(cyanoamino)-N-(5-cyclohexyl-1,3-thiazol-2-yl)pyrrolidine-1-carboxamide

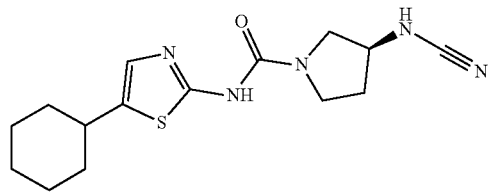 [SMILES: N#CN[C@H]1CCN(C(=O)Nc2ncc(C3CCCCC3)s2)C1]

¹H NMR (400 MHz, DMSO-d6) δ 10.51 (br s, 1H), 7.13 (s, 1H), 7.01 (s, 1H), 3.92-3.89 (m, 1H), 3.51-3.39 (m, 4H), 2.72-2.70 (m, 1H), 2.08-2.06 (m, 1H), 1.95-1.92 (m, 3H), 1.74-1.72 (m, 3H), 1.34-1.31 (m, 4H), 1.26-1.16 (m, 1H).

LC-MS (ESI) m/z: 320.4 [M+H]⁺

Compound 2-3. (3R)-3-(cyanoamino)-N-(5-cyclohexyl-1,3-thiazol-2-yl)pyrrolidine-1-carboxamide

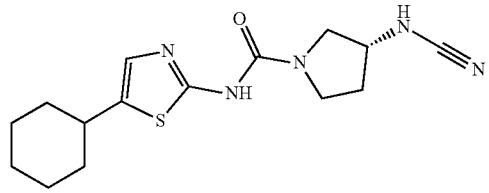

¹H NMR (400 MHz, DMSO-d6) δ 10.51 (br s, 1H), 7.13 (s, 1H), 7.01 (s, 1H), 3.89 (s, 1H), 3.51-3.39 (m, 4H), 2.72-2.70 (m, 1H), 2.09-2.07 (m, 1H), 1.99-1.92 (m, 3H), 1.74-1.66 (m, 3H), 1.34-1.31 (m, 4H), 1.26-1.16 (m, 1H).

LC-MS (ESI) m/z 320.1 [M+H]⁺

Example 12-1. (1R,3S)-3-(cyanoamino)-N-(5-phenyl-1,3-thiazol-2-yl)cyclopentane-1-carboxamide (Compound 12-1)

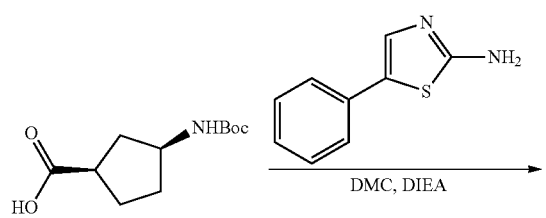

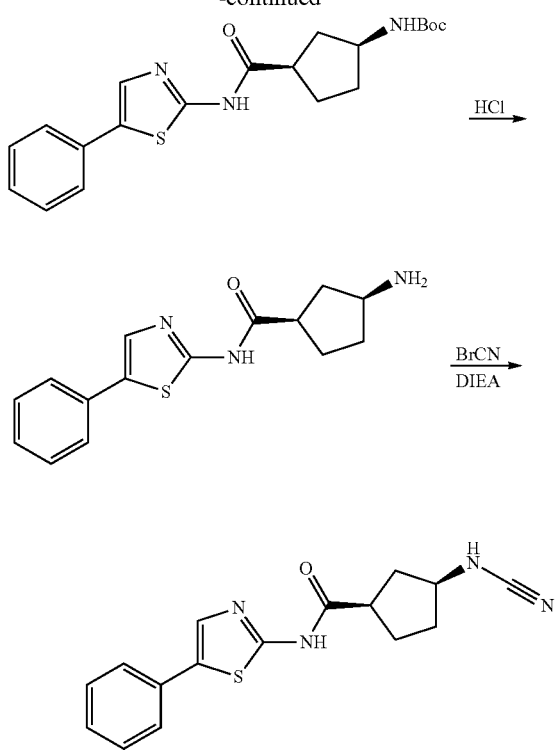

A half-dram vial was charged with (1R,3S)-3-((tert-butoxycarbonyl)amino)cyclopentane-1-carboxylic acid (0.2 M in 1,4-dioxane, 225 µL, 45 µmol), 5-phenylthiazol-2-amine (0.2 M in 1,4-dioxane, 225 µL, 45 µmol) and DIEA (30 µL, neat, 172 µmol), then a solution of 2-chloro-1,3-dimethylimidazolinium chloride (0.2 M in DCE, 275 µL, 55 µmol) was added. The vial was sealed and shaken at room temperature for 16 h. The reaction mixture was diluted with brine (500 µL) and extracted with ethyl acetate (2×500 µL). The combined organic layers were evaporated to dryness under a stream of N₂ and 1,4-dioxane (250 µL) was added to the residue. The vial was sealed and shaken at 50° C. for 15 min to dissolve the residue, then cooled to room temperature. HCl (4 M in 1,4-dioxane, 150 µL, 600 µmol) was added, the vial was sealed and shaken at room temperature for 3 h. The solvent was evaporated and DMA (200 µL) and DIEA (50 µL, neat, 287 µmol) were added. The vial was sealed and shaken at 50° C. for 15 min to dissolve the residue, then cooled to room temperature. Cyanogen bromide (0.4 M in DMA, 225 µL, 90 µmol) was added, the vial was sealed and shaken at room temperature for 3 h. DMSO (300 µL) and AcOH (45 µL) were added and the mixture was purified by mass triggered preparative HPLC. The product-containing fractions were combined and concentrated in a Genevac to afford (1R,3S)-3-(cyanoamino)-N-(5-phenyl-1,3-thiazol-2-yl)cyclopentane-1-carboxamide as an off-white solid. LC-MS (ESI) m/z 313 [M+H]⁺

The following compounds were synthesized according to Example 12-1:

| Compound 12-2 | 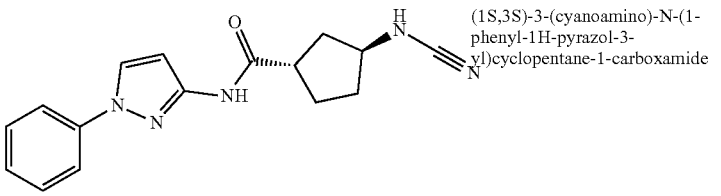 | (1S,3S)-3-(cyanoamino)-N-(1-phenyl-1H-pyrazol-3-yl)cyclopentane-1-carboxamide | LC-MS (ESI) m/z 296.2 [M + H]+ |
|---|---|---|---|
| Compound 12-3 | 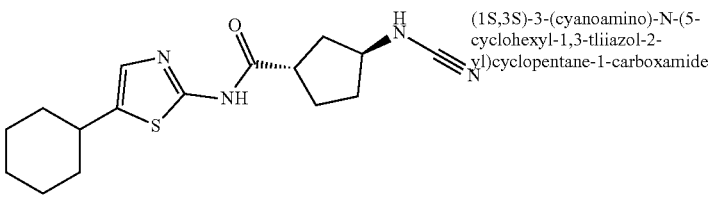 | (1S,3S)-3-(cyanoamino)-N-(5-cyclohexyl-1,3-tliiazol-2-yl)cyclopentane-1-carboxamide | LC-MS (ESI) m/z 319.2 [M + H]+ |
| Compound 12-4 | 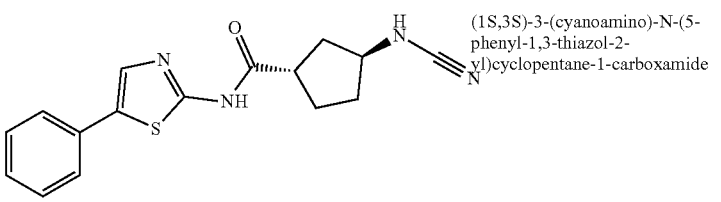 | (1S,3S)-3-(cyanoamino)-N-(5-phenyl-1,3-thiazol-2-yl)cyclopentane-1-carboxamide | LC-MS (ESI) m/z 313.2 [M + H]+ |
| Compound 12-5 | 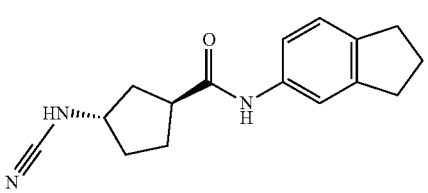 | (1S,3S)-3-(cyanoamino)-N-(2,3-dihydro-1H-inden-5-yl)cyclopentane-1-carboxamide | LC-MS (ESI) m/z 370.2 [M + H]+ |
| Compound 12-6 | 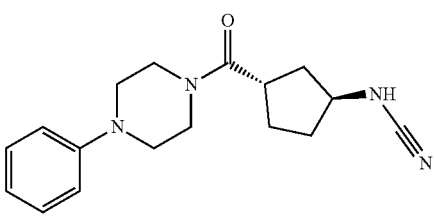 [SMILES: N#CN[C@H]1CC[C@H](C(=O)N2CCN(c3ccccc3)CC2)C1] | {[(1S,3S)-3-(4-phenylpiperazine-1-carbonyl)cyclopentyl]amino}carbonitrile | LC-MS (ESI) m/z 299.2 [M + H]+ |
| Compound 12-7 | 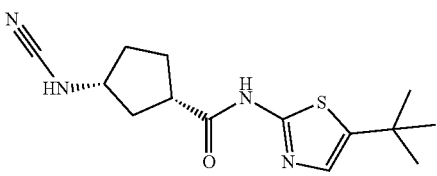 | (1S,3R)-N-(5-tert-butyl-1,3-thiazol-2-yl)-3-(cyanoamino)cyclopentane-1-carboxamide | LC-MS (ESI) m/z 293.2 [M + H]+ |
| Compound 12-8 | 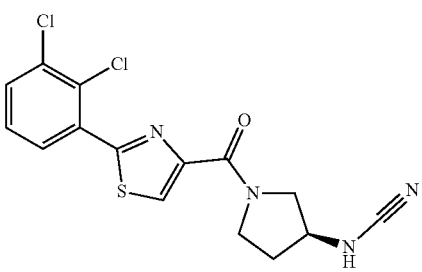 [SMILES: N#CN[C@H]1CCN(C(=O)c2csc(-c3cccc(Cl)c3Cl)n2)C1] | {[(3S)-1-[2-(2,3-dichlorophenyl)-1,3-thiazole-4-carbonyl]pyrrolidin-3-yl]amino}carbonitrile | LC-MS (ESI) m/z 367 [M + H]+ |

| | | | |
|---|---|---|---|
| Compound 12-9 | 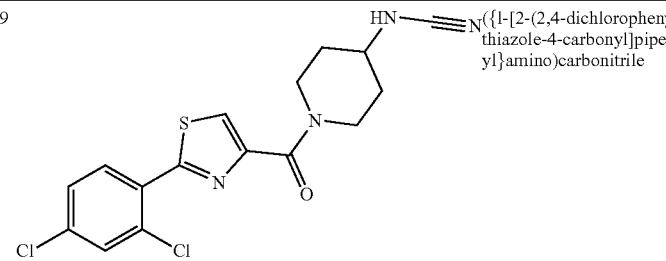 | ({1-[2-(2,4-dichlorophenyl)-1,3-thiazole-4-carbonyl]piperidin-4-yl}amino)carbonitrile | LC-MS (ESI) m/z 381 [M + H ]+ |

Example A: Biochemical Assay:
Ubiquitin-Rhodamine 110 Assay for USP30
Activity (USP30 Inhibitor Biochemical Assay)

In some embodiments, the compounds of the invention are USP30 inhibitor compounds having an IC$_{50}$ value of 1 micromolar or less (e.g., between 0.001 micromolar and 1 micromolar) as determined by the following USP30 Inhibitor Biochemical Assay. In some embodiments, the compounds of the invention are USP30 inhibitor compounds having an IC$_{50}$ value of less than 0.5 micromolar (e.g., between 0.001 micromolar and 0.5 micromolar) as determined by the following USP30 Inhibitor Biochemical Assay. In some embodiments the compounds of the invention are preferably USP30 inhibitor compounds having an IC$_{50}$ value of less than 0.1 micromolar (e.g., between 0.001 micromolar and 0.1 micromolar) as determined by the following USP30 Inhibitor Biochemical Assay.

The assay was performed in a final volume of 9 μL in assay buffer containing 20 mM Tris-HCl (pH 8.0, (1M Tris-HCl, pH 8.0 solution; Corning 46-031-CM)), 1 mM GSH (L-glutathione reduced, Sigma-Aldrich, G4251-100G), 0.03% BGG (0.22 μM filtered, Sigma, G7516-25G), and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 25 μM to 1.3 nM, top to lowest dose, respectively. Concentration and incubation times were optimized for the maximal signal-to-background while maintaining initial velocity conditions at a fixed substrate concentration. The final concentration of USP30 (human recombinant USP30, Boston Biochem, cat. # E-582) in the assay was 0.2 nM. Final substrate (Ub-Rh110; Ubiquitin-Rhodamine 110, UbiQ-126) concentration was 25 nM with [Ub-Rh110]<<Km. 3 μL of 2×USP30 was added to assay plates (pre-stamped with compound), preincubated for 30 minutes and then treated with 3 μL of 2×Ub-Rh110. Plates were incubated for 30 minutes at room temperature before addition of 3 μL of stop solution (final concentration of 10 mM citric acid (Sigma, 251275-500G)). Fluorescence was read on the Envision (excitation at 485 nm and emission at 535 nm; Perkin Elmer) or on the PheraSTAR (excitation at 485 nm and emission at 535 nm; BMG Labtech).

For all assay formats data were reported as percent inhibition compared with control wells based on the following equation: % inh=1−((FLU−Ave$_{Low}$)/(Ave$_{High}$−Ave$_{Low}$)) where FLU=measured Fluorescence, Ave$_{Low}$=average Fluorescence of no enzyme control (n=16), and Ave$_{High}$=average Fluorescence of DMSO control (n=16). IC$_{50}$ values were determined by curve fitting of the standard 4 parameter logistic fitting algorithm included in the Activity Base software package: IDBS XE Designer Model205. Data is fitted using the Levenburg Marquardt algorithm.

The activity of compounds in the USP30 biochemical IC$_{50}$ assay (IC$_{50}$ ranges) according to the present disclosure are reported in the tables A1 to A3 below according to the following:
"−": inactive, "+": 10-25 μM, "++": 1-10 μM, "+++": 0.1-1 μM, "++++": <0.1 μM.

TABLE A1

| Example No. | Structure | Chemical Name | USP30 potency range |
|---|---|---|---|
| Compound 1-1 | 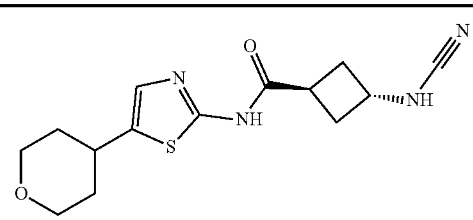 | trans-3-(cyanoamino)-N-[5-(oxan-4-yl)-1,3-thiazol-2-yl]cyclobutane-1-carboxamide | ++ |
| Compound 2-1 | 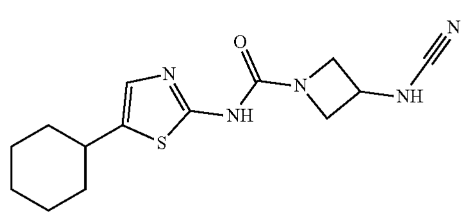 [SMILES: N#CNC1CN(C(=O)Nc2ncc(C3CCCCC3)s2)C1] | 3-(cyanoamino)-N-(5-cyclohexyl-1,3-thiazol-2-yl)azetidine-1-carboxamide | ++ |

TABLE A1-continued

| Example No. | Structure | Chemical Name | USP30 potency range |
|---|---|---|---|
| Compound 3-1 | 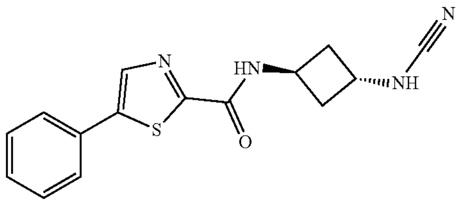 [SMILES: N#CN[C@H]1C[C@H](NC(=O)c2ncc(-c3ccccc3)s2)C1] | 5-phenyl-N-[(trans)-3-(cyanoamino)cyclobutyl]-1,3-thiazole-2-carboxamide | ++ |
| Compound 4-1 | 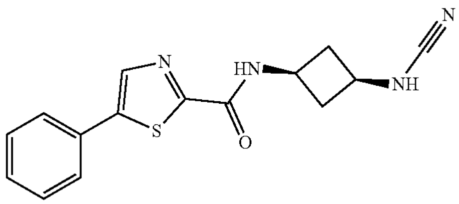 [SMILES: N#CN[C@H]1C[C@@H](NC(=O)c2ncc(-c3ccccc3)s2)C1] | 5-phenyl-N-[(cis)-3-(cyanoamino)cyclobutyl]-1,3-thiazole-2-carboxamide | ++ |
| Compound 5-1 | 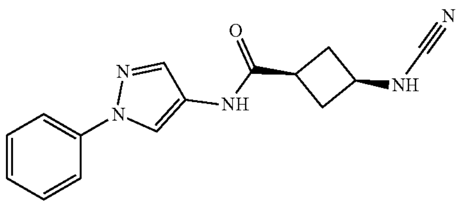 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide | ++ |
| Compound 5-2 | 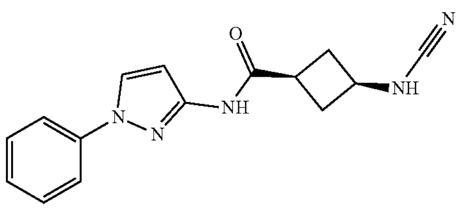 | cis-3-(cyanoamino)-N-(1-phenyl-1H-pyrazol-3-yl)cyclobutane-1-carboxamide | + |
| Compound 5-3 | 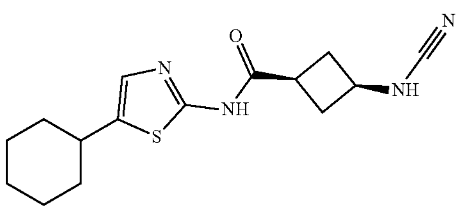 [SMILES: N#CN[C@H]1C[C@@H](C(=O)Nc2ncc(C3CCCCC3)s2)C1] | cis-3-(cyanoamino)-N-(5-cyclohexyl-1,3-thiazol-2-yl)cyclobutane-1-carboxamide | ++ |
| Compound 5-4 | 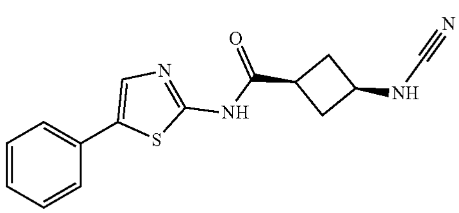 [SMILES: N#CN[C@H]1C[C@@H](C(=O)Nc2ncc(-c3ccccc3)s2)C1] | cis-3-(cyanoamino)-N-(5-phenyl-1,3-thiazol-2-yl)cyclobutane-1-carboxamide | ++ |
| Compound 5-5 | 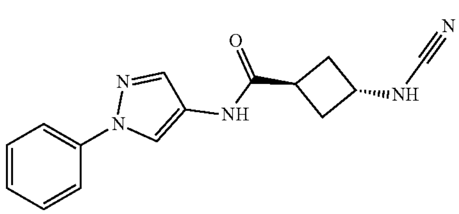 [SMILES: N#CN[C@H]1C[C@H](C(=O)Nc2cnn(-c3ccccc3)c2)C1] | trans-3-(cyanoamino)-N-(1-phenyl-1H-pyrazol-4-yl)cyclobutane-1-carboxamide | ++ |

TABLE A1-continued

| Example No. | Structure | Chemical Name | USP30 potency range |
|---|---|---|---|
| Compound 5-6 | 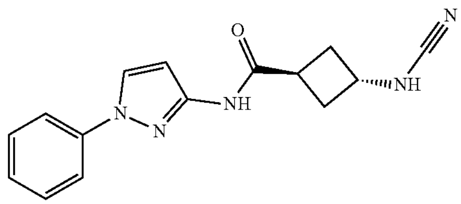 [SMILES: N#CN[C@H]1C[C@H](C(=O)Nc2ccn(-c3ccccc3)n2)C1] | trans-3-(cyanoamino)-N-(1-phenyl-1H-pyrazol-3-yl)cyclobutane-1-carboxamide | ++ |
| Compound 5-7 | 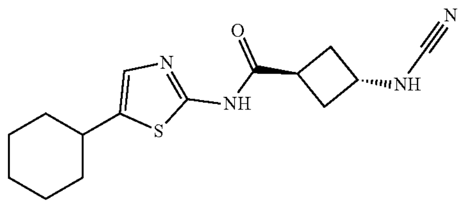 [SMILES: N#CN[C@H]1C[C@H](C(=O)Nc2ncc(C3CCCCC3)s2)C1] | trans-3-(cyanoamino)-N-(5-cyclohexyl-1,3-thiazol-2-yl)cyclobutane-1-carboxamide | +++ |
| Compound 5-8 | 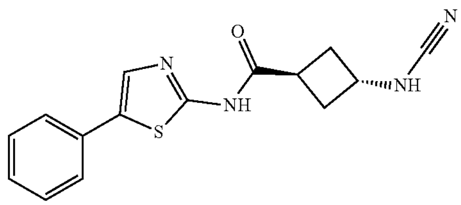 [SMILES: N#CN[C@H]1C[C@H](C(=O)Nc2ncc(-c3ccccc3)s2)C1] | trans-3-(cyanoamino)-N-(5-phenyl-1,3-thiazol-2-yl)cyclobutane-1-carboxamide | ++ |
| Compound 5-9 | 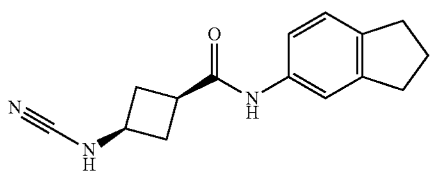 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide | ++ |
| Compound 5-10 | 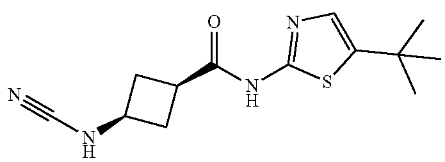 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide | + |
| Compound 5-11 | 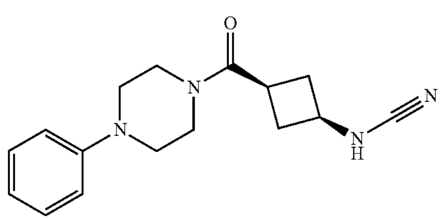 [SMILES: N#CN[C@H]1C[C@@H](C(=O)N2CCN(c3ccccc3)CC2)C1] | {[cis-3-(4-phenylpiperazine-1-carbonyl)cyclobutyl]amino}carbonitrile | + |
| Compound 5-12 | 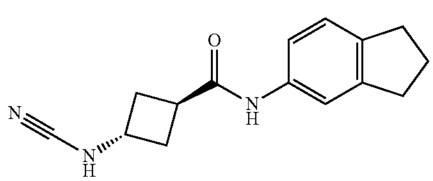 [SMILES: N#CN[C@H]1C[C@H](C(=O)Nc2ccc3c(c2)CCC3)C1] | trans-3-(cyanoamino)-N-(2,3-dihydro-1H-inden-5-yl)cyclobutane-1-carboxamide | ++ |
| Compound 5-13 | 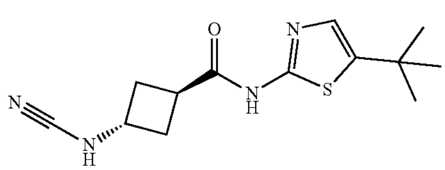 | trans-N-(5-tert-butyl-1,3-thiazol-2-yl)-3-(cyanoamino)cyclobutane-1-carboxamide | +++ |

TABLE A1-continued

| Example No. | Structure | Chemical Name | USP30 potency range |
|---|---|---|---|
| Compound 5-14 | 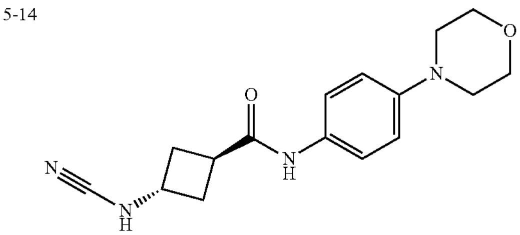 | trans-3-(cyanoamino)-N-[4-(morpholin-4-yl)phenyl]cyclobutane-1-carboxamide | + |

TABLE A2

| Example No. | Structure | Chemical Name | USP30 potency range |
|---|---|---|---|
| Compound 1-2 | 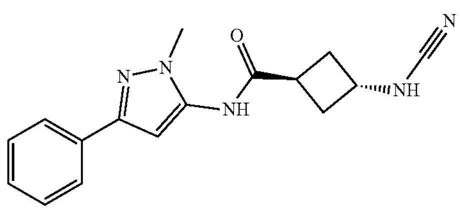 [SMILES: Cn1nc(-c2ccccc2)cc1NC(=O)[C@H]1C[C@H](NC#N)C1] | (1r,3r)-3-(cyanoamino)-N-(1-methyl-3-phenyl-1H-pyrazol-5-yl)cyclobutane-1-carboxamide | +++ |
| Compound 1-3 | 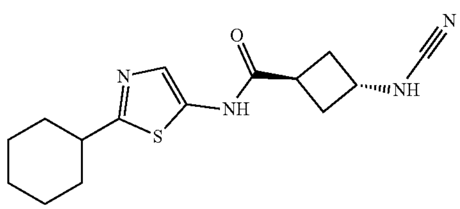 [SMILES: N#CN[C@H]1C[C@H](C(=O)Nc2cnc(C3CCCCC3)s2)C1] | (1r,3r)-3-(cyanoamino)-N-(2-cyclohexyl-1,3-thiazol-5-yl)cyclobutane-1-carboxamide | ++++ |
| Compound 1-4 | 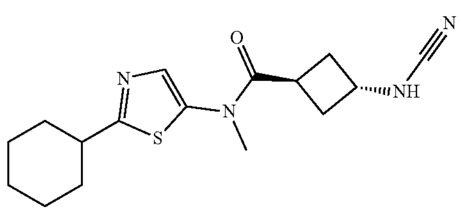 [SMILES: CN(c1cnc(C2CCCCC2)s1)C(=O)[C@H]1C[C@H](NC#N)C1] | (1r,3r)-3-(cyanoamino)-N-(2-cyclohexyl-1,3-thiazol-5-yl)-N-methylcyclobutane-1-carboxamide | +++ |
| Compound 1-5 | 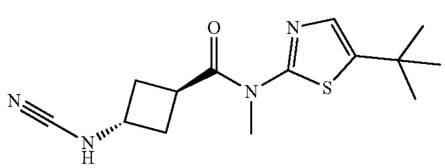 [SMILES: CN(c1ncc(C(C)(C)C)s1)C(=O)[C@H]1C[C@H](NC#N)C1] | (1r,3r)-N-(5-tert-butyl-1,3-thiazol-2-yl)-3-(cyanoamino)-N-methylcyclobutane-1-carboxamide | +++ |
| Compound 1-6 | 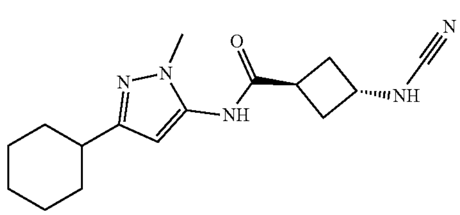 [SMILES: Cn1nc(C2CCCCC2)cc1NC(=O)[C@H]1C[C@H](NC#N)C1] | (1r,3r)-3-(cyanoamino)-N-(3-cyclohexyl-1-methyl-1H-pyrazol-5-yl)cyclobutane-1-carboxamide | +++ |

TABLE A2-continued

| Example No. | Chemical Name | USP30 potency range |
|---|---|---|
| Compound 1-7 | (1r,3r)-3-(cyanoamino)-N-(2-cyclohexyl-4-methyl-1,3-thiazol-5-yl)cyclobutane-1-carboxamide | +++ |
| Compound 1-8 | (1r,3r)-3-(cyanoamino)-N-{2-[2-(propan-2-yloxy)phenyl]-1,3-thiazol-5-yl}cyclobutane-1-carboxamide | +++ |
| Compound 1-9 | (1r,3r)-3-(cyanoamino)-N-[2-(3,3-difluorocyclobutyl)-1,3-thiazol-5-yl]cyclobutane-1-carboxamide | +++ |
| Compound 1-10 | (1r,3r)-N-(4-chloro-5-cyclohexyl-1,3-thiazol-2-yl)-3-(cyanoamino)cyclobutane-1-carboxamide | ++++ |
| Compound 1-11 | (1r,3s)-3-(cyanoamino)-N-(2-cyclohexyl-1,3-thiazol-5-yl)-1-methylcyclobutane-1-carboxamide | ++++ |
| Compound 1-12 | (1r,3r)-3-(cyanoamino)-N-{2-[(1S)-2,2-dimethylcyclohexyl]-1,3-thiazol-5-yl}cyclobutane-1-carboxamide | ++++ |
| Compound 1-13 | (1r,3r)-3-(cyanoamino)-N-{2-[(1R)-2,2-dimethylcyclohexyl]-1,3-thiazol-5-yl}cyclobutane-1-carboxamide | +++ |

TABLE A2-continued

| Example No. | Structure | Chemical Name | USP30 potency range |
|---|---|---|---|
| Compound 1-14 | 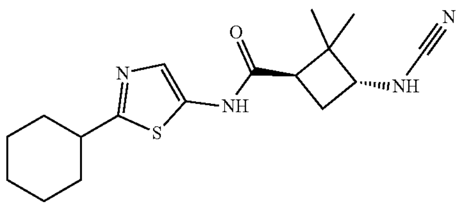 [SMILES: CC1(C)[C@H](NC#N)C[C@H]1C(=O)Nc1cnc(C2CCCCC2)s1] | (1r,3r)-N-(4-chloro-2-cyclohexyl-1,3-thiazol-5-yl)-3-(cyanoamino)cyclobutane-1-carboxamide | +++ |
| Compound 1-15 | 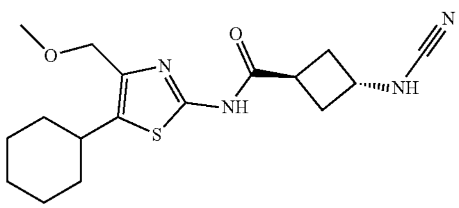 [SMILES: COCc1nc(NC(=O)[C@H]2C[C@H](NC#N)C2)sc1C1CCCCC1] | (1R,3R)-3-(cyanoamino)-N-(2-cyclohexyl-1,3-thiazol-5-yl)-2,2-dimethylcyclobutane-1-carboxamide | +++ |
| Compound 1-16 | 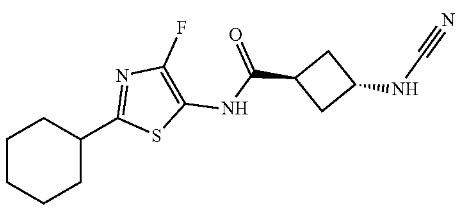 | (1r,3r)-3-(cyanoamino)-N-[5-cyclohexyl-4-(methoxymethyl)-1,3-thiazol-2-yl]cyclobutane-1-carboxamide | ++++ |
| Compound 1-17 | 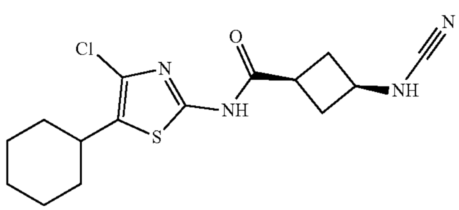 [SMILES: N#CN[C@H]1C[C@@H](C(=O)Nc2nc(Cl)c(C3CCCCC3)s2)C1] | (1r,3r)-3-(cyanoamino)-N-(2-cyclohexyl-4-fluoro-1,3-thiazol-5-yl)cyclobutane-1-carboxamide | +++ |
| Compound 1-18 | 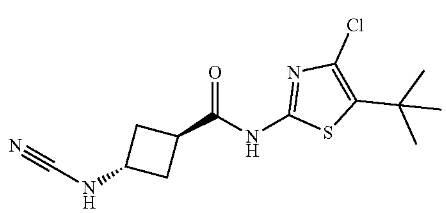 [SMILES: CC(C)(C)c1sc(NC(=O)[C@H]2C[C@H](NC#N)C2)nc1Cl] | (1s,3s)-N-(4-chloro-5-cyclohexyl-1,3-thiazol-2-yl)-3-(cyanoamino)cyclobutane-1-carboxamide | +++ |
| Compound 1-19 | 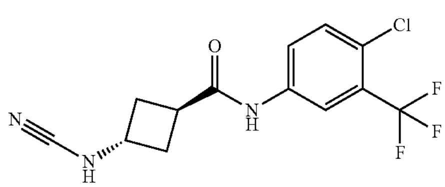 [SMILES: N#CN[C@H]1C[C@H](C(=O)Nc2ccc(Cl)c(C(F)(F)F)c2)C1] | (1r,3r)-N-(5-tert-butyl-4-chloro-1,3-thiazol-2-yl)-3-(cyanoamino)cyclobutane-1-carboxamide | ++++ |
| Compound 1-20 | 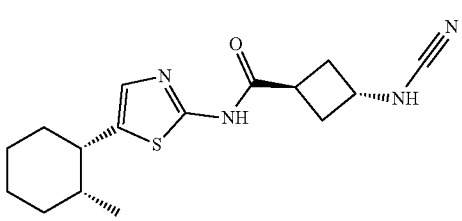 [SMILES: C[C@@H]1CCCC[C@@H]1c1cnc(NC(=O)[C@H]2C[C@H](NC#N)C2)s1] | (1r,3r)-N-[4-chloro-3-(trifluoromethyl)phenyl]-3-(cyanoamino)cyclobutane-1-carboxamide | ++ |

TABLE A2-continued

| Example No. | Chemical Name | USP30 potency range |
|---|---|---|
| Compound 1-21 | (1r,3r)-3-(cyanoamino)-N-{5-[(1S,2R)-2-methylcyclohexyl]-1,3-thiazol-2-yl}cyclobutane-1-carboxamide | +++ |
| Compound 1-22 | (1r,3r)-3-(cyanoamino)-N-{5-[(1R,2S)-2-methylcyclohexyl]-1,3-thiazol-2-yl}cyclobutane-1-carboxamide | +++ |
| Compound 1-23 | (1r,3r)-3-(cyanoamino)-N-{5-[(1S,2S)-2-methylcyclohexyl]-1,3-thiazol-2-yl}cyclobutane-1-carboxamide | ++++ |
| Compound 1-24 | (1r,3r)-3-(cyanoamino)-N-{5-[(1R,2R)-2-methylcyclohexyl]-1,3-thiazol-2-yl}cyclobutane-1-carboxamide | ++++ |
| Compound 1-25 | (1r,3r)-3-(cyanoamino)-N-(5-cyclohexyl-4-cyclopropyl-1,3-thiazol-2-yl)cyclobutane-1-carboxamide | ++++ |
| Compound 1-26 | (1r,3r)-3-(cyanoamino)-N-[5-cyclohexyl-4-(1-cyclopropyl-1H-pyrazol-4-yl)-1,3-thiazol-2-yl]cyclobutane-1-carboxamide | ++++ |
| Compound 1-27 | (1r,3r)-3-(cyanoamino)-N-[4-(trifluoromethyl)pyridin-2-yl]cyclobutane-1-carboxamide | +++ |

TABLE A2-continued

| Example No. | Structure | Chemical Name | USP30 potency range |
|---|---|---|---|
| Compound 1-28 | 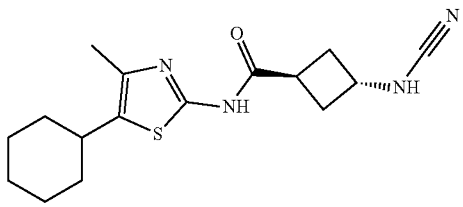 [SMILES: Cc1nc(NC(=O)[C@H]2C[C@H](NC#N)C2)sc1C1CCCCC1] | (1r,3r)-3-(cyanoamino)-N-{5-[(2S)-oxan-2-yl]-1,3-thiazol-2-yl}cyclobutane-1-carboxamide | ++ |
| Compound 1-29 | 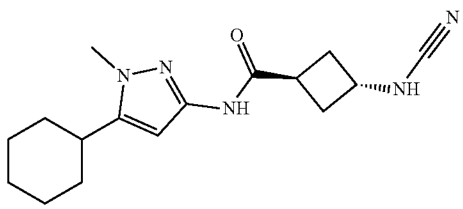 [SMILES: Cn1nc(NC(=O)[C@H]2C[C@H](NC#N)C2)cc1C1CCCCC1] | (1r,3r)-3-(cyanoamino)-N-(5-cyclohexyl-4-methyl-1,3-thiazol-2-yl)cyclobutane-1-carboxamide | ++++ |
| Compound 1-30 | 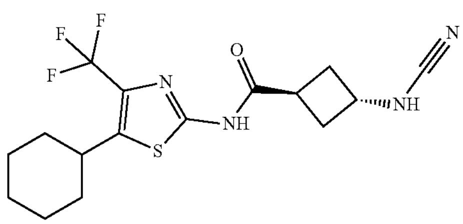 [SMILES: N#CN[C@H]1C[C@H](C(=O)Nc2nc(C(F)(F)F)c(C3CCCCC3)s2)C1] | (1r,3r)-3-(cyanoamino)-N-(5-cyclohexyl-1-methyl-1H-pyrazol-3-yl)cyclobutane-1-carboxamide | +++ |
| Compound 1-31 | 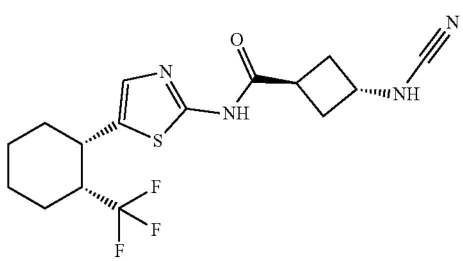 [SMILES: N#CN[C@H]1C[C@H](C(=O)Nc2ncc([C@H]3CCCC[C@H]3C(F)(F)F)s2)C1] | (1r,3r)-3-(cyanoamino)-N-[5-cyclohexyl-4-(trifluoromethyl)-1,3-thiazol-2-yl]cyclobutane-1-carboxamide | ++++ |
| Compound 1-32 | 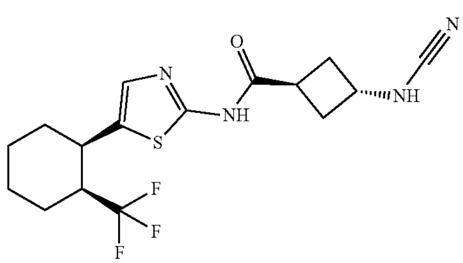 [SMILES: N#CN[C@H]1C[C@H](C(=O)Nc2ncc([C@@H]3CCCC[C@@H]3C(F)(F)F)s2)C1] | (1r,3r)-3-(cyanoamino)-N-{5-[(1S,2R)-2-(trifluoromethyl)cyclohexyl]-1,3-thiazol-2-yl}cyclobutane-1-carboxamide | +++ |
| Compound 1-33 | 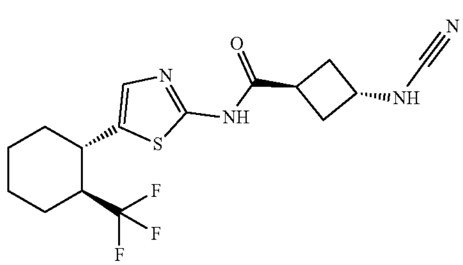 [SMILES: N#CN[C@H]1C[C@H](C(=O)Nc2ncc([C@H]3CCCC[C@@H]3C(F)(F)F)s2)C1] | (1r,3r)-3-(cyanoamino)-N-{5-[(1R,2S)-2-(trifluoromethyl)cyclohexyl]-1,3-thiazol-2-yl}cyclobutane-1-carboxamide | +++ |

TABLE A2-continued

| Example No. | Structure | Chemical Name | USP30 potency range |
|---|---|---|---|
| Compound 1-34 | 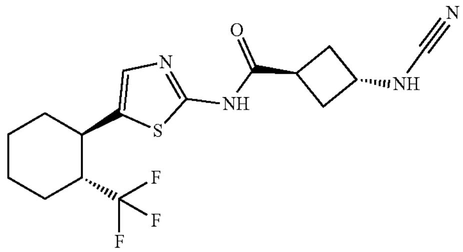 [SMILES: N#CN[C@H]1C[C@H](C(=O)Nc2ncc([C@@H]3CCCC[C@H]3C(F)(F)F)s2)C1] | (1r,3r)-3-(cyanoamino)-N-{5-[(1S,2S)-2-(trifluoromethyl)cyclohexyl]-1,3-thiazol-2-yl}cyclobutane-1-carboxamide | +++ |
| Compound 1-35 | 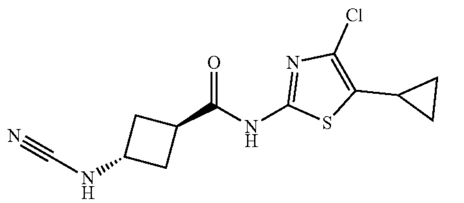 [SMILES: N#CN[C@H]1C[C@H](C(=O)Nc2nc(Cl)c(C3CC3)s2)C1] | (1r,3r)-3-(cyanoamino)-N-{5-[(1R,2R)-2-(trifluoromethyl)cyclohexyl]-1,3-thiazol-2-yl}cyclobutane-1-carboxamide | +++ |
| Compound 1-36 | 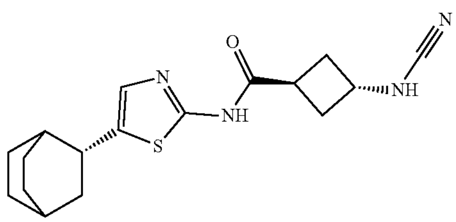 [SMILES: N#CN[C@H]1C[C@H](C(=O)Nc2ncc([C@@H]3CC4CCC3CC4)s2)C1] | (1r,3r)-N-(4-chloro-5-cyclopropyl-1,3-thiazol-2-yl)-3-(cyanoamino)cyclobutane-1-carboxamide | ++++ |
| Compound 1-37 | 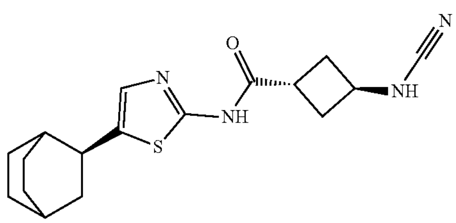 [SMILES: N#CN[C@H]1C[C@H](C(=O)Nc2ncc([C@H]3CC4CCC3CC4)s2)C1] | (1r,3r)-N-{5-[(2R)-bicyclo[2.2.2]octan-2-yl]-1,3-thiazol-2-yl}-3-(cyanoamino)cyclobutane-1-carboxamide | ++++ |
| Compound 1-38 | 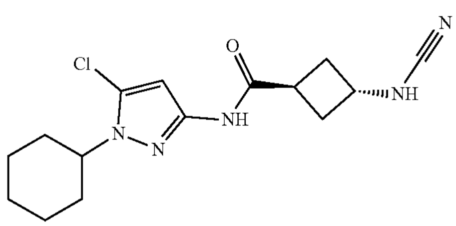 [SMILES: N#CN[C@H]1C[C@H](C(=O)Nc2cc(Cl)n(C3CCCCC3)n2)C1] | (1r,3r)-N-{5-[(2S)-bicyclo[2.2.2]octan-2-yl]-1,3-thiazol-2-yl}-3-(cyanoamino)cyclobutane-1-carboxamide | +++ |
| Compound 1-39 | 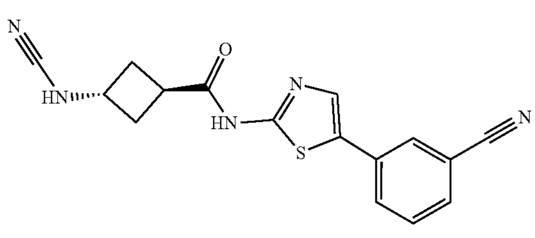 [SMILES: N#CN[C@H]1C[C@H](C(=O)Nc2ncc(-c3cccc(C#N)c3)s2)C1] | (1r,3r)-N-(5-chloro-1-cyclohexyl-1H-pyrazol-3-yl)-3-(cyanoamino)cyclobutane-1-carboxamide | +++ |

TABLE A2-continued

| Example No. | Structure | Chemical Name | USP30 potency range |
|---|---|---|---|
| Compound 1-40 | 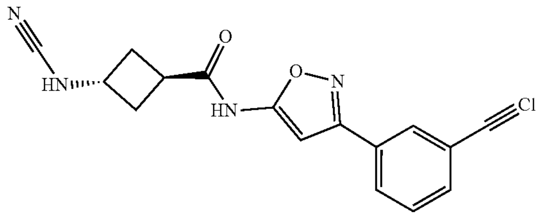 | (1r,3r)-3-(cyanoamino)-N-[5-(3-cyanophenyl)-1,3-thiazol-2-yl]cyclobutane-1-carboxamide | +++ |
| Compound 1-41 | 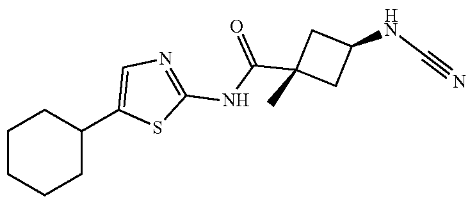 [SMILES: C[C@]1(C(=O)Nc2ncc(C3CCCCC3)s2)C[C@H](NC#N)C1] | (1r,3r)-N-[3-(3-chlorophenyl)-1,2-oxazol-5-yl]-3-(cyanoamino)cyclobutane-1-carboxamide | +++ |
| Compound 1-42 | 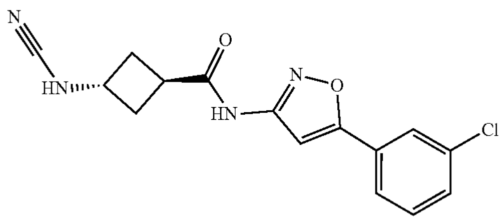 [SMILES: N#CN[C@H]1C[C@H](C(=O)Nc2cc(-c3cccc(Cl)c3)on2)C1] | (1r,3s)-3-(cyanoamino)-N-(5-cyclohexyl-1,3-thiazol-2-yl)-1-methylcyclobutane-1-carboxamide | +++ |
| Compound 1-43 | 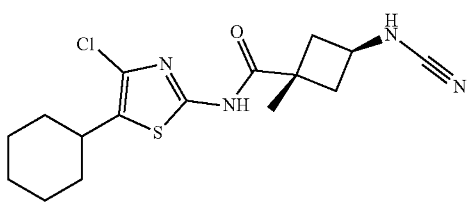 [SMILES: C[C@]1(C(=O)Nc2nc(Cl)c(C3CCCCC3)s2)C[C@H](NC#N)C1] | (1r,3r)-N-[5-(3-chlorophenyl)-1,2-oxazol-3-yl]-3-(cyanoamino)cyclobutane-1-carboxamide | +++ |
| Compound 1-44 | 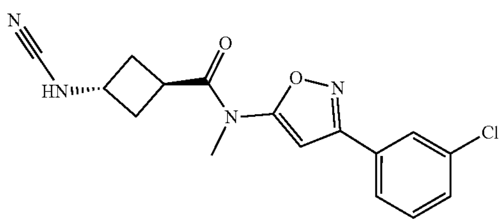 [SMILES: CN(c1cc(-c2cccc(Cl)c2)no1)C(=O)[C@H]1C[C@H](NC#N)C1] | (1r,3s)-N-(4-chloro-5-cyclohexyl-1,3-thiazol-2-yl)-3-(cyanoamino)-1-methylcyclobutane-1-carboxamide | ++++ |
| Compound 1-45 | 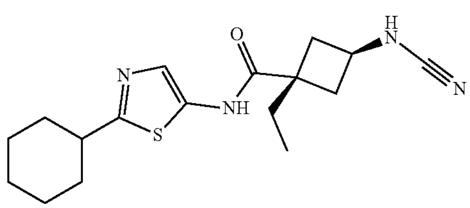 [SMILES: CC[C@]1(C(=O)Nc2cnc(C3CCCCC3)s2)C[C@H](NC#N)C1] | (1r,3r)-N-[3-(3-chlorophenyl)-1,2-oxazol-5-yl]-3-(cyanoamino)-N-methylcyclobutane-1-carboxamide | +++ |
| Compound 1-46 | 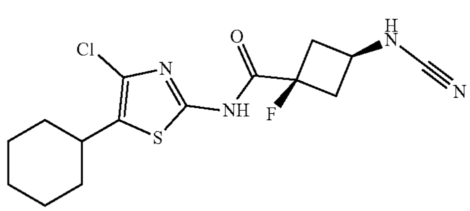 [SMILES: N#CN[C@H]1C[C@](F)(C(=O)Nc2nc(Cl)c(C3CCCCC3)s2)C1] | (1r,3s)-3-(cyanoamino)-N-(2-cyclohexyl-1,3-thiazol-5-yl)-1-ethylcyclobutane-1-carboxamide | +++ |

TABLE A2-continued

| Example No. | Structure | Chemical Name | USP30 potency range |
|---|---|---|---|
| Compound 1-47 | 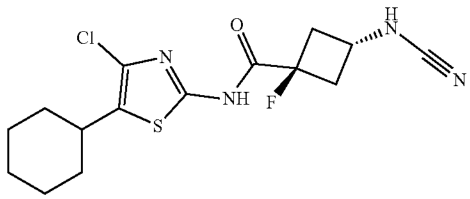 [SMILES: N#CN[C@H]1C[C@@](F)(C(=O)Nc2nc(Cl)c(C3CCCCC3)s2)C1] | (1s,3s)-N-(4-chloro-5-cyclohexyl-1,3-thiazol-2-yl)-3-(cyanoamino)-1-fluorocyclobutane-1-carboxamide | +++ |
| Compound 1-48 | 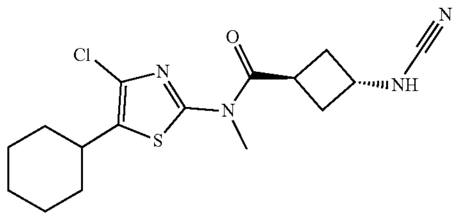 [SMILES: CN(c1nc(Cl)c(C2CCCCC2)s1)C(=O)[C@H]1C[C@H](NC#N)C1] | (1r,3r)-N-(4-chloro-5-cyclohexyl-1,3-thiazol-2-yl)-3-(cyanoamino)-1-fluorocyclobutane-1-carboxamide | ++++ |
| Compound 1-49 | 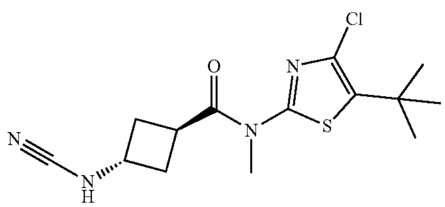 [SMILES: CN(c1nc(Cl)c(C(C)(C)C)s1)C(=O)[C@H]1C[C@H](NC#N)C1] | (1r,3r)-N-(4-chloro-5-cyclohexyl-1,3-thiazol-2-yl)-3-(cyanoamino)-N-methylcyclobutane-1-carboxamide | ++++ |
| Compound 1-50 | 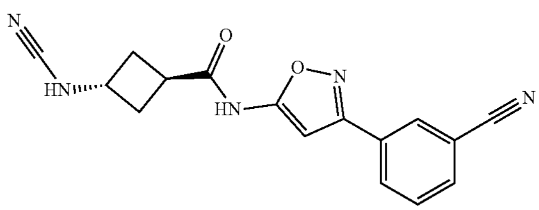 [SMILES: N#CN[C@H]1C[C@H](C(=O)Nc2cc(-c3cccc(C#N)c3)no2)C1] | (1r,3r)-N-(5-tert-butyl-4-chloro-1,3-thiazol-2-yl)-3-(cyanoamino)-N-methylcyclobutane-1-carboxamide | ++++ |
| Compound 1-51 | 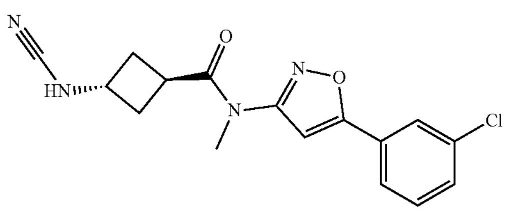 [SMILES: CN(c1cc(-c2cccc(Cl)c2)on1)C(=O)[C@H]1C[C@H](NC#N)C1] | (1r,3r)-3-(cyanoamino)-N-[3-(3-cyanophenyl)-1,2-oxazol-5-yl]cyclobutane-1-carboxamide | +++ |
| Compound 1-52 | 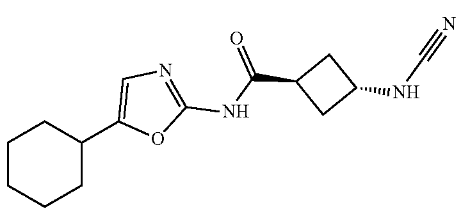 | (1r,3r)-N-[5-(3-chlorophenyl)-1,2-oxazol-3-yl]-3-(cyanoamino)-N-methylcyclobutane-1-carboxamide | +++ |
| Compound 1-53 | 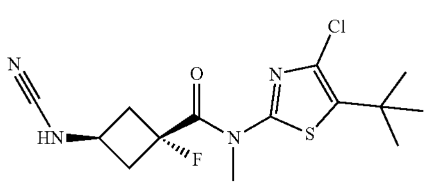 [SMILES: CN(c1nc(Cl)c(C(C)(C)C)s1)C(=O)[C@]1(F)C[C@H](NC#N)C1] | (1r,3r)-3-(cyanoamino)-N-(5-cyclohexyl-1,3-oxazol-2-yl)cyclobutane-1-carboxamide | +++ |

TABLE A2-continued

| Example No. | Structure | Chemical Name | USP30 potency range |
|---|---|---|---|
| Compound 1-54 | 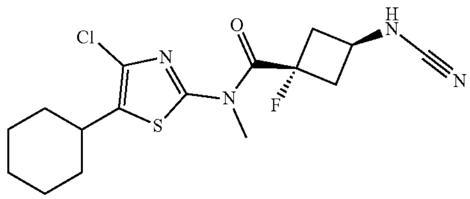 [SMILES: CN(c1nc(Cl)c(C2CCCCC2)s1)C(=O)[C@]1(F)C[C@H](NC#N)C1] | (1r,3r)-N-(5-tert-butyl-4-chloro-1,3-thiazol-2-yl)-3-(cyanoamino)-1-fluoro-N-methylcyclobutane-1-carboxamide | ++++ |
| Compound 1-55 | 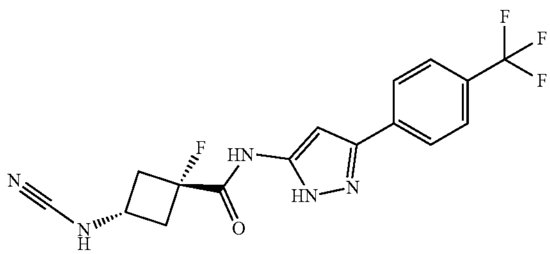 [SMILES: N#CN[C@H]1C[C@](F)(C(=O)Nc2cc(-c3ccc(C(F)(F)F)cc3)n[nH]2)C1] | (1r,3r)-N-(4-chloro-5-cyclohexyl-1,3-thiazol-2-yl)-3-(cyanoamino)-1-fluoro-N-methylcyclobutane-1-carboxamide | ++++ |
| Compound 1-56 | 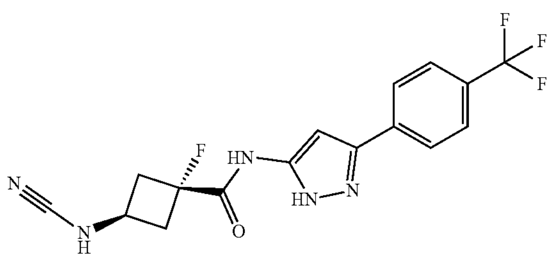 [SMILES: N#CN[C@H]1C[C@@](F)(C(=O)Nc2cc(-c3ccc(C(F)(F)F)cc3)n[nH]2)C1] | (1s,3s)-3-(cyanoamino)-1-fluoro-N-{3-[4-(trifluoromethyl)phenyl]-1H-pyrazol-5-yl}cyclobutane-1-carboxamide | +++ |
| Compound 1-57 | 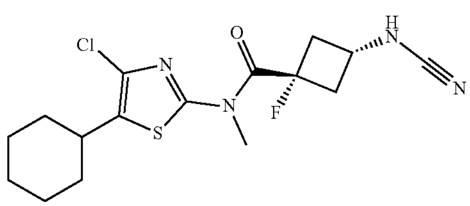 [SMILES: CN(c1nc(Cl)c(C2CCCCC2)s1)C(=O)[C@]1(F)C[C@@H](NC#N)C1] | (1r,3r)-3-(cyanoamino)-1-fluoro-N-{3-[4-(trifluoromethyl)phenyl]-1H-pyrazol-5-yl}cyclobutane-1-carboxamide | +++ |
| Compound 1-58 | 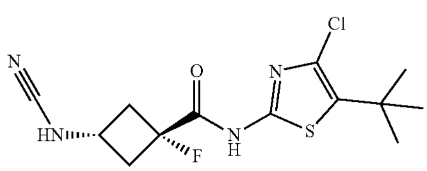 [SMILES: CC(C)(C)c1sc(NC(=O)[C@]2(F)C[C@@H](NC#N)C2)nc1Cl] | (1s,3s)-N-(4-chloro-5-cyclohexyl-1,3-thiazol-2-yl)-3-(cyanoamino)-1-fluoro-N-methylcyclobutane-1-carboxamide | +++ |
| Compound 1-59 | 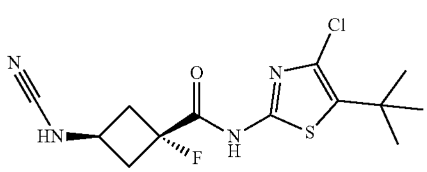 [SMILES: CC(C)(C)c1sc(NC(=O)[C@]2(F)C[C@H](NC#N)C2)nc1Cl] | (1s,3s)-N-(5-tert-butyl-4-chloro-1,3-thiazol-2-yl)-3-(cyanoamino)-1-fluorocyclobutane-1-carboxamide | +++ |
| Compound 1-60 | 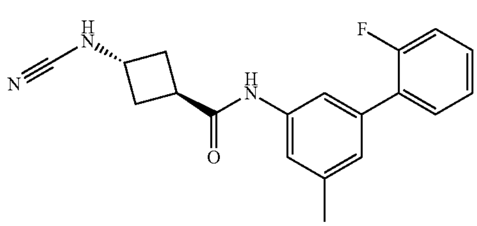 [SMILES: Cc1cc(NC(=O)[C@H]2C[C@H](NC#N)C2)cc(-c2ccccc2F)c1] | (1r,3r)-N-(5-tert-butyl-4-chloro-1,3-thiazol-2-yl)-3-(cyanoamino)-1-fluorocyclobutane-1-carboxamide | ++++ |

TABLE A2-continued

| Example No. | Chemical Name | USP30 potency range |
|---|---|---|
| Compound 1-61 | (1r,3r)-3-(cyanoamino)-N-[3-(2-fluorophenyl)-5-methylphenyl]cyclobutane-1-carboxamide | +++ |
| Compound 1-62 | (1r,3r)-N-(3-chloro-5-cyclohexylphenyl)-3-(cyanoamino)cyclobutane-1-carboxamide | ++++ |
| Compound 1-63 | (1r,3r)-3-(cyanoamino)-N-[4-fluoro-3-(piperidin-1-yl)phenyl]cyclobutane-1-carboxamide | +++ |
| Compound 1-64 | (1r,3r)-3-(cyanoamino)-N-(7-cyclobutoxy-1,3-benzothiazol-2-yl)cyclobutane-1-carboxamide | +++ |
| Compound 1-65 | (1r,3r)-3-(cyanoamino)-N-(7-cyclobutoxy-1,3-benzothiazol-2-yl)-1-fluorocyclobutane-1-carboxamide | ++++ |
| Compound 1-66 | (1s,3s)-3-(cyanoamino)-N-(7-cyclobutoxy-1,3-benzothiazol-2-yl)-1-fluorocyclobutane-1-carboxamide | +++ |
| Compound 1-67 | (1r,3r)-3-(cyanoamino)-N-{[(1R,2R,5R)-6,6-dimethylbicyclo[3.1.1]heptan-2-yl]methyl}cyclobutane-1-carboxamide | +++ |

TABLE A2-continued

| Example No. | Structure | Chemical Name | USP30 potency range |
|---|---|---|---|
| Compound 1-68 | 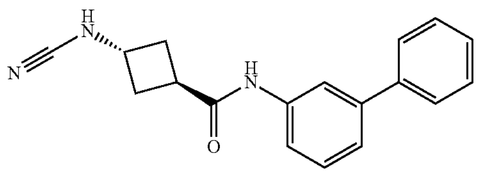 [SMILES: N#CN[C@H]1C[C@H](C(=O)Nc2cccc(-c3ccccc3)c2)C1] | (1r,3r)-N-[4-(4-chlorophenyl)-1,3-thiazol-2-yl]-3-(cyanoamino)cyclobutane-1-carboxamide | +++ |
| Compound 1-69 | 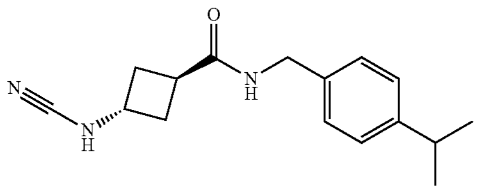 [SMILES: CC(C)c1ccc(CNC(=O)[C@H]2C[C@H](NC#N)C2)cc1] | (1r,3r)-3-(cyanoamino)-N-(3-phenylphenyl)cyclobutane-1-carboxamide | +++ |
| Compound 1-70 | 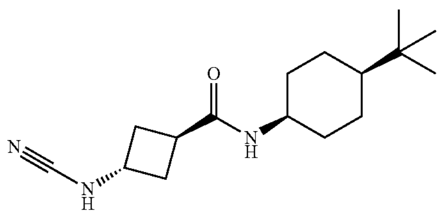 [SMILES: CC(C)(C)[C@H]1CC[C@@H](NC(=O)[C@H]2C[C@H](NC#N)C2)CC1] | (1r,3r)-3-(cyanoamino)-N-{[4-(propan-2-yl)phenyl]methyl}cyclobutane-1-carboxamide | ++++ |
| Compound 1-71 | 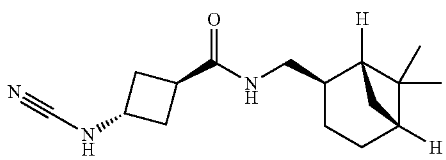 [SMILES: CC1(C)[C@@H]2CC[C@@H](CNC(=O)[C@H]3C[C@H](NC#N)C3)[C@H]1C2] | (1r,3r)-3-(cyanoamino)-N-[(1s,4s)-4-tert-butylcyclohexyl]cyclobutane-1-carboxamide | +++ |
| Compound 1-72 | 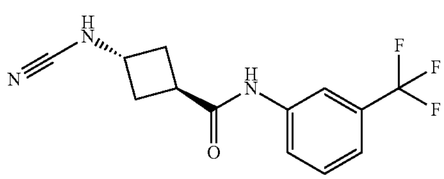 | (1r,3r)-3-(cyanoamino)-N-{[(1R,2R,5R)-6,6-dimethylbicyclo[3.1.1]heptan-2-yl]methyl}cyclobutane-1-carboxamide | +++ |
| Compound 1-73 | 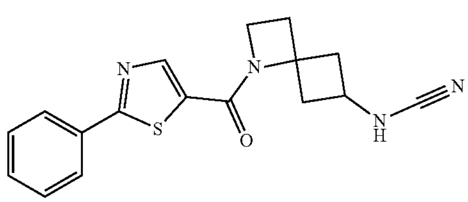 [SMILES: N#CNC1CC2(CCN2C(=O)c2cnc(-c3ccccc3)s2)C1] | (1r,3r)-3-(cyanoamino)-N-[3-(trifluoromethyl)phenyl]cyclobutane-1-carboxamide | +++ |
| Compound 3-2 | 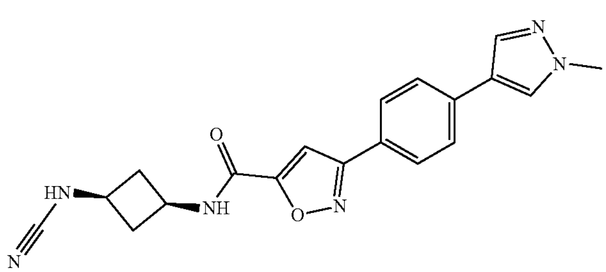 [SMILES: Cn1cc(-c2ccc(-c3cc(C(=O)N[C@H]4C[C@@H](NC#N)C4)on3)cc2)cn1] | {[1-(2-phenyl-1,3-thiazole-5-carbonyl)-1-azaspiro[3.3]heptan-6-yl]amino}carbonitrile | +++ |

TABLE A2-continued

| Example No. | Structure | Chemical Name | USP30 potency range |
|---|---|---|---|
| Compound 3-3 | 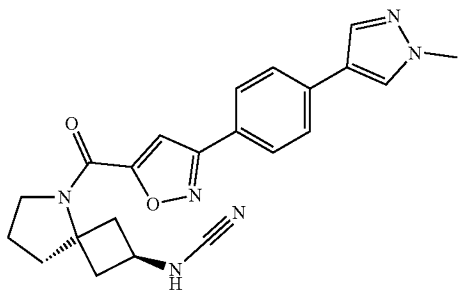 | 3-[4-(1-methyl-1H-pyrazol-4-yl)phenyl]-N-[(1s,3s)-3-(cyanoamino)cyclobutyl]-1,2-oxazole-5-carboxamide | +++ |
| Compound 3-4 | 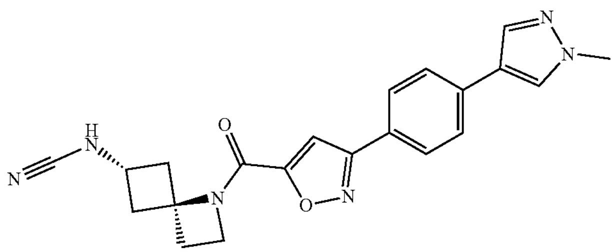 [SMILES: Cn1cc(-c2ccc(-c3cc(C(=O)N4CC[C@]45C[C@@H](NC#N)C5)on3)cc2)cn1] | {[(2r,4s)-5-{3-[4-(1-methyl-1H-pyrazol-4-yl)phenyl]-1,2-oxazole-5-carbonyl}-5-azaspiro[3.4]octan-2-yl]amino}carbonitrile | +++ |
| Compound 3-5 | 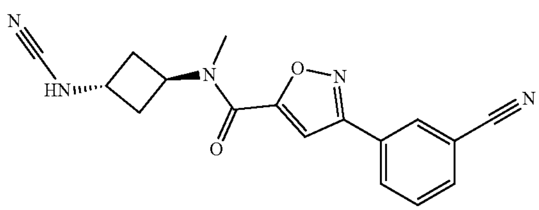 [SMILES: CN(C(=O)c1cc(-c2cccc(C#N)c2)no1)[C@H]1C[C@H](NC#N)C1] | {[(4r,6s)-1-{3-[4-(1-methyl-1H-pyrazol-4-yl)phenyl]-1,2-oxazole-5-carbonyl}-1-azaspiro[3.3]heptan-6-yl]amino}carbonitrile | +++ |
| Compound 3-6 | 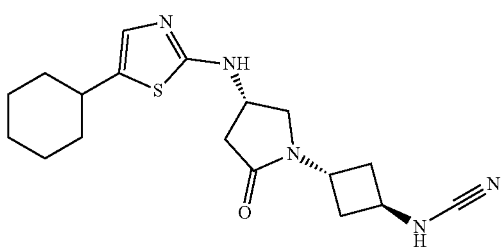 [SMILES: N#CN[C@H]1C[C@H](N2C[C@@H](Nc3ncc(C4CCCCC4)s3)CC2=O)C1] | 3-(3-cyanophenyl)-N-methyl-N-[(1r,3r)-3-(cyanoamino)cyclobutyl]-1,2-oxazole-5-carboxamide | ++ |
| Compound 6-1 | 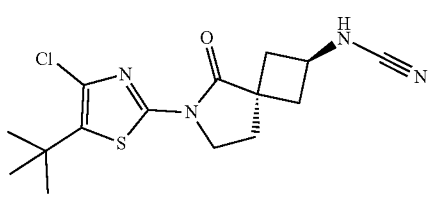 [SMILES: CC(C)(C)c1sc(N2CC[C@]3(C[C@H](NC#N)C3)C2=O)nc1Cl] | {[(1r,3r)-3-[(4S)-4-[(5-cyclohexyl-1,3-thiazol-2-yl)amino]-2-oxopyrrolidin-1-yl]cyclobutyl]amino}carbonitrile | +++ |
| Compound 7-1 | 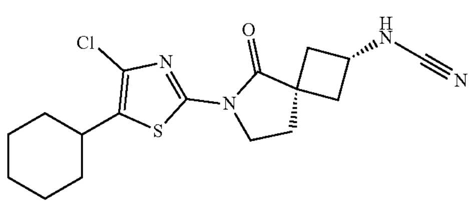 [SMILES: N#CN[C@H]1C[C@@]2(CCN(c3nc(Cl)c(C4CCCCC4)s3)C2=O)C1] | {[(2r,4s)-6-(5-tert-butyl-4-chloro-1,3-thiazol-2-yl)-5-oxo-6-azaspiro[3.4]octan-2-yl]amino}carbonitrile | ++++ |

TABLE A2-continued

| Example No. | Chemical Name | USP30 potency range |
|---|---|---|
| Compound 7-2 | {[(2s,4r)-6-(4-chloro-5-cyclohexyl-1,3-thiazol-2-yl)-5-oxo-6-azaspiro[3.4]octan-2-yl]amino}carbonitrile | +++ |
| Compound 7-3 | {[(2r,4s)-6-(4-chloro-5-cyclohexyl-1,3-thiazol-2-yl)-5-oxo-6-azaspiro[3.4]octan-2-yl]amino}carbonitrile | ++++ |
| Compound 8-1 | (1r,3r)-N-(5-tert-butyl-4-chloro-1,3-thiazol-2-yl)-3-(cyanoamino)-1-methoxycyclobutane-1-carboxamide | ++++ |
| Compound 9-1 | (1s,3s)-N-(5-tert-butyl-4-chloro-1,3-thiazol-2-yl)-1-chloro-3-(cyanoamino)cyclobutane-1-carboxamide | ++++ |
| Compound 9-2 | (1r,3r)-N-(5-tert-butyl-4-chloro-1,3-thiazol-2-yl)-1-chloro-3-(cyanoamino)cyclobutane-1-carboxamide | +++ |

Table A3

| Example No. | Chemical Name | USP30 potency range |
|---|---|---|
| Compound 10-1 | cis-4-(cyanoamino)-N-(5-cyclohexyl-1,3-thiazol-2-yl)cyclohexane-1-carboxamide | +++ |
| Compound 10-2 | trans-4-(cyanoamino)-N-(5-cyclohexyl-1,3-thiazol-2-yl)cyclohexane-1-carboxamide | ++ |
| Compound 10-3 | (1R,2R)-2-(cyanoamino)-N-(5-cyclohexyl-1,3-thiazol-2-yl)cyclopentane-1-carboxamide | ++ |

TABLE A2-continued

| Example No. | Structure | Chemical Name | USP30 potency range |
|---|---|---|---|
| Compound 10-4 | 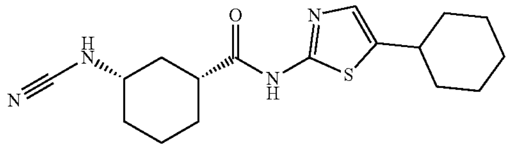 [SMILES: N#CN[C@H]1CCC[C@@H](C(=O)Nc2ncc(C3CCCCC3)s2)C1] | (1R,3S)-3-(cyanoamino)-N-(5-cyclohexyl-1,3-thiazol-2-yl)cyclohexane-1-carboxamide | − |
| Compound 10-5 | 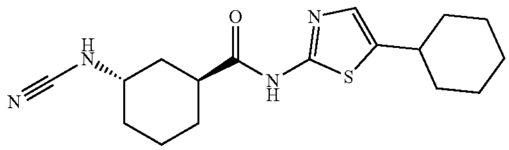 [SMILES: N#CN[C@H]1CCC[C@H](C(=O)Nc2ncc(C3CCCCC3)s2)C1] | (1S,3S)-3-(cyanoamino)-N-(5-cyclohexyl-1,3-thiazol-2-yl)cyclohexane-1-carboxamide | − |
| Compound 10-6 | 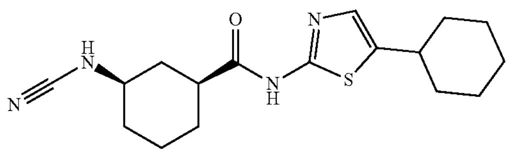 [SMILES: N#CN[C@@H]1CCC[C@H](C(=O)Nc2ncc(C3CCCCC3)s2)C1] | (1S,3R)-3-(cyanoamino)-N-(5-cyclohexyl-1,3-thiazol-2-yl)cyclohexane-1-carboxamide | ++ |
| Compound 10-7 | 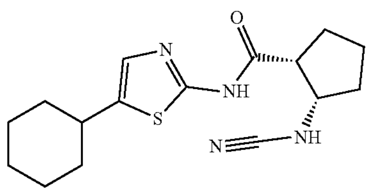 [SMILES: N#CN[C@H]1CCC[C@H]1C(=O)Nc1ncc(C2CCCCC2)s1] | (1R,2S)-2-(cyanoamino)-N-(5-cyclohexyl-1,3-thiazol-2-yl)cyclopentane-1-carboxamide | ++ |
| Compound 10-8 | 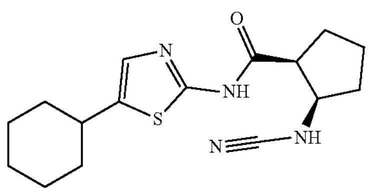 [SMILES: N#CN[C@@H]1CCC[C@@H]1C(=O)Nc1ncc(C2CCCCC2)s1] | (1S,2R)-2-(cyanoamino)-N-(5-cyclohexyl-1,3-thiazol-2-yl)cyclopentane-1-carboxamide | ++ |
| Compound 10-9 | 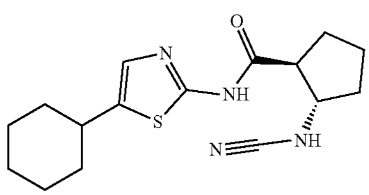 [SMILES: N#CN[C@H]1CCC[C@@H]1C(=O)Nc1ncc(C2CCCCC2)s1] | (1S,2S)-2-(cyanoamino)-N-(5-cyclohexyl-1,3-thiazol-2-yl)cyclopentane-1-carboxamide | ++ |
| Compound 1-10 | 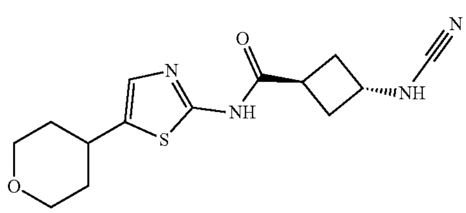 [SMILES: N#CN[C@H]1C[C@H](C(=O)Nc2ncc(C3CCOCC3)s2)C1] | trans-3-(cyanoamino)-N-[5-(oxan-4-yl)-1,3-thiazol-2-yl]cyclobutane-1-carboxamide | ++ |
| Compound 10-10 | 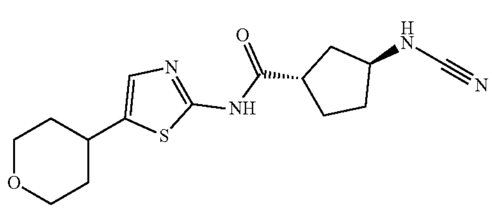 [SMILES: N#CN[C@H]1CC[C@H](C(=O)Nc2ncc(C3CCOCC3)s2)C1] | (1S,3S)-3-(cyanoamino)-N-[5-(oxan-4-yl)-1,3-thiazol-2-yl]cyclopentane-1-carboxamide | ++ |

TABLE A2-continued

| Example No. | Structure | Chemical Name | USP30 potency range |
|---|---|---|---|
| Compound 10-11 | 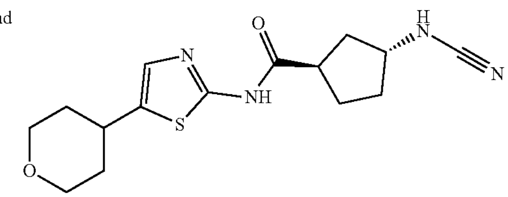 | (1R,3R)-3-(cyanoamino)-N-[5-(oxan-4-yl)-1,3-thiazol-2-yl]cyclopentane-1-carboxamide | + |
| Compound 11-1 | 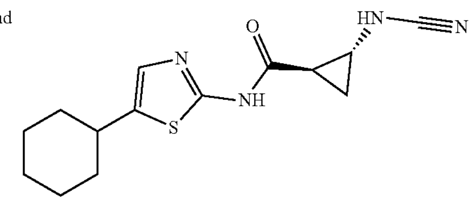 | trans-2-(cyanoamino)-N-(5-cyclohexyl-1,3-thiazol-2-yl)cyclopropane-1-carboxamide | ++ |
| Compound 11-2 | 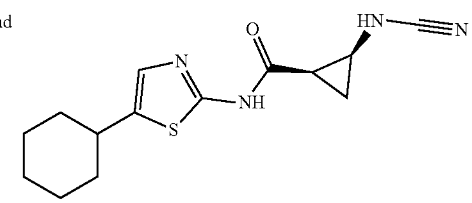 | cis-2-(cyanoamino)-N-(5-cyclohexyl-1,3-thiazol-2-yl)cyclopropane-1-carboxamide | ++ |
| Compound 2-2 | 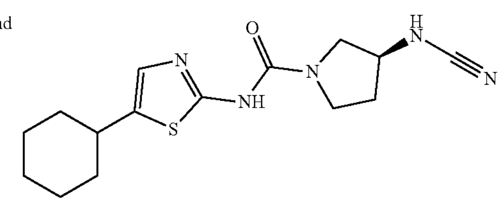 | (3S)-3-(cyanoamino)-N-(5-cyclohexyl-1,3-thiazol-2-yl)pyrrolidine-1-carboxamide | ++ |
| Compound 2-3 | 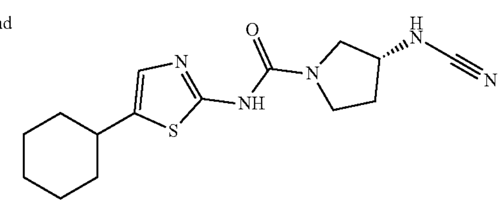 | (3R)-3-(cyanoamino)-N-(5-cyclohexyl-1,3-thiazol-2-yl)pyrrolidine-1-carboxamide | ++ |
| Compound 12-1 | 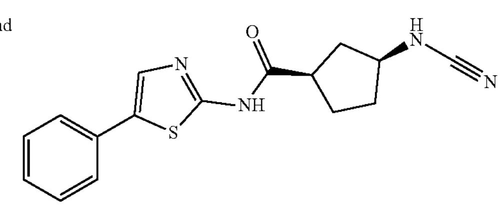 | (1R,3S)-3-(cyanoamino)-N-(5-phenyl-1,3-thiazol-2-yl)cyclopentane-1-carboxamide | ++ |
| Compound 12-2 | 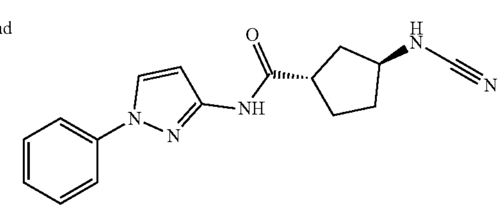 | (1S,3S)-3-(cyanoamino)-N-(1-phenyl-1H-pyrazol-3-yl)cyclopentane-1-carboxamide | + |

TABLE A2-continued

| Example No. | Chemical Name | USP30 potency range |
|---|---|---|
| Compound 12-3 | (1S,3S)-3-(cyanoamino)-N-(5-cyclohexyl-1,3-thiazol-2-yl)cyclopentane-1-carboxamide | +++ |
| Compound 12-4 | (1S,3S)-3-(cyanoamino)-N-(5-phenyl-1,3-thiazol-2-yl)cyclopentane-1-carboxamide | ++ |
| Compound 12-5 | (1S,3S)-3-(cyanoamino)-N-(2,3-dihydro-1H-inden-5-yl)cyclopentane-1-carboxamide | + |
| Compound 12-6 | {[(1S,3S)-3-(4-phenylpiperazine-1-carbonyl)cyclopentyl]amino}carbonitrile | − |
| Compound 12-7 | (1S,3R)-N-(5-tert-butyl-1,3-thiazol-2-yl)-3-(cyanoamino)cyclopentane-1-carboxamide | ++ |
| Compound 12-8 | {[(3S)-1-[2-(2,3-dichlorophenyl)-1,3-thiazole-4-carbonyl]pyrrolidin-3-yl]amino}carbonitrile | ++ |
| Compound 12-9 | ({1-[2-(2,4-dichlorophenyl)-1,3-thiazole-4-carbonyl]piperidin-4-yl}amino)carbonitrile | ++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

Embodiments of the disclosure are set out in the following numbered clauses:

1. At least one chemical entity chosen from compounds of Formula (I):

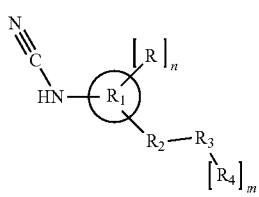

and pharmaceutically acceptable salts, solvates, prodrugs, stereoisomers, and tautomers thereof,
wherein:
R is independently chosen from hydrogen, OH, CN, ($C_1$-$C_6$) alkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, and ($C_3$-$C_6$) heterocycloalkyl groups;
n is 0, 1, or 2;
wherein, if n is 2, the R groups can combine to form a fused ring system with $R_1$;
$R_1$ is chosen from 3-6 membered cyclic or heterocyclic groups;
$R_2$, is chosen from $C(X)_n$, $S(O)_2$, $N(X)$, heteroatom linkers, $N(X)S(O)_2$, $N(X)S(O)_2N(X)$, carbonylalkyl groups, and carbonylheteroalkyl groups, wherein the alkyl portion of carbonylalkyl and carbonylheteroalkyl groups can optionally cyclize with R, $R_1$, or $R_3$;
X is independently chosen from hydrogen, alkyl groups, and heteroalkyl groups, wherein the alkyl and heteroalkyl groups can optionally cyclize with R, $R_1$, or $R_3$ or with another X group when multiple X groups are present;
$R_3$ is chosen from hydrogen, halogens, alkyl groups, heteroalkyl groups, haloalkyl groups, alkoxy groups, heteroalkoxy groups, haloalkoxy groups, carbonylalkyl groups, carbonylheteroalkyl groups, cyclic groups, heterocyclic groups, aryl groups, and heteroaryl groups, wherein any rings are optionally substituted with 1 or 2 R groups;
$R_4$ is independently chosen from alkyl groups, heteroalkyl groups, haloalkyl groups, alkoxy groups, cycloalkoxy groups, heteroalkoxy groups, haloalkoxy groups, carboxyalkyl groups, heterocarboxyalkyl groups, cyclic groups, heterocyclic groups, aryl groups and heteroaryl groups, wherein any rings are optionally substituted with 1 or 2 Y groups;
Y is independently chosen from hydrogen, OH, CN, $N(X)_2$, ($C_1$-$C_6$) alkyl groups, ($C_1$-$C_6$) heteroalkyl groups, ($C_1$-$C_6$) alkoxy groups, ($C_1$-$C_6$) haloalkyl groups, ($C_1$-$C_6$) haloalkoxy groups, halogen, ($C_3$-$C_6$) cycloalkyl groups, ($C_3$-$C_6$) heterocycloalkyl groups, ($C_5$-$C_8$) aryl groups, and ($C_4$-$C_8$) heteroaryl groups; and
m is 0, 1, or 2.
2. The chemical entity of clause 1, wherein $R_1$ is chosen from cyclopropane, cyclobutane, cyclopentane, and cyclohexane.
3. The chemical entity of clause 1, wherein $R_1$ is chosen from cyclobutane and cyclopentane.
4. The chemical entity of clause 1, wherein $R_1$ is chosen from heterocyclic groups.
5. The chemical entity of clause 1, wherein $R_1$ is a pyrrolidine.
6. The chemical entity of clause 1, wherein $R_2$ is chosen from carbonylalkyl and heterocarbonylalkyl groups.
7. The chemical entity of clause 1, wherein $R_2$ is chosen from amides, reversed amides, and ureas.
8. The chemical entity of clause 1, wherein $R_2$ is an amide.
9. The chemical entity of clause 1, wherein $R_3$ is chosen from aryl and heteroaryl rings.
10. The chemical entity of clause 1, wherein $R_3$ is chosen from thiazole, indenyl, pyrazole, and phenyl rings.
11. The chemical entity of clause 1, wherein $R_3$ is chosen from cyclic and heterocyclic rings.
12. The chemical entity of clause 1, wherein m is 0.
13. The chemical entity of clause 1, wherein $R_4$ is chosen from cyclic and heterocyclic rings optionally substituted with 1 or 2 R.
14. The chemical entity of clause 1, wherein $R_4$ is chosen from alkyl, heteroalkyl, and haloalkyl groups.
15. The chemical entity of clause 1, wherein $R_4$ is chosen from aryl and heteroaryl rings optionally substituted with 1 or 2 R.
16. The chemical entity of clause 1, wherein R is chosen from halogens.
17. The chemical entity of clause 1, chosen from the following compounds:

| Example No. | Structure | Chemical Name |
|---|---|---|
| Compound 10-1 | 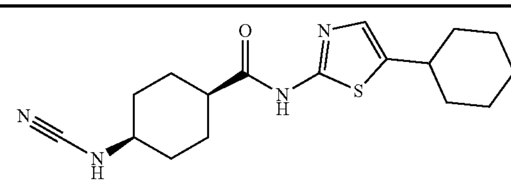 | cis-4-(cyanoamino)-N-(5-cyclohexyl-1,3-thiazol-2-yl)cyclohexane-1-carboxamide |
| Compound 10-2 | 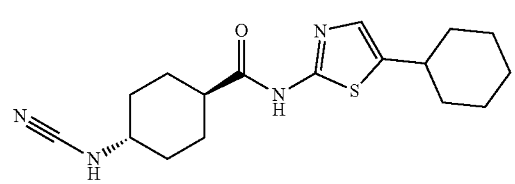 [SMILES: N#CN[C@H]1CC[C@H](C(=O)Nc2ncc(C3CCCCC3)s2)CC1] | trans-4-(cyanoamino)-N-(5-cyclohexyl-1,3-thiazol-2-yl)cyclohexane-1-carboxamide |

| Example No. | Structure | Chemical Name |
|---|---|---|
| Compound 10-3 | 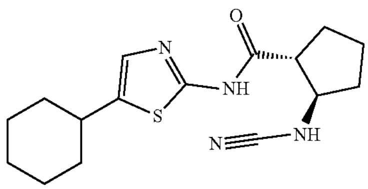 [SMILES: N#CN[C@@H]1CCC[C@H]1C(=O)Nc1ncc(C2CCCCC2)s1] | (1R,2R)-2-(cyanoamino)-N-(5-cyclohexyl-1,3-thiazol-2-yl)cyclopentane-1-carboxamide |
| Compound 10-4 | 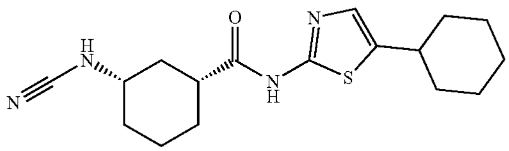 [SMILES: N#CN[C@H]1CCC[C@@H](C(=O)Nc2ncc(C3CCCCC3)s2)C1] | (1R,3S)-3-(cyanoamino)-N-(5-cyclohexyl-1,3-thiazol-2-yl)cyclohexane-1-carboxamide |
| Compound 10-5 | 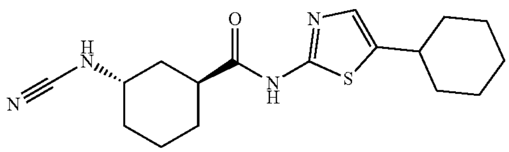 [SMILES: N#CN[C@H]1CCC[C@H](C(=O)Nc2ncc(C3CCCCC3)s2)C1] | (1S,3S)-3-(cyanoamino)-N-(5-cyclohexyl-1,3-thiazol-2-yl)cyclohexane-1-carboxamide |
| Compound 10-6 | 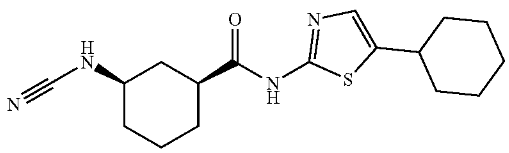 [SMILES: N#CN[C@@H]1CCC[C@H](C(=O)Nc2ncc(C3CCCCC3)s2)C1] | (1S,3R)-3-(cyanoamino)-N-(5-cyclohexyl-1,3-thiazol-2-yl)cyclohexane-1-carboxamide |
| Compound 10-7 | 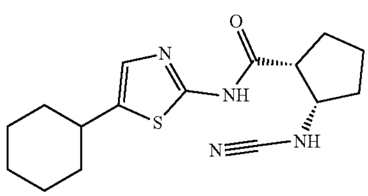 [SMILES: N#CN[C@H]1CCC[C@H]1C(=O)Nc1ncc(C2CCCCC2)s1] | (1R,2S)-2-(cyanoamino)-N-(5-cyclohexyl-1,3-thiazol-2-yl)cyclopentane-1-carboxamide |
| Compound 10-8 | 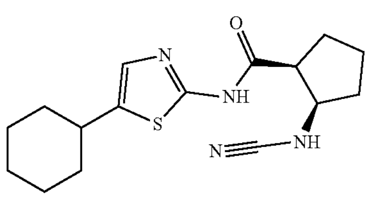 [SMILES: N#CN[C@@H]1CCC[C@@H]1C(=O)Nc1ncc(C2CCCCC2)s1] | (1S,2R)-2-(cyanoamino)-N-(5-cyclohexyl-1,3-thiazol-2-yl)cyclopentane-1-carboxamide |
| Compound 10-9 | 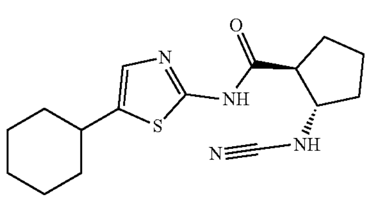 [SMILES: N#CN[C@H]1CCC[C@@H]1C(=O)Nc1ncc(C2CCCCC2)s1] | (1S,2S)-2-(cyanoamino)-N-(5-cyclohexyl-1,3-thiazol-2-yl)cyclopentane-1-carboxamide |
| Compound 1-1 | 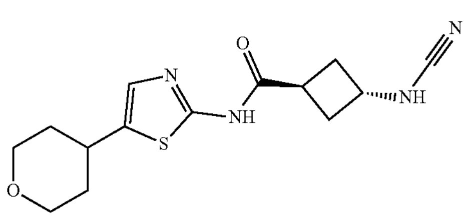 [SMILES: N#CN[C@H]1C[C@H](C(=O)Nc2ncc(C3CCOCC3)s2)C1] | trans-3-(cyanoamino)-N-[5-(oxan-4-yl)-1,3-thiazol-2-yl]cyclobutane-1-carboxamide |

| Example No. | Structure | Chemical Name |
|---|---|---|
| Compound 10-10 | 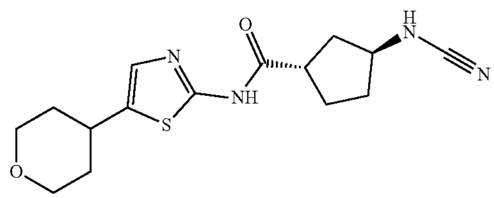 [SMILES: N#CN[C@H]1CC[C@H](C(=O)Nc2ncc(C3CCOCC3)s2)C1] | (1S,3S)-3-(cyanoamino)-N-[5-(oxan-4-yl)-1,3-thiazol-2-yl]cyclopentane-1-carboxamide |
| Compound 10-11 | 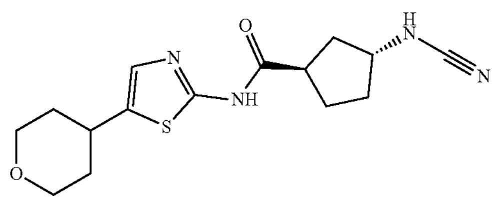 [SMILES: N#CN[C@@H]1CC[C@@H](C(=O)Nc2ncc(C3CCOCC3)s2)C1] | (1R,3R)-3-(cyanoamino)-N-[5-(oxan-4-yl)-1,3-thiazol-2-yl]cyclopentane-1-carboxamide |
| Compound 11-1 | 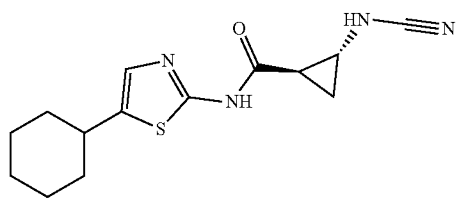 [SMILES: N#CN[C@@H]1C[C@H]1C(=O)Nc1ncc(C2CCCCC2)s1] | trans-2-(cyanoamino)-N-(5-cyclohexyl-1,3-thiazol-2-yl)cyclopropane-1-carboxamide |
| Compound 11-2 | 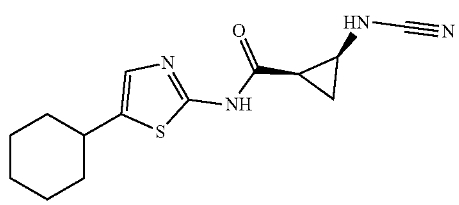 [SMILES: N#CN[C@H]1C[C@H]1C(=O)Nc1ncc(C2CCCCC2)s1] | cis-2-(cyanoamino)-N-(5-cyclohexyl-1,3-thiazol-2-yl)cyclopropane-1-carboxamide |
| Compound 2-1 | 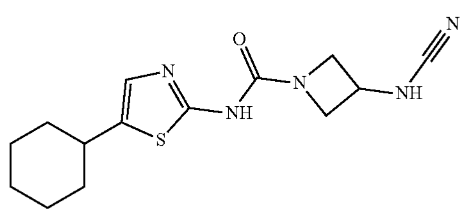 [SMILES: N#CNC1CN(C(=O)Nc2ncc(C3CCCCC3)s2)C1] | 3-(cyanoamino)-N-(5-cyclohexyl-1,3-thiazol-2-yl)azetidine-1-carboxamide |
| Compound 2-2 | 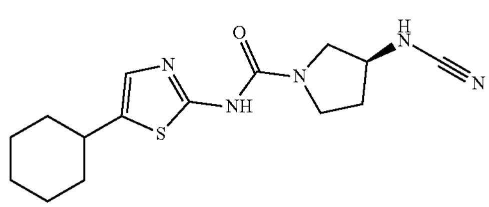 [SMILES: N#CN[C@H]1CCN(C(=O)Nc2ncc(C3CCCCC3)s2)C1] | (3S)-3-(cyanoamino)-N-(5-cyclohexyl-1,3-thiazol-2-yl)pyrrolidine-1-carboxamide |
| Compound 2-3 | 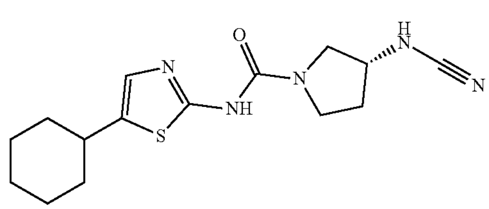 [SMILES: N#CN[C@@H]1CCN(C(=O)Nc2ncc(C3CCCCC3)s2)C1] | (3R)-3-(cyanoamino)-N-(5-cyclohexyl-1,3-thiazol-2-yl)pyrrolidine-1-carboxamide |

-continued

| Example No. | Structure | Chemical Name |
|---|---|---|
| Compound 3-1 | 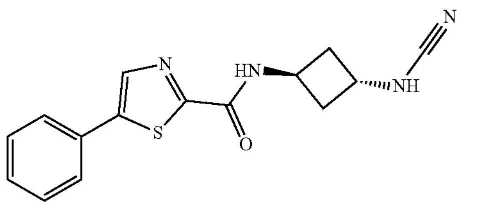 [SMILES: N#CN[C@H]1C[C@H](NC(=O)c2ncc(-c3ccccc3)s2)C1] | 5-phenyl-N-[(trans)-3-(cyanoamino)cyclobutyl]-1,3-thiazole-2-carboxamide |
| Compound 4-1 | 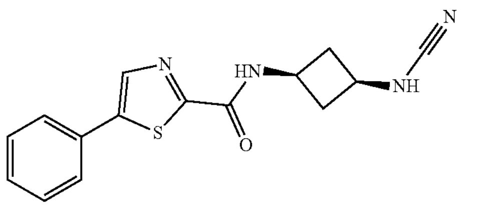 [SMILES: N#CN[C@H]1C[C@@H](NC(=O)c2ncc(-c3ccccc3)s2)C1] | 5-phenyl-N-[(cis)-3-(cyanoamino)cyclobutyl]-1,3-thiazole-2-carboxamide |
| Compound 12-1 | 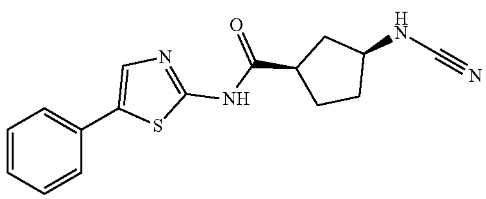 [SMILES: N#CN[C@H]1CC[C@@H](C(=O)Nc2ncc(-c3ccccc3)s2)C1] | (1R,3S)-3-(cyanoamino)-N-(5-phenyl-1,3-thiazol-2-yl)cyclopentane-1-carboxamide |
| Compound 12-2 | 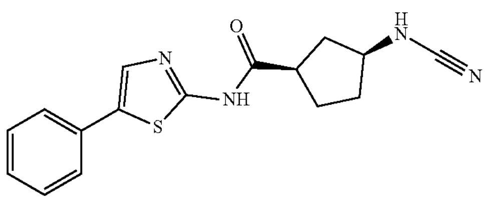 [SMILES: N#CN[C@H]1CC[C@@H](C(=O)Nc2ncc(-c3ccccc3)s2)C1] | (1S,3S)-3-(cyanoamino)-N-(1-phenyl-1H-pyrazol-3-yl)cyclopentane-1-carboxamide |
| Compound 12-3 | 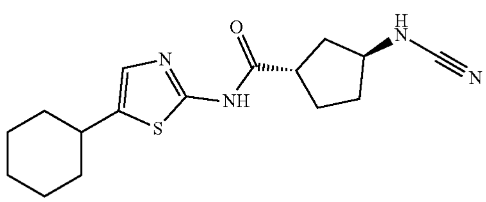 [SMILES: N#CN[C@H]1CC[C@H](C(=O)Nc2ncc(C3CCCCC3)s2)C1] | (1S,3S)-3-(cyanoamino)-N-(5-cyclohexyl-1,3-thiazol-2-yl)cyclopentane-1-carboxamide |
| Compound 12-4 | 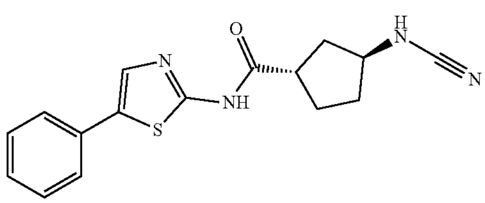 [SMILES: N#CN[C@H]1CC[C@H](C(=O)Nc2ncc(-c3ccccc3)s2)C1] | (1S,3S)-3-(cyanoamino)-N-(5-phenyl-1,3-thiazol-2-yl)cyclopentane-1-carboxamide |
| Compound 5-1 | 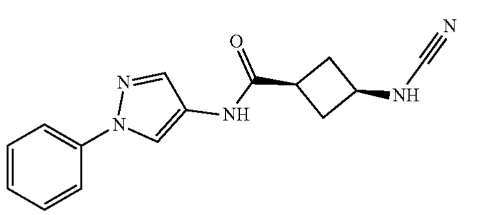 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide |

| Example No. | Structure | Chemical Name |
| --- | --- | --- |
| Compound 5-2 | 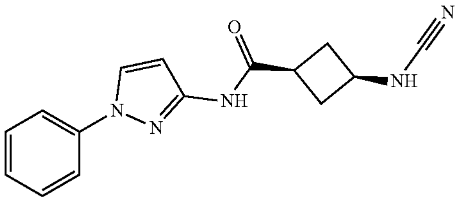 [SMILES: N#CN[C@H]1C[C@@H](C(=O)Nc2ccn(-c3ccccc3)n2)C1] | cis-3-(cyanoamino)-N-(1-phenyl-1H-pyrazol-3-yl)cyclobutane-1-carboxamide |
| Compound 5-3 | 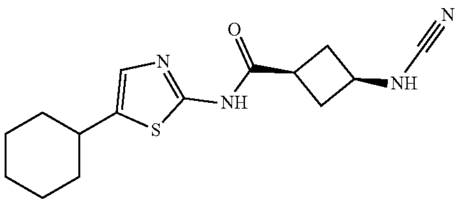 [SMILES: N#CN[C@H]1C[C@@H](C(=O)Nc2ncc(C3CCCCC3)s2)C1] | cis-3-(cyanoamino)-N-(5-cyclohexyl-1,3-thiazol-2-yl)cyclobutane-1-carboxamide |
| Compound 5-4 | 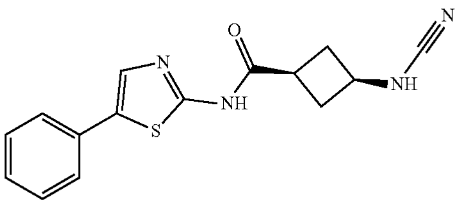 [SMILES: N#CN[C@H]1C[C@@H](C(=O)Nc2ncc(-c3ccccc3)s2)C1] | cis-3-(cyanoamino)-N-(5-phenyl-1,3-thiazol-2-yl)cyclobutane-1-carboxamide |
| Compound 5-5 | 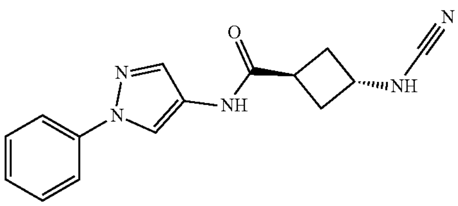 [SMILES: N#CN[C@H]1C[C@H](C(=O)Nc2cnn(-c3ccccc3)c2)C1] | trans-3-(cyanoamino)-N-(1-phenyl-1H-pyrazol-4-yl)cyclobutane-1-carboxamide |
| Compound 5-6 | 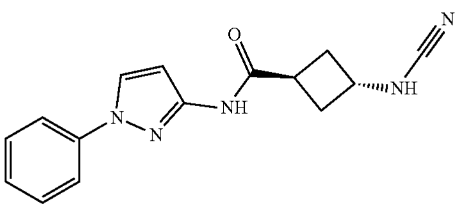 [SMILES: N#CN[C@H]1C[C@H](C(=O)Nc2ccn(-c3ccccc3)n2)C1] | trans-3-(cyanoamino)-N-(1-phenyl-1H-pyrazol-3-yl)cyclobutane-1-carboxamide |
| Compound 5-7 | 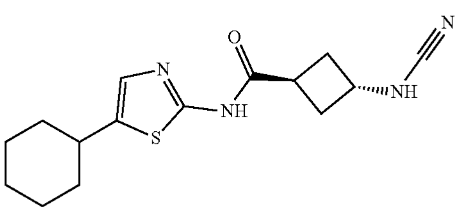 [SMILES: N#CN[C@H]1C[C@H](C(=O)Nc2ncc(C3CCCCC3)s2)C1] | trans-3-(cyanoamino)-N-(5-cyclohexyl-1,3-thiazol-2-yl)cyclobutane-1-carboxamide |
| Compound 5-8 | 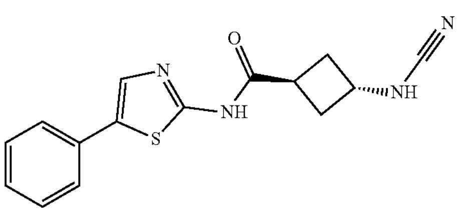 [SMILES: N#CN[C@H]1C[C@H](C(=O)Nc2ncc(-c3ccccc3)s2)C1] | trans-3-(cyanoamino)-N-(5-phenyl-1,3-thiazol-2-yl)cyclobutane-1-carboxamide |

-continued

| Example No. | Structure | Chemical Name |
|---|---|---|
| Compound 12-5 | 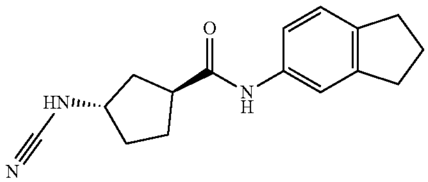 [SMILES: N#CN[C@H]1CC[C@H](C(=O)Nc2ccc3c(c2)CCC3)C1] | (1S,3S)-3-(cyanoamino)-N-(2,3-dihydro-1H-inden-5-yl)cyclopentane-1-carboxamide |
| Compound 12-6 | 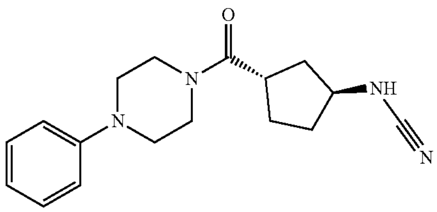 [SMILES: N#CN[C@H]1CC[C@H](C(=O)N2CCN(c3ccccc3)CC2)C1] | {[(1S,3S)-3-(4-phenylpiperazine-1-carbonyl)cyclopentyl]-amino}carbonitrile |
| Compound 12-7 | 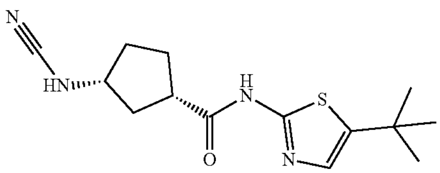 [SMILES: CC(C)(C)c1cnc(NC(=O)[C@H]2CC[C@@H](NC#N)C2)s1] | (1S,3R)-N-(5-tert-butyl-1,3-thiazol-2-yl)-3-(cyanoamino)cyclopentane-1-carboxamide |
| Compound 5-9 | 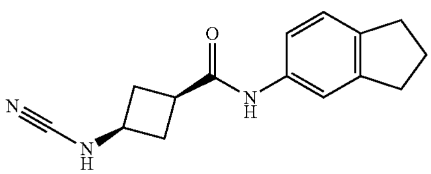 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide |
| Compound 5-10 | 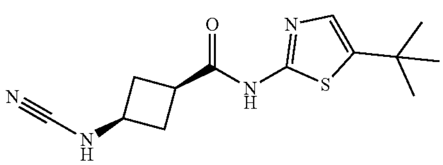 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide |
| Compound 5-11 | 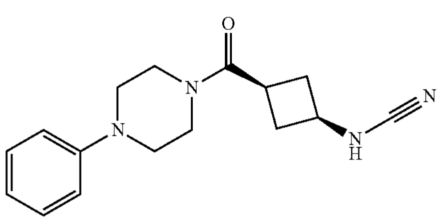 [SMILES: N#CN[C@H]1C[C@@H](C(=O)N2CCN(c3ccccc3)CC2)C1] | {[cis-3-(4-phenylpiperazine-1-carbonyl)cyclobutyl]amino}carbonitrile |
| Compound 5-12 | 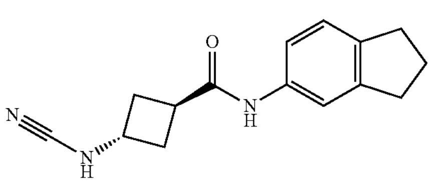 [SMILES: N#CN[C@H]1C[C@H](C(=O)Nc2ccc3c(c2)CCC3)C1] | trans-3-(cyanoamino)-N-(2,3-dihydro-1H-inden-5-yl)cyclobutane-1-carboxamide |
| Compound 5-13 | 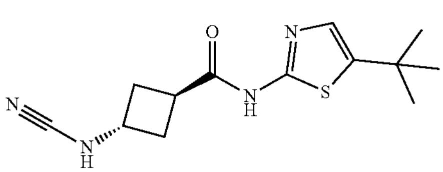 [SMILES: CC(C)(C)c1cnc(NC(=O)[C@H]2C[C@H](NC#N)C2)s1] | trans-N-(5-tert-butyl-1,3-thiazol-2-yl)-3-(cyanoamino)cyclobutane-1-carboxamide |

| Example No. | Structure | Chemical Name |
|---|---|---|
| Compound 5-14 | 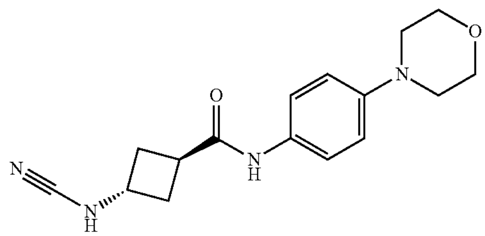 [SMILES: N#CN[C@H]1C[C@H](C(=O)Nc2ccc(N3CCOCC3)cc2)C1] | trans-3-(cyanoamino)-N-[4-(morpholin-4-yl)phenyl]cyclobutane-1-carboxamide |
| Compound 12-8 | 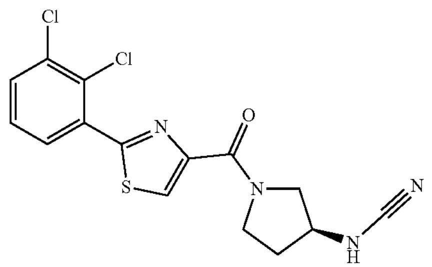 [SMILES: N#CN[C@H]1CCN(C(=O)c2csc(-c3cccc(Cl)c3Cl)n2)C1] | {[(3S)-1-[2-(2,3-dichlorophenyl)-1,3-thiazole-4-carbonyl]pyrrolidin-3-yl]amino}carbonitrile |
| Compound 12-9 | | ({1-[2-(2,4-dichlorophenyl)-1,3-thiazole-4-carbonyl]piperidin-4-yl}amino)carbonitrile | and pharmaceutically acceptable salts, solvates, prodrugs, stereoisomers, and tautomers thereof.

18. A composition comprising at least one chemical entity of any one of clauses 1-17, and a pharmaceutically acceptable carrier.

19. A method of inhibiting USP30 in vitro comprising administering to a Ubiquitin-Rhodamine 110 assay for USP30 activity an effective amount of at least one chemical entity of any one of clauses 1-17.

20. A method for treating at least one disease, disorder, or condition associated with mitochondrial dysfunction comprising administering to a patient in need thereof an effective amount of at least one chemical entity of any one of clauses 1-17.

21. The method of clause 20, wherein the at least one disease, disorder, or condition is chosen from neurodegenerative diseases, motor neuron diseases, metabolic disorders, cardio-vascular diseases, psychiatric diseases, osteoarthritis, and cancer.

22. The method of clause 21, wherein the neurodegenerative disease is chosen from Alzheimer's disease, Parkinson's disease, dementia, Prion disease, corticobasal degeneration, Posterior Cortical Atrophy, Primary Progressive Aphasia, Progressive Supranuclear Palsy, Pick's disease, Chronic Traumatic Encephelopathy, Traumatic Brain Injury, peripheral neuropathy, and multiple sclerosis.

23. The method of clause 21, wherein the motor neuron disease is chosen from Amyltrophic Lateral Sclerosis (ALS), Huntington's disease, Spinocerebellar Ataxia, Ataxia, and Spinal Muscular Atrophy.

24. The method of clause 21 wherein the metabolic disorder is chosen from diabetes, mitochondrial encephalomyopathy, Stroke-Like Episodes (MELAS), mitochondrial myopathy, encephalopathy, lactic acidosis, Leber's hereditary optic neuropathy (LHON), neuropathy, ataxia, retinitis pigmentosa-maternally inherited Leigh syndrome (NARP-MILS), Danon disease, diabetic nephropathy, retinitis pigmentosa-maternally inherited Leigh syndrome (NARP-MILS), multiple sulfatase deficiency (MSD), mucolipidosis II (ML II), mucolipidosis III (ML III), mucolipidosis IV (ML IV), GM1-gangliosidosis (GM1), neuronal ceroid-lipofuscinoses (NCL1), Alpers disease, Barth syndrome, Beta-oxidation defects, carnitine-acyl-carnitine deficiency, carnitine deficiency, creatine deficiency syndrome, co-enzyme Q 10 deficiency, complex I deficiency, complex II deficiency, CPT I deficiency, CPT II deficiency, glutaric aciduria type II, Kearns-Sayre syndrome, lactic acidosis, long-chain acyl-CoA dehydrogenase deficiency (LCHAD), Leigh disease complex III deficiency, complex IV deficiency, complex V deficiency, COX deficiency, chronic progressive external syndrome, lethal infantile cardiomyopathy (LIC), Luft disease, glutaric aciduria type II, medium-chain acyl-CoA dehydrogenase deficiency (MCAD), myoclonic epilepsy and ragged-red fiber (MERRF) syndrome, mitochondrial cytopathy, mitochondrial recessive ataxia syndrome, mitochondrial DNA depletion syndrome, myoneurogastrointestinal disorder and encephalopathy, Pearson syndrome, pyruvate dehydrogenase deficiency, pyruvate carboxylase deficiency, POLG ophthalmoplegia syndrome mutations, medium/short-chain 3-hydroxyacyl-CoA dehydrogenase (M/SCHAD) deficiency, and very long-chain acyl-CoA dehydrogenase (VLCAD) deficiency.

25. The method of clause 21 wherein the cardiovascular disorder is chosen from transthyretin amyloidosis, heart failure, ischemic heart disease leading to cardiac infarction, and cardiac amyloidosis.

26. The method of clause 21 wherein the psychiatric disease is chosen from schizophrenia, depression, and general anxiety disorder.

27. The method of clause 21, wherein the cancer is chosen from bladder cancer, breast cancer, cervical cancer, colorectal cancer, esophageal cancer, gastric cancer, head and neck cancer, hematologic cancer, lung cancer, liver cancer, lymphoma, neurological cancer, ovarian, pancreatic cancer, prostate cancer, renal cancer, sarcoma, skin cancer, thyroid cancer, and uterine cancer.

The invention claimed is:
1. A compound of Formula (II):

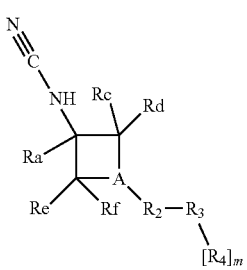

(II)

or a pharmaceutically acceptable salt thereof, wherein:
A is N or $CR_b$;
$R_a$ is hydrogen;
$R_b$ is selected from the group consisting of hydrogen, halogen, ($C_1$-$C_6$) alkyl optionally substituted with one or more $R_5$, and ($C_1$-$C_6$) alkoxy optionally substituted with one or more $R_5$; or
$R_b$ and X together form a ($C_3$-$C_6$) spirocyclic cycloalkyl or ($C_3$-$C_6$) spirocyclic heterocycloalkyl;
each of $R_c$, $R_d$, $R_e$ and $R_f$ is independently selected from the group consisting of hydrogen and ($C_1$-$C_6$) alkyl optionally substituted with one or more $R_5$;
$R_2$ is selected from the group consisting of C(O)N(X) and N(X)C(O);
X is independently chosen from hydrogen, alkyl, and heteroalkyl, wherein the alkyl and heteroalkyl can optionally cyclize with $R_3$;
$R_3$ is selected from the group consisting of ($C_1$-$C_6$) alkyl, ($C_3$-$C_6$) cycloalkyl, ($C_1$-$C_6$) heteroalkyl, aryl having 1 to 3 aromatic rings and optionally substituted with 1 or 2 R groups, and heteroaryl having 1 to 3 aromatic rings and optionally substituted with 1 or 2 R groups;
$R_4$ is independently chosen from alkyl, cycloalkyl, heteroalkyl, haloalkyl, alkoxy, cycloalkoxy, heteroalkoxy, haloalkoxy, carboxyalkyl, heterocarboxyalkyl, cyclic, heterocyclic, aryl, and heteroaryl, wherein any rings are optionally substituted with 1 or 2 Y groups;
$R_5$ is selected from the group consisting of hydrogen, halogen, OH, ($C_1$-$C_3$) alkyl, and ($C_1$-$C_3$) alkoxy;
R is independently chosen from hydrogen, OH, CN, ($C_1$-$C_6$) alkyl, ($C_1$-$C_6$) alkoxy, ($C_1$-$C_6$) haloalkyl, ($C_1$-$C_6$) haloalkoxy, halogen, ($C_3$-$C_6$) cycloalkyl, ($C_3$-$C_6$) heterocycloalkyl, ($C_3$-$C_6$) cycloalkyloxy, and ($C_1$-$C_6$) alkoxyalkyl;
Y is independently chosen from hydrogen, OH, CN, $N(X)_2$, ($C_1$-$C_6$) alkyl, ($C_1$-$C_6$) heteroalkyl, ($C_1$-$C_6$) alkoxy, ($C_1$-$C_6$) haloalkyl, ($C_1$-$C_6$) haloalkoxy, halogen, ($C_3$-$C_6$) cycloalkyl, ($C_3$-$C_6$) heterocycloalkyl, ($C_5$-$C_8$) aryl, ($C_4$-$C_8$) heteroaryl, and ($C_4$-$C_8$) heteroaryl substituted with ($C_1$-$C_3$) alkyl; and
m is 0, 1, or 2.

2. The compound of claim 1, wherein each of $R_c$, $R_d$, $R_e$, and $R_f$ is independently selected from the group consisting of hydrogen and ($C_1$-$C_6$) alkyl.

3. The compound of claim 1, wherein $R_3$ is aryl having 1 to 3 aromatic rings and optionally substituted with 1 or 2 R groups or heteroaryl having 1 to 3 aromatic rings and optionally substituted with 1 or 2 R groups.

4. The compound of claim 3, wherein $R_4$ is cycloalkyl optionally substituted with 1 or 2 Y groups or aryl optionally substituted with 1 or 2 Y groups.

5. The compound of claim 4, wherein $R_4$ is cycloalkyl optionally substituted with 1 or 2 Y groups.

6. The compound of claim 3, wherein $R_3$ is heteroaryl having 1 aromatic ring containing two heteroatoms and optionally substituted with 1 or 2 R groups.

7. The compound of claim 6, wherein $R_3$ is a thiazole ring.

8. The compound of claim 6, wherein $R_4$ is cycloalkyl optionally substituted with 1 or 2 Y groups.

9. The compound of claim 1, wherein the compound is of Formula (III):

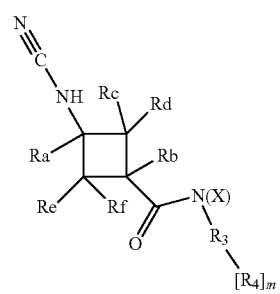

(III)

or a pharmaceutically acceptable salt thereof.

10. The compound of claim 9, wherein X is hydrogen.

11. The compound of claim 9, wherein each of $R_c$, $R_d$, $R_e$, and $R_f$ is hydrogen.

12. The compound of claim 11, wherein $R_3$ is aryl having 1 to 3 aromatic rings and optionally substituted with 1 or 2 R groups or heteroaryl having 1 to 3 aromatic rings and optionally substituted with 1 or 2 R groups.

13. The compound of claim 12, wherein $R_3$ is heteroaryl having 1 aromatic ring containing two heteroatoms and optionally substituted with 1 or 2 R groups.

14. The compound of claim 13, wherein $R_3$ is a thiazole ring.

15. The compound of claim 13, wherein $R_4$ is cycloalkyl optionally substituted with 1 or 2 Y groups.

16. The compound of claim 12, wherein $R_4$ is cycloalkyl optionally substituted with 1 or 2 Y groups or aryl optionally substituted with 1 or 2 Y groups.

17. The compound of claim 16, wherein $R_4$ is cycloalkyl optionally substituted with 1 or 2 Y groups.

18. The compound of claim 9, wherein m is 0.

19. The compound of claim 1, wherein each of $R_c$, $R_d$, $R_e$, and $R_f$ is hydrogen.

20. The compound of claim 19, wherein $R^b$ is selected from the group consisting of hydrogen and ($C_1$-$C_6$) alkyl groups.

21. The compound of claim 1, wherein $R^b$ is selected from the group consisting of hydrogen, halogen, ($C_1$-$C_6$) alkyl groups, and ($C_1$-$C_6$) alkoxy groups.

22. The compound of claim 1, wherein the compound is selected from:

| | | |
|---|---|---|
| Compound 1-1 | 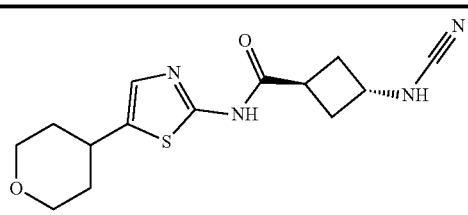 | trans-3-(cyanoamino)-N-[5-(oxan-4-yl)-1,3-thiazol-2-yl]cyclobutane-1-carboxamide; |
| Compound 2-1 | 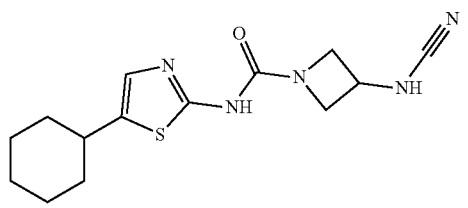 [SMILES: N#CNC1CN(C(=O)Nc2ncc(C3CCCCC3)s2)C1] | 3-(cyanoamino)-N-(5-cyclohexyl-1,3-thiazol-2-yl)azetidine-1-carboxamide; |
| Compound 3-1 | 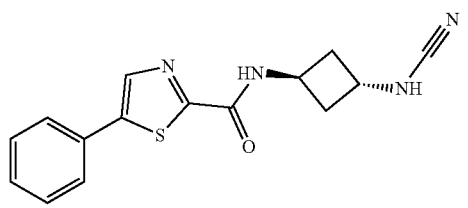 [SMILES: N#CN[C@H]1C[C@H](NC(=O)c2ncc(-c3ccccc3)s2)C1] | 5-phenyl-N-[(trans)-3-(cyanoamino)cyclobutyl]-1,3-thiazole-2-carboxamide; |
| Compound 4-1 | 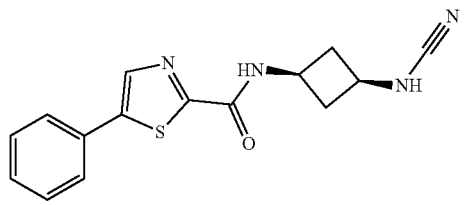 | 5-phenyl-N-[(cis)-3-(cyanoamino)cyclobutyl]-1,3-thiazole-2-carboxamide; |
| Compound 5-1 | 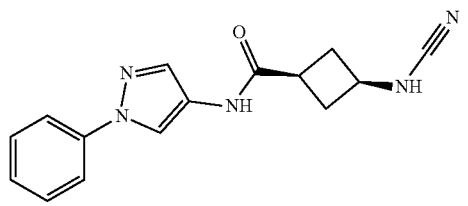 [SMILES: N#CN[C@H]1C[C@@H](C(=O)Nc2cnn(-c3ccccc3)c2)C1] | cis-3-(cyanoamino)-N-(1-phenyl-1H-pyrazol-4-yl)cyclobutane-1-carboxamide; |
| Compound 5-2 | 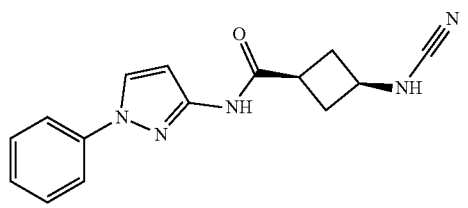 [SMILES: N#CN[C@H]1C[C@@H](C(=O)Nc2ccn(-c3ccccc3)n2)C1] | cis-3-(cyanoamino)-N-(1-phenyl-1H-pyrazol-3-yl)cyclobutane-1-carboxamide; |
| Compound 5-3 | 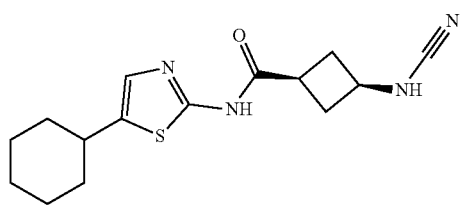 [SMILES: N#CN[C@H]1C[C@@H](C(=O)Nc2ncc(C3CCCCC3)s2)C1] | cis-3-(cyanoamino)-N-(5-cyclohexyl-1,3-thiazol-2-yl)cyclobutane-1-carboxamide; |

-continued

| | | |
|---|---|---|
| Compound 5-4 | 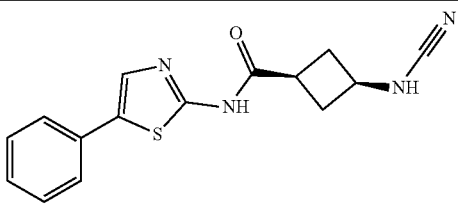 | cis-3-(cyanoamino)-N-(5-phenyl-1,3-thiazol-2-yl)cyclobutane-1-carboxamide; |
| Compound 5-5 | 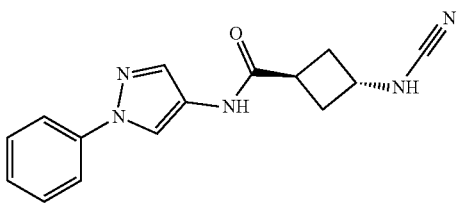 [SMILES: N#CN[C@H]1C[C@H](C(=O)Nc2cnn(-c3ccccc3)c2)C1] | trans-3-(cyanoamino)-N-(1-phenyl-1H-pyrazol-4-yl)cyclobutane-1-carboxamide; |
| Compound 5-6 | 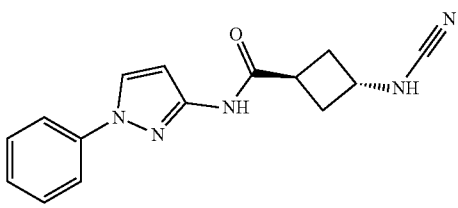 [SMILES: N#CN[C@H]1C[C@H](C(=O)Nc2ccn(-c3ccccc3)n2)C1] | trans-3-(cyanoamino)-N-(1-phenyl-1H-pyrazol-3-yl)cyclobutane-1-carboxamide; |
| Compound 5-7 | 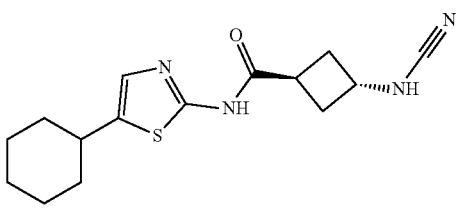 | trans-3-(cyanoamino)-N-(5-cyclohexyl-1,3-thiazol-2-yl)cyclobutane-1-carboxamide; |
| Compound 5-8 | 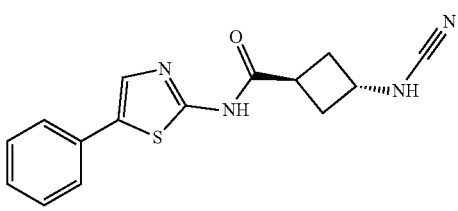 [SMILES: N#CN[C@H]1C[C@H](C(=O)Nc2ncc(-c3ccccc3)s2)C1] | trans-3-(cyanoamino)-N-(5-phenyl-1,3-thiazol-2-yl)cyclobutane-1-carboxamide; |
| Compound 5-9 | 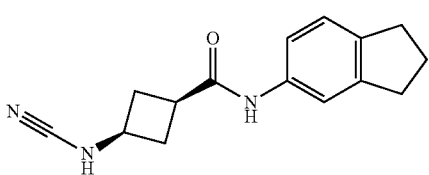 [SMILES: N#CN[C@H]1C[C@@H](C(=O)Nc2ccc3c(c2)CCC3)C1] | cis-3-(cyanoamino)-N-(2,3-dihydro-1H-inden-5-yl)cyclobutane-1-carboxamide; |
| Compound 5-10 | 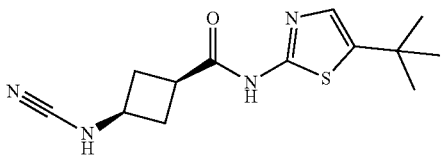 [SMILES: CC(C)(C)c1cnc(NC(=O)[C@H]2C[C@@H](NC#N)C2)s1] | cis-N-(5-tert-butyl-1,3-thiazol-2-yl)-3-(cyanoamino)cyclobutane-1-carboxamide; |
| Compound 5-11 | 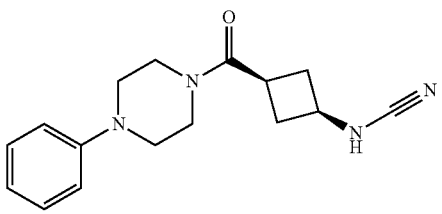 [SMILES: N#CN[C@H]1C[C@@H](C(=O)N2CCN(c3ccccc3)CC2)C1] | {[cis-3-(4-phenylpiperazine-1-carbonyl)cyclobutyl]amino}carbonitrile; |

| | | |
|---|---|---|
| Compound 5-12 | 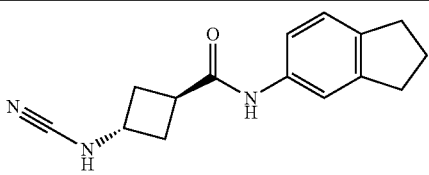 | trans-3-(cyanoamino)-N-(2,3-dihydro-1H-inden-5-yl)cyclobutane-1-carboxamide; |
| Compound 5-13 | 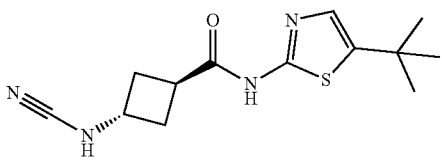 [SMILES: CC(C)(C)c1cnc(NC(=O)[C@H]2C[C@H](NC#N)C2)s1] | trans-N-(5-tert-butyl-1,3-thiazol-2-yl)-3-(cyanoamino)cyclobutane-1-carboxamide; |
| Compound 5-14 | 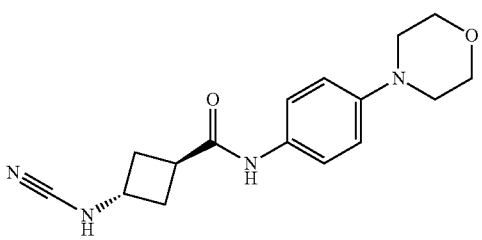 [SMILES: N#CN[C@H]1C[C@H](C(=O)Nc2ccc(N3CCOCC3)cc2)C1] | trans-3-(cyanoamino)-N-[4-(morpholin-4-yl)phenl]cyclobutane-1-carboxamide; |
| Compound 1-2 | 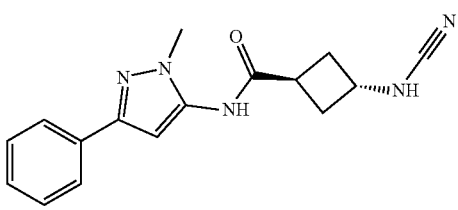 [SMILES: Cn1nc(-c2ccccc2)cc1NC(=O)[C@H]1C[C@H](NC#N)C1] | (1r,3r)-3-(cyanoamino)-N-(1-methyl-3-phenyl-1H-pyrazol-5-yl)cyclobutane-1-carboxamide; |
| Compound 1-3 | 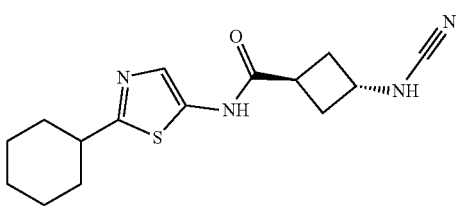 [SMILES: N#CN[C@H]1C[C@H](C(=O)Nc2cnc(C3CCCCC3)s2)C1] | (1r,3r)-3-(cyanoamino)-N-(2-cyclohexyl-1,3-thiazol-5-yl)cyclobulane-1-carboxamide; |
| Compound 1-4 | 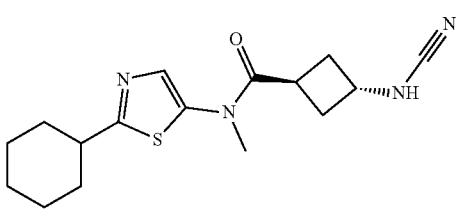 [SMILES: CN(c1cnc(C2CCCCC2)s1)C(=O)[C@H]1C[C@H](NC#N)C1] | (1r,3r)-3-(cyanoamino)-N-(2-cyclohexyl-1,3-thiazol-5-yl)-N-methylcyclobutane-1-carboxamide; |
| Compound 1-5 | 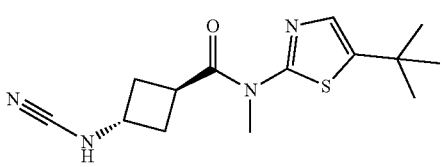 [SMILES: CN(c1ncc(C(C)(C)C)s1)C(=O)[C@H]1C[C@H](NC#N)C1] | (1r,3r)-N-(5-tert-butyl-1,3-thiazol-2-yl)-3-(cyanoamino)-N-methylcyclobutane-1-carboxamide; |
| Compound 1-6 | 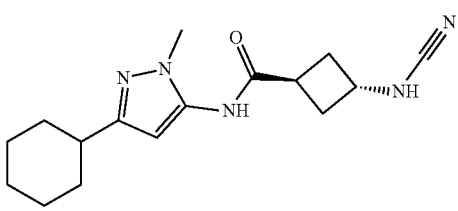 [SMILES: Cn1nc(C2CCCCC2)cc1NC(=O)[C@H]1C[C@H](NC#N)C1] | (1r,3r)-3-(cyanoamino)-N-(3-cyclohexyl-1-methyl-1H-pyrazol-5-yl)cyclobutane-1-carboxamide; |

-continued

| | | |
|---|---|---|
| Compound 1-7 | 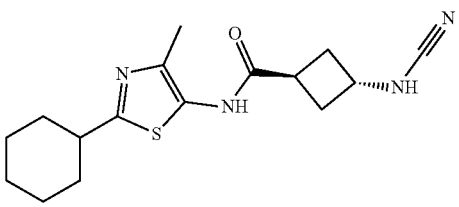 | (1r,3r)-3-(cyanoamino)-N-(2-cyclohexyl-4-methyl-1,3-thiazol-5-yl)cyclobutane-1-carboxamide; |
| Compound 1-8 | 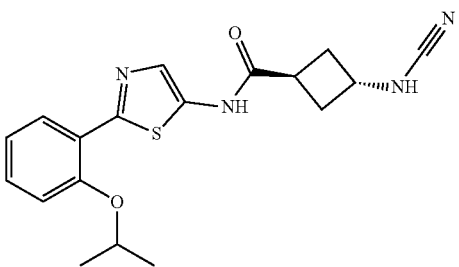 [SMILES: CC(C)Oc1ccccc1-c1ncc(NC(=O)[C@H]2C[C@H](NC#N)C2)s1] | (1r,3r)-3-(cyanoamino)-N-{2-[2-(propan-2-yloxy)phenyl]-1,3-thiazol-5-yl}cyclobutane-1-carboxamide; |
| Compound 1-9 | 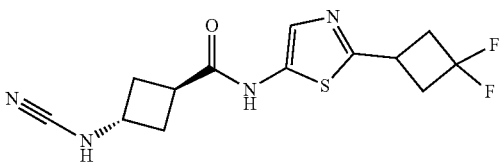 [SMILES: N#CN[C@H]1C[C@H](C(=O)Nc2cnc(C3CC(F)(F)C3)s2)C1] | (1r,3r)-3-(cyanoamino)-N-[2-(3,3-difluorocyclobutyl)-1,3-thiazol-5-yl]cyclobutane-1-carboxamide; |
| Compound 1-10 | 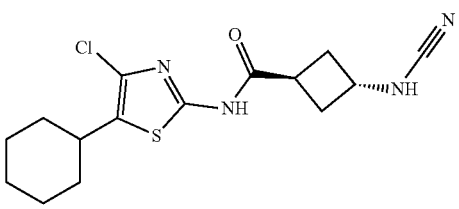 [SMILES: N#CN[C@H]1C[C@H](C(=O)Nc2nc(Cl)c(C3CCCCC3)s2)C1] | (1r,3r)-N-(4-chloro-5-cyclohexyl-1,3-thiazol-2-yl)-3-(cyanoamino)cyclobutane-1-carboxamide; |
| Compound 1-11 | 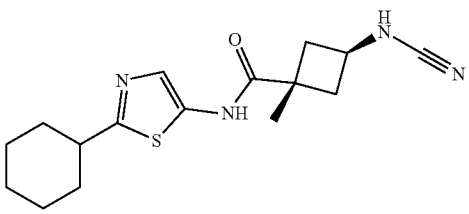 [SMILES: C[C@]1(C(=O)Nc2cnc(C3CCCCC3)s2)C[C@H](NC#N)C1] | (1r,3s)-3-(cyanoamino)-N-(2-cyclohexyl-1,3-thiazol-5-yl)-1-methylcyclobulane-1-carboxamide; |
| Compound 1-12 | 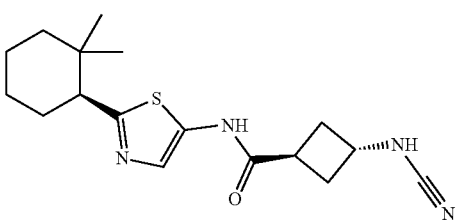 [SMILES: CC1(C)CCCC[C@@H]1c1ncc(NC(=O)[C@H]2C[C@H](NC#N)C2)s1] | (1r,3r)-3-(cyanoamino)-N-{2-[(1S)-2,2-dimethylcyclohexyl]-1,3-thiazol-5-yl}cyclobutane-1-carboxamide; |
| Compound 1-13 | 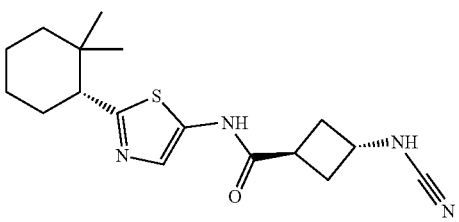 [SMILES: CC1(C)CCCC[C@H]1c1ncc(NC(=O)[C@H]2C[C@H](NC#N)C2)s1] | (1r,3r)-3-(cyanoamino)-N-{2-[(1S)-2,2-dimethylcyclohexyl]-1,3-thiazol-5-yl}cyclobutane-1-carboxamide; |

-continued

| | | |
|---|---|---|
| Compound 1-14 | 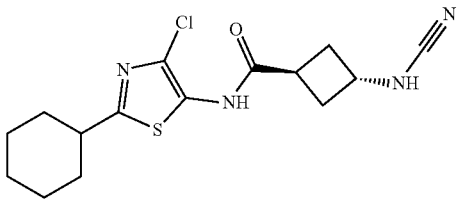 | (1r,3r)-N-(4-chloro-2-cyclohexyl-1,3-thiazol-5-yl)-3-(cyanoamino)cyclobutane-1-carboxamide; |
| Compound 1-15 | 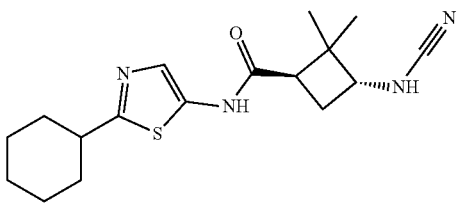 [SMILES: CC1(C)[C@H](NC#N)C[C@H]1C(=O)Nc1cnc(C2CCCCC2)s1] | (1R,3R)-3-(cyanoamino)-N-(2-cyclohexyl-1,3-thiazol-5-yl)-2,2-dimethylcyclobutane-1-carboxamide; |
| Compound 1-16 | 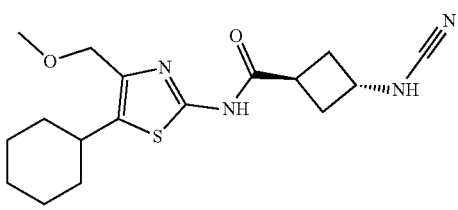 [SMILES: COCc1nc(NC(=O)[C@H]2C[C@H](NC#N)C2)sc1C1CCCCC1] | (1r,3r)-3-(cyanoamino)-N-[5-cyclohexyl-4-(methoxymethyl)-1,3-thiazol-2-yl]cyclobutane-1-carboxamide; |
| Compound 1-17 | 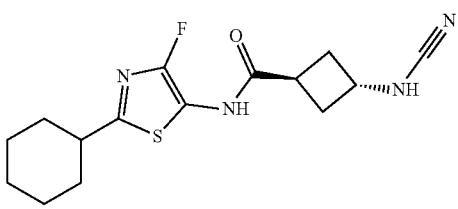 | (1r,3r)-3-(cyanoamino)-N-(2-cyclohexyl-4-fluoro-1,3-thiazol-5-yl)cyclobutane-1-carboxamide; |
| Compound 1-18 | 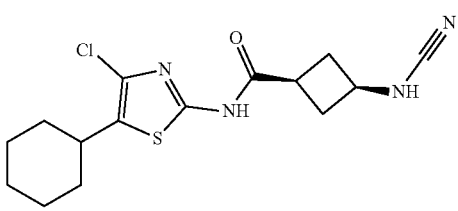 [SMILES: N#CN[C@H]1C[C@@H](C(=O)Nc2nc(Cl)c(C3CCCCC3)s2)C1] | (1s,3s)-N-(4-chloro-5-cyclohexyl-1,3-thiazol-2-yl)-3-(cyanoamino)cyclobutane-1-carboxamide; |
| Compound 1-19 | 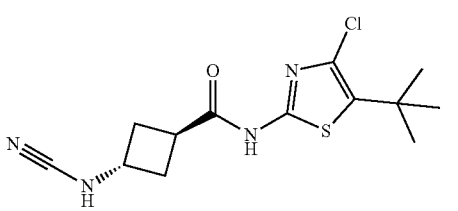 | (1r,3r)-N-(5-tert-butyl-4-chloro-1,3-thiazol-2-yl)-3-(cyanoamino)cyclobutane-1-carboxamide; |
| Compound 1-20 | 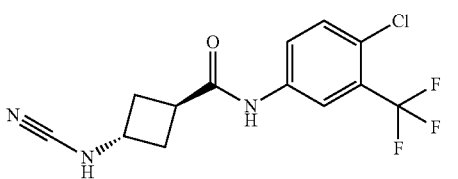 [SMILES: N#CN[C@H]1C[C@H](C(=O)Nc2ccc(Cl)c(C(F)(F)F)c2)C1] | (1r,3r)-N-[4-chloro-3-(trifluoromethyl)phenyl]-3-(cyanoamino)cyclobutane-1-carboxamide; |

-continued

| | | |
|---|---|---|
| Compound 1-21 | 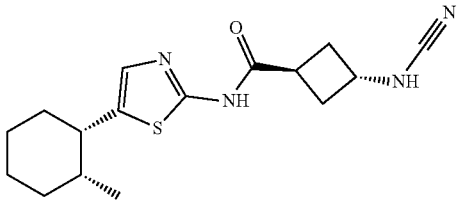 [SMILES: C[C@@H]1CCCC[C@@H]1c1cnc(NC(=O)[C@H]2C[C@H](NC#N)C2)s1] | (1r,3r)-3-(cyanoamino)-N-{5-[(1S,2R)-2-methylcyclohexyl]-1,3-thiazol-2-yl}cyclobutane-1-carboxamide; |
| Compound 1-22 | 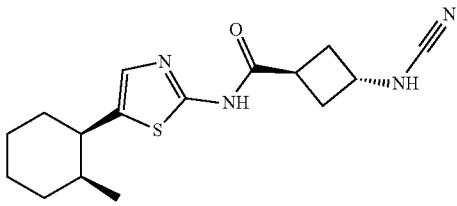 [SMILES: C[C@H]1CCCC[C@H]1c1cnc(NC(=O)[C@H]2C[C@H](NC#N)C2)s1] | (1r,3r)-3-(cyanoamino)-N-{5-[(1R,2S)-2-methylcyclohexyl]-1,3-thiazol-2-yl}cyclobutane-1-carboxamide; |
| Compound 1-23 | 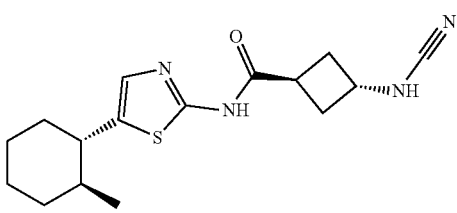 [SMILES: C[C@H]1CCCC[C@@H]1c1cnc(NC(=O)[C@H]2C[C@H](NC#N)C2)s1] | (1r,3r)-3-(cyanoamino)-N-{5-[(1S,2S)-2-methylcyclohexyl]-1,3-thiazol-2-yl}cyclobutane-1-carboxamide; |
| Compound 1-24 | 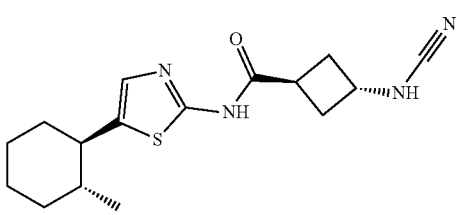 [SMILES: C[C@@H]1CCCC[C@H]1c1cnc(NC(=O)[C@H]2C[C@H](NC#N)C2)s1] | (1r,3r)-3-(cyanoamino)-N-{5-[(1R,2R)-2-methylcyclohexyl]-1,3-thiazol-2-yl}cyclobutane-1-carboxamide; |
| Compound 1-25 | 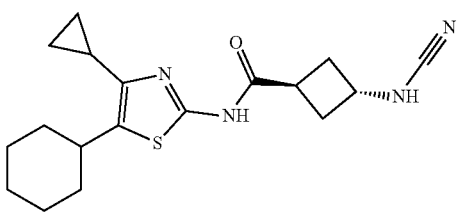 [SMILES: N#CN[C@H]1C[C@H](C(=O)Nc2nc(C3CC3)c(C3CCCCC3)s2)C1] | (1r,3r)-3-(cyanoamino)-N-(5-cyclohexyl-4-cyclopropyl-1,3-thiazol-2-yl)cyclobutane-1-carboxamide; |
| Compound 1-26 | 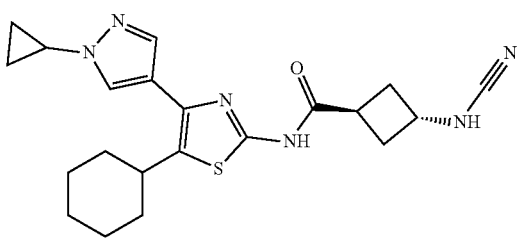 [SMILES: N#CN[C@H]1C[C@H](C(=O)Nc2nc(-c3cnn(C4CC4)c3)c(C3CCCCC3)s2)C1] | (1r,3r)-3-(cyanoamino)-N-[5-cyclohexyl-4-(1-cyclopropyl-1H-pyrazol-4-yl)-1,3-thiazol-2-yl]cyclobutane-1-carboxamide; |
| Compound 1-27 | 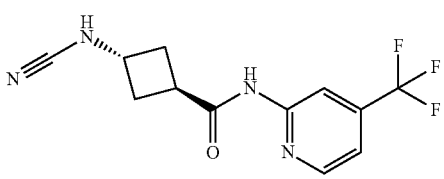 [SMILES: N#CN[C@H]1C[C@H](C(=O)Nc2cc(C(F)(F)F)ccn2)C1] | (1r,3r)-3-(cyanoamino)-N-[4-(trifluoromethyl)pyridin-2-yl]cyclobutane-1-carboxamide; |

-continued

| | | |
|---|---|---|
| Compound 1-28 | 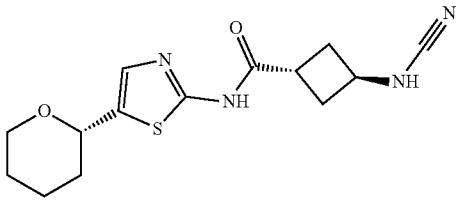 [SMILES: N#CN[C@H]1C[C@H](C(=O)Nc2ncc([C@@H]3CCCCO3)s2)C1] | (1r,3r)-3-(cyanoamino)-N-{5-[(2S)-oxan-2-yl]-1,3-thiazol-2-yl}cyclobutane-1-carboxamide; |
| Compound 1-29 | 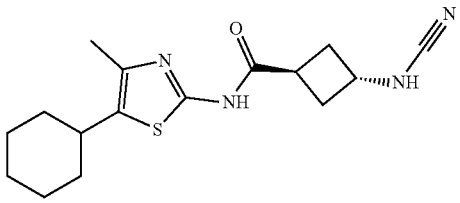 [SMILES: Cc1nc(NC(=O)[C@H]2C[C@H](NC#N)C2)sc1C1CCCCC1] | (1r,3r)-3-(cyanoamino)-N-(5-cyclohexyl-4-methyl-1,3-thiazol-2-yl)cyclobutane-1-carboxamide; |
| Compound 1-30 | 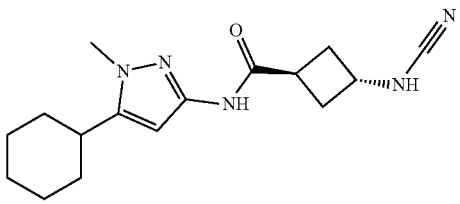 [SMILES: Cn1nc(NC(=O)[C@H]2C[C@H](NC#N)C2)cc1C1CCCCC1] | (1r,3r)-3-(cyanoamino)-N-(5-cyclohexyl-1-methyl-1H-pyrazol-3-yl)cyclobutane-1-carboxamide; |
| Compound 1-31 | 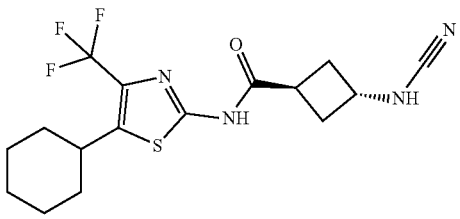 [SMILES: N#CN[C@H]1C[C@H](C(=O)Nc2nc(C(F)(F)F)c(C3CCCCC3)s2)C1] | (1r,3r)-3-(cyanoamino)-N-[5-cyclohexyl-4-(trifluoromethyl)-1,3-thiazol-2-yl]cyclobutane-1-carboxamide; |
| Compound 1-32 | 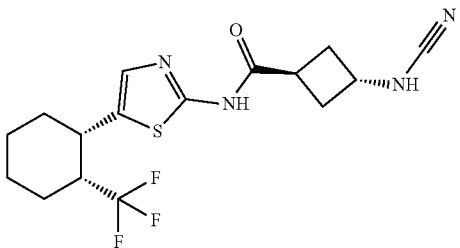 [SMILES: N#CN[C@H]1C[C@H](C(=O)Nc2ncc([C@H]3CCCC[C@H]3C(F)(F)F)s2)C1] | (1r,3r)-3-(cyanoamino)-N-[5-[(1S,2R)-2-(trifluoromethyl)cyclohexyl]-1,3-thiazol-2-yl}cyclobutane-1-carboxamide; |
| Compound 1-33 | 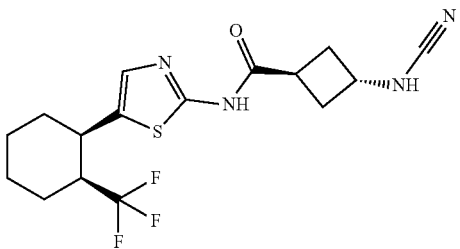 [SMILES: N#CN[C@H]1C[C@H](C(=O)Nc2ncc([C@@H]3CCCC[C@@H]3C(F)(F)F)s2)C1] | (1r,3r)-3-(cyanoamino)-N-{5-[(1R,2S)-2-(trifluoromethyl)cyclohexyl]-1,3-thiazol-2-yl}cyclobutane-1-carboxamide; |
| Compound 1-34 | 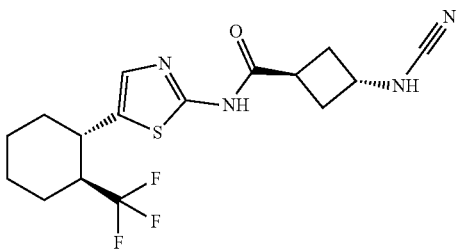 [SMILES: N#CN[C@H]1C[C@H](C(=O)Nc2ncc([C@H]3CCCC[C@@H]3C(F)(F)F)s2)C1] | (1r,3r)-3-(cyanoamino)-N-{5-[(1S,2S)-2-(trifluoromethyl)cyclohexyl]-1,3-thiazol-2-yl}cyclobutane-1-carboxamide; |

-continued

| | | |
|---|---|---|
| Compound 1-35 | 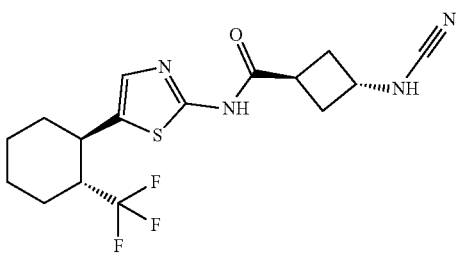 [SMILES: N#CN[C@H]1C[C@H](C(=O)Nc2ncc([C@@H]3CCCC[C@H]3C(F)(F)F)s2)C1] | (1r,3r)-3-(cyanoamino)-N-{5-[(1R,2R)-2-(trifluoromethyl)cyclohexyl]-1,3-thiazol-2-yl}cyclobutane-1-carboxamide; |
| Compound 1-36 | 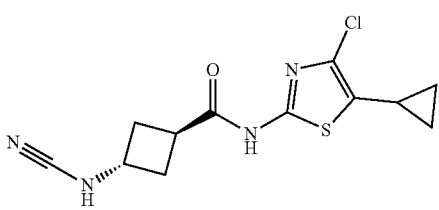 [SMILES: N#CN[C@H]1C[C@H](C(=O)Nc2nc(Cl)c(C3CC3)s2)C1] | (1r,3r)-N-(4-chloro-5-cyclopropyl-1,3-thiazol-2-yl)-3-(cyanoamino)cyclobutane-1-carboxamide; |
| Compound 1-37 | 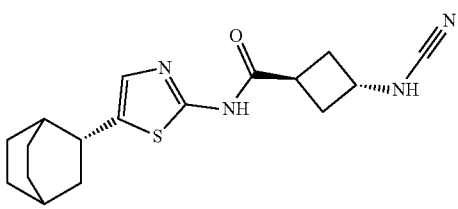 [SMILES: N#CN[C@H]1C[C@H](C(=O)Nc2ncc([C@@H]3CC4CCC3CC4)s2)C1] | (1r,3r)-N-{5-[(2R)-bicyclo[2.2.2]octan-2-yl]-1,3-thiazol-2-yl}-3-(cyanoamino)cyclobutane-1-carboxamide; |
| Compound 1-38 | 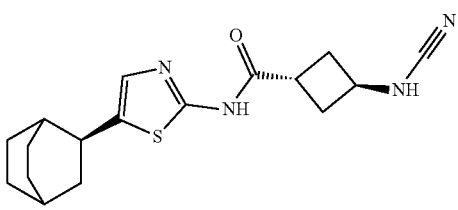 [SMILES: N#CN[C@H]1C[C@H](C(=O)Nc2ncc([C@H]3CC4CCC3CC4)s2)C1] | (1r,3r)-N-{5-[(2S)-bicyclo[2.2.2]octan-2-yl]-1,3-thiazol-2-yl}-3-(cyanoamino)cyclobutane-1-carboxamide; |
| Compound 1-39 | 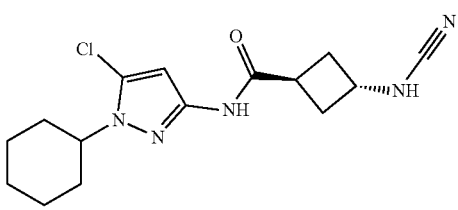 [SMILES: N#CN[C@H]1C[C@H](C(=O)Nc2cc(Cl)n(C3CCCCC3)n2)C1] | (1r,3r)-N-(5-chloro-1-cyclohexyl-1H-pyrazol-3-yl)-3-(cyanoamino)cyclobutane-1-carboxamide; |
| Compound 1-40 | 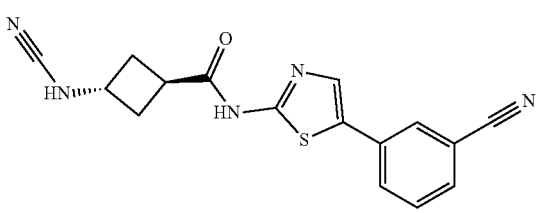 [SMILES: N#CN[C@H]1C[C@H](C(=O)Nc2ncc(-c3cccc(C#N)c3)s2)C1] | (1r,3r)-3-(cyanoamino)-N-[5-(3-cyanophenyl)-1,3-thiazol-2-yl]cyclobutane-1-carboxamide; |
| Compound 1-41 | 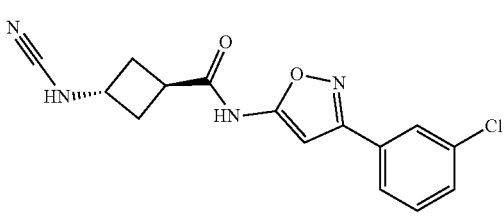 [SMILES: N#CN[C@H]1C[C@H](C(=O)Nc2cc(-c3cccc(Cl)c3)no2)C1] | (1r,3r)-N-[3-(3-chlorophenyl)-1,2-oxazol-5-yl]-3-(cyanoamino)cyclobutane-1-carboxamide; |

-continued

| | | |
|---|---|---|
| Compound 1-42 | 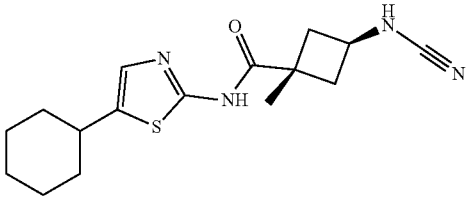 [SMILES: C[C@]1(C(=O)Nc2ncc(C3CCCCC3)s2)C[C@H](NC#N)C1] | (1r,3s)-3-(cyanoamino)-N-(5-cyclohexyl-1,3-thiazol-2-yl)-1-methylcyclobutane-1-carboxamide; |
| Compound 1-43 | 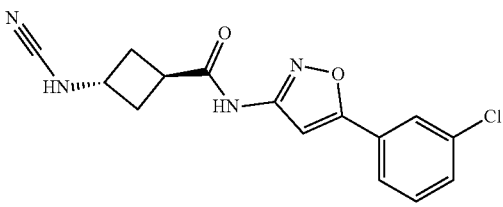 [SMILES: N#CN[C@H]1C[C@H](C(=O)Nc2cc(-c3cccc(Cl)c3)on2)C1] | (1r,3r)-N-[5-(3-chlorophenyl)-1,2-oxazol-3-yl]-3-(cyanoamino)cyclobutane-1-carboxamide; |
| Compound 1-44 | 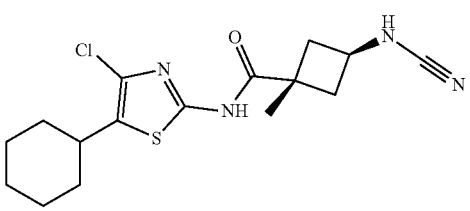 [SMILES: C[C@]1(C(=O)Nc2nc(Cl)c(C3CCCCC3)s2)C[C@H](NC#N)C1] | (1r,3s)-N-(4-chloro-5-cyclohexyl-1,3-thiazol-2-yl)-3-(cyanoamino)-1-methylcyclobutane-1-carboxamide; |
| Compound 1-45 | 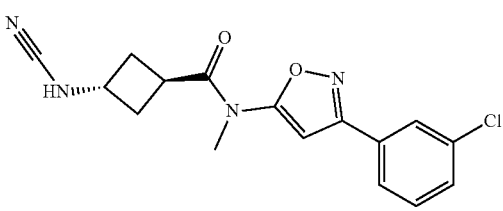 [SMILES: CN(c1cc(-c2cccc(Cl)c2)no1)C(=O)[C@H]1C[C@H](NC#N)C1] | (1r,3r)-N-[3-(3-chlorophenyl)-1,2-oxazol-5-yl]-3-(cyanoamino)-N-methylcyclobutane-1-carboxamide; |
| Compound 1-46 | 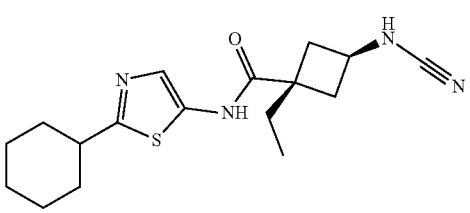 [SMILES: CC[C@]1(C(=O)Nc2cnc(C3CCCCC3)s2)C[C@H](NC#N)C1] | (1r,3s)-3-(cyanoamino)-N-(2-cyclohexyl-1,3-thiazol-5-yl)-1-ethylcyclobutane-1-carboxamide; |
| Compound 1-47 | 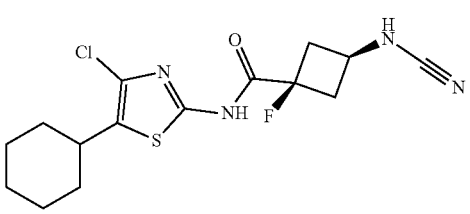 [SMILES: N#CN[C@H]1C[C@](F)(C(=O)Nc2nc(Cl)c(C3CCCCC3)s2)C1] | (1s,3s)-N-(4-chloro-5-cyclohexyl-1,3-thiazol-2-yl)-3-(cyanoamino)-1-fluorocyclobutane-1-carboxamide; |
| Compound 1-48 | 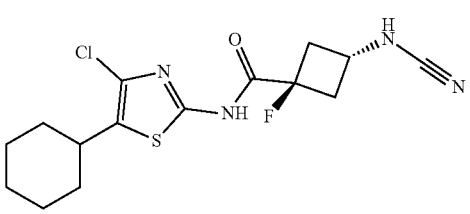 [SMILES: N#CN[C@H]1C[C@@](F)(C(=O)Nc2nc(Cl)c(C3CCCCC3)s2)C1] | (1r,3r)-N-(4-chloro-5-cyclohexyl-1,3-thiazol-2-yl)-3-(cyanoamino)-1-fluorocyclobutane-1-carboxamide; |

-continued

| | | |
|---|---|---|
| Compound 1-49 | 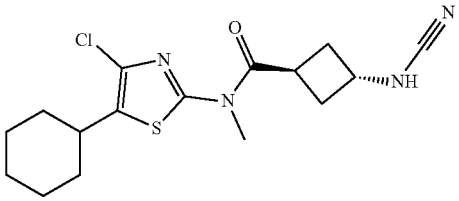 [SMILES: CN(c1nc(Cl)c(C2CCCCC2)s1)C(=O)[C@H]1C[C@H](NC#N)C1] | (1r,3r)-N-(4-chloro-5-cyclohexyl-1,3-thiazol-2-yl)-3-(cyanoamino)-N-methylcyclobutane-1-carboxamide; |
| Compound 1-50 | 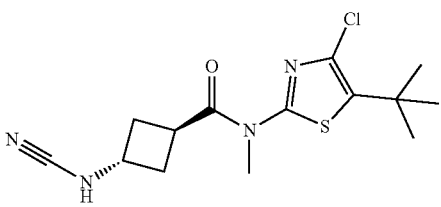 [SMILES: CN(c1nc(Cl)c(C(C)(C)C)s1)C(=O)[C@H]1C[C@H](NC#N)C1] | (1r,3r)-N-(5-tert-butyl-4-chloro-1,3-thiazol-2-yl)-3-(cyanoamino)-N-methylcyclobutane-1-carboxamide; |
| Compound 1-51 | 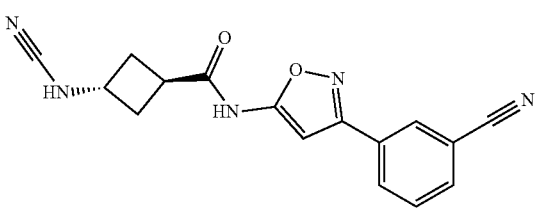 [SMILES: N#CN[C@H]1C[C@H](C(=O)Nc2cc(-c3cccc(C#N)c3)no2)C1] | (1r,3r)-3-(cyanoamino)-N-[3-(3-cyanophenyl)-1,2-oxazol-5-yl]cyclobutane-1-carboxamide; |
| Compound 1-52 | 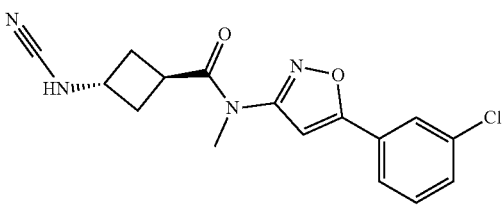 [SMILES: CN(c1cc(-c2cccc(Cl)c2)on1)C(=O)[C@H]1C[C@H](NC#N)C1] | (1r,3r)-N-[5-(3-chlorophenyl)-1,2-oxazol-3-yl]-3-(cyanoamino)-N-methylcyclobutane-1-carboxamide; |
| Compound 1-53 | 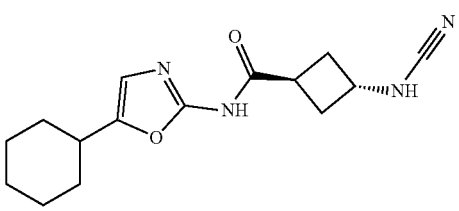 | (1r,3r)-3-(cyanoamino)-N-(5-cyclohexyl-1,3-oxazol-2-yl)cyclobutane-1-carboxamide; |
| Compound 1-54 | 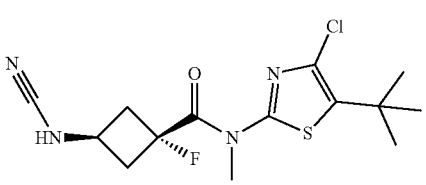 [SMILES: CN(c1nc(Cl)c(C(C)(C)C)s1)C(=O)[C@]1(F)C[C@H](NC#N)C1] | (1r,3r)-N-(5-tert-butyl-4-chloro-1,3-thiazol-2-yl)-3-(cyanoamino)-1-fluoro-N-methylcyclobutane-1-carboxamide; |
| Compound 1-55 | 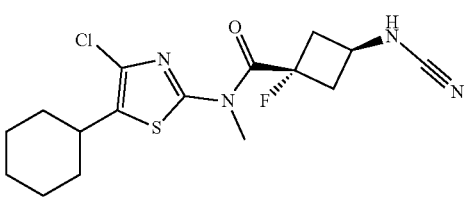 [SMILES: CN(c1nc(Cl)c(C2CCCCC2)s1)C(=O)[C@]1(F)C[C@H](NC#N)C1] | (1r,3r)-N-(4-chloro-5-cyclohexyl-1,3-thiazol-2-yl)-3-(cyanoamino)-1-fluoro-N-methylcyclobutane-1-carboxamide; |

-continued

Compound 1-56 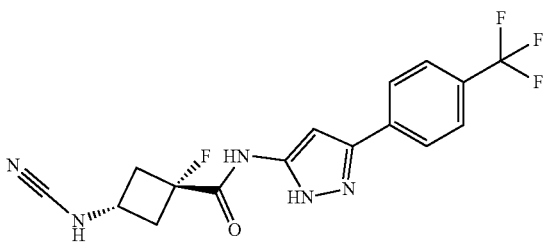 [SMILES: N#CN[C@H]1C[C@](F)(C(=O)Nc2cc(-c3ccc(C(F)(F)F)cc3)n[nH]2)C1] (1s,3s)-3-(cyanoamino)-1-fluoro-N-{3-[4-(trifluoromethyl)phenyl]-1H-pyrazol-5-yl}cyclobutane-1-carboxamide;

Compound 1-57 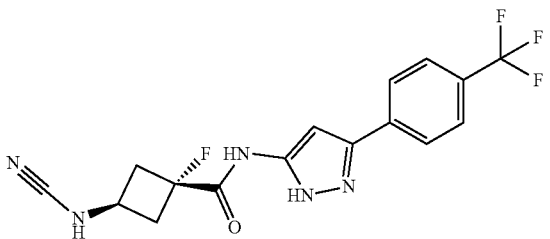 [SMILES: N#CN[C@H]1C[C@@](F)(C(=O)Nc2cc(-c3ccc(C(F)(F)F)cc3)n[nH]2)C1] (1r,3r)-3-(cyanoamino)-1-fluoro-N-{3-[4-(trifluoromethyl)phenyl]-1H-pyrazol-5-yl}cyclobutane-1-carboxamide;

Compound 1-58 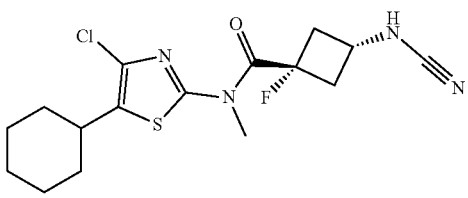 [SMILES: CN(c1nc(Cl)c(C2CCCCC2)s1)C(=O)[C@]1(F)C[C@@H](NC#N)C1] (1s,3s)-N-(4-chloro-5-cyclohexyl-1,3-thiazol-2-N-3-(cyanoamino)-1-fluoro-N-methylcyclobutane-1-carboxamide;

Compound 1-59 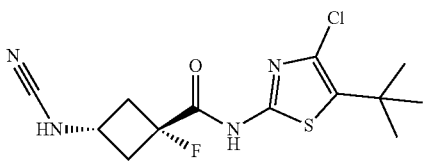 (1s,3s)-N-(5-tert-butyl-4-chloro-1,3-thiazol-2-yl)-3-(cyanoamino)-1-fluorocyclobutane-1-carboxamide;

Compound 1-60 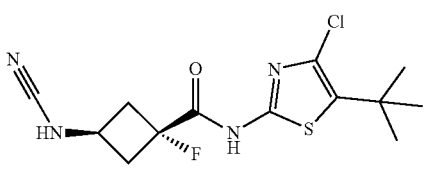 [SMILES: CC(C)(C)c1sc(NC(=O)[C@]2(F)C[C@H](NC#N)C2)nc1Cl] (1r,3r)-N-(5-tert-butyl-4-chloro-1,3-thiazol-2-yl)-3-(cyanoamino)-1-fluorocyclobutane-1-carboxamide;

Compound 1-61 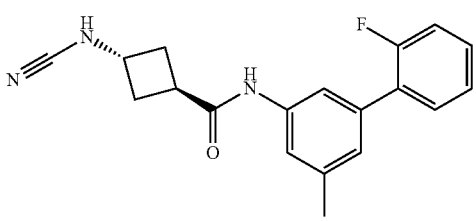 [SMILES: Cc1cc(NC(=O)[C@H]2C[C@H](NC#N)C2)cc(-c2ccccc2F)c1] (1r,3r)-3-(cyanoamino)-N-[3-(2-fluorophenyl)-5-methylphenyl]cyclobutane-1-carboxamide;

Compound 1-62 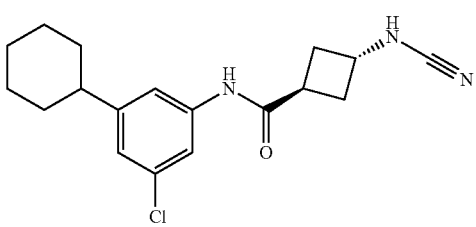 [SMILES: N#CN[C@H]1C[C@H](C(=O)Nc2cc(Cl)cc(C3CCCCC3)c2)C1] (1r,3r)-N-(3-chloro-5-cyclohexylphenyl)-3-(cyanoamino)cyclobutane-1-carboxamide;

| | | |
|---|---|---|
| Compound 1-63 | 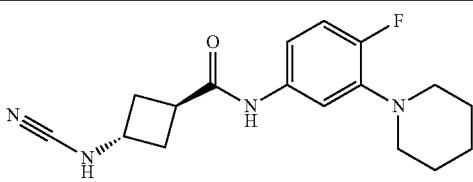 | (1r,3r)-3-(cyanoamino)-N-[4-fluoro-3-(piperidin-1-yl)phenyl]cyclobutane-1-carboxamide; |
| Compound 1-64 | 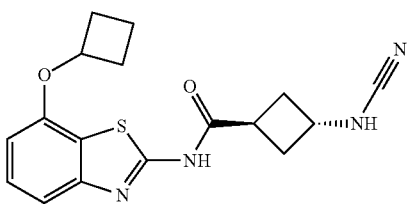 [SMILES: N#CN[C@H]1C[C@H](C(=O)Nc2nc3cccc(OC4CCC4)c3s2)C1] | (1r,3r)-3-(cyanoamino)-N-(7-cyclobutoxy-1,3-benzothiazol-2-yl)cyclobutane-1-carboxamide; |
| Compound 1-65 | 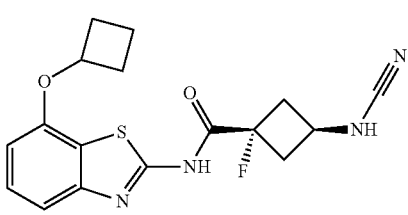 | (1r,3r)-3-(cyanoamino)-N-(7-cyclobutoxy-1,3-benzothiazol-2-yl)-1-fluorocyclobutane-1-carboxamide; |
| Compound 1-66 | 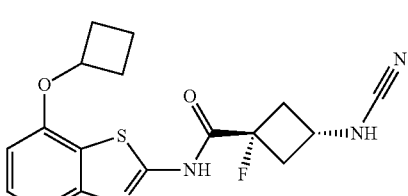 | (1s,3s)-3-(cyanoamino)-N-(7-cyclobutoxy-1,3-benzothiazol-2-yl)-1-fluorocyclobutane-1-carboxamide; |
| Compound 1-67 | 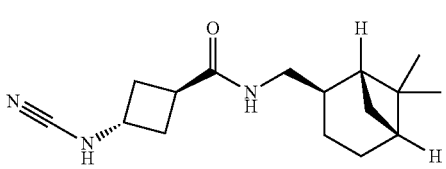 [SMILES: CC1(C)[C@@H]2CC[C@@H](CNC(=O)[C@H]3C[C@H](NC#N)C3)[C@H]1C2] | (1r,3r)-3-(cyanoamino)-N-{[(1R,2R,5R)-6,6-dimethylbicyclo[3.1.1]-heptane-2-yl]methyl}cyclobutane-1-carboxamide; |
| Compound 1-68 | 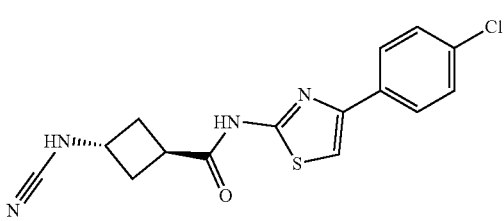 [SMILES: N#CN[C@H]1C[C@H](C(=O)Nc2nc(-c3ccc(Cl)cc3)cs2)C1] | (1r,3r)-N-[4-(4-chlorophenyl)-1,3-thiazol-2-yl]-3-(cyanoamino)cyclobutane-1-carboxamide; |
| Compound 1-69 | 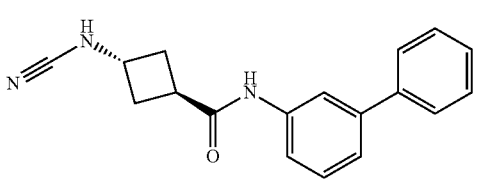 [SMILES: N#CN[C@H]1C[C@H](C(=O)Nc2cccc(-c3ccccc3)c2)C1] | (1r,3r)-3-(cyanoamino)-N-(3-phenylphenyl)cyclobutane-1-carboxamide; |
| Compound 1-70 | 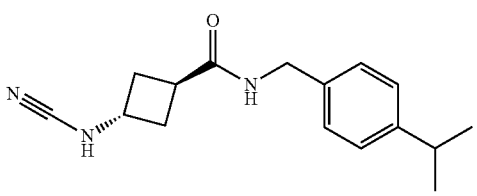 [SMILES: CC(C)c1ccc(CNC(=O)[C@H]2C[C@H](NC#N)C2)cc1] | (1r,3r)-3-(cyanoamino)-N-{[4-(propan-2-yl)phenyl]methyl}cyclobutane-1-carboxamide; |

| | | |
|---|---|---|
| Compound 1-71 | 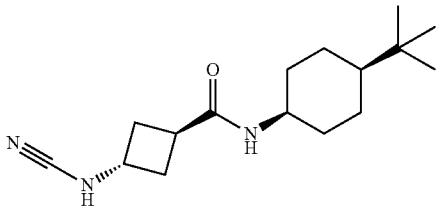 [SMILES: CC(C)(C)[C@H]1CC[C@@H](NC(=O)[C@H]2C[C@H](NC#N)C2)CC1] | (1r,3r)-3-(cyanoamino)-N-[(1s,4s)-4-tert-butylcyclohexyl]cyclobutane-1-carboxamide; |
| Compound 1-72 | 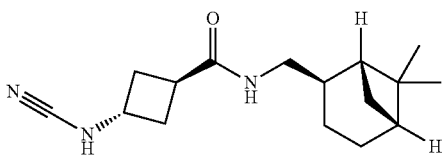 | (1r,3r)-3-(cyanoamino)-N-{[(1R,2R,5R)-6,6-dimethylbicyclo[3.1.1]heptan-2-yl]methyl}cyclobutane-1-carboxamide; |
| Compound 1-73 | 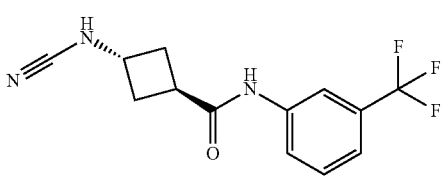 [SMILES: N#CN[C@H]1C[C@H](C(=O)Nc2cccc(C(F)(F)F)c2)C1] | (1r,3r)-3-(cyanoamino)-N-[3-(trifluoromethyl)phenyl]-cyclcobutane-1-carboxamide; |
| Compound 3-2 | 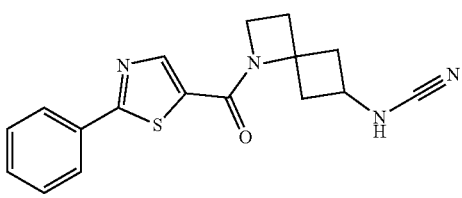 [SMILES: N#CNC1CC2(CCN2C(=O)c2cnc(-c3ccccc3)s2)C1] | {[1-(2-phenyl-1,3-thiazole-5-carbonyl)-1-azaspiro[3.3]heptan-6-yl]amino}carbonitrile; |
| Compound 3-3 | 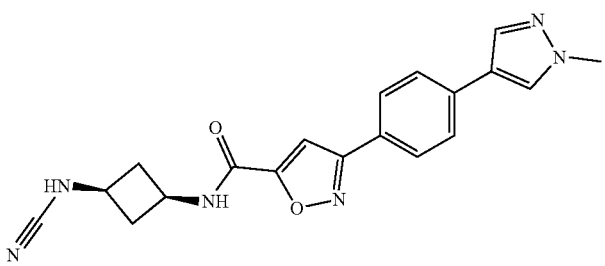 [SMILES: Cn1cc(-c2ccc(-c3cc(C(=O)N[C@H]4C[C@@H](NC#N)C4)on3)cc2)cn1] | 3-[4-(1-methyl-1H-pyrazol-4-yl)phenyl]-N-[(1,s,3s)-3-(cyanoamino)cyclobutyl]-1,2-oxazole-5-carboxamide, |
| Compound 3-4 | 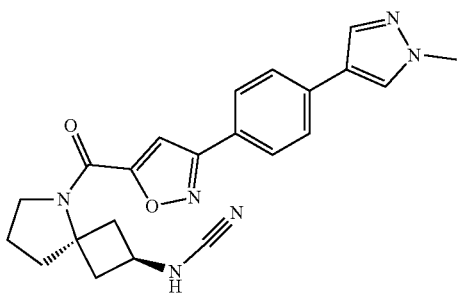 [SMILES: Cn1cc(-c2ccc(-c3cc(C(=O)N4CCC[C@]45C[C@H](NC#N)C5)on3)cc2)cn1] | {[(2r,4s)-5-{3-[4-(1-methyl-1H-pyrazol-4-yl)phenyl]-1,2-oxazole-5-carbonyl}-5-azaspiro[3.4]octan-2-yl]amino}carbonitrile; |
| Compound 3-5 | 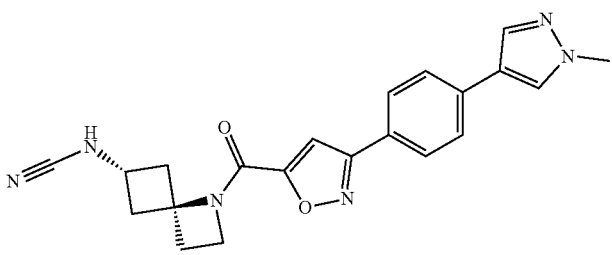 [SMILES: Cn1cc(-c2ccc(-c3cc(C(=O)N4CC[C@]45C[C@@H](NC#N)C5)on3)cc2)cn1] | {[(4r,6s)-1-{3-[4-(1methyl-1H-pyrazol-4-yl)phenyl]-1,2-oxazole-5-carbonyl}-1-azaspiro[3.3]heptan-6-yl]amino}carbonitrile; |

-continued

| | | |
|---|---|---|
| Compound 3-6 | | 3-(3-cyanophenyl)-N-methyl-N-[(1r,3r)-3-(cyanoamino)cyclobutyl]-1,2-oxazole-5-carboxamide; |
| Compound 6-1 | | {[(1r,3r)-3-[(4S)-4-[(5-cyclohexyl-1,3-thiazol-2-yl)amino]-2-oxopyrrolidin-1-yl]cyclobutyl]amino}-carbonitrile; |
| Compound 7-1 | | {[(2r,4s)-6-(5-tert-butyl-4-chloro-1,3-thiazol-2-yl)-5-oxo-6-azaspiro[3.4]octan-2-yl]amino}carbonitrile; |
| Compound 7-2 | | {[(2s,4r)-6-(4-chloro-5-cyclohexyl-1,3-thiazol-2-yl)-5-oxo-6-azaspiro[3.4]octan-2-yl]amino}carbonitrile; |
| Compound 7-3 | | {[(2r,4s)-6-(4-chloro-5-cyclohexyl-1,3-thiazol-2-yl)-5-oxo-6-azaspiror[3.4]octan-2-yl]amino}carbonitrile; |
| Compound 8-1 | | (1r,3r)-N-(5-tert-butyl-4-chloro-1,3-thiazol-2-yl)-3-(cyanoamino)-1-methoxycyclobutane-1-carboxamide; |
| Compound 9-1 | | (1s,3s)-N-(5-tert-butyl-4-chloro-1,3-thiazol-2-yl)-1-chloro-3-(cyanoamino)cyclobutane-1-carboxamide; |
| Compound 9-2 | | (1r,3r)-N-(5-tert-butyl-4-chloro-1,3-thiazol-2-yl)-1-chloro-3-(cyanoamino)cyclobutane-1-carboxamide; and | or a pharmaceutically acceptable salt thereof.

23. A pharmaceutical composition comprising the compound of claim 1 or a pharmaceutically acceptable salt thereof and a pharmaceutically acceptable carrier.

24. A pharmaceutical composition comprising the compound of claim 22 or a pharmaceutically acceptable salt thereof and a pharmaceutically acceptable carrier.

* * * * *